US009879177B2

(12) United States Patent
Heun et al.

(10) Patent No.: US 9,879,177 B2
(45) Date of Patent: Jan. 30, 2018

(54) METAL COMPLEXES COMPRISING CONDENSED HETEROAROMATIC RINGS

(71) Applicant: Merck Patent GmbH, Darmstadt (DE)

(72) Inventors: Susanne Heun, Bad Soden (DE); Nils Koenen, Darmstadt (DE); Cheng-Han Yang, Fangshan Township (TW); Luisa De Cola, Muenster (DE)

(73) Assignee: Merck Patent GmbH (DE)

( * ) Notice: Subject to any disclaimer, the term of this patent is extended or adjusted under 35 U.S.C. 154(b) by 382 days.

(21) Appl. No.: 14/402,360

(22) PCT Filed: Apr. 26, 2013

(86) PCT No.: PCT/EP2013/001261
§ 371 (c)(1),
(2) Date: Nov. 20, 2014

(87) PCT Pub. No.: WO2013/174471
PCT Pub. Date: Nov. 28, 2013

(65) Prior Publication Data
US 2015/0105843 A1  Apr. 16, 2015

(30) Foreign Application Priority Data

May 24, 2012 (EP) ..................... 12004059

(51) Int. Cl.
| | | |
|---|---|---|
| C09K 11/06 | (2006.01) | |
| A61N 5/06 | (2006.01) | |
| C07F 15/00 | (2006.01) | |
| H01L 51/00 | (2006.01) | |
| H05B 33/10 | (2006.01) | |
| H01L 51/50 | (2006.01) | |

(52) U.S. Cl.
CPC ............ *C09K 11/06* (2013.01); *A61N 5/06* (2013.01); *A61N 5/0616* (2013.01); *C07F 15/0033* (2013.01); *H01L 51/0085* (2013.01); *H01L 51/5012* (2013.01); *H05B 33/10* (2013.01); *A61N 5/062* (2013.01); *A61N 2005/065* (2013.01); *A61N 2005/0653* (2013.01); *A61N 2005/0663* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *C09K 2211/185* (2013.01); *H01L 51/5016* (2013.01); *Y02E 10/549* (2013.01); *Y02P 70/521* (2015.11)

(58) Field of Classification Search
CPC .... A61N 2005/0652; A61N 2005/0653; A61N 2005/0663; A61N 5/06; A61N 5/0616; A61N 5/062; C07F 15/0033; C09K 11/06; C09K 2211/1007; C09K 2211/1011; C09K 2211/1029; C09K 2211/1044; C09K 2211/1059; C09K 2211/1088; C09K 2211/1092; C09K 2211/185; H01L 51/0085; H01L 51/5012; H01L 51/5016; H05B 33/10; Y02E 10/549; Y02P 70/521

See application file for complete search history.

(56) References Cited

U.S. PATENT DOCUMENTS

| | | |
|---|---|---|
| 2004/0013905 A1 | 1/2004 | Tsuboyama et al. |
| 2006/0286404 A1 | 12/2006 | Wu |
| 2008/0160182 A1 | 7/2008 | Kathirgamanathan et al. |
| 2008/0217606 A1 | 9/2008 | Cheng et al. |
| 2009/0039771 A1 | 2/2009 | Oshiyama et al. |
| 2011/0049496 A1 | 3/2011 | Fukuzaki |
| 2011/0204333 A1 | 8/2011 | Xia et al. |
| 2013/0116755 A1 | 5/2013 | Anemian et al. |
| 2014/0135498 A1 | 5/2014 | Fukuzaki |

FOREIGN PATENT DOCUMENTS

| | | | |
|---|---|---|---|
| CN | 101107884 A | 1/2008 | |
| CN | 101200478 A | 6/2008 | |
| EP | 1238981 A2 | 9/2002 | |
| JP | 2004067658 A | 3/2004 | |
| JP | 2008529212 A | 7/2008 | |
| JP | 2011089103 A | 5/2011 | |
| JP | 201277069 A | 4/2012 | |
| KR | 20100090156 A | 8/2010 | |
| TW | 200844103 A | 11/2008 | |
| WO | WO-2005/118606 A1 | 12/2005 | |
| WO | WO-2006077402 A1 | 7/2006 | |
| WO | WO-2010090362 A1 | 8/2010 | |
| WO | WO-2010090925 A1 | 8/2010 | |
| WO | WO-2010111175 A1 | 9/2010 | |
| WO | WO 2010/111175 * | 6/2011 | ........... C07D 207/16 |
| WO | WO-2011/069590 A1 | 6/2011 | |

(Continued)

OTHER PUBLICATIONS

Hwang, F., et al., "Iridium(III) Complexes with Orthometalated Quinoxaline Ligands: Subtle Tuning of Emission to the Saturated Red Color", Inorganic Chemistry, vol. 44, No. 5, (2005), pp. 1344-1353.

International Search Report for PCT/EP2013/001261 dated Jul. 4, 2013.

Tsujimoto, H., et al., "White Electroluminescence Obtained from a Polymer Light-Emitting Diode Containing Two Phosphorescent Iridium(III) Complexes in an Emitting Layer", Journal of the Japan Society of Colour Material, vol. 83, No. 5, (2010), pp. 207-214.

He, W., et al., "A series of iridium complexes equipped with inert shields: Highly efficient bluish green emitters with reduced self quenching effect in solid state", Inorganic Chimica Acta, 2011, vol. 365, pp. 78-84.

(Continued)

*Primary Examiner* — Erich A Leeser
(74) *Attorney, Agent, or Firm* — Drinker Biddle & Reath LLP

(57) ABSTRACT

The present invention relates inter alia to a new class of heteroleptic metal complexes comprising condensed aromatic heterocyclic rings, their preparation and use.

22 Claims, No Drawings

(56) References Cited

FOREIGN PATENT DOCUMENTS

| WO | WO-2011106344 A1 | 9/2011 |
| WO | WO-2011110275 A2 | 9/2011 |
| WO | WO-2011110277 A1 | 9/2011 |
| WO | WO-2012007103 A1 | 1/2012 |
| WO | WO-2012010238 A1 | 1/2012 |

OTHER PUBLICATIONS

Lee, S-J., et al., "Synthesis and Characterization of Red-Emitting Iridium(III) Complexes for Solution-Processable Phosphorescent Organic Light Emitting Diodes", Advanced Functional Materials, 2009, vol. 19, pp. 2205-2212.

Tsujimoto, H., et al., "Pure red electrophosphorescence from polymer light-emitting diodes doped with highly emissive bis-cyclometalated iridium(III) complexes", Journal of Organometallic Chemistry, 2010, vol. 695, pp. 1972-1978.

Japanese Office Action dated Feb. 7, 2017 for application No. JP 2015-513034.

Chinese Office Action for application No. 201380027223.0, dated Jul. 4, 2016.

* cited by examiner

METAL COMPLEXES COMPRISING CONDENSED HETEROAROMATIC RINGS

CROSS-REFERENCE TO RELATED APPLICATIONS

This application is a national stage application (under 35 U.S.C. § 371) of PCT/EP2013/001261, filed Apr. 26, 2013, which claims benefit of European Application No. 12004059.7, filed May 24, 2012, both of which are incorporated herein by reference in their entirety.

The present invention relates to new organic metal complexes, formulations and compositions comprising them, their use in electronic devices and their preparation.

The structure of organic electroluminescent devices (OLEDs) in which organic semiconductors are used as functional materials is described, for example, in U.S. Pat. Nos. 4,539,507, 5,151,629, EP 0676461 and WO 98/27136. The emitting materials being employed for this purpose are increasingly often organometallic complexes which exhibit phosphorescence instead of fluorescence (M. A. Baldo et al., Appl. Phys. Lett. 1999, 75, 4-6). For quantum-mechanical reasons, an up to four-fold increase in energy and power efficiency is possible using organometallic compounds as phosphorescent emitters. In accordance with the prior art, the triplet emitters in phosphorescent OLEDs are, in particular, iridium and platinum complexes, which are typically cyclometallated. The emitters currently available emit light in the range from blue to red.

WO 2010/090362 discloses heteroleptic complexes. The ligands require a specific push-pull substitution pattern. The authors disclose only complexes with the same push-pull-substitution pattern on the phenylpyridine ligand, which is present twice, and all complexes show light-blue emission only. The photoluminescence (PL) efficiencies disclosed are very low (42% max.), and due to the compactness of the emitters, they are clearly intended for use in evaporated devices.

US 2006/0286404 also discloses heteroleptic light-blue emitters. The phenylpyridine ligand here is also F-substituted twice, but contrary to WO 2010/090362 there is no push-functionality. The emitter complexes can also bear (2-pyridyl)-1,2,4-triazole-type ligands. The emitters are used in rather complicated multi-layer devices only, but only one example mentions an efficiency, which is rather low and could just as well be reached with singlet emitters.

US 2008/0217606 discloses heteroleptic red and orange emitters. The metal complexes can comprise 2-naphthalene-1-yl-quinoline or (1,2,3-triazol-4-yl)pyridine ligands. However, all device examples shown are evaporated devices with hole-blocking and electron transport layers.

H. Tsujimoto et al. disclose (J. Jpn. Soc. Colour Mater. 83, (5), 207-214, 2010) a heteroleptic Ir(III)-emitter having a bis[2-(dibenzo[b,d]furan-4-yl) quinolinato-N,$C^{3'}$] ligand and a substituted acetylacetonate (acac) ligand. The Ir(III)-complex shows red electroluminescence and is employed together with a blue emitter in one emissive layer in order to yield white emission. The acac ligand was modified in order to enhance processability, but the efficiencies are low and the voltages high.

The prior art reveals that there is still need for organic light emitting devices such as organic light emitting diodes (OLEDs) and organic light emitting electrochemical cells (OLEDs) which exhibit triplet emission, in particular with respect to high efficiency, low operating voltage and long lifetime of the device. In addition, synthesis and purification of the light emitting metal complexes are often difficult. There is thus a need for emitters which can be manufactured easily so that they are suitable for commercial production. Moreover, there is a need to provide phosphorescent emitters which show improved shelf-life, improved processability (e.g. improved solubility to use printing techniques in the display production process), color and photoluminescence (PL) quantum yields. In addition, not all colors are readily available since much emphasis has been put on saturated RGB materials to obtain high color gamut displays and to achieve a high color rendering index (CRI) in lighting applications. Stable emitters for yellow or orange with high efficiency, long lifetime, good shelf-life and improved processability that can be easily manufactured even on large scale are required for many different applications such as decorative purposes, effect illumination, life science applications (phototherapy) or in the automotive industry (e.g. lane change signals), but also for low-cost lighting applications where two-color whites (light-blue and yellow-orange) are sufficient. These emitters are currently scarce and have not fulfilled the above mentioned requirements.

The underlying problem of the present invention is to overcome the drawbacks of the prior art as described above.

Surprisingly, it has been found that certain metal chelate complexes described in greater detail below solve the problems of the prior art. Particularly, the compounds and devices according to the present invention show excellent efficiencies, a preferential color, good stabilities, long shelf-life, improved solubility, good processability, and can be manufactured easily. Devices can be made in a simple device setup and still lead to high EL efficiencies and good lifetimes.

The invention relates to a compound of the following general Formula (1),

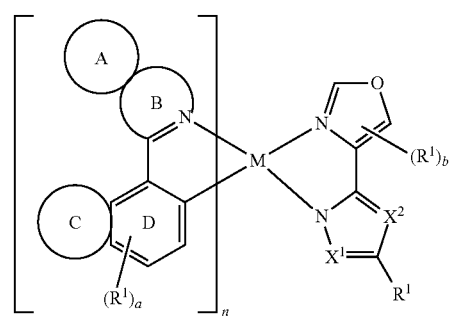

Formula (1)

wherein A and B together represent a condensed heteroaromatic ring system wherein both A and B can be unsubstituted or identically or differently be substituted with one or more $R^1$;

wherein A can be any aromatic or heteroaromatic ring or any aromatic or heteroaromatic polycyclic ring system;

wherein B represents any monocyclic heteroaromatic ring;

wherein C represents a chemical structure having the Formula (2) which is condensed to ring D at any positions via the positions indicated by the sign # in Formula (2);

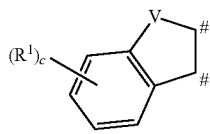

Formula (2)

and where the remaining indices and symbols are defined as follows:

a is 0, 1 or 2;
b is 0, 1 or 2;
is 0, 1, 2, 3 or 4;
M is a metal selected from the group consisting of iridium, rhodium, platinum and palladium, preferably iridium, platinum and palladium, particularly preferably iridium and platinum and very particularly preferably iridium;
n is 2 for M equal to iridium or rhodium and n is 1 for M equal to platinum or palladium; if n is 2, the two ligands comprising the rings A, B, C and D can be identical or different from each other, preferably they are identical;
$R^1$ is identical or different from each other on each occurrence and selected from H, D, F, Cl, Br, I, $N(R^2)_2$, CN, $NO_2$, $Si(R^2)_3$, $B(R^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more substituents $R^2$, where one or more non-adjacent $CH_2$ groups may be replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms which may in each case be substituted by one or more substituents $R^2$, or an aryloxy or heteroaryloxy group having 5 to 60 aromatic ring atoms, which may be substituted by one or more substituents $R^2$, or a diarylamino group, diheteroarylamino group or arylheteroarylamino group having 10 to 40 aromatic ring atoms, which may be substituted by one or more substituents $R^2$, or a combination of two or more of these groups; two or more groups $R^1$ here may also form a mono- or polycyclic, aliphatic, aromatic and/or benzo-fused ring system with one another.
$R^2$ is, identical or different on each occurrence, H, D, F, Cl, Br, I, $N(R^3)_2$, CN, $NO_2$, $Si(R^3)_3$, $B(R^3)_2$, $C(=O)R^3$, $P(=O)(R^3)_2$, $S(=O)R^3$, $S(=O)_2R^3$, $OSO_2R^3$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more substituents $R^3$, where one or more non-adjacent $CH_2$ groups may be replaced by $R^3C=CR^3$, $C\equiv C$, $Si(R^3)_2$, $Ge(R^3)_2$, $Sn(R^3)_2$, $C=O$, $C=S$, $C=Se$, $C=NR^3$, $P(=O)(R^3)$, SO, $SO_2$, $NR^3$, O, S or $CONR^3$ and where one or more H atoms may be replaced by D, F, Cl, Br, I, CN or $NO_2$, or an aromatic or heteroaromatic ring system having 5 to 60 aromatic ring atoms, which may in each case be substituted by one or more substituents $R^3$, or an aryloxy or heteroaryloxy group having 5 to 60 aromatic ring atoms, which may be substituted by one or more substituents $R^3$, or a diarylamino group, diheteroarylamino group or arylheteroarylamino group having 10 to 40 aromatic ring atoms, which may be substituted by one or more substituents $R^3$, or a combination of two or more of these groups; two or more adjacent substituents $R^2$ here may form a mono- or polycyclic, aliphatic or aromatic ring system with one another;
$R^3$ is identical or different on each occurrence and selected from H, D, F or an aliphatic, aromatic and/or heteroaromatic hydrocarbon having 1 to 20 C atoms, in which, in addition, one or more H atoms may be replaced by F; two or more substituents $R^3$ here may also form a mono- or polycyclic, aliphatic or aromatic ring system with one another;
Q is identical or different on each occurrence and selected from $R^1C=CR^1$, $R^1C=N$, O, S, $SO_2$, $SiR^1_2$, Se or $NR^1$, preferably $R^1C=CR^1$, S or $NR^1$; particularly preferably $R^1C=CR^1$ or S, and very particularly preferably $R^1C=CR^1$;
$X^1$ and $X^2$ are identical or different on each occurrence, selected from $CR^1$ or N, wherein at least one of $X^1$ and $X^2$ is N;
V is identical or different on each occurrence and selected from $NR^1$, O, S, $SO_2$, $SiR^1_2$, $BR^1$ or Se, preferably $NR^1$, O, S, particularly preferably S or O, and very particularly preferably O.

An aryl group in the sense of this invention contains 6 to 40 C atoms; a heteroaryl group in the sense of this invention contains 2 to 40 C atoms and at least one heteroatom, with the proviso that the sum of C atoms and heteroatoms is at least 5. The heteroatoms are preferably selected from N, and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, phenanthrene, quinoline, isoquinoline, etc.

An aromatic ring system in the sense of this invention contains 6 to 60 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system also includes systems in which a plurality of aryl or heteroaryl groups are interrupted by a non-aromatic unit (preferably less than 10% of the atoms other than H), such as, for example, an $sp^3$-hybridised C, N or O atom or a carbonyl group. Thus, for example, systems such as 9,9'-spirobifluorene, 9,9-diarylfluorene, triarylamine, diaryl ether, stilbene, etc., are also intended to be taken to mean aromatic ring systems for the purposes of this invention, and likewise systems in which two or more aryl groups are interrupted, for example, by a linear or cyclic alkyl group or by a silyl group.

A cyclic alkyl, alkoxy or thioalkoxy group in the sense of this invention is taken to mean a monocyclic, bicyclic or polycyclic group.

For the purposes of the present invention, a $C_1$- to $C_{40}$-alkyl group, in which, in addition, individual H atoms or $CH_2$ groups may be substituted by the above-mentioned groups, is taken to mean, for example, methyl, ethyl, n-propyl, i-propyl, n-butyl, i-butyl, s-butyl, t-butyl, 2-methylbutyl, n-pentyl, s-pentyl, tert-pentyl, 2-pentyl, cyclopentyl, n-hexyl, s-hexyl, tert-hexyl, 2-hexyl, 3-hexyl, cyclohexyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, trifluoromethyl, pentafluoroethyl or 2,2,2-trifluoroethyl. An alkenyl group is taken to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is taken to mean, for example, ethynyl, propynyl, butynyl, pentynyl, hexynyl, heptynyl or octynyl. A $C_1$- to $C_{40}$-alkoxy group is taken to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system having 5-60 aromatic ring atoms, which may also in each case be substituted by the substituents R mentioned above and which may be linked to the aromatic or heteroaromatic ring system via any desired positions, is taken to mean, for example, groups derived from benzene, napththalene, phenanthrene, benzophenanthrene, fluoranthene, benzofluoranthene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phen-anthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzo-pyridazine, pyrimidine, benzopyrimidine, quinoxaline, pyrazine, phenazine, phenoxazine, phenothiazine, fluorubin, naphthyridine, azacarbazole, benzo-carboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

The compounds of the Formula (1) may be electrically charged or uncharged. In a preferred embodiment, the compounds of the Formula (1) are electrically neutral. The neutral species are especially well suited for application in OLED devices or most other typical organic semiconductor devices. A charged compound can be obtained, for example, if $X^1$ or $X^2$ is an alkyl-substituted nitrogen atom, which results in a positively charged complex. For charge compensation the metal complex needs to be accompanied by a counter ion which is taken out of the group of non-coordinating ionic species such as $J^-$, $BF_4^-$, $PF_6^-$, etc. Charged complexes have advantages in organic light emitting electrochemical cells (OLECs, LECs, LEECs).

Preference is given to a compound according to Formula (1), wherein ring A has the general structure as shown in Formula (3)

Formula (3)

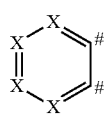

wherein X is identical or different on each occurrence and selected from $CR^1$ or N, and wherein the signs # indicate the positions in ring A which are condensed to ring B. Preferably X in Formula (3) is in each occurrence equal to $CR^1$.

Particular preference is given to a compound according to Formula (1), wherein ring A has the general structure as shown in Formula (3), wherein X is identical or different on each occurrence either $CR^1$ or N, and wherein the signs # indicate the positions in ring A which are condensed to ring B and wherein the substituents $R^1$, if present, do not form further fused rings.

In a preferred embodiment $X^1$ is N and $X^2$ is $CR^1$. In another preferred embodiment both $X^1$ and $X^2$ are N.

Thus, preference is given to a compound having one of the following Formulae (4) and (5)

Formula (4)

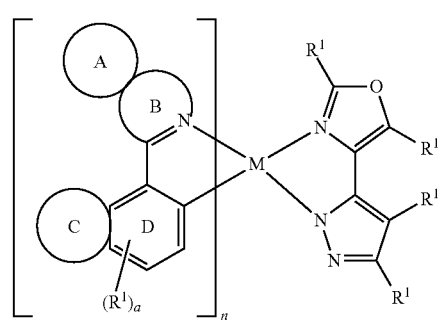

Formula (5)

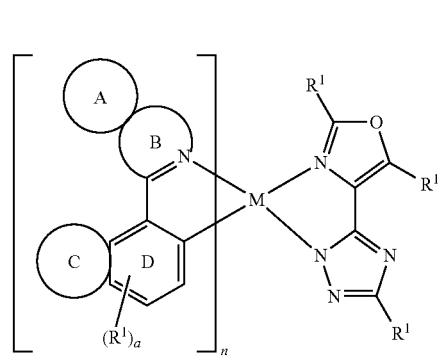

wherein the symbols and indices are defined as above and wherein ring A has the general structure as shown in Formula (3), and wherein the substituents $R^1$ in ring C, if present, do not form further fused rings.

Preferably, ring B is a 6-membered ring, and particularly preferably ring B is a 6-membered ring consisting of one N— and 5 C-ring atoms which may be further substituted with one or more $R^1$.

The present invention relates to the following metal complexes having one of the Formulae (6) to (8).

Formula (6)
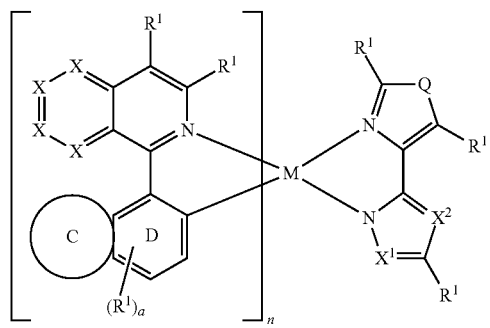
Formula (7)
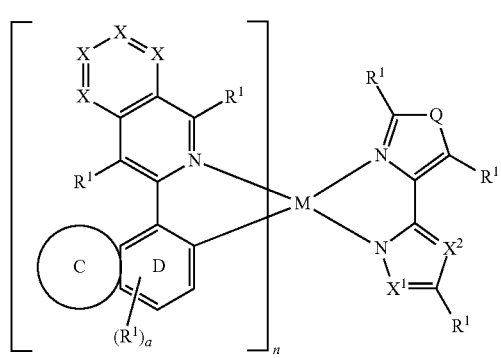
Formula (8)
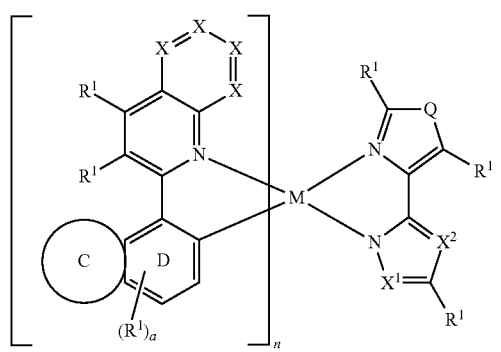
Very particular preference is given to a compound having one of the following Formulae (9) to (26)
Formula (9)
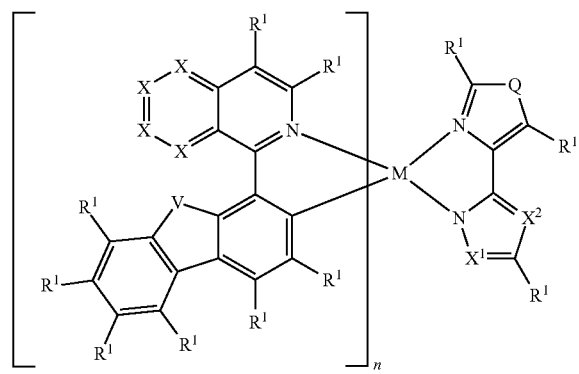
Formula (10)
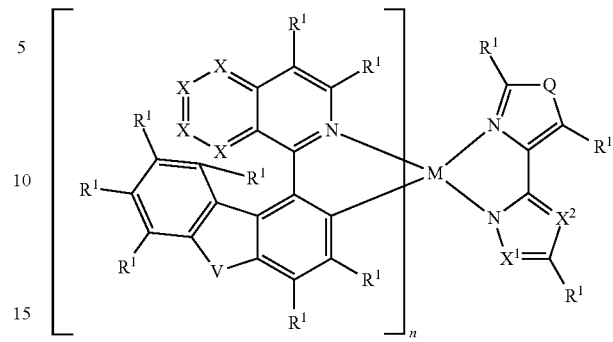
Formula (11)
Formula (12)
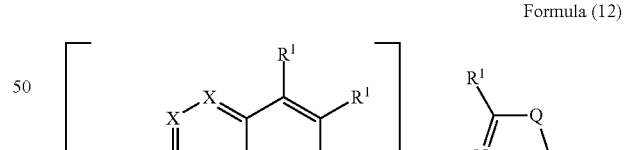

Formula (13)
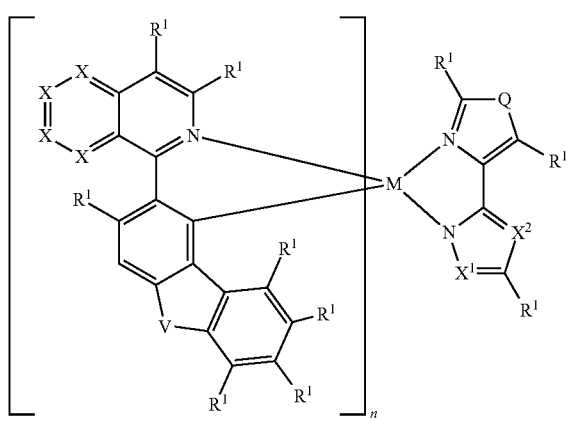
Formula (14)
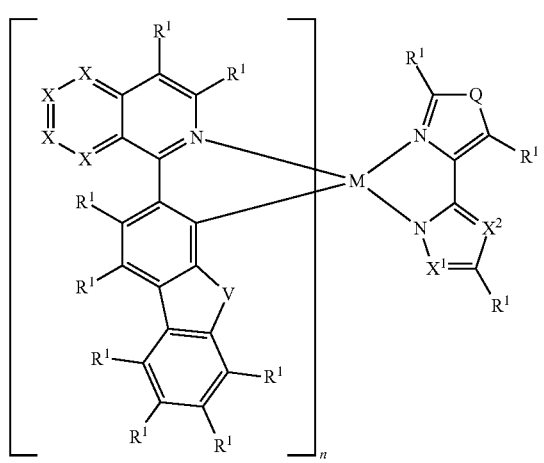
Formula (15)
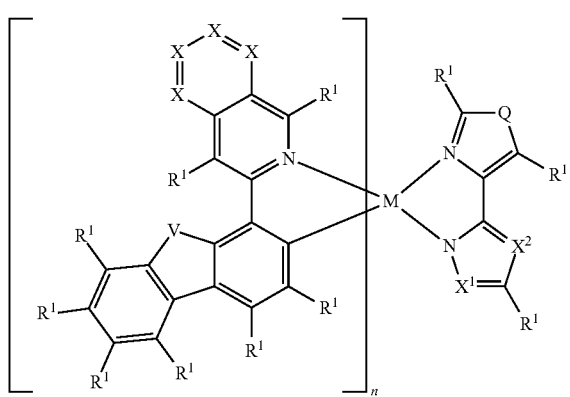
Formula (16)
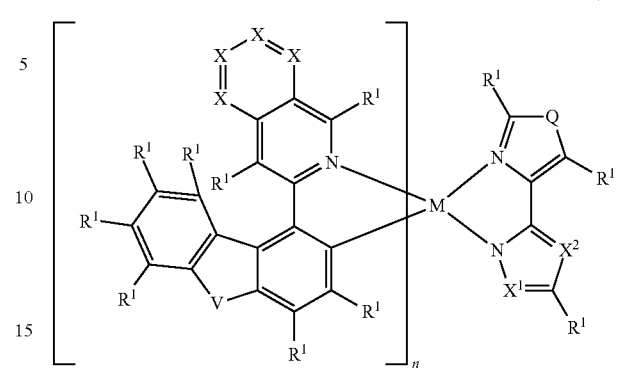
Formula (17)
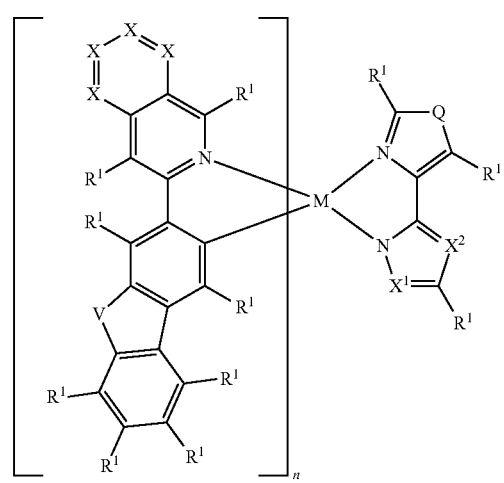
Formula (18)
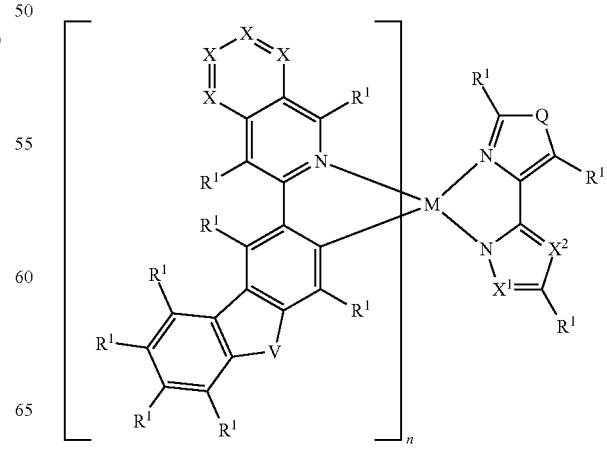

Formula (19)
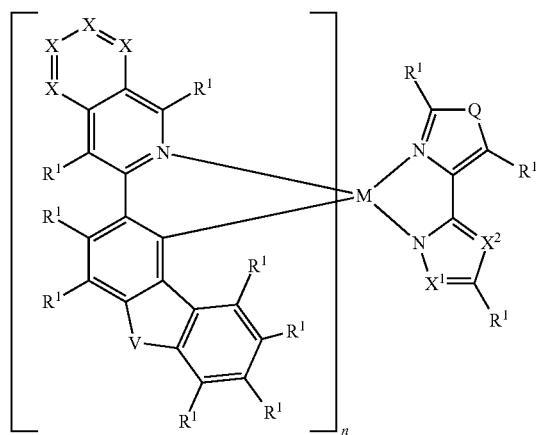
Formula (20)
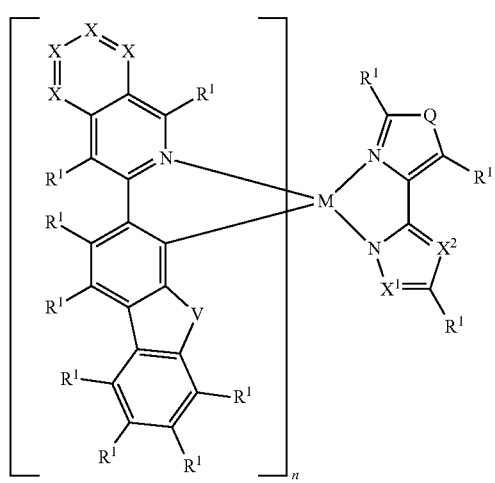
Formula (21)
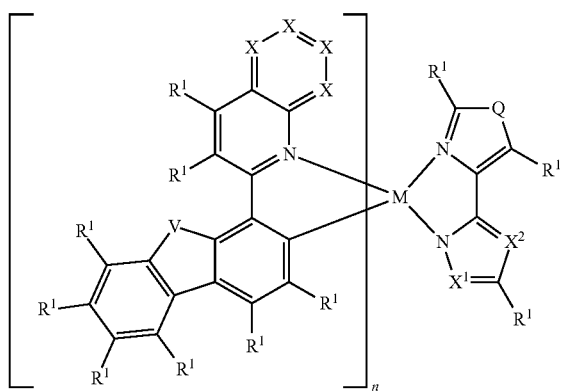
Formula (22)
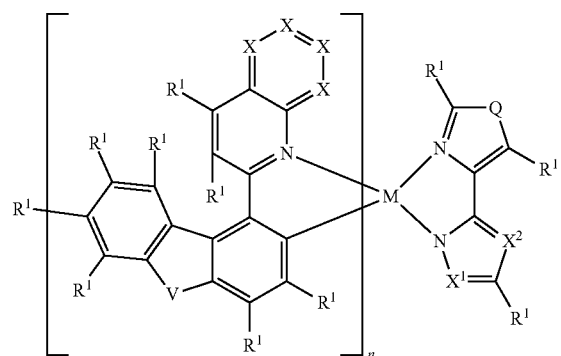
Formula (23)
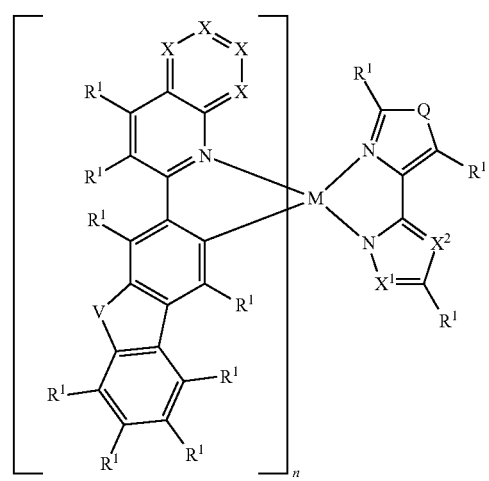
Formula (24)

Formula (25)

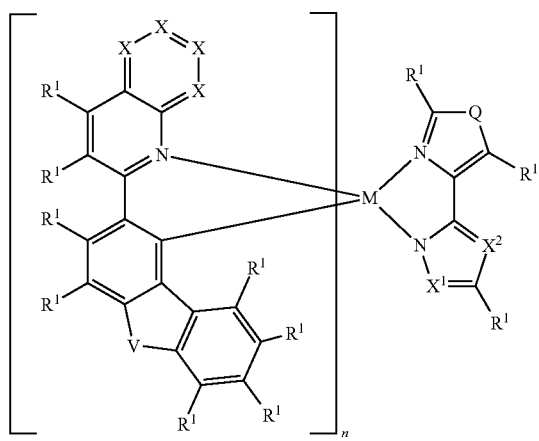

Formula (26)

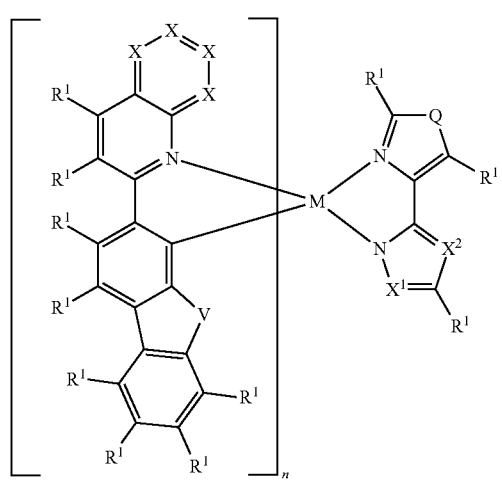

wherein the indices and symbols are defined as above.

In a further preferred embodiment the present invention relates to a compound having one of the Formulae (9) to (12), (15) to (18) and (21) to (24), particularly preferably a compound having one of the Formulae (9), (11), (12), (15), (17), (18), (21), (23) and (24), very particularly preferably a compound having one of the Formulae (9), (15), and (21), and even more preferably a compound having the Formula (21).

Preferably Q in Formulae (1) to (26) is $R^1C=CR^1$.

The present invention further relates to a compound having one of the following Formulae (27) and (28)

Formula (27)

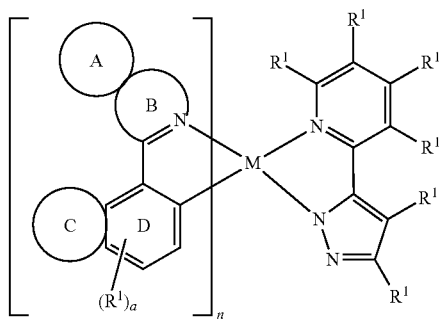

Formula (28)

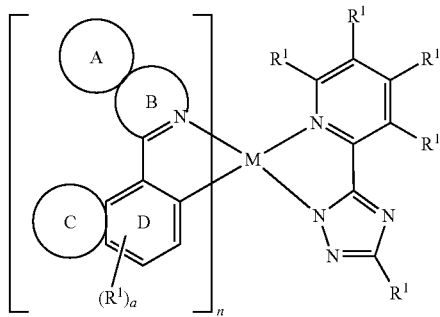

The present invention further relates to a compound having one of the following Formulae (29) to (46)

Formula (29)

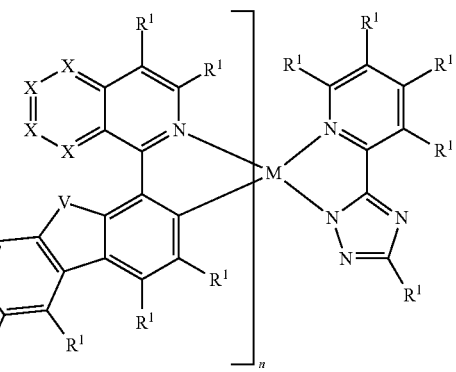

Formula (30)

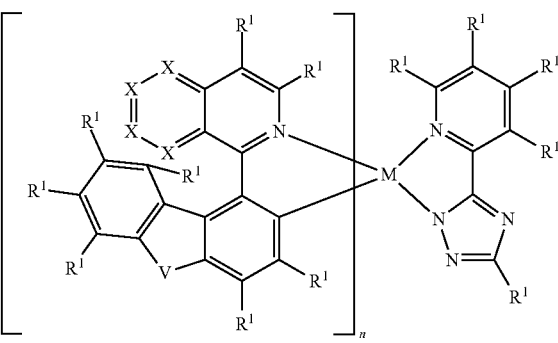

Formula (31)
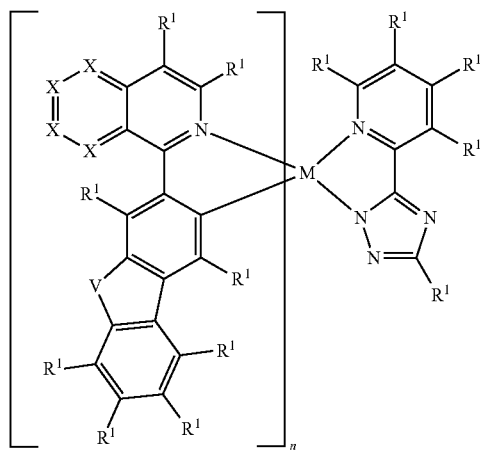
Formula (32)
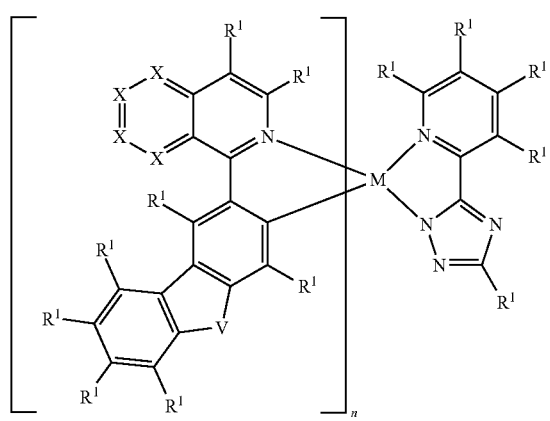
Formula (33)
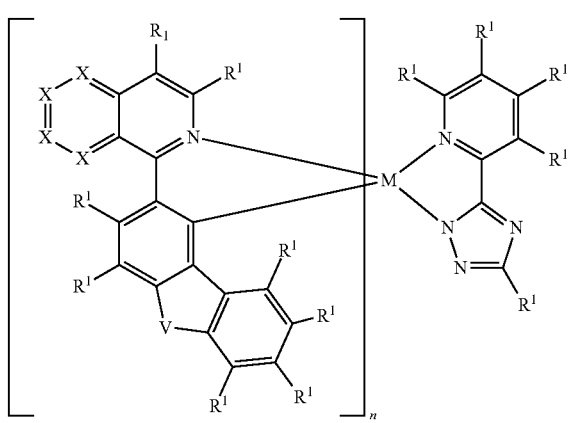
Formula (34)
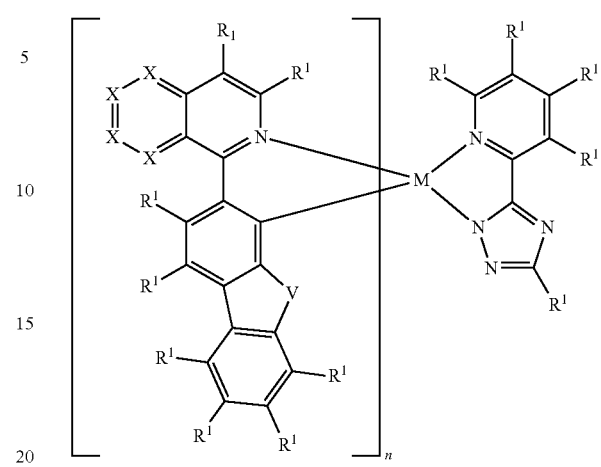
Formula (35)
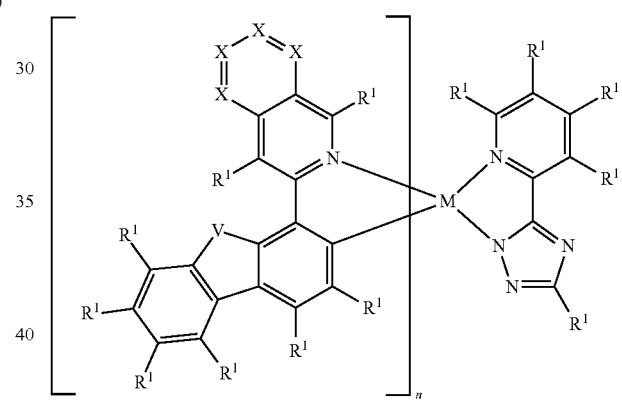
Formula (36)
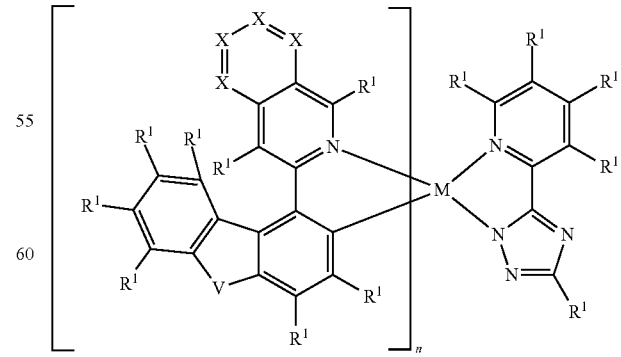

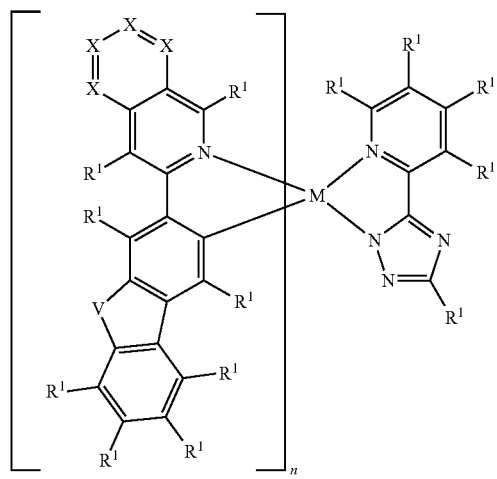
Formula (37)
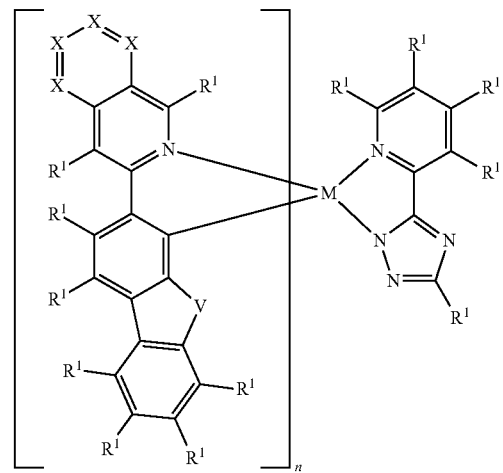
Formula (40)
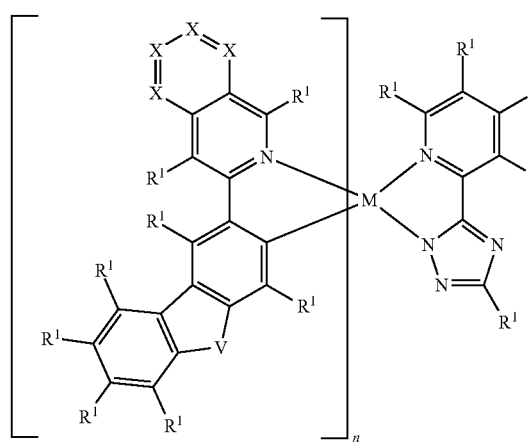
Formula (38)
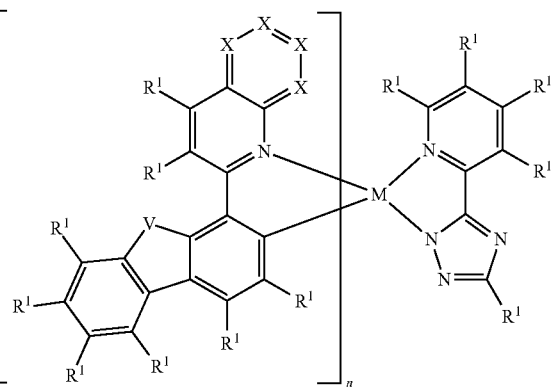
Formula (41)
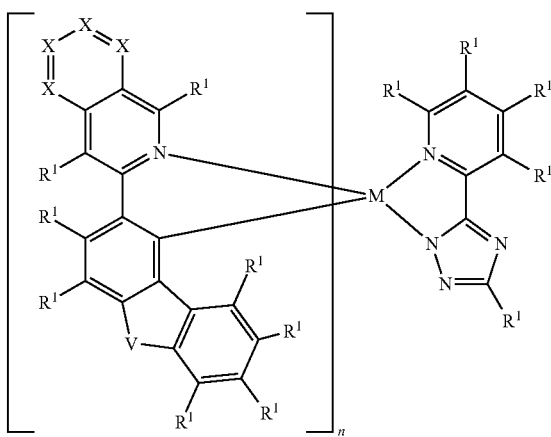
Formula (39)
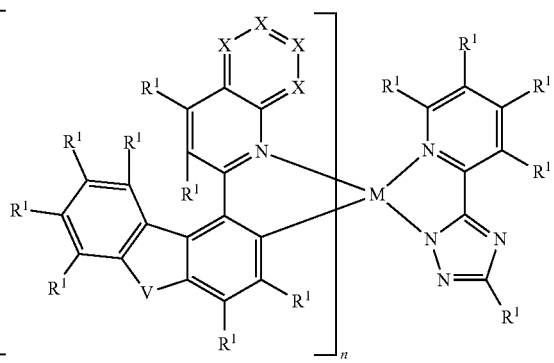
Formula (42)

Formula (43)

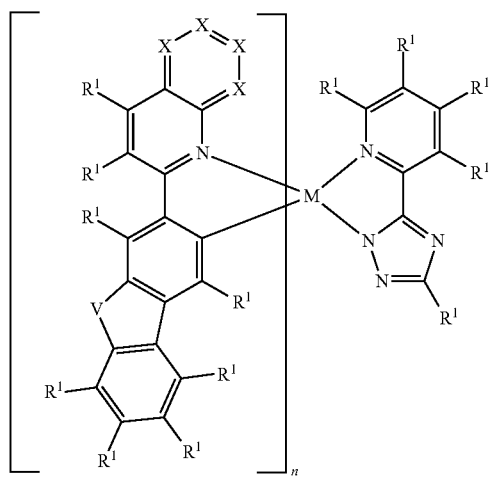

Formula (46)

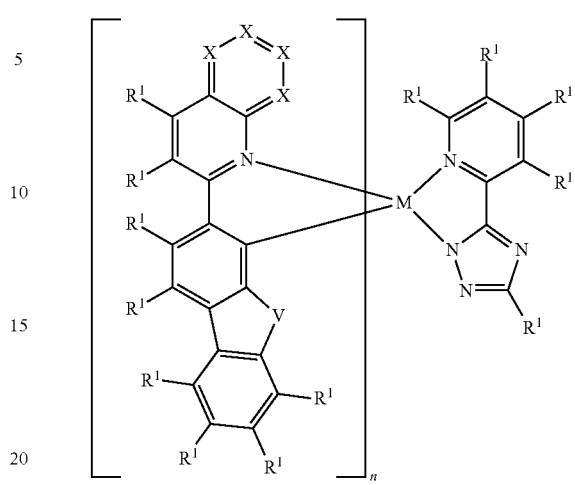

Formula (44)

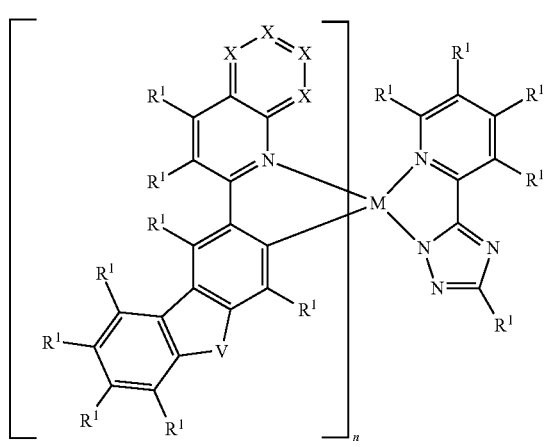

Formula (45)

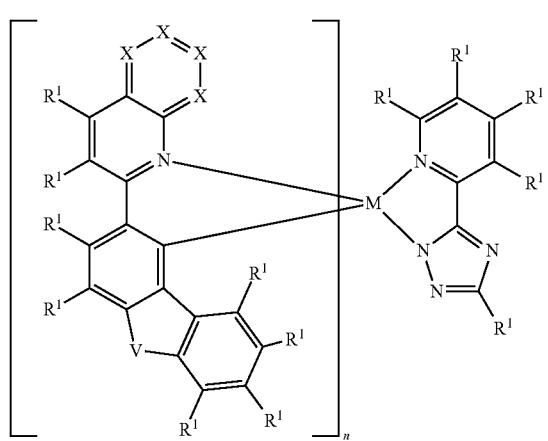

In a further preferred embodiment the present invention relates to a compound having one of the Formulae (29) to (32), (35) to (38) and (41) to (44), particularly preferably a compound having one of the Formulae (29), (31), (32), (35), (37), (38), (41), (43), and (44), very particularly preferably a compound having one of the Formulae (29), (35), and (41), and even more preferably a compound having the Formula (41).

The present invention further relates to a compound having one of the following Formulae (47) to (64)

Formula (47)


Formula (48)

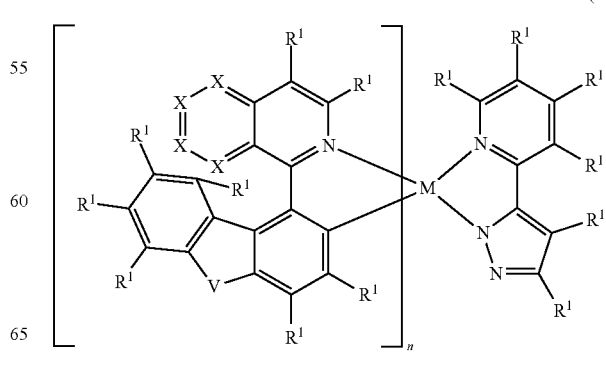

Formula (49)
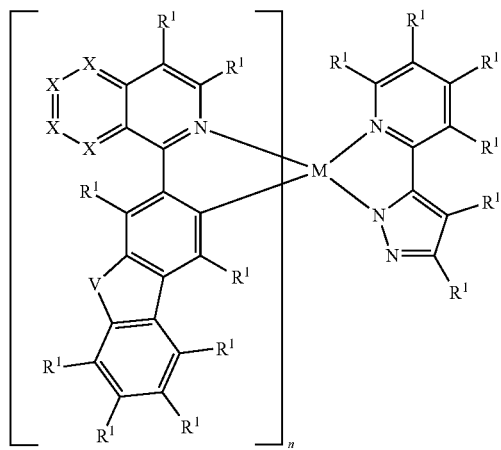
Formula (50)
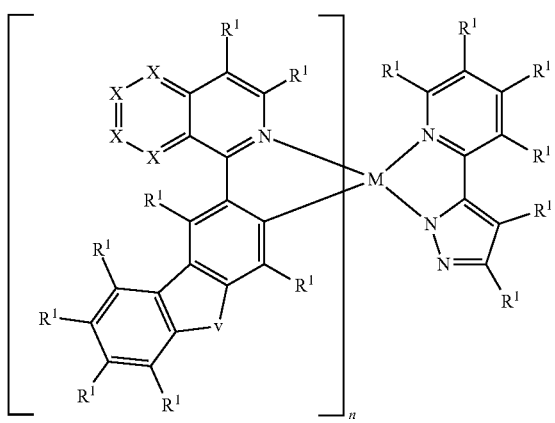
Formula (51)
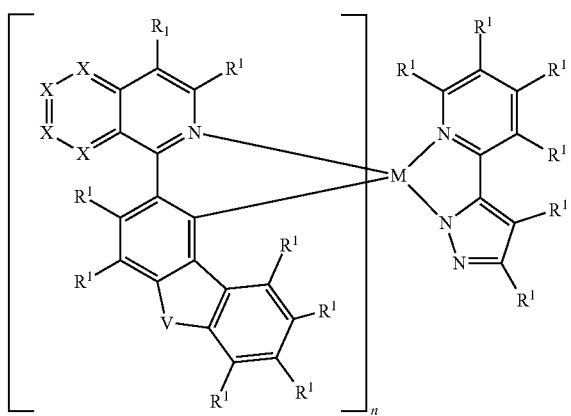
Formula (52)
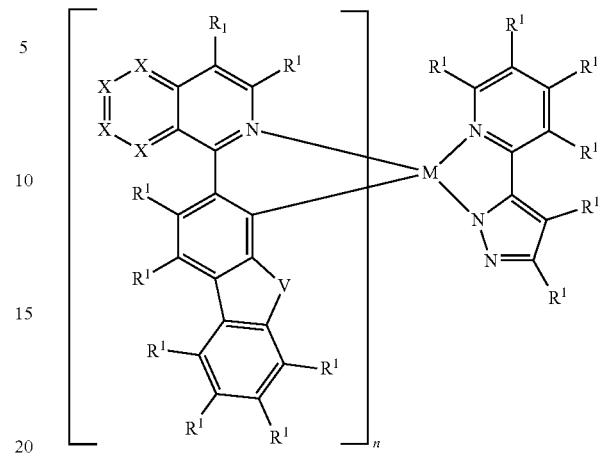
Formula (53)
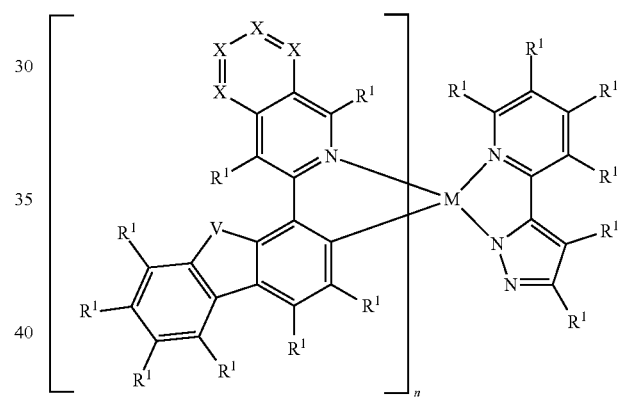
Formula (54)
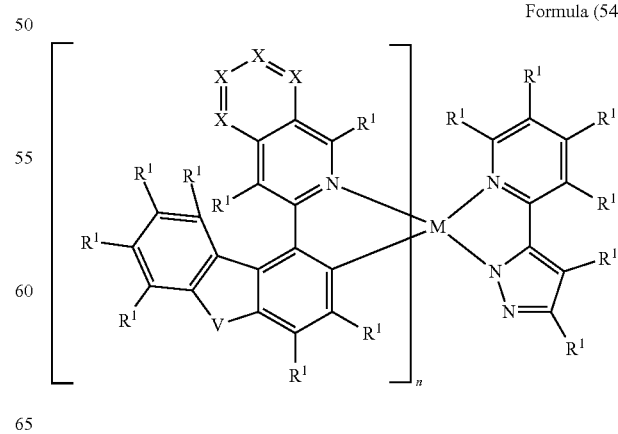

-continued
Formula (55)
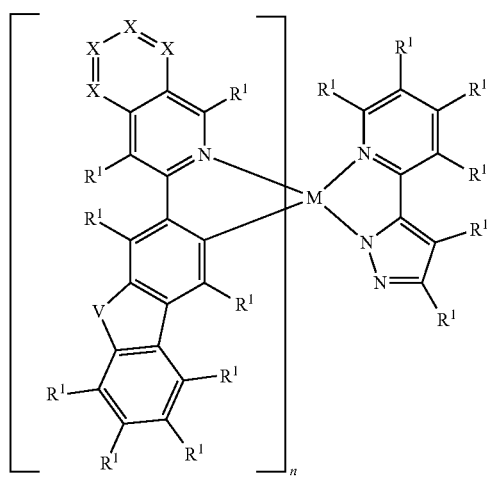
Formula (56)
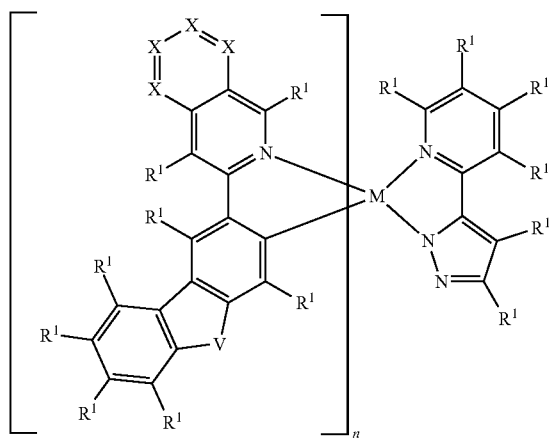
Formula (57)
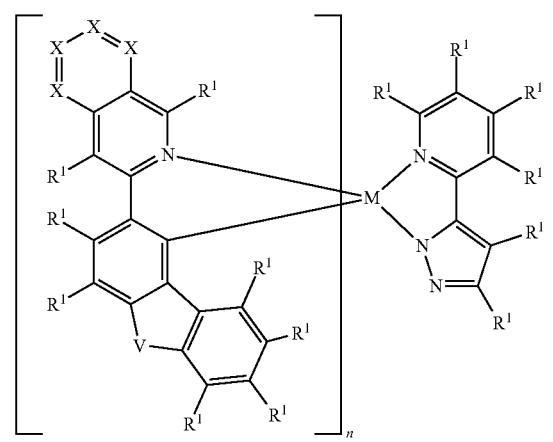
Formula (58)
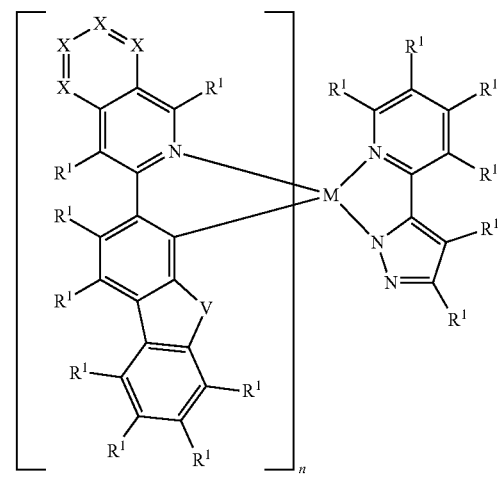
Formula (59)
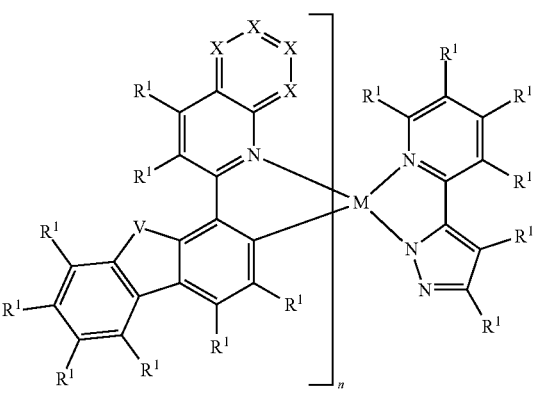
Formula (60)
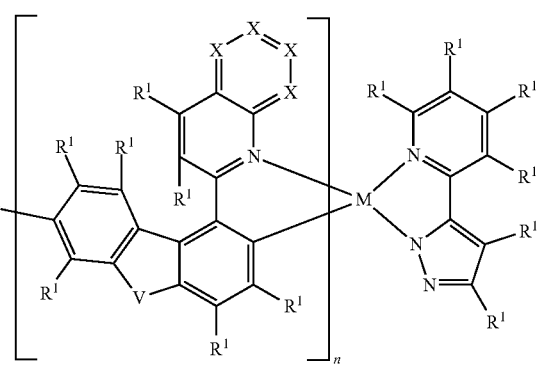

Formula (61)

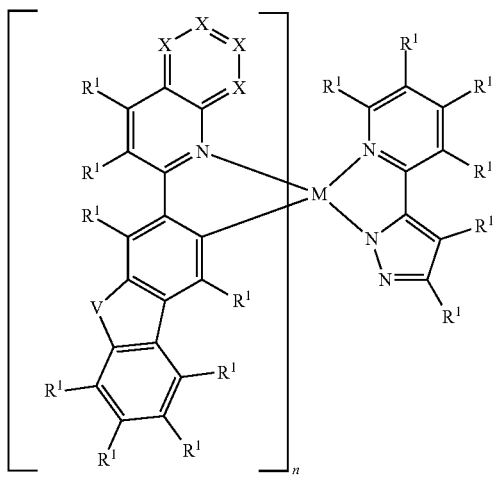

Formula (62)

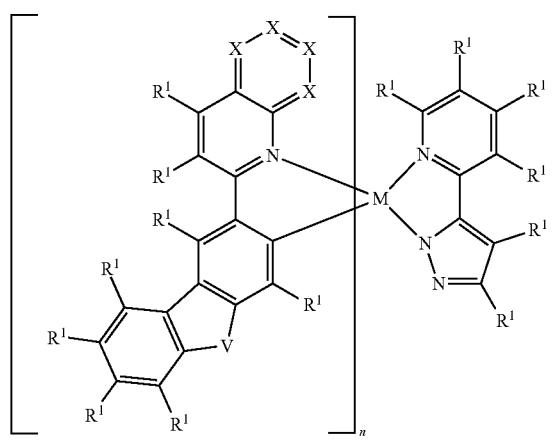

Formula (63)

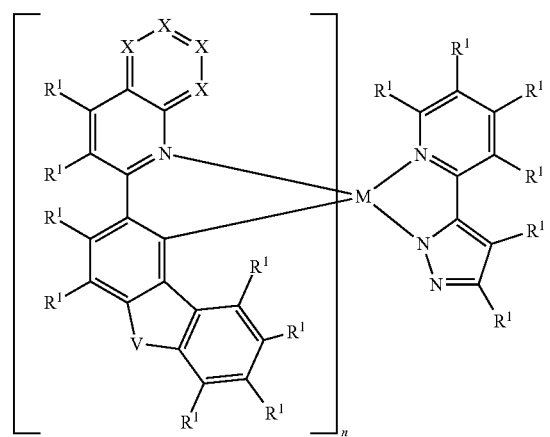

Formula (64)

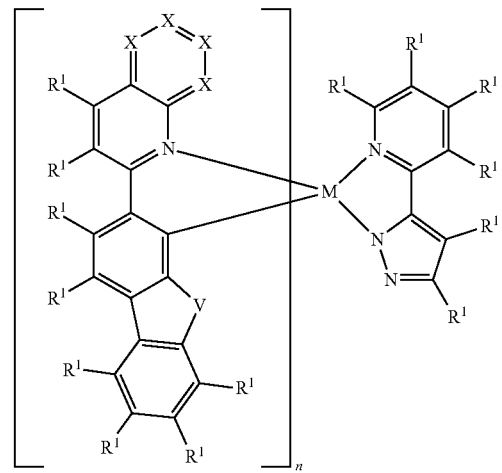

In a further preferred embodiment the present invention relates to a compound having one of the Formulae (47) to (50), (53) to (56) and (59) to (62), particularly preferably a compound having one of the Formulae (47), (49), (50), (53), (55), (56), (59), (61), and (62), very particularly preferably a compound having one of the Formulae (47), (53), and (59), and even more preferably a compound having the Formula (59).

Particular preference is given to a compound of Formula (65), wherein compound of Formula (66) is condensed to compound of Formula (65) via positions #1 and #2 to positions*1, *2 or *3 in any possible and reasonable combination.

Formula (65)

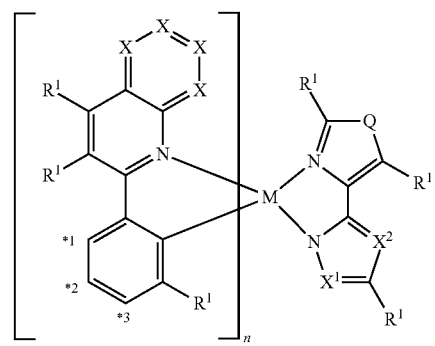

Formula (66)

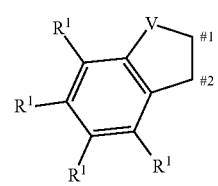

Very particular preference is given to a compound of Formula (65) wherein the compound having the general Formula (66) is condensed to Formula (65) via position #1 to *1 or to *3 and #2 to *2.

Even more preference is given to a compound according to Formula (65) where condensation takes place via #1 to *1 and #2 to *2.

Preferably, two or more substituents $R^1$ in the compounds of Formulae (1) to (66) do not form a mono- or polycyclic, aliphatic, aromatic and/or benzo-fused ring system with one another.

Preferably, the substituents $R^1$ are identical or different from each other on each occurrence and selected from H, D, F, Cl, Br, I, $N(R^2)_2$, CN, $NO_2$, $Si(R^2)_3$, $B(R^2)_2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more substituents $R^2$, where one or more non-adjacent $CH_2$ groups may be replaced by $R^2C=CR^2$, $C\equiv C$, $Si(R^2)_2$, C=O, C=S, C=Se, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more substituents $R^2$, or an aryloxy or heteroaryloxy group having 5 to 60 aromatic ring atoms, which may be substituted by one or more substituents $R^2$, or a diarylamino group, diheteroarylamino group or arylheteroarylamino group having 10 to 40 aromatic ring atoms, which may be substituted by one or more substituents $R^2$, or a combination of two or more of these groups.

Particularly preferably $R^1$ is identical or different from each other on each occurrence and selected from H, D, F, Cl, Br, I, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more substituents $R^2$, where one or more H atoms may be replaced by D, F, Cl, Br, I.

Very particularly preferably $R^1$ is identical or different from each other on each occurrence and selected from H, D, F, Cl, Br, I, a straight-chain alkyl having 1 to 40 C atoms or a branched or cyclic alkyl having 3 to 40 C atoms, each of which may be substituted by one or more substituents $R^2$, and where one or more H atoms may be replaced by D, F, Cl, Br, I.

Even more preferably $R^1$ is identical or different from each other on each occurrence and selected from H, D, F, Cl, Br, I, a straight-chain alkyl having 1 to 40 C atoms, preferably 1 to 30 C atoms, very particularly 1 to 20 C atoms and very particularly preferably 1 to 10 C atoms, or a branched or cyclic alkyl having 3 to 40 C atoms, preferably 3 to 30 C atoms, very particularly 3 to 20 C atoms and very particularly preferably 3 to 10 C atoms where one or more H atoms may be replaced by D, F, Cl, Br, I.

Further preference is given to a compound having the Formula (67)

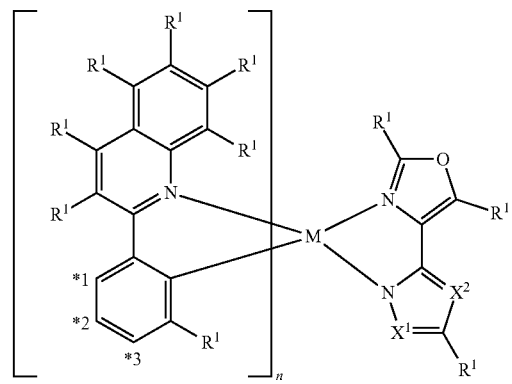

Formula (67)

wherein the aforementioned about Formula (65) concerning the condensation of Formula (66) is also valid for compounds according to Formula (67).

The present invention also relates to the compounds having the Formulae (68) and (69), preferably Formula (68).

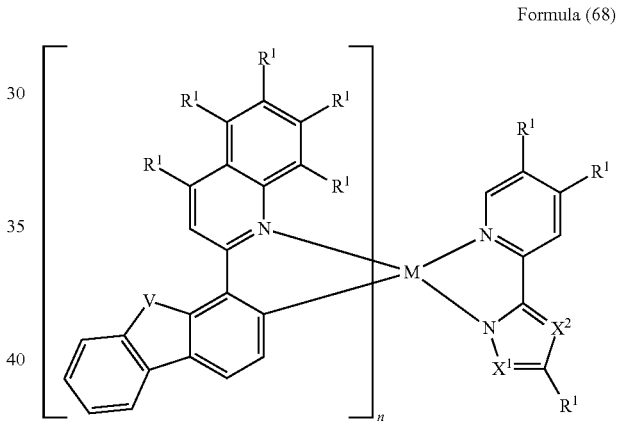

Formula (68)

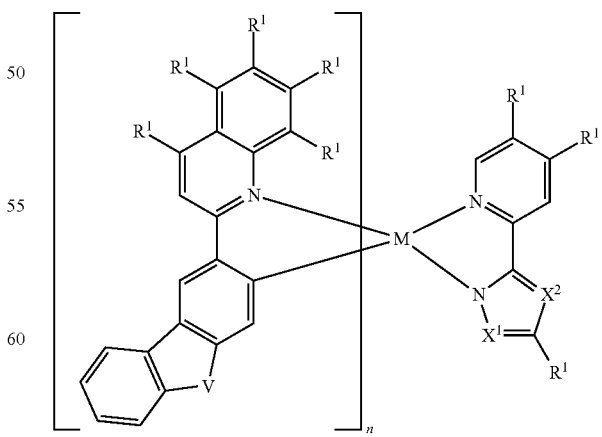

Formula (69)

The present invention also relates to the compounds having the Formulae (70) and (71), preferably Formula (70).

Formula (70)
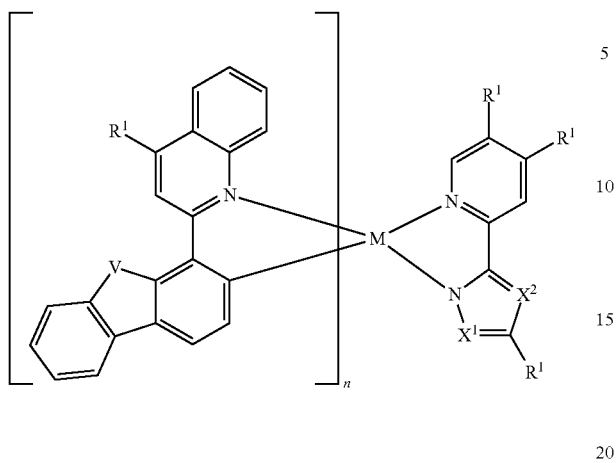
Formula (71)
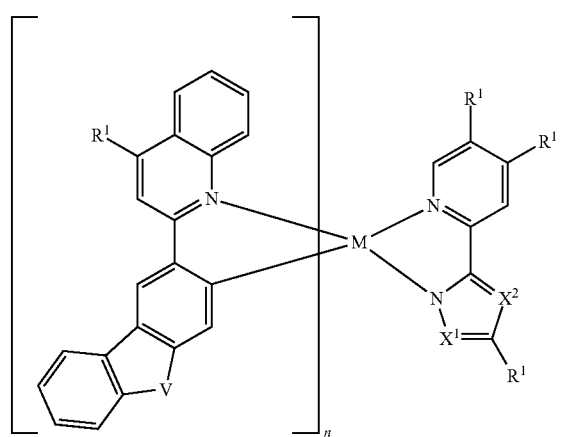
The present invention also relates to the compounds having the Formulae (72) and (73), preferably Formula (72).
Formula (72)
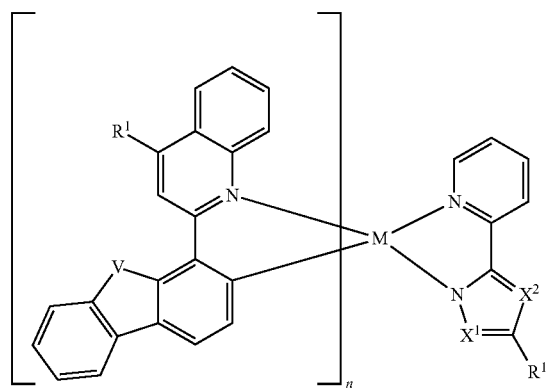
Formula (73)
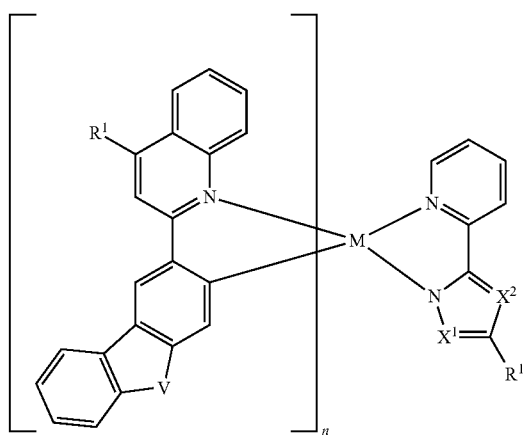
The present invention also relates to the compounds having the Formulae (74) and (75), preferably Formula (74).
Formula (74)
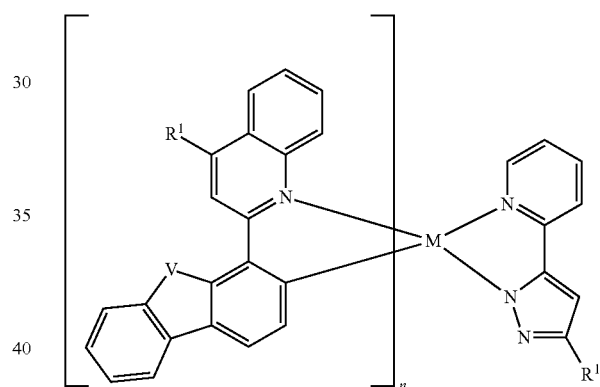
Formula (75)
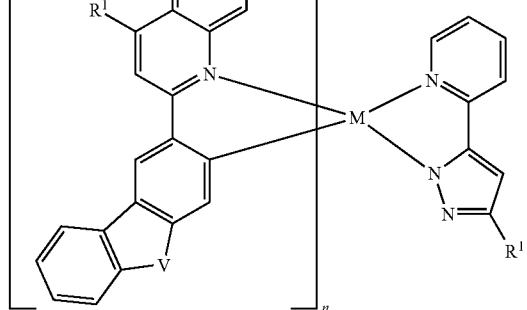
The present invention also relates to the compounds having the Formulae (76) and (77), preferably Formula (76).

Formula (76)

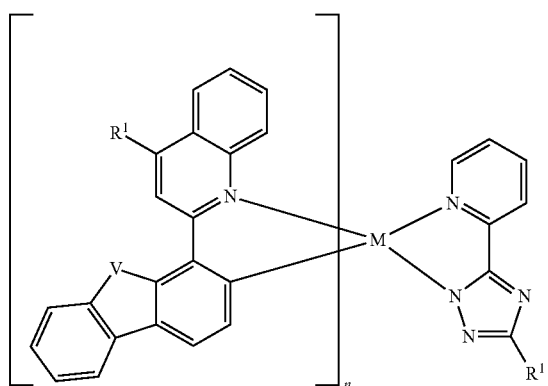

Formula (77)

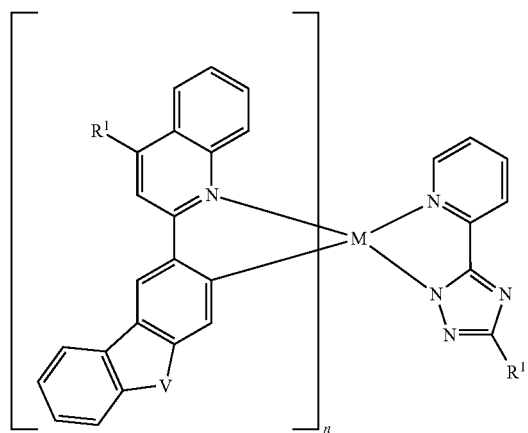

The present invention also relates to the compounds having the Formulae (78) and (79), preferably Formula (78).

Formula (78)

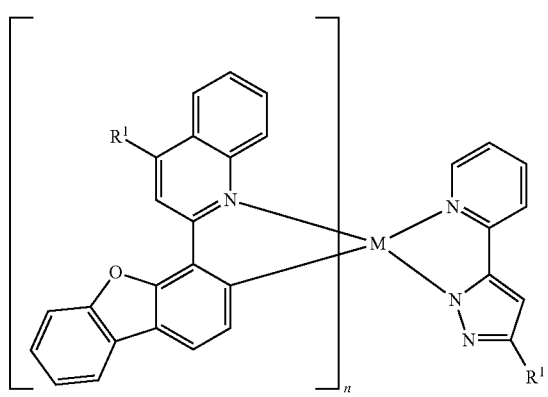

Formula (79)

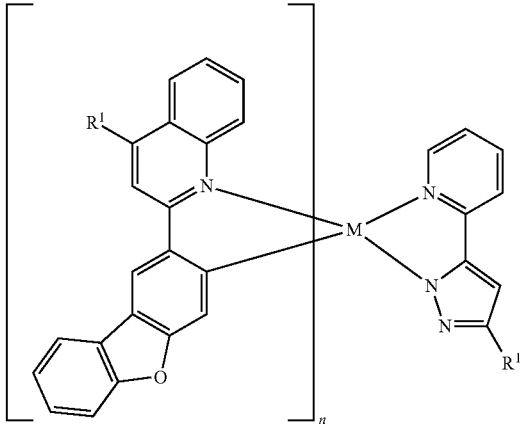

The present invention also relates to the compounds having the Formulae (80) and (81), preferably Formula (80).

Formula (80)

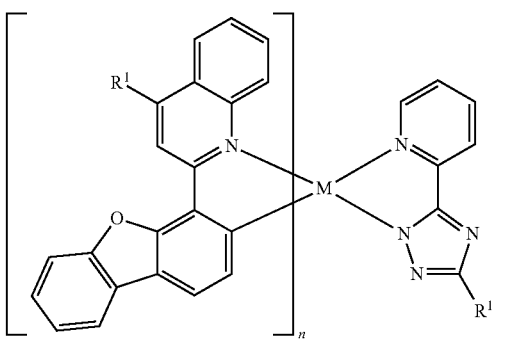

Formula (81)

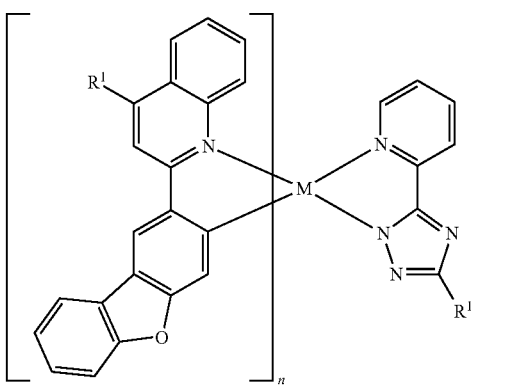

In one particularly preferred embodiment the present invention relates to a compound having one of the above mentioned Formulae wherein M is Ir(III), n is 2 and $R^1$ is identical or different from each other on each occurrence and selected from H, D, F, Cl, Br, I, a straight-chain alkyl having 1 to 40 C atoms, preferably 1 to 30 C atoms, very particularly 1 to 20 C atoms and very particularly preferably 1 to 10 C atoms, or a branched or cyclic alkyl having 3 to 40 C atoms, preferably 3 to 30 C atoms, very particularly 3 to 20 C atoms and very particularly preferably 3 to 10 C atoms where one or more H atoms may be replaced by D, F, Cl, Br, I.

Further to the above mentioned preferred substituents $R^1$, $R^1$ can preferably be identical or different from each other on each occurrence and selected from H and the general structures having the Formulae (82) to (98), wherein Y is identical or different from each other on each occurrence, $CR^2$, N, P, or $PR^2_2$, preferably $CR^2$ or N and wherein $R^2$ is defined as above.

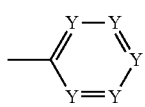

Formula (82)

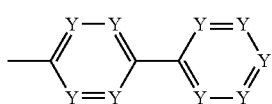

Formula (83)

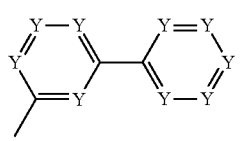

Formula (84)

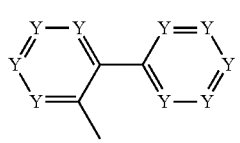

Formula (85)

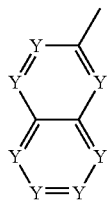

Formula (86)

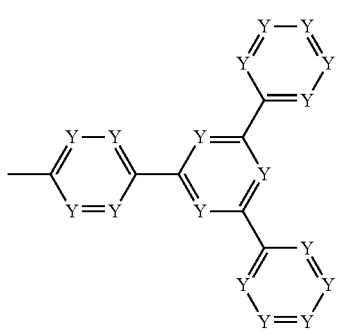

Formula (87)

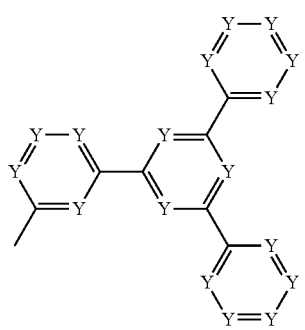

Formula (88)

-continued

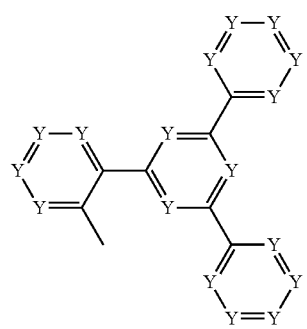

Formula (89)

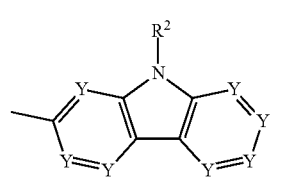

Formula (90)

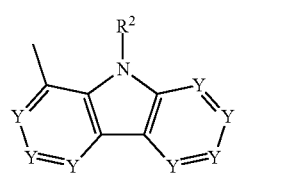

Formula (91)

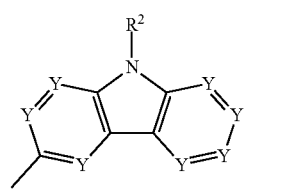

Formula (92)

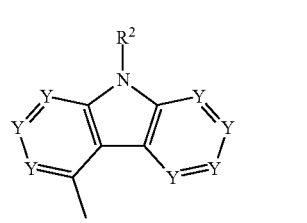

Formula (93)

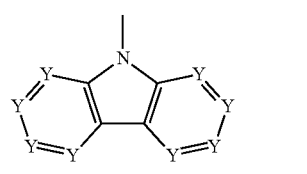

Formula (93a)

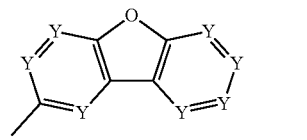

Formula (93b)

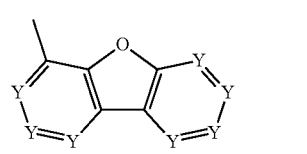

Formula (93c)

Formula (94)

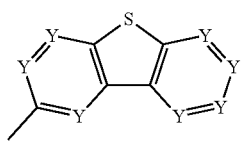

Formula (95)

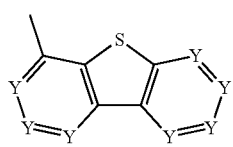

Formula (96)

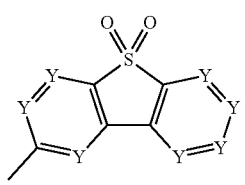

Formula (97)

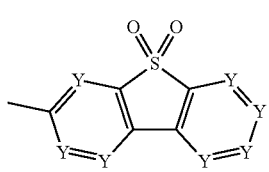

Formula (98)

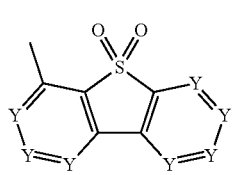

These bulky substituents are especially useful to further increase the processability of the complexes. The carbazoles and sulfoxides have an additional function since they increase the singlet-triplet intersystem crossing rate. Their preferred position is in the trans-position from #1 and #2 in Formula (66).

Particular preference is given to $R^1$ that is identical or different from each other on each occurrence, selected from H and the following Formulae (99) to (272). These substituents $R^1$ can be identical or different from each other on each occurrence, and be substituted with one or more $R^3$, wherein $R^3$ is defined as above.

Formula (99)

Formula (100)

Formula (101)

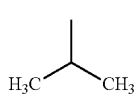

Formula (102)

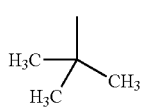

Formula (103)

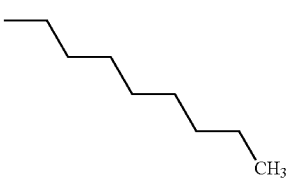

Formula (104)

Formula (105)

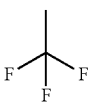

Formula (106)

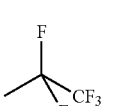

Formula (107)

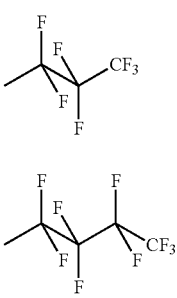

Formula (108)

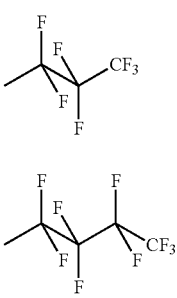

Formula (109)

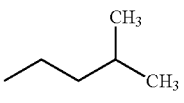

Formula (110)

Formula (111)

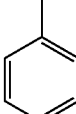

Formula (112)

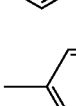

Formula (113)

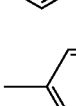

Formula (114)

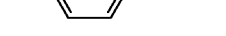

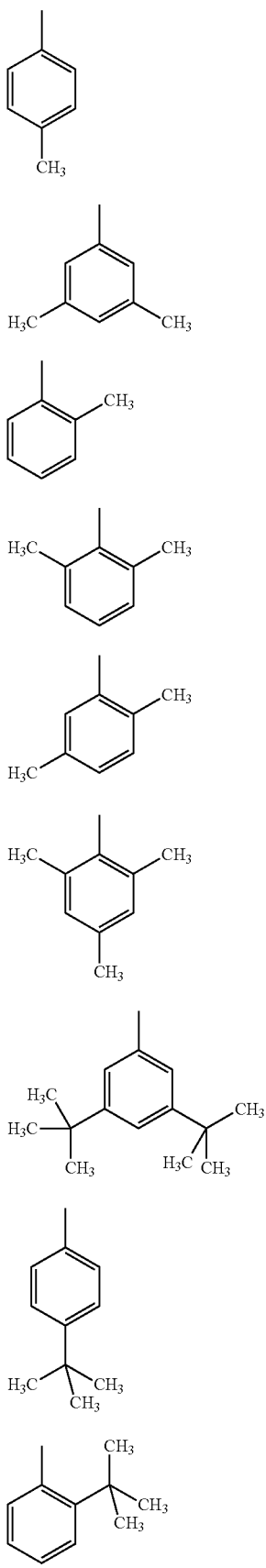
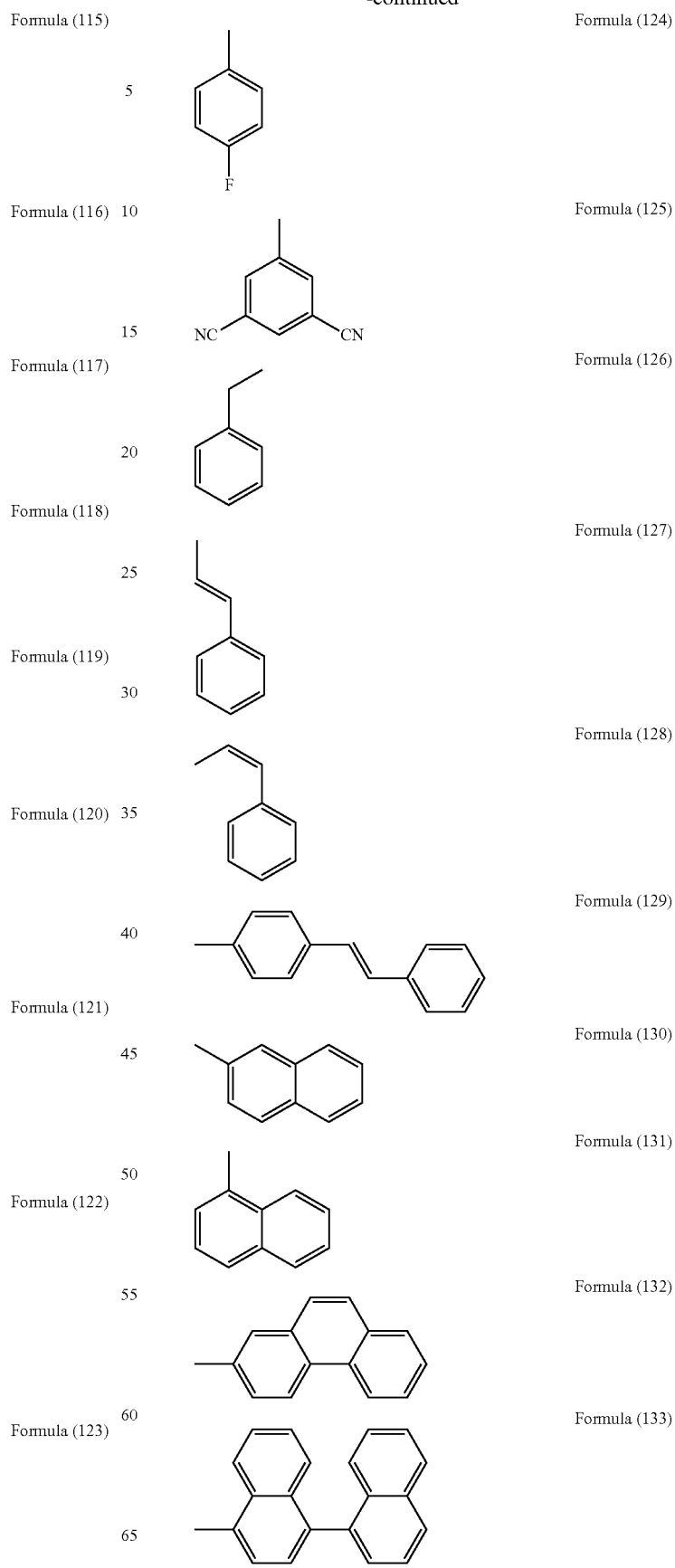

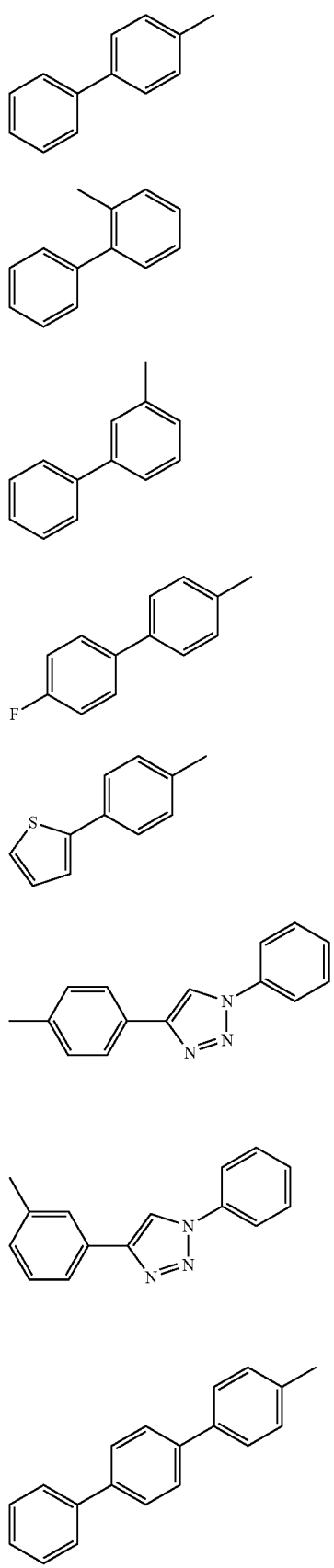
Formula (134)
Formula (135)
Formula (136)
Formula (137)
Formula (138)
Formula (139)
Formula (140)
Formula (141)
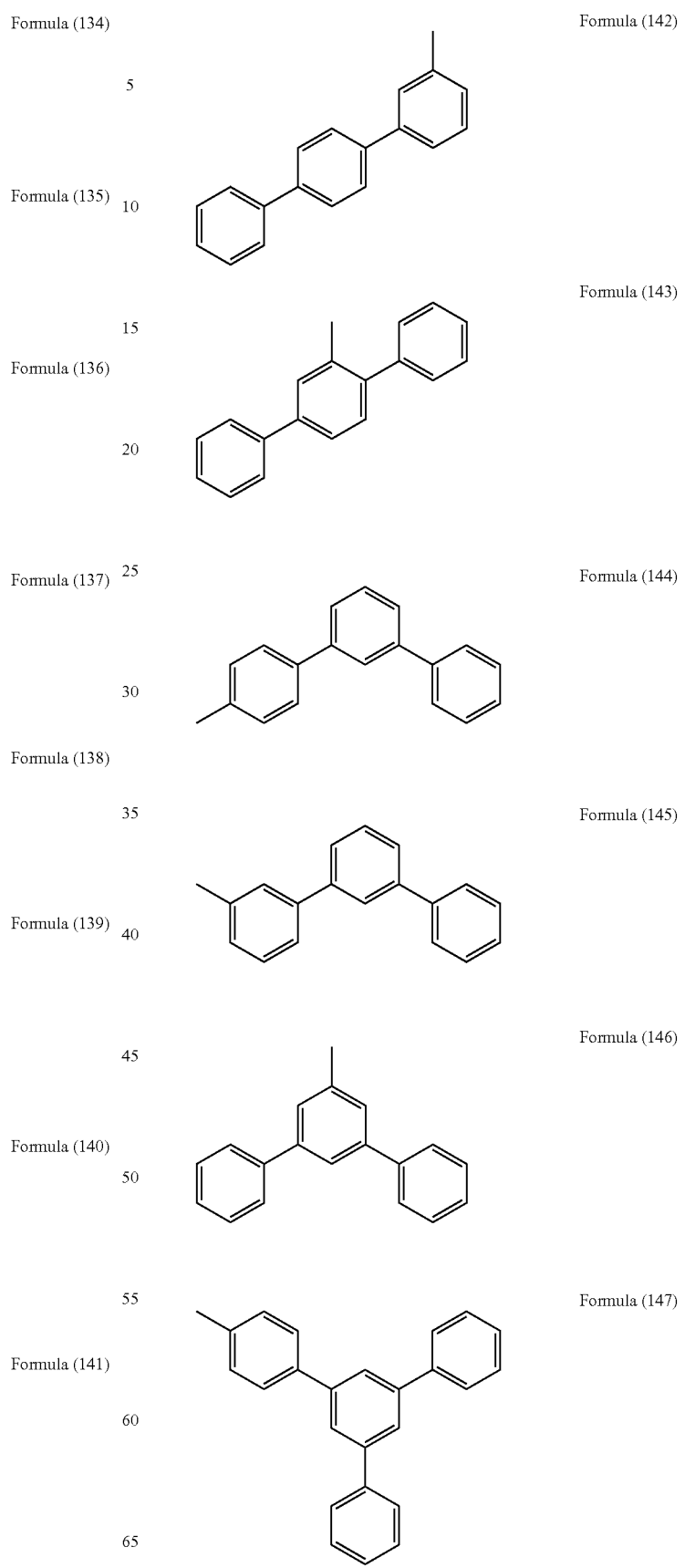
Formula (142)
Formula (143)
Formula (144)
Formula (145)
Formula (146)
Formula (147)

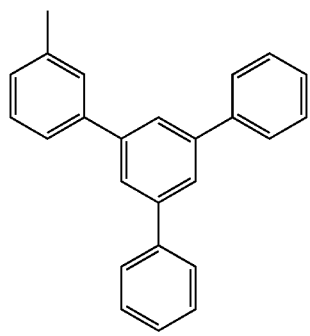
Formula (148)
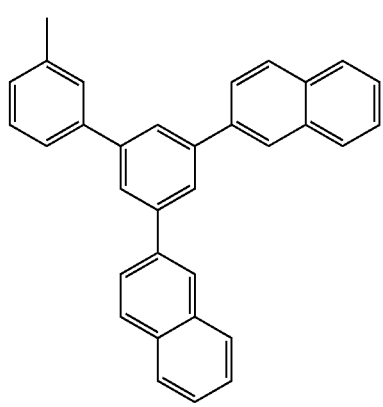
Formula (152)
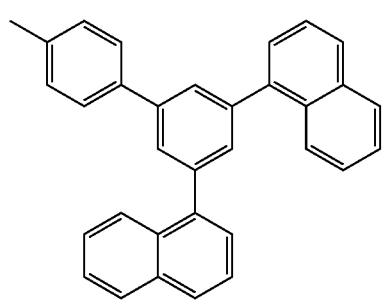
Formula (149)
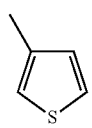
Formula (153)
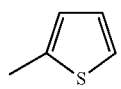
Formula (154)
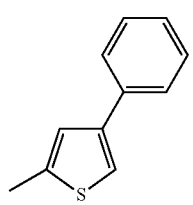
Formula (155)
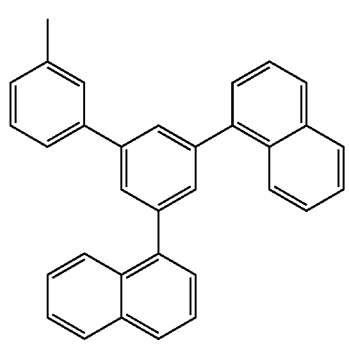
Formula (150)
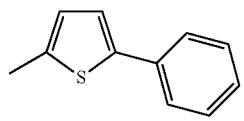
Formula (156)
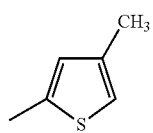
Formula (157)
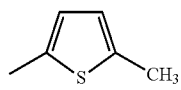
Formula (158)
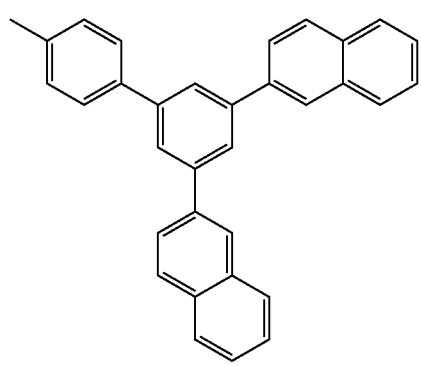
Formula (151)
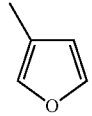
Formula (159)
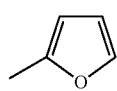
Formula (160)
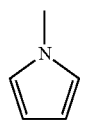
Formula (161)

-continued
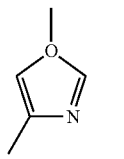
Formula (150)
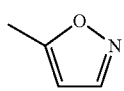
Formula (151)
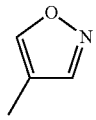
Formula (152)
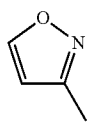
Formula (153)
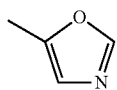
Formula (154)
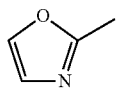
Formula (155)
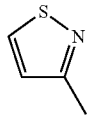
Formula (156)
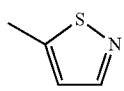
Formula (157)
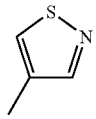
Formula (158)
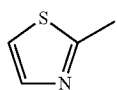
Formula (159)
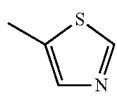
Formula (160)
Formula (161)
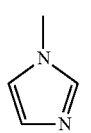
Formula (162)
-continued
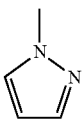
Formula (163)
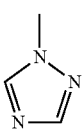
Formula (164)
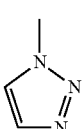
Formula (165)
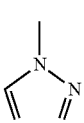
Formula (166)
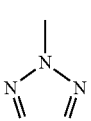
Formula (167)
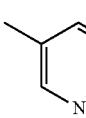
Formula (168)
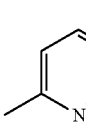
Formula (169)
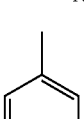
Formula (170)
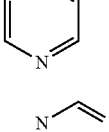
Formula (171)
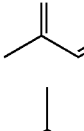
Formula (172)
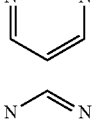
Formula (173)
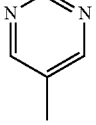
Formula (174)
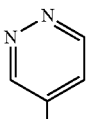
Formula (175)

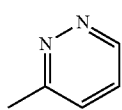
Formula (187)
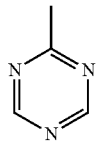
Formula (188)
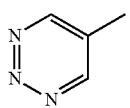
Formula (189)
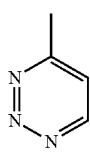
Formula (190)
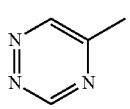
Formula (191)
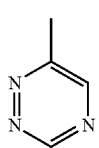
Formula (192)
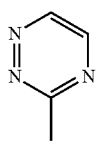
Formula (193)
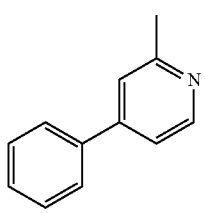
Formula (194)
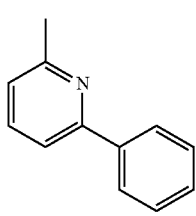
Formula (195)
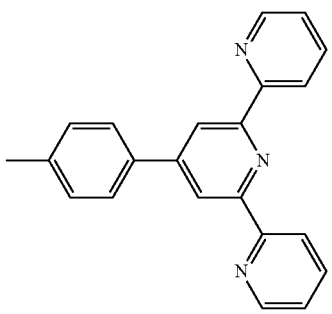
Formula (196)
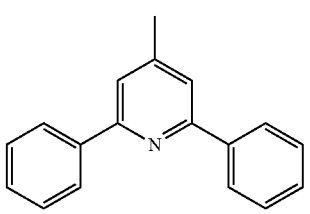
Formula (197)
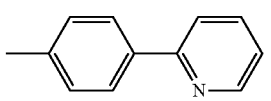
Formula (198)
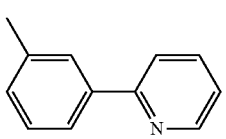
Formula (199)
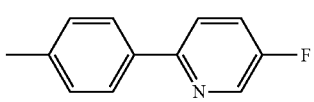
Formula (200)
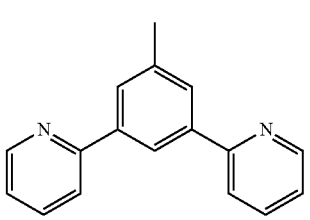
Formula (201)
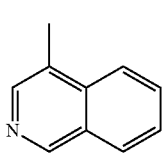
Formula (202)
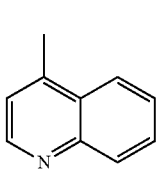
Formula (203)
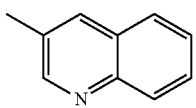
Formula (204)

Formula (205)
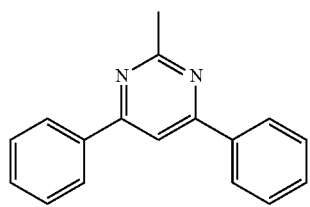
Formula (206)
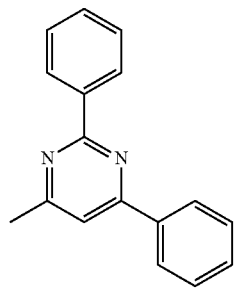
Formula (207)
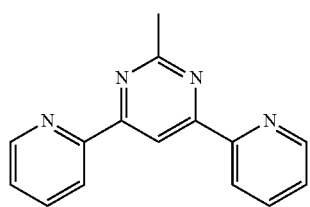
Formula (208)
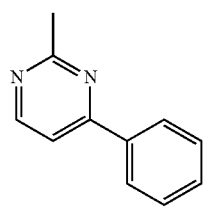
Formula (209)
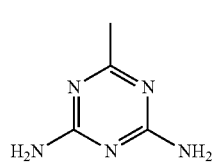
Formula (210)
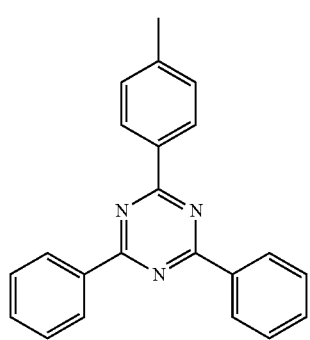
Formula (211)
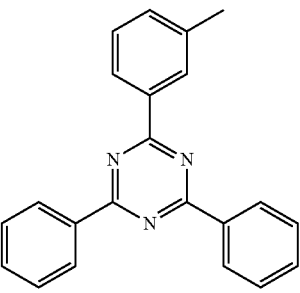
Formula (212)
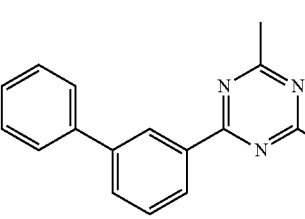
Formula (213)
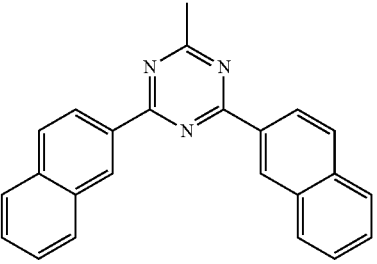
Formula (214)
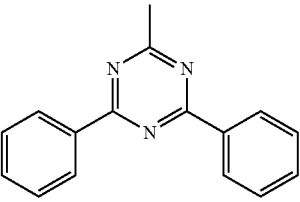
Formula (215)
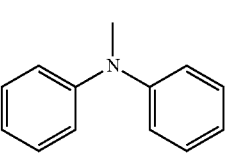
Formula (216)
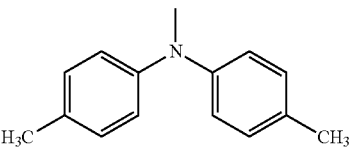
Formula (217)
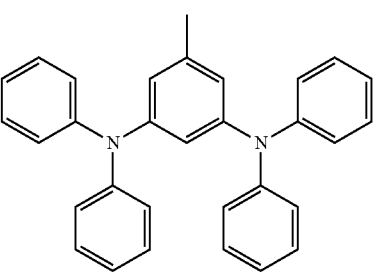

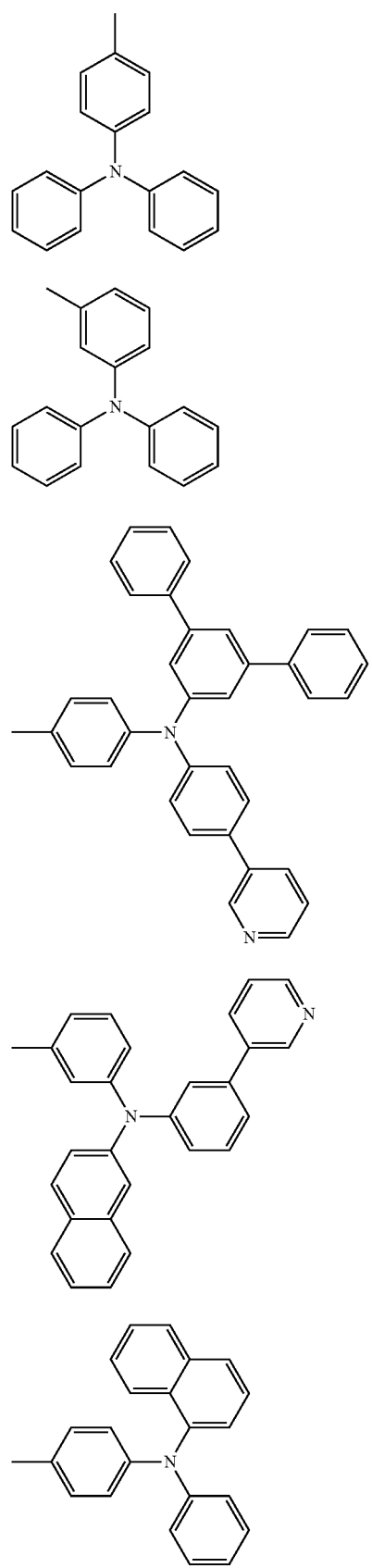
Formula (218)
Formula (219)
Formula (220)
Formula (221)
Formula (222)
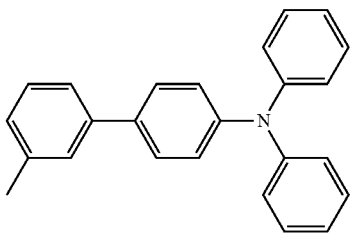
Formula (223)
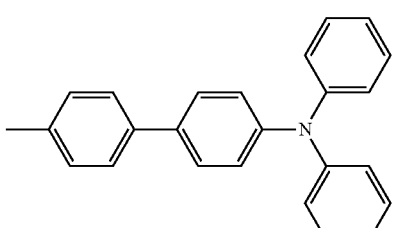
Formula (224)
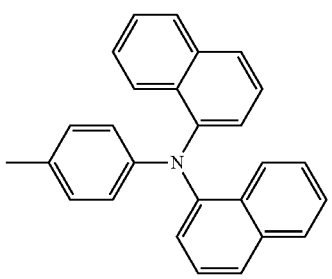
Formula (225)
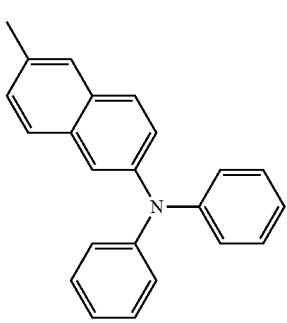
Formula (226)
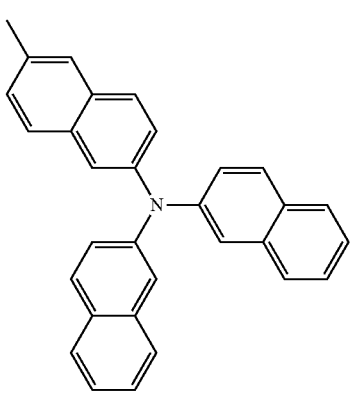
Formula (227)

Formula (228)
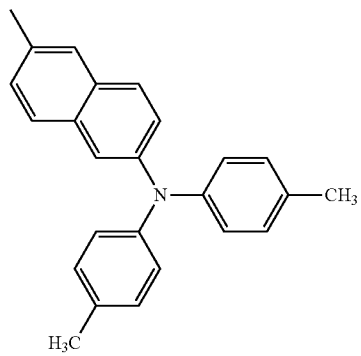
Formula (229)
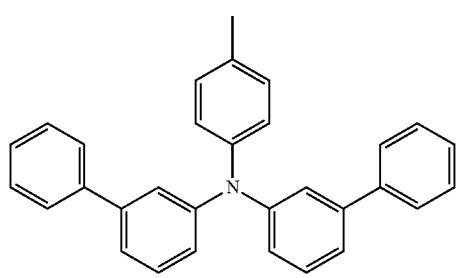
Formula (230)
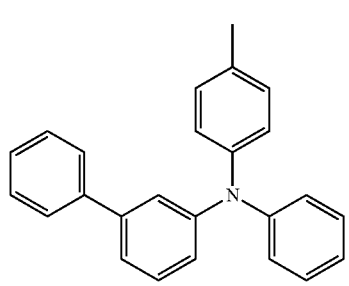
Formula (231)
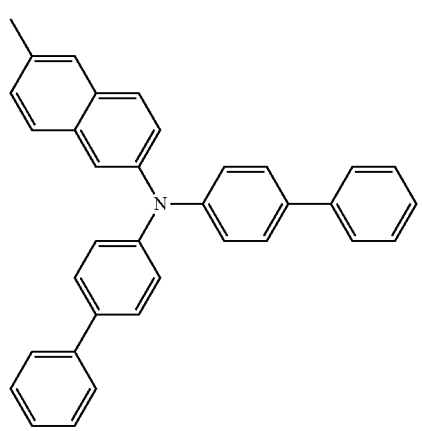
Formula (232)
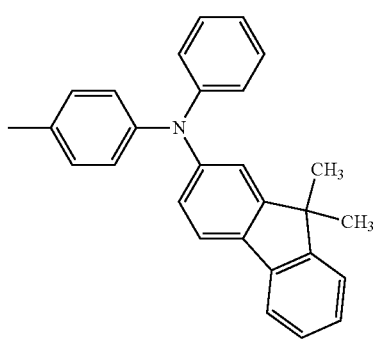
Formula (233)
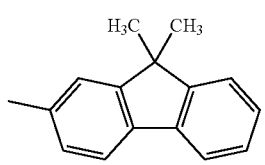
Formula (234)
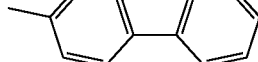
Formula (235)
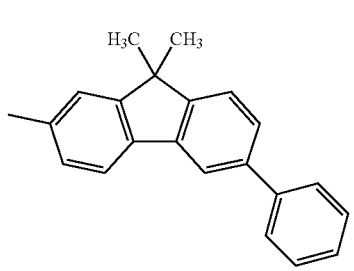
Formula (236)
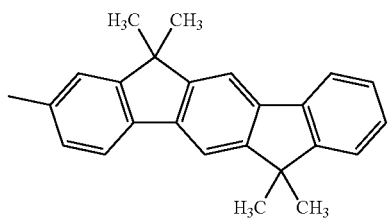
Formula (237)
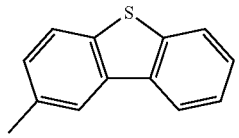
Formula (238)
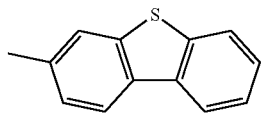

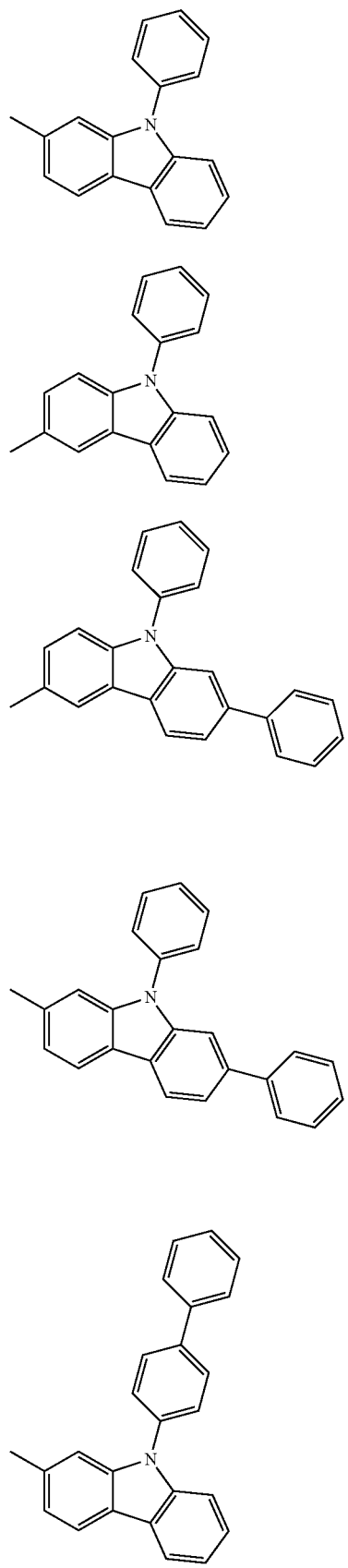
Formula (239)
Formula (240)
Formula (241)
Formula (242)
Formula (243)
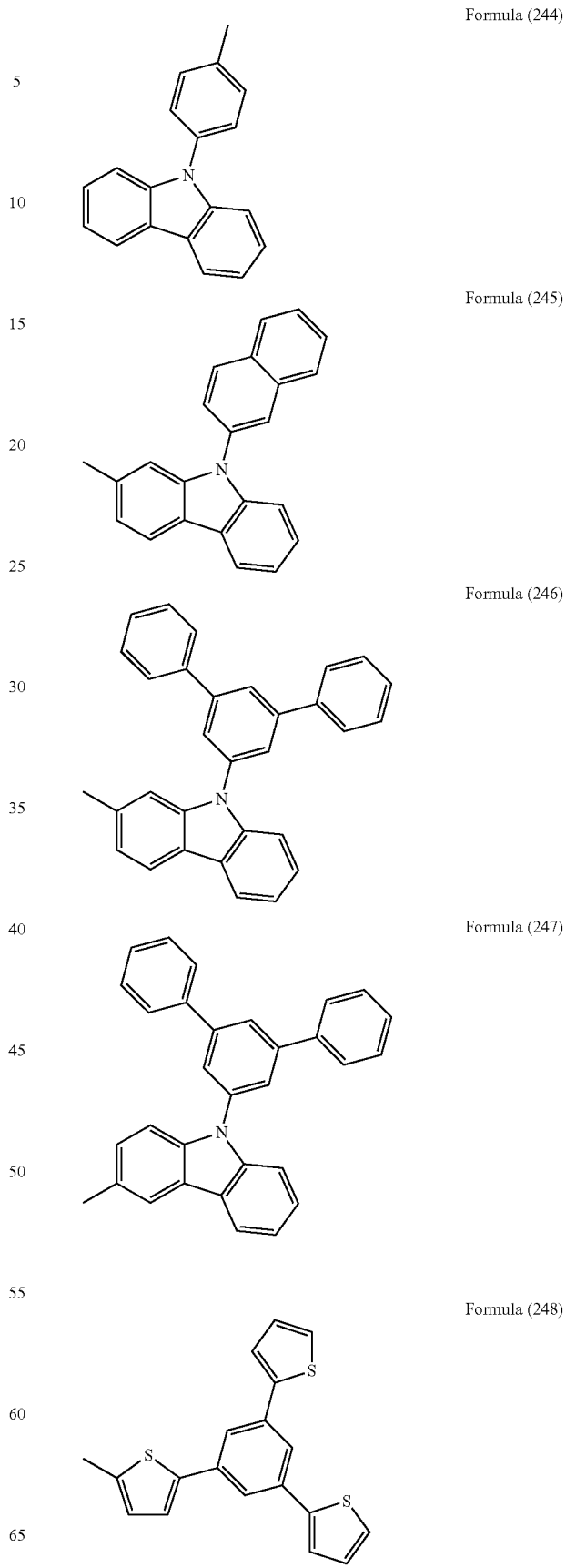
Formula (244)
Formula (245)
Formula (246)
Formula (247)
Formula (248)

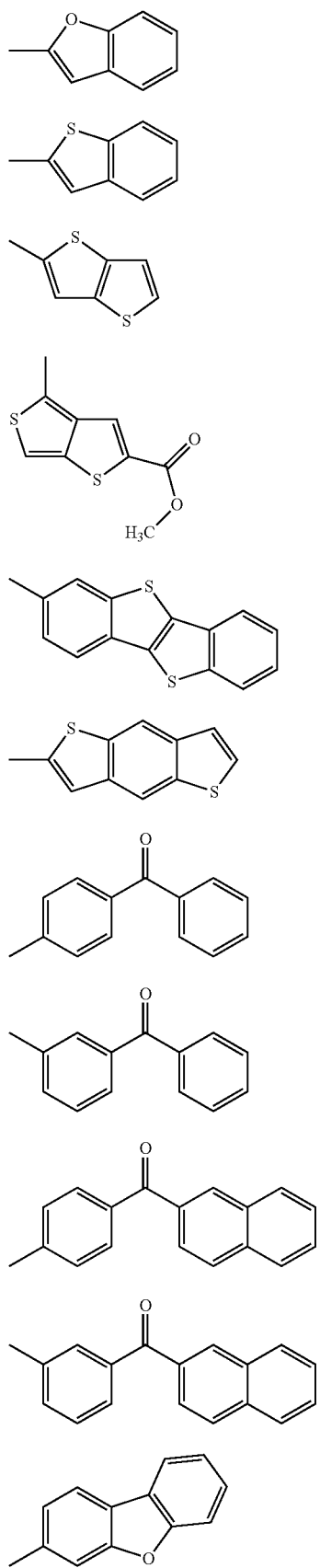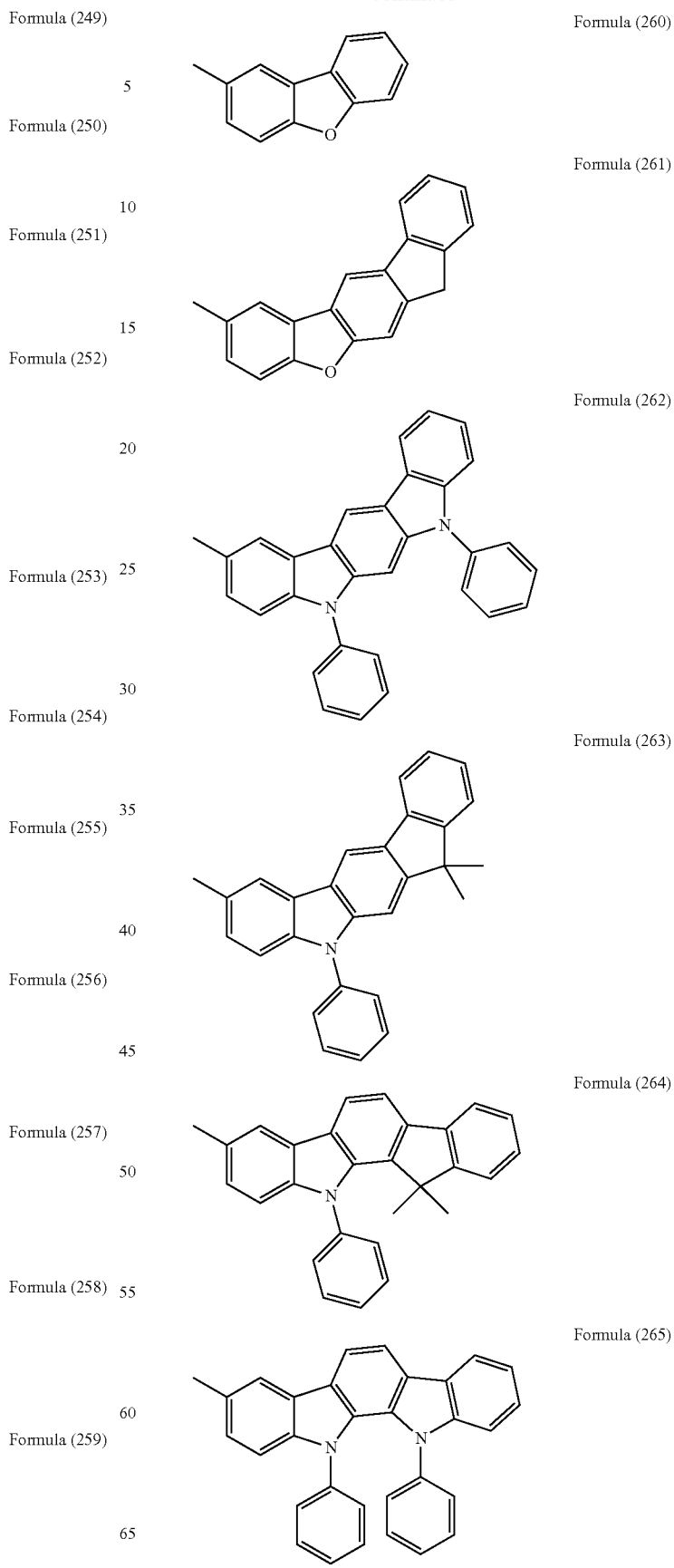

Formula (266)
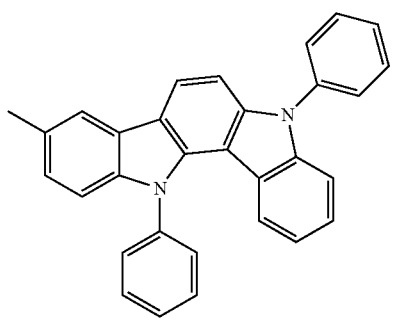

Formula (267)
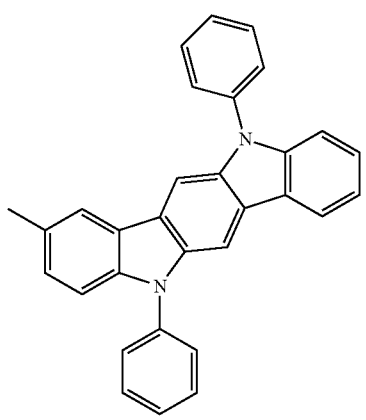

Formula (268)
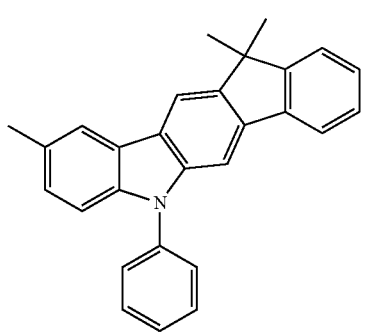

Formula (269)
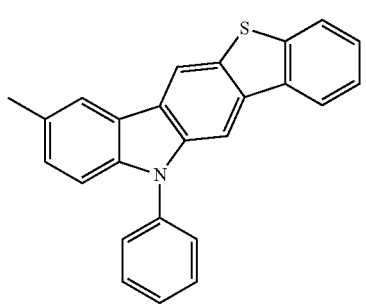

Formula (270)
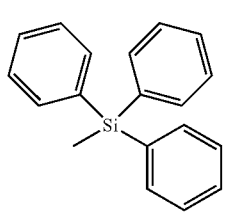

Formula (271)
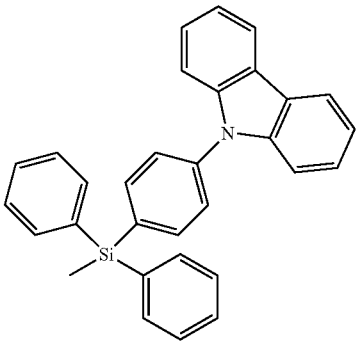

Formula (272)
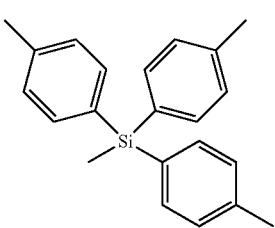

Depending on the exact structure of the complex according to Formula (1) it is often preferable to have a bridge connecting one or more of the ligands to increase the overall stability of the complex. To facilitate the visualization of the options, Formula (1) can be written as $$[L\text{-}]_n M\text{-}L'$$
Formula (273)

wherein L represents one or more of the ligands having the general Formula (274)

Formula (274)
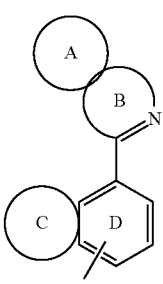

and L' represents the ligand having the general Formula (275)

Formula (275)
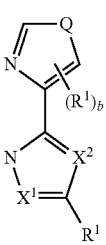

and wherein the indices and symbols have the meaning as defined above.

Preferred structures having bridged ligands are the metal complexes of the following Formulae (276) to (280):

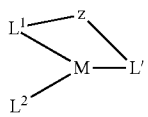

Formula (276)

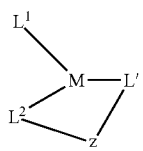

Formula (277)

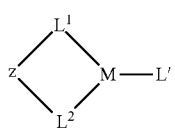

(Formula (278))

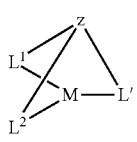

Formula (279)

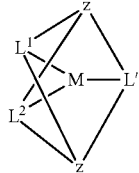

Formula (280)

Preferably Z represents a single bond or a bridging unit containing 1 to 80 atoms from the third, fourth, fifth and/or sixth main group and/or the transmission metals group (IUPAC group 3 to 12 and 13 to 16) or a 3- to 6-membered homo- or heterocycle which covalently bonds the ligands L to one another or L to L'. The bridging unit Z here may also have an asymmetric structure, i.e. the linking of Z to L or L' needs not to be identical. In a preferred embodiment of the invention, one or more bridging units Z are present and can link one or more of the ligands L and L' either directly from the rings A, B, C or D or from one of the substituents $R^1$, meaning that the ligands have a bidentate or tridentate or polydentate or polypodal character. This results in the formation of macrocyclic ligands or cryptates.

The bridging unit Z may be neutral, singly, doubly or triply negatively charged or singly, doubly or triply positively charged. Z is preferably neutral or singly negatively positively charged. The charge of Z here is preferably selected so that overall a neutral complex arises.

If Z is a trivalent group, i.e. bridges two ligands L to L' or two ligands L to one another or one ligand L to L', Z is preferably selected, identical or different on each occurrence, from the group consisting of B, $B(R^2)^-$, $B(C(R^2)_2)_3$, $(R^2)B(C(R^2)_2)_3^-$, $B(O)_3$, $(R^2)B(O)_3^-$, $B(C(R^2)_2C(R^2)_2)_3$, $(R^2)B(C(R^2)_2C(R^2)_2)_3^-$, $B(C(R^2)_2O)_3$, $(R^2)B(C(R^2)_2O)_3^-$, $B(OC(R^2)_2)_3$, $(R^2)B(OC(R^2)_2)_3^-$, $C(R^2)$, $CO^-$, $CN(R^2)_2$, $(R^2)C(C(R^2)_2)_3$, $(R^2)C(O)_3$, $(R^2)C(C(R^2)_2C(R^2)_2)_3$, $(R^2)C(C(R^2)_2O)_3$, $(R^2)C(OC(R^2)_2)_3$, $(R^2)C(Si(R^2)_2)_3$, $(R^2)C(Si(R^2)_2C(R^2)_2)_3$, $(R^2)C(C(R^2)_2Si(R^2)_2)_3$, $(R^2)C(Si(R^2)_2Si(R^2)_2)_3$, $Si(R^2)$, $(R^2)Si(C(R^2)_2)_3$, $(R^2)Si(O)_3$, $(R^2)Si(C(R^2)_2C(R^2)_2)_3$, $(R^2)Si(OC(R^2)_2)_3$, $(R^2)Si(C(R^2)_2O)_3$, $(R^2)Si(Si(R^2)_2)_3$, $(R^2)Si(Si(R^2)_2C(R^2)_2)_3$, $(R^2)Si(C(R^2)_2Si(R^2)_2)_3$, $(R^2)Si(Si(R^2)_2Si(R^2)_2)_3$, N, NO, $N(R^2)^+$, $N(C(R^2)_2)_3$, $(R^2)N(C(R^2)_2)_3^+$, $N(C=O)_3$, $N(C(R^2)_2C(R^2)_2)_3$, $(R^2)N(C(R^2)_2C(R^2)_2)_3^+$, P, $P(R^2)^+$, PO, PS, PSe, PTe, $P(O)_3$, $PO(O)_3$, $P(OC(R^2)_2)_3$, $PO(OC(R^2)_2)_3$, $P(C(R^2)_2)_3$, $P(R^2)(C(R^2)_2)_3^+$, $PO(C(R^2)_2)_3$, $P(C(R^2)_2C(R^2)_2)_3$, $P(R^2)(C(R^2)_2C(R^2)_2)_3^+$, $PO(C(R^2)_2C(R^2)_2)_3$, $S^+$, $S(C(R^2)_2)_3^+$, $S(C(R^2)_2C(R^2)_2)_3^+$,
or a unit of the Formulae (281) to (284),

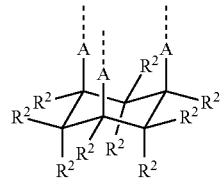

Formula (281)

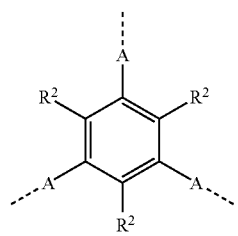

Formula (282)

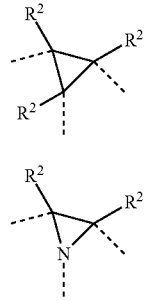

Formula (283)

Formula (284)

where the dashed bonds in each case indicate the bonding to the ligands L or L', and A is selected, identical or different on each occurrence, from the group consisting of a single bond, O, S, S(=O), S(=O)$_2$, $NR^2$, $PR^2$, P(=O)$R^2$, P(=N$R^2$), C($R^2$)$_2$, C(=O), C(=N$R^2$), C(=C($R^2$)$_2$), Si($R^2$)$_2$ or $BR^2$. The other symbols used have the meanings mentioned above.

If Z is a divalent group, i.e. bridges two ligands L to one another or one ligand L to L', Z is preferably selected, identical or different on each occurrence, from the group consisting of $BR^2$, $B(R^2)_2^-$, $C(R^2)_2$, C(=O), Si($R^2$)$_2$, $NR^2$, $PR^2$, $P(R^2)_2^+$, P(=O)($R^2$), P(=S)($R^2$), $AsR^2$, As(=O)($R^2$), As(=S)($R^2$), O, S, Se, or a unit of the Formulae (285) to (294),

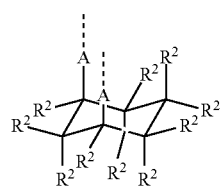

Formula (285)

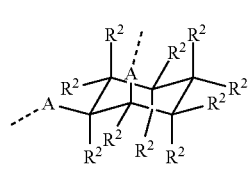

Formula (286)

Formula (287)
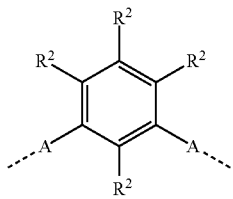

Formula (288)
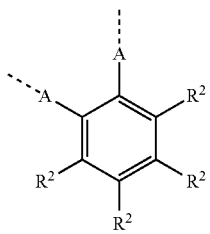

Formula (289)
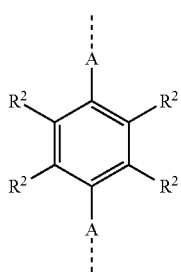

Formula (290)
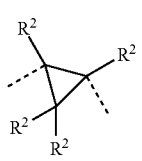

Formula (291)
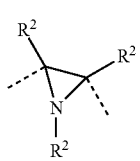

Formula (292)
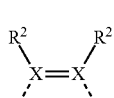

Formula (293)
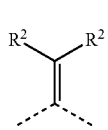

Formula (294)
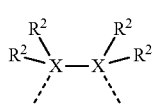

where the dashed bonds in each case indicate the bonding to the ligands L or L', and the further symbols used in each case have the meanings mentioned above.

Also preferred are complexes where the ligands L and/or V themselves contain a bridging unit Z connecting the upper and lower part of the ligand as shown exemplarily in Formulae (295) and (295a).

Formula (295)
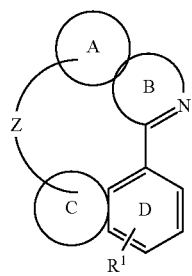

Formula (295a)
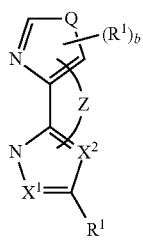

The bridging unit Z in Formula (295) can be realized as a covalent or a coordinative bond from ring A to C or D or from ring B to C or D. In case of Formula (295a) the bridging unit Z connects both independent ring systems. Preferably $X^2$ in Formula (295a) is —C=C— connected to the bridging unit Z.

Some preferred exemplary structures are shown in Formulae (296) to (305)

Formula (296)
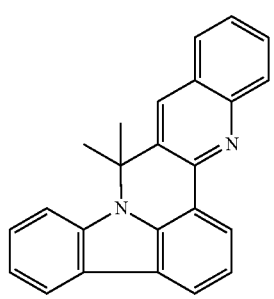

Formula (297)
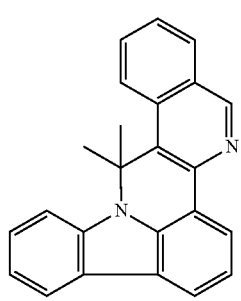

-continued

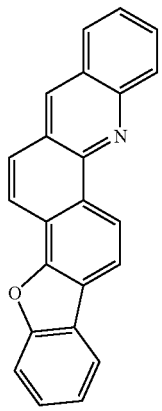
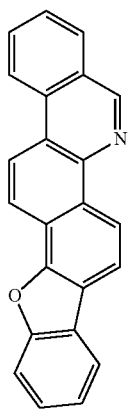
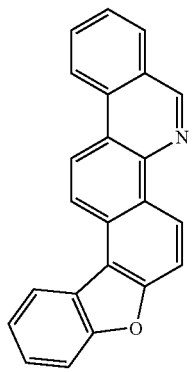
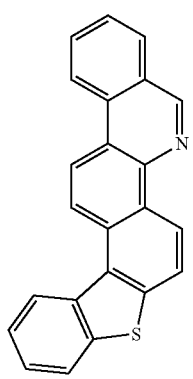

Formula (298)
Formula (299)
Formula (300)
Formula (301)

-continued

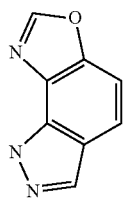
Formula (302)

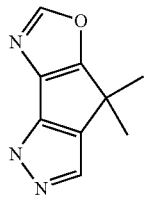
Formula (303)

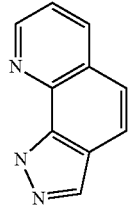
Formula (304)

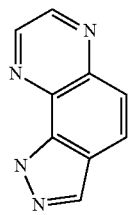
Formula (305)

The present invention further relates to a process for the preparation of the metal-complex compounds of the Formula (1). The reaction comprises the following steps 1 to.

Step 1

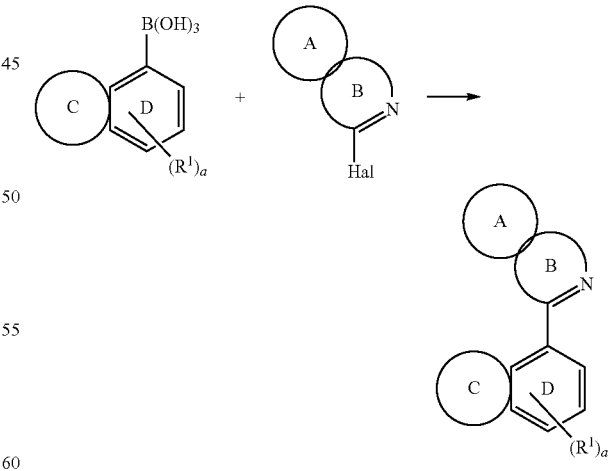

wherein the symbols and indices are defined as above and Hal stands for halogens like Cl, Br, I and functional groups which can undergo C—C-coupling reactions like pseudo-halides (triflate, etc.).

Step 1 is preferably carried out in the presence of a palladium catalyst, particularly preferably in the presence of Pd(PPh$_3$)$_4$. To the reaction mixture a base, preferably sodium carbonate, is added, and the reaction is carried out under reflux for up to 30 h. The reaction is carried out in organic solvents, preferably in a mixture of 1,2-dimethoxy-ethane and ethanol.

Step 2

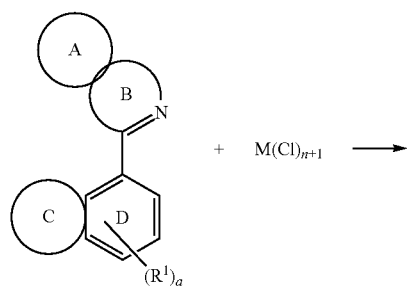

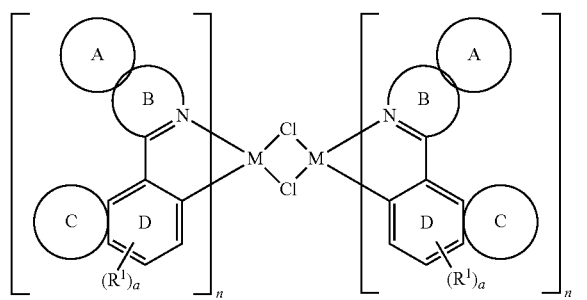

Step 2 is preferably carried out by mixing the ligand with a metal chloride in an organic solvent, preferably 2-ethoxy-ethanol. The mixture is heated to reflux preferably for up to 48 h.

Step 3

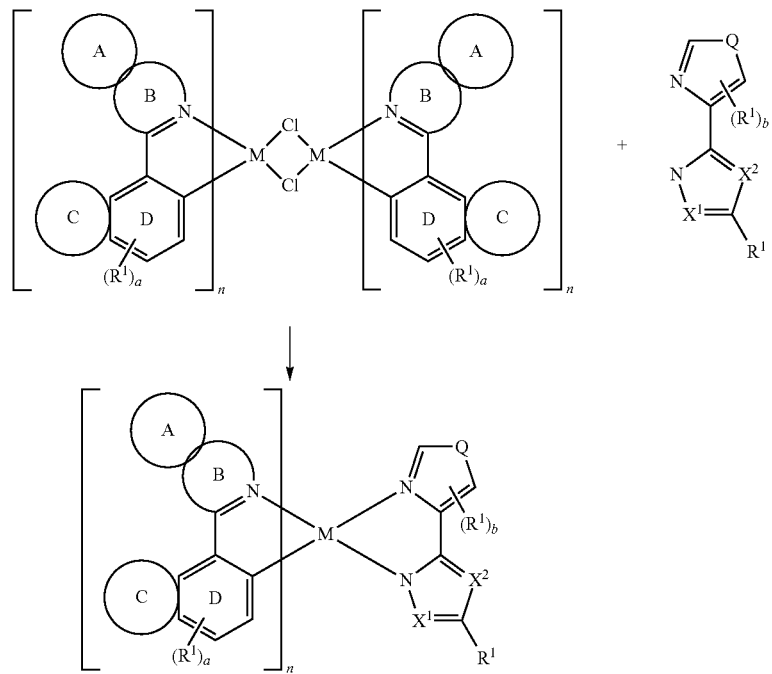

In step 3, the third ligand is added to the chloro-complex solution together with a base, preferably sodium carbonate. The reaction is carried out in an organic solvent, preferably in ethoxyethanol, under reflux for up to 5 h.

To gain triple heteroleptic complexes the metallation reaction is carried out by mixing Ir(acac)$_3$ and 3 different ligands in an organic solvent, preferably glycerol, under reflux for up to 20 h.

These processes enable the compounds of the Formula (1) according to the invention to be obtained in high purity, typically greater than 97% (determined by means of $^1$H-NMR and/or HPLC). Further purification can be easily achieved by recrystallization from a mixture of dichloromethane and methanol.

The synthetic methods explained here enable the preparation of, inter alia, the compounds of the Formulae (306) to (350) according to the invention depicted below.

Formula (306)

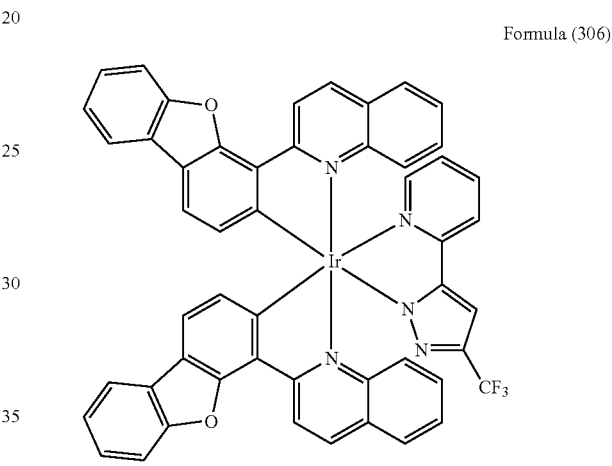

Formula (307)
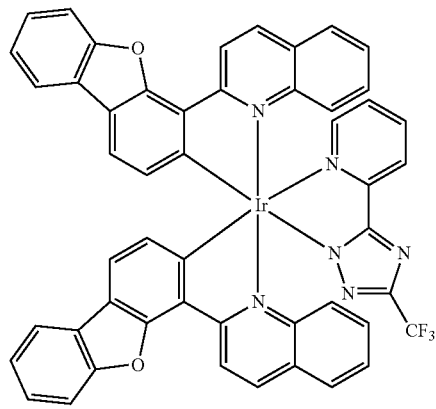
Formula (310)
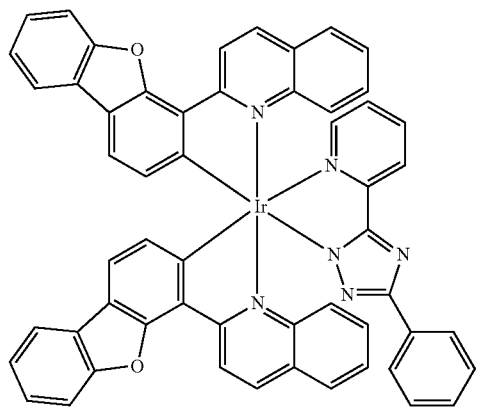
Formula (308)
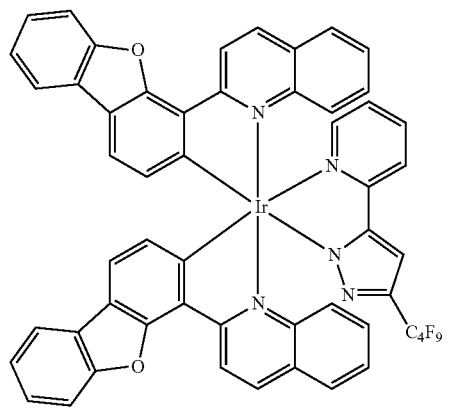
Formula (311)
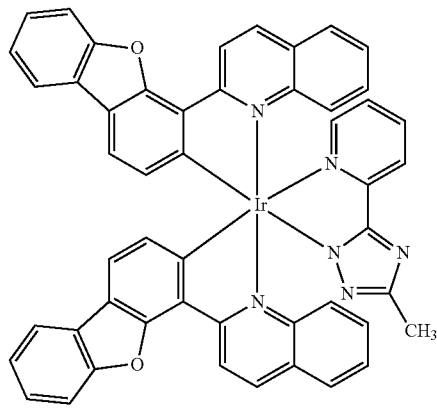
Formula (309)
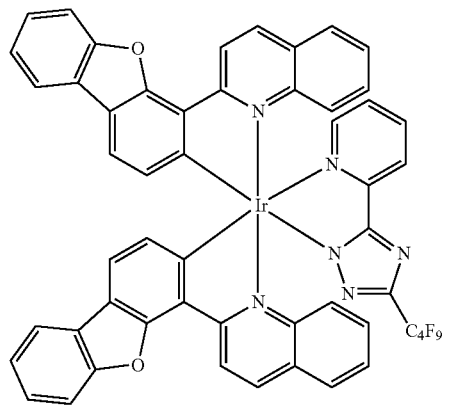
Formula (312)
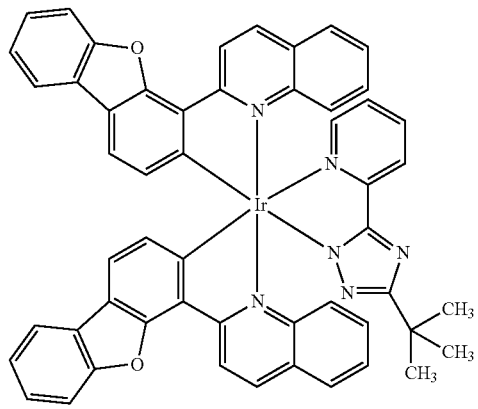

Formula (313)
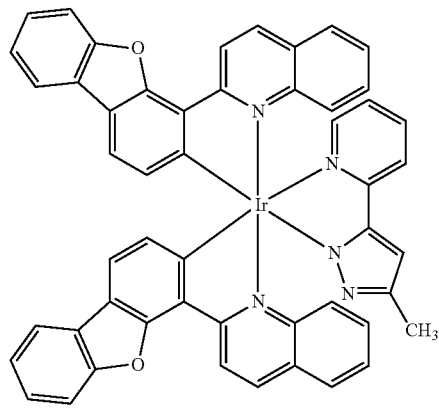
Formula (314)
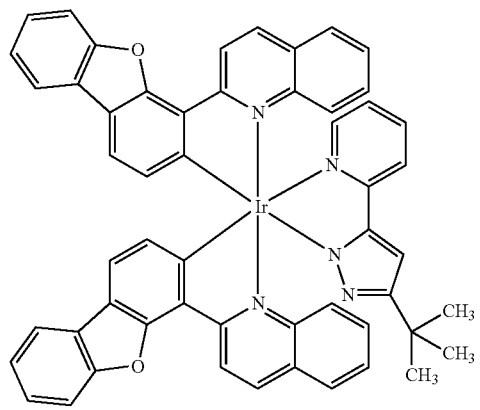
Formula (315)
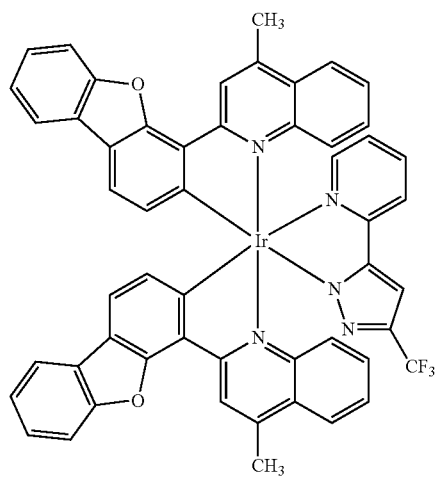
Formula (316)
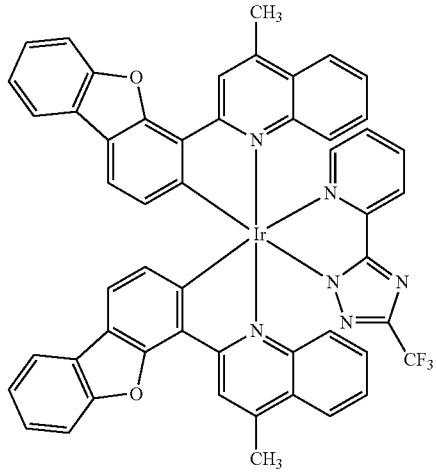
Formula (317)
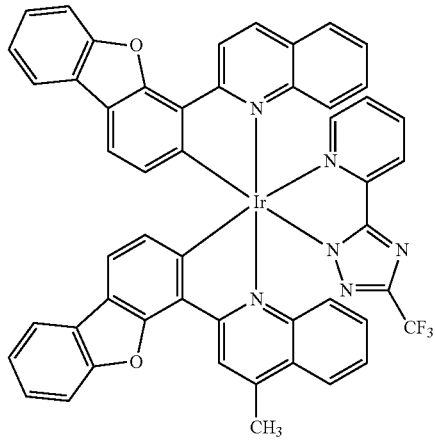
Formula (318)
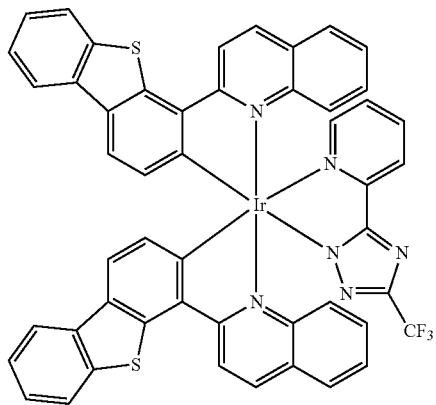

Formula (319)
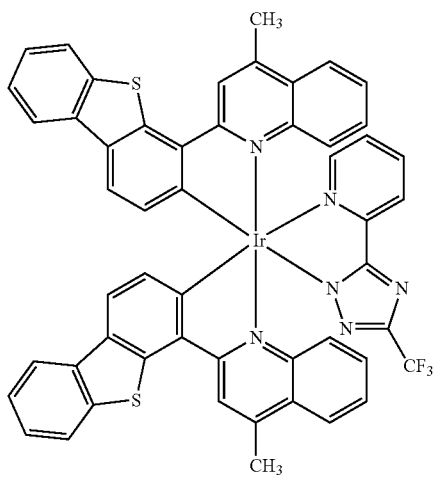
Formula (320)
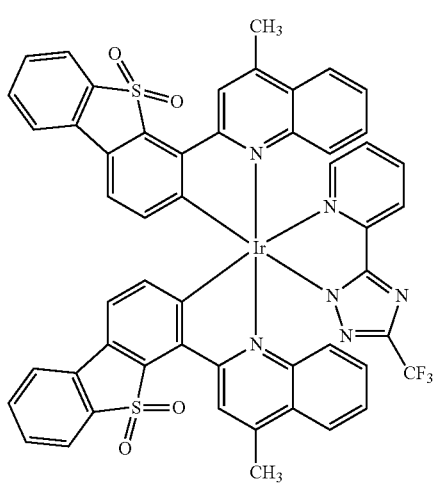
Formula (321)
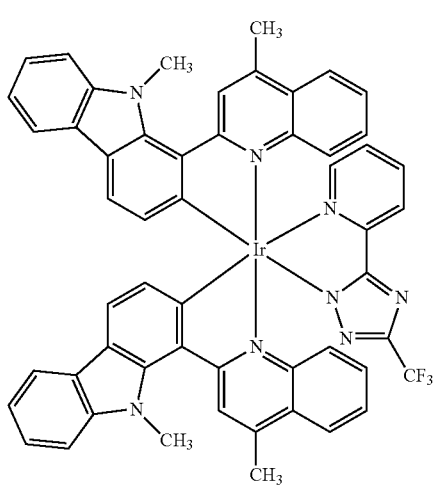
Formula (322)
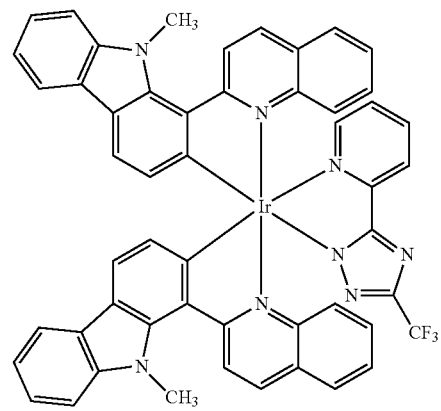
Formula (323)
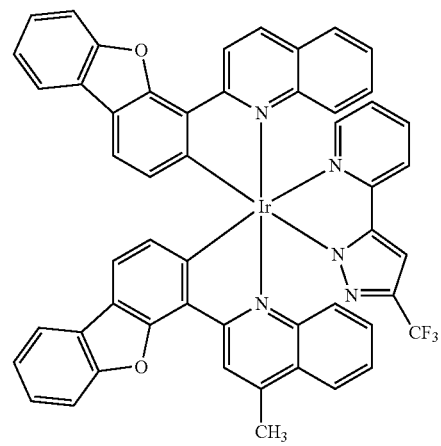
Formula (324)
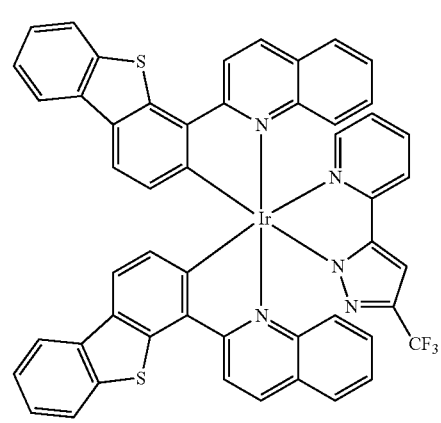

Formula (325)
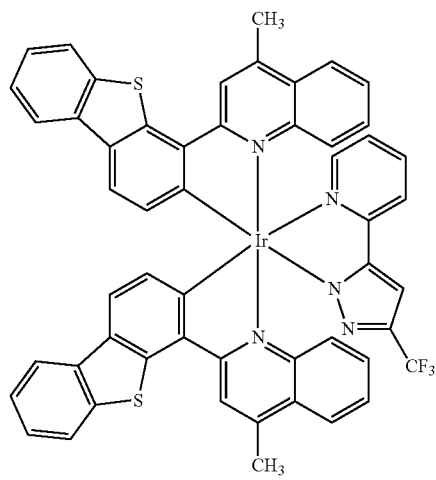
Formula (326)
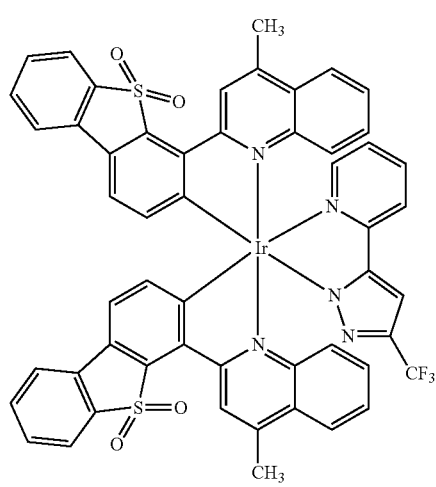
Formula (327)
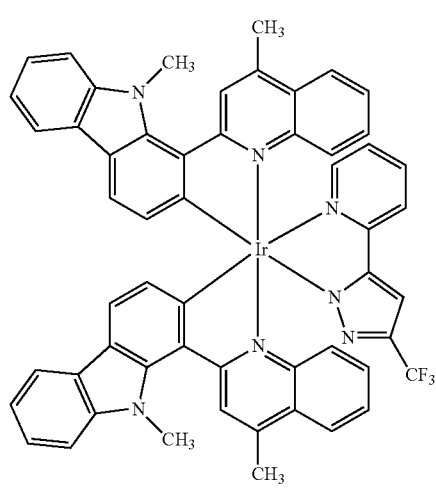
Formula (328)
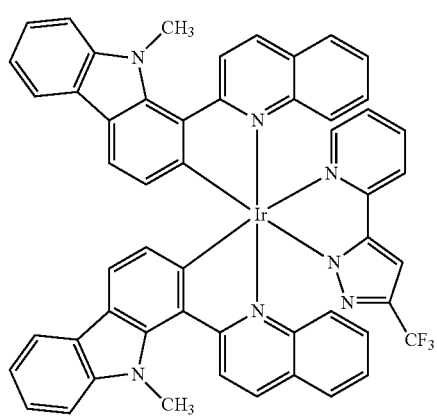
Formula (329)
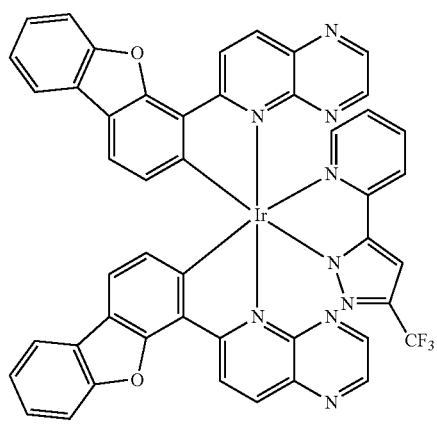
Formula (330)
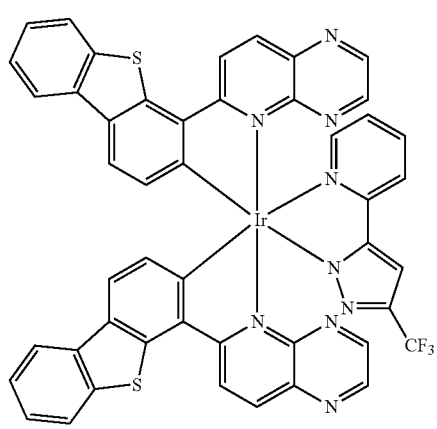

Formula (331)
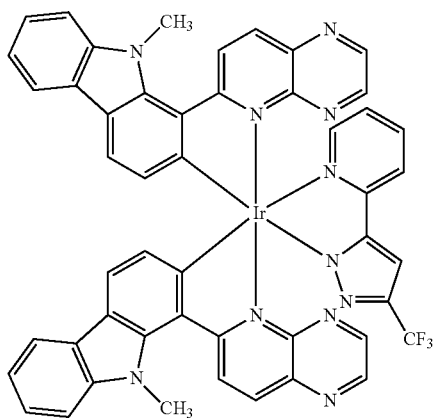
Formula (332)
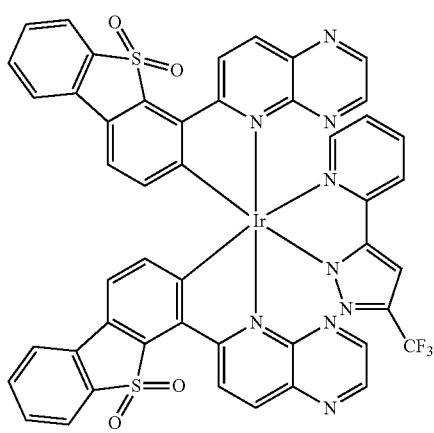
Formula (333)
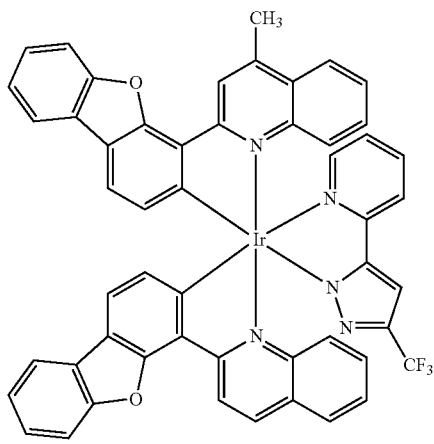
Formula (334)
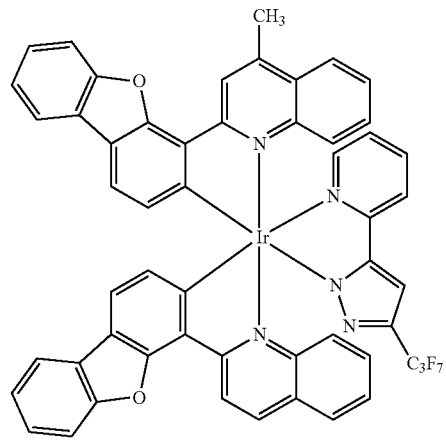
Formula (335)
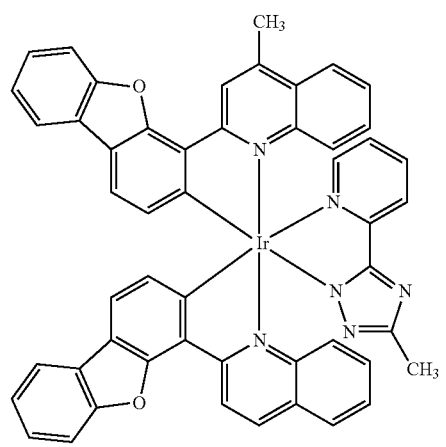
Formula (336)
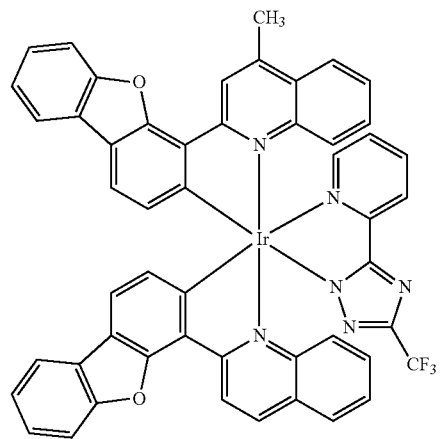

77
-continued
Formula (337)
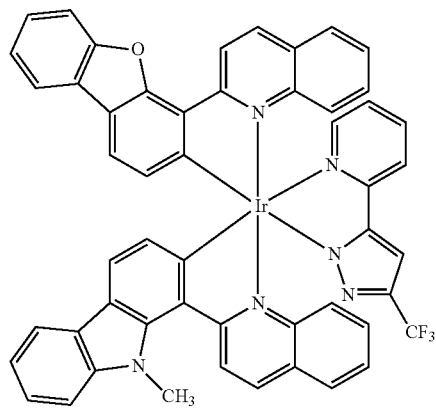
Formula (338)
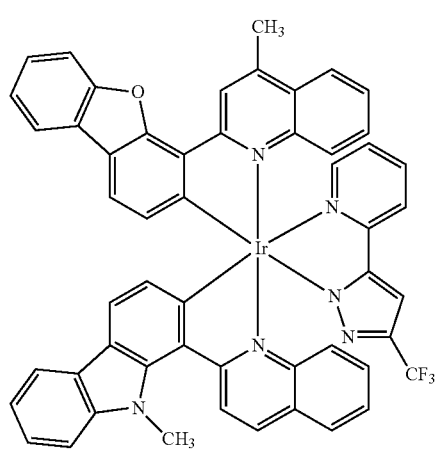
Formula (339)
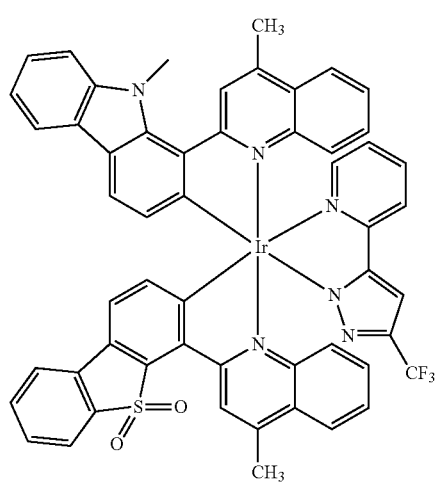
78
-continued
Formula (340)
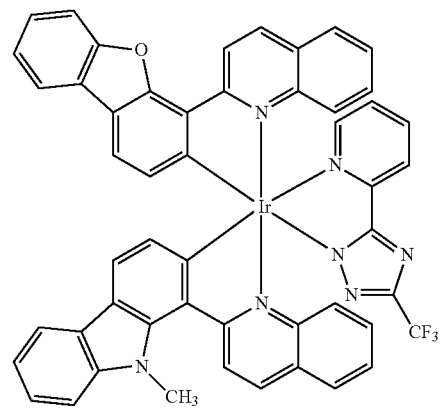
Formula (341)
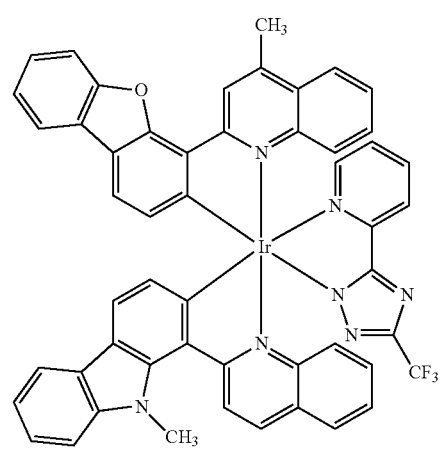
Formula (342)
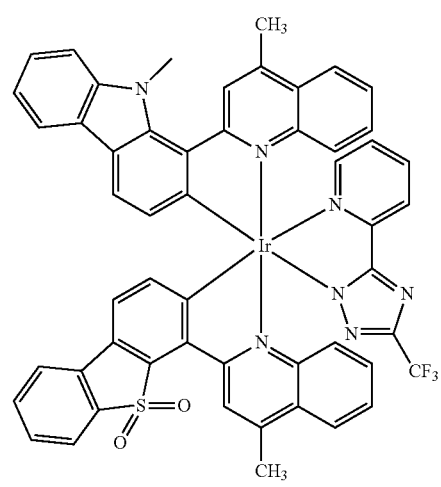

Formula (343)
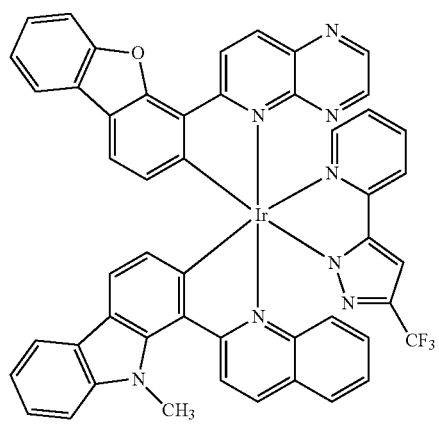
Formula (344)
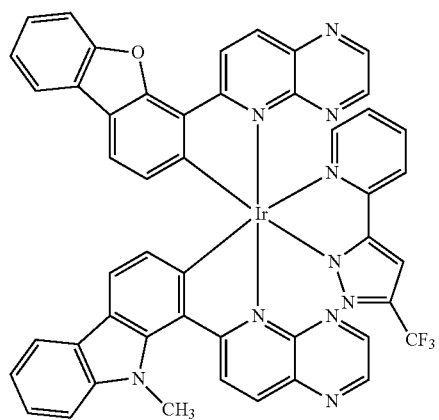
Formula (345)
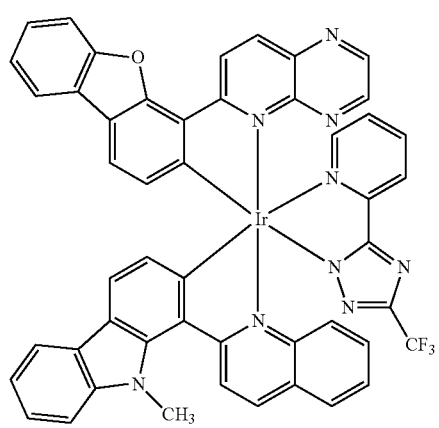
Formula (346)
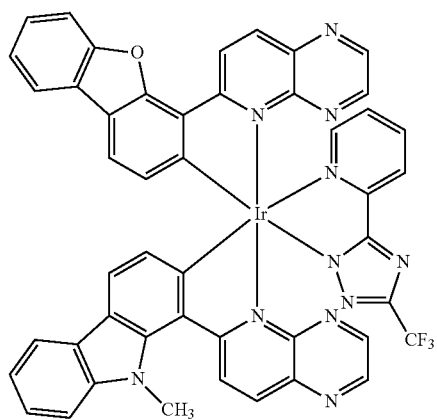
Formula (347)
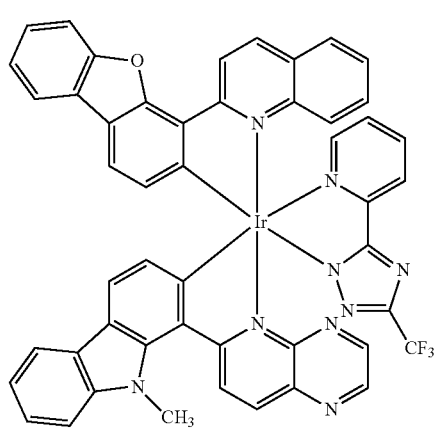
Formula (348)
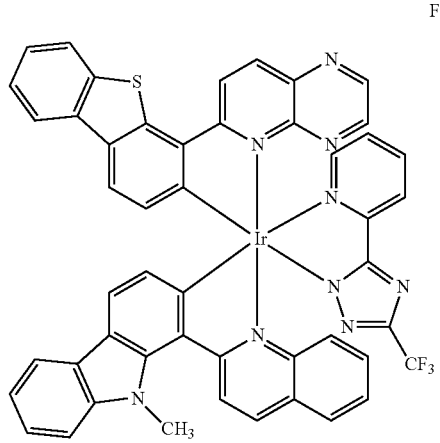

-continued

Formula (349)

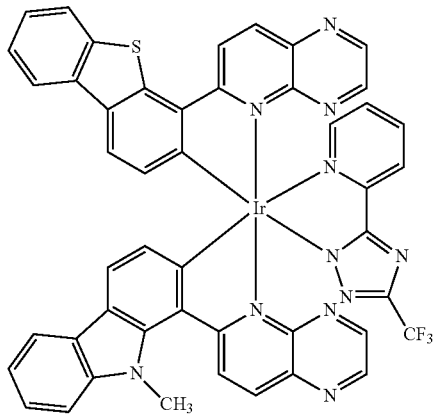

Formula (350)

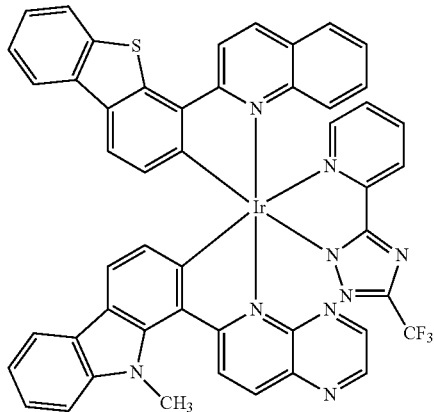

The complexes of Formula (1) and the preferred embodiments mentioned above can be used as active components in electronic devices. An electronic device is taken to mean a device which comprises an anode, a cathode and at least one layer that comprises at least one organic or organometallic compound. The electronic device according to this invention thus comprises an anode, a cathode and at least one layer which comprises at least one compound of Formula (1) as indicated above. Preferred electronic devices are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quenching devices (O-FQDs), light-emitting electrochemical cells (LECs or LEECs) or organic laser diodes (O-lasers), comprising, in at least one layer at least one compound of the Formula (1) indicated above. Particular preference is given to organic electroluminescent devices.

Active components are generally organic or inorganic materials which are introduced between the anode and cathode, for example charge-injection, charge-transport or charge-blocking materials, but in particular emission materials and matrix materials. The compounds according to this invention exhibit particularly good properties as emission material in organic electroluminescent devices. Organic electroluminescent devices are therefore a preferred embodiment of the invention.

An organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, charge-generation layers and/or organic or inorganic pin junctions. It is likewise possible for interlayers, which have, for example, an exciton-blocking function and/or control the charge balance in the electroluminescent device, to be introduced between two emitting layers. However, it should be pointed out that each of these layers does not necessarily have to be present. The organic electroluminescent device may comprise one or more emitting layers. If more than one emission layer is present, their emission maxima are also preferably different and cover a range from 380 nm to 780 nm, resulting in white emission. Particular preference is given to three-layer systems, where the three layers exhibit blue, green and orange or red emission (for the basic structure see, for example, WO 2005/011013), two layer systems for cheaper two-color whites, or systems which comprise even more than three emitting layers.

In a preferred embodiment of the invention, the organic electroluminescent device comprises the compound of the Formula (1) or the preferred embodiments mentioned above as emitting compound in one or more emitting layers.

In a particularly preferred embodiment of the invention the organic electroluminescent device has an emission layer processed from solution comprising at least one host material and a material according to Formula (1). The host material can be one or more soluble small molecules and/or one or more polymers. Low-molecular weight additives or polymeric compounds may be added for rheological reasons and/or film formation. Other layers containing active components of the device including additional emission layers may be either evaporated or solution-processed.

Very particularly preferred is an embodiment in which all layers up to the emission layer are solution-processed. Even more preferred is a simplified device setup that does not require an evaporated organic electron transport layer.

Also preferred are white luminescent devices made of a light-blue triplet emitter and an orange emitter according to Formula (1) combined in one emission layer in a concentration ratio that renders a two-color white.

Equally preferred are white luminescent devices with a solution processed emission layer comprising the material according to Formula (1) with an evaporated or solution processed singlet blue layer on top, balanced in concentration and charge distribution to render a two-color-white device.

If the compound of the Formula (1) is used as emitting compound in an emission layer, it is preferably employed in combination with one or more matrix materials. The mixture of the compound of the Formula (1) and the matrix material comprises between 1 and 99% by weight, preferably between 2 and 50% by weight, particularly preferably between 3 and 40% by weight, in particular between 5 and 30% by weight, of the compound of the formula (1), based on the entire mixture comprising emitter and matrix material. Correspondingly, the mixture comprises between 99 and 1% by weight, preferably between 98 and 50% by weight, particularly preferably between 97 and 60% by weight, in particular between 95 and 70% by weight, of the matrix material, based on the entire mixture comprising emitter and matrix material.

Suitable matrix materials for the compounds according to the invention are ketones, phosphine oxides, sulfoxides and sulfones, for example in accordance with WO 2004/013080, WO 2004/093207, WO 2006/005627 or the application DE 102008033943, triarylamines, carbazole derivatives, such as for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with the applications DE 102009023155 and DE 102009031021, azacarbazoles, for example in according with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with the application DE 102008036982, WO 2007/063754 or WO 2008/056746, zinc complexes, for example in accordance with EP 652273 or in accordance with WO 2009/062578, diaza- or tetraazasilole derivatives, for example in accordance with the application DE 102008056688, or diazaphosphole derivatives, for example in accordance with application DE 102009022858.

It may also be preferred to employ a plurality of different matrix materials as a mixture, e.g. one or more electron-transporting matrix material and one or more hole-transporting matrix material. A preferred combination is, for example, the use of an aromatic ketone or a triazine with a triarylamine derivative or a carbazole derivative as mixed matrix for the metal complex according to the invention. Preference is likewise also given to mixtures of a hole- or electron-transporting material with a material which is involved in neither hole transport nor electron transport, as disclosed, for example, in DE 102009014513.

In a further preferred embodiment of the present invention, the compounds according to the invention can be employed in mixtures with one or more further emitters. Particular preference is given here to a mixture of the compounds according to the invention with one or more phosphorescent emitters where the concentration of each is balanced in such a way that the emitter according to Formula (1) is the one the electroluminescence comes from.

In a further preferred embodiment of the present invention, the emitter mixtures comprise 3, particularly preferably 2 and very particularly preferably one compound according to the invention.

In a particularly preferred embodiment of the present invention, the emitter mixtures comprise precisely one of the compounds according to the invention and precisely one further emitter. This further emitter thus acts like a matrix material.

The compound according to the present invention can, as outlined above, be mixed with further matrix materials. Besides matrix materials the compounds according to the present invention can also be mixed with any other organic functional material that is typically employed in electronic devices. Thus, the present invention also relates to a composition comprising at least one compound according to Formula (1) and at least one organic functional material selected from hole transport material (HTM), hole injection material (HIM), electron transport material (ETM), electron injection material (EIM), hole blocking material (HBM), exciton blocking material (ExBM), host or matrix material, fluorescent emitter, phosphorescent emitter, preferably matrix materials.

Preferred matrix materials are selected from ketones, phosphinoxides, sulfoxides, sulfones, triarylamines, carbazoles, indolocarbazoles, indenocarbazoles, azacarbazoles, bipolar matrix materials, silanes, azaborolenes, boronesters, triazines, zinc complexes, diaza- or tetraazasiloles or diazaphospholes or mixtures thereof.

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys of an alkali or alkaline-earth metal and silver, for example an alloy of magnesium and silver. In the case of multilayered structures, further metals which have a relatively high work function, such as, for example, Ag, may also be used in addition to the said metals, in which case combinations of the metals, such as, for example, Ca/Ag or Ba/Ag, are generally used. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, $Li_2O$, $BaF_2$, MgO, NaF, CsF, $Cs_2CO_3$, etc.). The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent in order to enable either irradiation of the organic material (O-SCs) or the outcoupling of light (OLEDs/PLEDs, O-lasers). A preferred structure uses a transparent anode. Preferred anode materials here are conductive mixed metal oxides. Particular preference is given to indium tin oxide (ITO) or indium zinc oxide (IZO). Preference is furthermore given to conductive doped organic materials, in particular conductive doped polymers.

In general, all materials as used for the layers in accordance with the prior art can be used in the further layers, and the person skilled in the art will be able to combine each of these materials with the materials according to the invention in an electronic device without inventive step.

The device is correspondingly (depending on the application) structured, provided with contacts and finally hermetically sealed, since the lifetime of devices of this type is drastically shortened in the presence of water and/or air.

Preference is furthermore given to an organic electroluminescent device, characterised in that one or more layers are applied by means of a sublimation process, in which the materials are vapour-deposited in vacuum sublimation units at an initial pressure of usually less than $10^{-5}$ mbar, preferably less than $10^{-6}$ mbar. It is also possible for the initial pressure to be even lower, for example less than $10^{-7}$ mbar.

Preference is likewise given to an organic electroluminescent device, characterised in that one or more layers are applied by means of OVPD (organic vapour phase deposition) or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., Appl. Phys. Lett. 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Since the compounds of the Formula (1) according to the invention have very good solubility in organic solvents, they are particularly suitable for processing from solution.

The organic electroluminescent device can also be produced as a hybrid system by applying one or more layers from solution and applying one or more other layers by vapour deposition. Thus, for example, it is possible to apply an emitting layer comprising a compound of the Formula (1) and a matrix material from solution and to apply a hole-blocking layer and/or an electron-transport layer on top by vacuum vapour deposition.

These processes are generally known to the person skilled in the art and can be applied by him without problems to organic electroluminescent devices comprising compounds of the Formula (1) or the preferred embodiments mentioned above.

For processing from solution, solutions or formulations of the compounds of the Formula (1) are necessary. It may also be preferred to use mixtures of two or more solvents. Suitable and preferred solvents are, for example, toluene, anisole, o-, m- or p-xylene, methyl benzoate, dimethylanisole, mesitylene, tetralin, veratrol, THF, methyl-THF, THP, chlorobenzene, dioxane, or mixtures of these solvents.

The present invention therefore furthermore relates to a solution or formulation comprising at least one compound of the Formula (1) and one or more solvents, in particular organic solvents. The way in which solutions of this type can be prepared is known to the person skilled in the art and is described, for example, in WO 02/072714, WO 03/019694 and the literature cited therein.

Some of the basic areas of application here are display or illumination technologies. Due to the potential simplicity of the devices, large area and thus very cheap device fabrication by any kind of printing method or roll-to-roll-processing is possible. One further preferred application is therefore the use of the materials according to Formula (1) in flexible devices which are then particularly well suited for phototherapy.

The present invention therefore furthermore relates to the use of the compounds or compositions according to the invention and devices comprising the compounds for the treatment, prophylaxis and diagnosis of diseases. The present invention furthermore relates to the use of the compounds or compositions according to the invention and devices comprising the compounds for the treatment and prophylaxis of cosmetic conditions.

The present invention furthermore relates to the use of the compounds or compositions according to the invention for the production of devices for the therapy, prophylaxis and/or diagnosis of therapeutic diseases and/or for cosmetic applications.

Phototherapy or light therapy is used in many medical and/or cosmetic areas. The compounds or compositions according to the invention and the devices comprising them can therefore be employed for the therapy and/or prophylaxis and/or diagnosis of all diseases and/or in any cosmetic applications for which the person skilled in the art considers the use of phototherapy. Besides irradiation, the term phototherapy also includes photodynamic therapy (PDT) and disinfection and sterilisation in general. Phototherapy or light therapy can be used for the treatment of not only humans or animals, but also any other type of living or non-living materials. These include, for example, fungi, bacteria, microbes, viruses, eukaryotes, prokaryonts, foods, drinks, water and drinking water.

The term phototherapy also includes any type of combination of light therapy and other types of therapy, such as, for example, treatment with active compounds. Many light therapies have the aim of irradiating or treating exterior parts of an object, such as the skin of humans and animals, wounds, mucous membranes, the eye, hair, nails, the nail bed, gums and the tongue. The treatment or irradiation according to the invention can in addition also be carried out inside an object in order, for example, to treat internal organs (heart, lung, etc.) or blood vessels or the breast.

The therapeutic and/or cosmetic areas of application according to the invention are preferably selected from the group of skin diseases and skin-associated diseases or changes or conditions, such as, for example, psoriasis, skin ageing, skin wrinkling, skin rejuvenation, enlarged skin pores, cellulite, oily/greasy skin, folliculitis, actinic keratosis, precancerous actinic keratosis, skin lesions, sun-damaged and sun-stressed skin, crows' feet, skin ulcers, acne, acne rosacea, scars caused by acne, acne bacteria, photomodulation of greasy/oily sebaceous glands and their surrounding tissue, jaundice, jaundice of the newborn, vitiligo, skin cancer, skin tumours, Crigler-Najjar, dermatitis, atopic dermatitis, diabetic skin ulcers and desensitisation of the skin.

Particular preference is given for the purposes of the invention to the treatment and/or prophylaxis of psoriasis, acne, cellulite, skin wrinkling, skin ageing, jaundice and vitiligo.

Very particular preference is given to the use of the light emitting devices comprising the compounds or compositions according to the present invention to reduce or prevent skin ageing and the formation of skin wrinkles. The treatment of skin with orange light in these cases is particularly beneficial.

Further areas of application according to the invention for the compounds or compositions and/or devices comprising them are selected from the group of inflammatory diseases, rheumatoid arthritis, pain therapy, treatment of wounds, neurological diseases and conditions, oedema, Paget's disease, primary and metastasising tumours, connective-tissue diseases or changes, changes in the collagen, fibroblasts and cell level originating from fibroblasts in tissues of mammals, irradiation of the retina, neovascular and hypertrophic diseases, allergic reactions, irradiation of the respiratory tract, sweating, ocular neovascular diseases, viral infections, particularly infections caused by herpes simplex or HPV (human papillomaviruses) for the treatment of warts and genital warts.

Particular preference is given for the purposes of the invention to the treatment and/or prophylaxis of rheumatoid arthritis, viral infections and pain.

Further areas of application according to the invention for the compounds or compositions and/or devices comprising them are selected from winter depression, sleeping sickness, irradiation for improving the mood, the reduction in pain, particularly muscular pain caused by, for example, tension or joint pain, elimination of the stiffness of joints and the whitening of the teeth (bleaching).

Further areas of application according to the invention for the compounds or compositions and/or devices comprising them are selected from the group of disinfections. The compounds or compositions according to the invention and/or the devices can be used for the treatment of any type of objects (non-living materials) or subjects (living materials such as, for example, humans and animals) for the purposes of disinfection. This includes, for example, the disinfection of wounds, the reduction in bacteria, the disinfection of surgical instruments or other articles, the disinfection of foods, of liquids, in particular water, drinking water and other drinks, the disinfection of mucous membranes and gums and teeth. Disinfection here is taken to mean the reduction in the living microbiological causative agents of undesired effects, such as bacteria and germs.

For the purposes of phototherapy, devices comprising the compounds or compositions according to the invention preferably emit light having a wavelength between 300 and 1250 nm, particularly preferably between 440 and 1000 nm, particularly preferably between 500 and 850 nm and very particularly preferably between 560 and 620 nm.

In a particularly preferred embodiment of the present invention, the compounds or compositions according to the invention are employed in an organic light-emitting diode (OLED) or an organic light-emitting electrochemical cell (OLEC) for the purposes of phototherapy. Both the OLED and the OLEC can have a planar or fibre-like structure having any desired cross section (for example round, oval, polygonal, square) with a single- or multilayered structure. These OLECs and/or OLEDs can be installed in other devices which comprise further mechanical, adhesive and/or electronic elements (for example battery and/or control unit for adjustment of the irradiation times, intensities and wavelengths). These devices comprising the OLECs and/or OLEDs according to the invention are preferably selected from the group comprising plasters, pads, tapes, bandages, cuffs, blankets, caps, sleeping bags, textiles and stents.

The use of OLED- or OLEC-devices for therapeutic and/or cosmetic purposes is particularly advantageous compared to the prior art since homogeneous irradiation with lower intensity is possible virtually anywhere and anytime. The irradiation can be carried out on an in- or outpatient basis, or especially for cosmetic purposes, even by the customers themselves without initiation by medical or cosmetic specialists. Thus, for example, bandages and plasters can be worn under clothing, so that irradiation is also possible during working hours, in leisure time or during sleep. Complex inpatient/outpatient treatments can in many cases be avoided or their frequency reduced. The devices according to the invention may be intended for re-use or be disposable articles, which can be disposed of after use once, twice or three times.

Further advantages over the prior art are, for example, lower evolution of heat and emotional aspects. Thus, newborn being treated owing to jaundice typically have to be irradiated blindfolded in an incubator without physical contact with the parents, which represents an emotional stress situation for parents and newborn. With the aid of a blanket according to the invention comprising the OLEDs and/or OLECs according to the invention, the emotional stress can be reduced significantly. In addition, better temperature control of the child is possible due to reduced heat production of the devices according to the invention compared with conventional irradiation equipment.

The new materials and electronic devices according to the invention, in particular organic electroluminescent devices, are distinguished by the following surprising advantages over the prior art:
1. Synthesis with high yield and purification of the compounds according to the present invention is easy, even on large scale. This makes upscaling straightforward and the materials suited for mass production of devices.
2. The compounds of the Formula (1) have very good solubility in a high number of common organic solvents and are therefore very highly suitable for processing from solution. This makes them ideally suited for applications that require low production costs, such as illumination and signage devices, and for roll-to-roll-processed devices on flexible substrates.
3. The compounds of Formula (1) and the electronic devices comprising them show improved stability and improved shelf life compared to similar compounds of the prior art.
4. Organic electroluminescent devices comprising compounds of the Formula (1) as emitting materials show excellent efficiencies and lifetimes. Even very simple devices have efficiencies and lifetimes sufficient for monochrome illumination and signage applications.
5. The emission color of the compounds according to Formula (1) is beneficial for a number of different applications, e.g. for the treatment or prevention of skin issues in phototherapeutic devices or for low cost two-color white devices for lighting applications.

These above-mentioned advantages are not accompanied by an impairment in the other electronic properties.

It should be pointed out that variations of the embodiments described in the present invention fall within the scope of this invention. Each feature disclosed in the present invention can, unless explicitly excluded, be replaced by alternative features which serve the same, an equivalent or a similar purpose. Thus, each feature disclosed in the present invention should, unless stated otherwise, be regarded as an example of a generic series or as an equivalent or similar feature.

All features of the present invention can be combined with one another in any way, unless certain features and/or steps are mutually exclusive. This applies, in particular, to preferred features of the present invention. Equally, features of non-essential combinations can be used separately (and not in combination).

It should furthermore be pointed out that many of the features, and in particular those of the preferred embodiments of the present invention, should be regarded as inventive themselves and not merely as part of the embodiments of the present invention. Independent protection may be granted for these features in addition or as an alternative to each invention claimed at present.

The teaching regarding technical action disclosed with the present invention can be abstracted and combined with other examples.

The invention is explained in greater detail by the following examples without wishing it to be restricted thereby.

WORKING EXAMPLES

Materials (Acronyms)

| Structure | Name (acronym) |
|---|---|
| 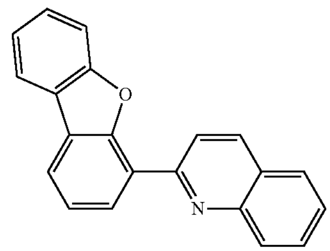 [SMILES: c1ccc2nc(-c3cccc4c3oc3ccccc34)ccc2c1] | 2-(dibenzo[b,d]furan-4-yl)quinoline (dbfqH) |

-continued

| Structure | Name (acronym) |
|---|---|
| 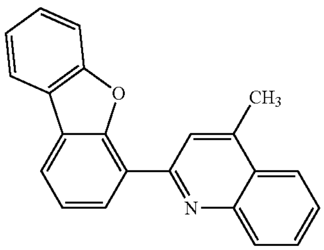 [SMILES: Cc1cc(-c2cccc3c2oc2ccccc23)nc2ccccc12] | 2-(dibenzo[b,d]furan-4-yl)-4-methylquinoline (dbfmqH) |
| 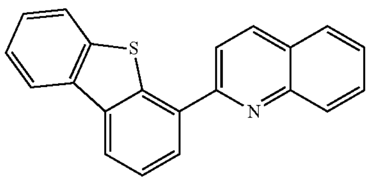 [SMILES: c1ccc2nc(-c3cccc4c3sc3ccccc34)ccc2c1] | 2-dibenzothiophene-4-yl-quinoline (dbtqH) |
| 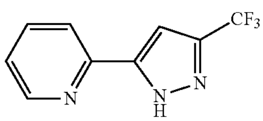 [SMILES: FC(F)(F)c1cc(-c2ccccn2)[nH]n1] | (2-(3-(trifluoromethyl)-1H-pyrazol-5-yl)pyridine) (fppzH) |
| 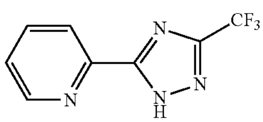 | 2-(3-(trifluoromethyl)-1H-1,2,4-triazol-5-yl)pyridine (fptzH) |
| 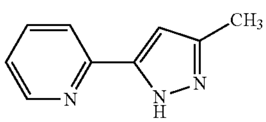 | 2-(3-methyl-1H-pyrazol-5-yl)pyridine (mppzH) |
| 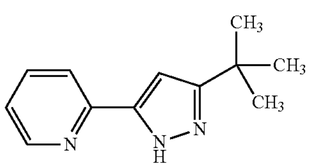 | 2-(3-(tert-butyl)-1H-pyrazol-5-yl)pyridine (bppzH) |
| 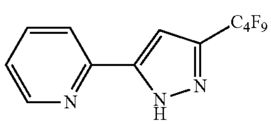 | 2-(3-(perfluorobutyl)-1H-pyrazol-5-yl)pyridine (hppzH) |
| 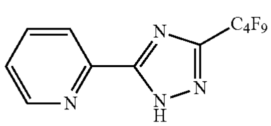 | 2-(3-(perfluorobutyl)-1H-1,2,4-triazol-5-yl)pyridine (hptzH) |
| 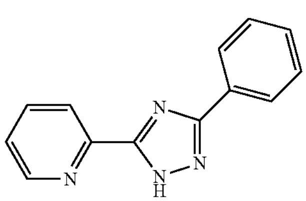 [SMILES: c1ccc(-c2n[nH]c(-c3ccccn3)n2)cc1] | 2-(3-phenyl-1H-1,2,4-triazol-5-yl)pyridine (pptzH) |
| 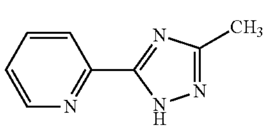 | 2-(3-methyl-1H-1,2,4-triazol-5-yl)pyridine (mptzH) |

-continued

| Structure | Name (acronym) |
|---|---|
| 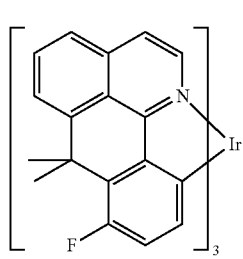 | 2-(3-tert-butyl)-1H-1,2,4-triazol-5-yl)pyridine (tptzH) |
| 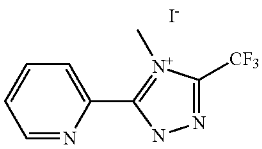 [SMILES: [I-] ; C[n+]1c(C(F)(F)F)n[nH]c1-c1ccccn1] | 2-(3-trifluoromethyl)-1H-[1,2,4]triazol-4-yl)-4-methyl-5-pyridin iodide (ftmpiH) |
| 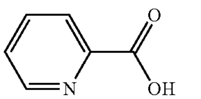 | picolinic acid (pic) |

Chemical syntheses of the ligands bppzH and mppzH are well known to one skilled in the art. They can be prepared according to Yu, Wei-Shan et al., JAGS, 125(36), 10800-10801; 2003.

Chemical syntheses of the ligands pptzH and mptzH are well known to one skilled in the art. They can be prepared according to Orselli, Enrico et al, Inorg. Chem., 46(26), 11082-11093; 2007.

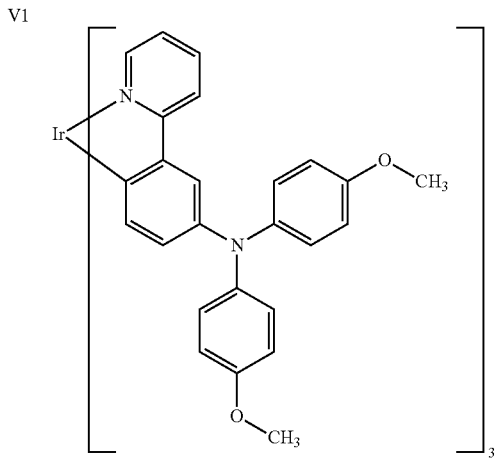

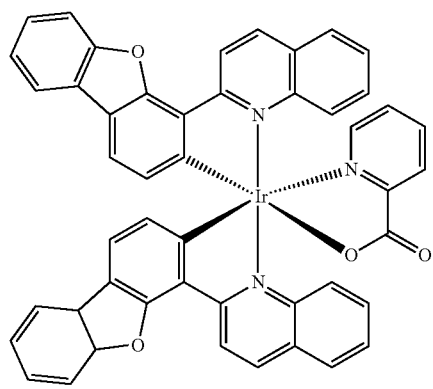

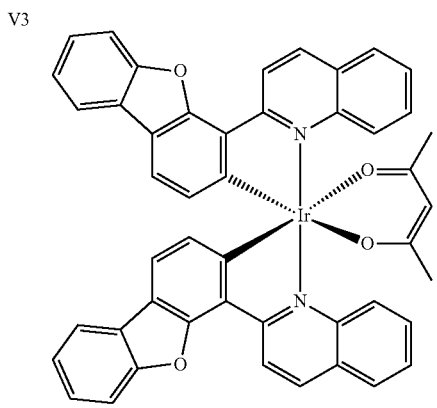

SSM-1
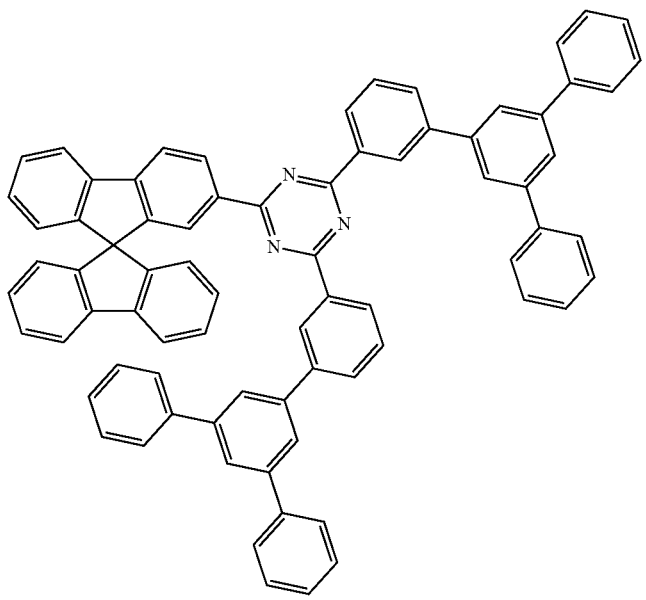
SSM-2
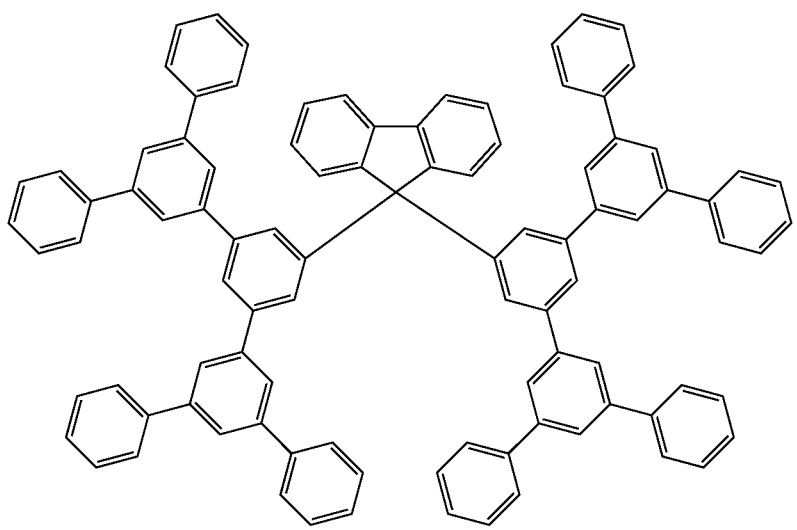
SSM-3
ET-1
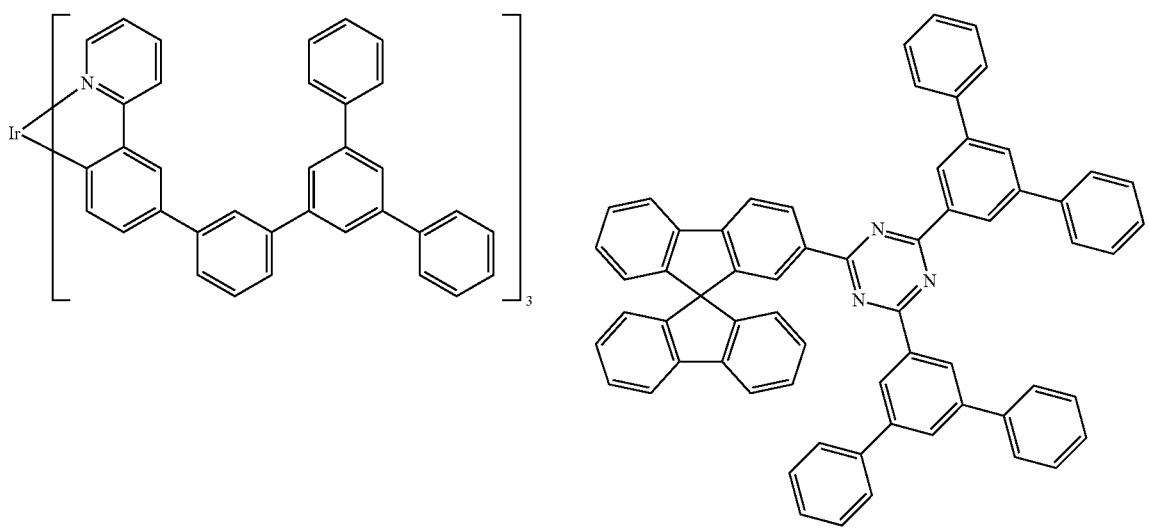

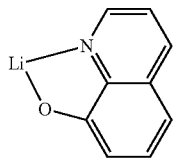

The compounds V1, V2, V4, SSM-1, SSM-2, SSM-3, ET-1 and ET-2 are well known from the prior art. As an example, the compounds V1, V2, V4, SSM-1, SSM-2, SSM-3 and ET-1 have been disclosed in WO 2005/033244, WO 2004/026886, JP 2012/77069, WO 2011/137922, WO 2012/048778, WO 2011/032626 and WO 2010/072300, respectively. Compound ET-2 can be purchased from ABCR GmbH & Co. KG, Karlsruhe. Compound V3 ([(dbfq)$_2$Ir(pic)]) is a complex showing deep red light emission. V3 can be prepared according to the procedure as outlined in Example 8, wherein pic (30 mg, 0.24 mmol) is used instead of fppzH. V4 can be obtained with 74% yield.

Example 1

Synthesis of 2-(dibenzo[b,d]furan-4-yl)quinoline (dbfqH)

To a mixture of 2-chloroisoquinoline (1.73 g, 10.5 mmol) and Pd(PPh$_3$)$_4$ (403 mg, 0.349 mmol) in 1,2-dimethoxyethane (50 mL) a solution of dibenzofuran-4-ylboronic acid (2.30 g, 10.9 mmol) in degassed ethanol (50 mL) is added, followed by addition of 2.6 M aqueous sodium carbonate solution (50 mL). Then, the mixture is heated under reflux for 19 h under inert atmosphere. After cooling, ethyl acetate (50 mL) and water (100 mL) are added, and the insoluble materials are removed by filtration. The filtrate is treated with a standard aqueous workup. The solvent is removed and the residue is purified by column chromatography to render a yellow solid.

Recrystallization from chloroform/hexane yields a white crystalline solid of the titled compound dbfqH in 84% yield (2.62 g, 8.87 mmol).

Example 2

Synthesis of ligands L1 to L44

In analogy to the preparation of (dbfqH) according to Example 1 the Suzuki coupling reaction can be used to prepare a variety of similar compounds such as compounds L1 to L44. The general preparation method is as follows: To a mixture of the halogen-compound (10.5 mmol; educt 2) and Pd(PPh$_3$)$_4$ (0.35 mmol, 1/30 eq.) in 1,2-dimethoxyethane (50 mL) a solution of boronic acid (11 mmol; educt 1) in degassed ethanol (50 mL) is added, followed by addition of 2.6 M aqueous sodium carbonate solution (50 mL). Then, the mixture is heated under reflux for 20 h under inert atmosphere. After cooling, ethyl acetate (50 mL) and water (100 mL) are added, and the insoluble materials are removed by filtration. The filtrate is treated with a standard aqueous workup. The solvent is removed and the residue is purified by column chromatography. Recrystallization from chloroform/hexane yields a white crystalline solid of the compound in about 65 to 90% yield.

The following ligands can be prepared according to the method provided herein:

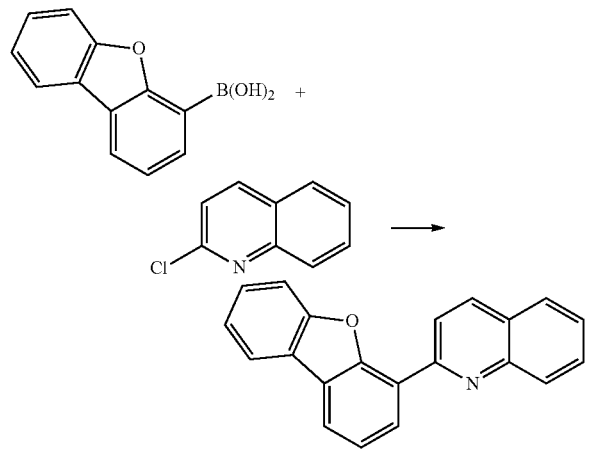

-continued
| Educt 1 | Educt 2 | Product | Yield |
|---|---|---|---|
| 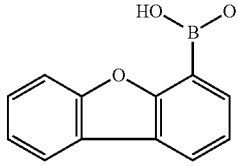<br>CAS 100124-06-9 | 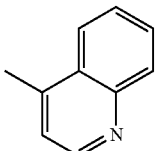<br>CAS 634-47-9 | 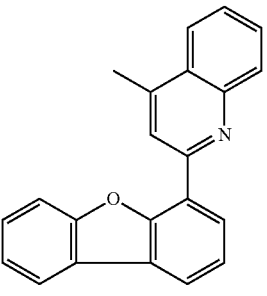<br>L2 | 78% |
| 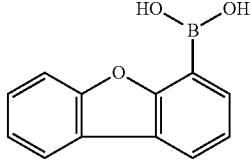<br>CAS 100124-06-9 | 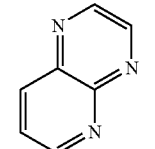<br>CAS 68236-03-3 | 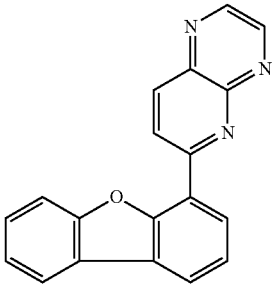<br>L3 | 81% |
| 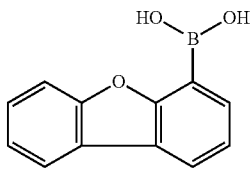<br>CAS 100124-06-9 | 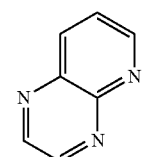<br>CAS 68236-03-3 | 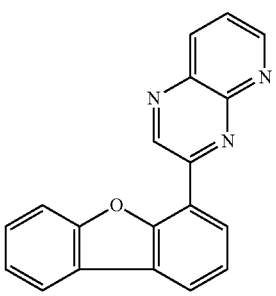<br>L4 | 73% |
| 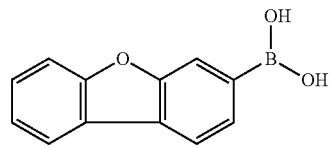<br>CAS 395087-89-5 | 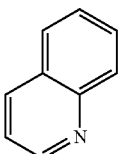<br>CAS 612-62-4 | 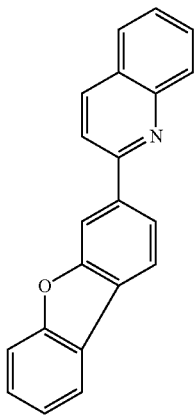<br>L5 | 69% |

-continued
| Educt 1 | Educt 2 | Product | Yield |
|---|---|---|---|
| 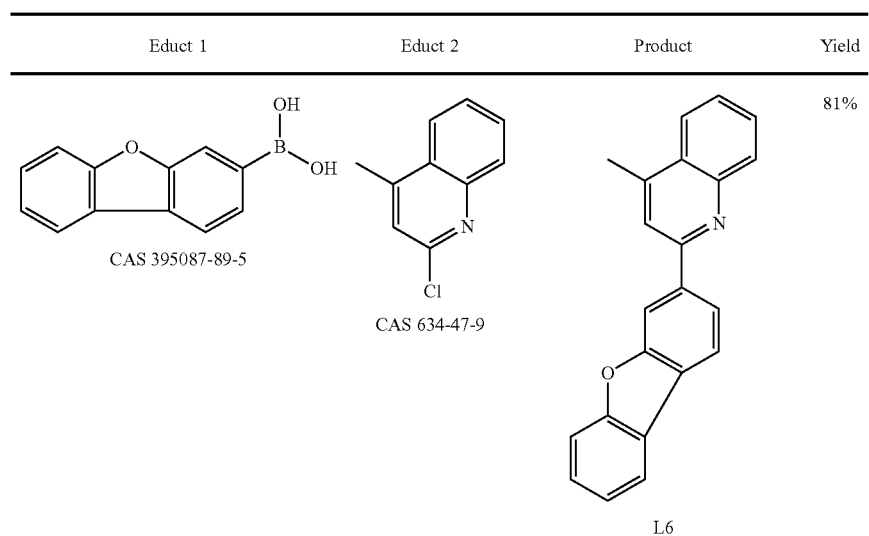 | | | 81% |
| 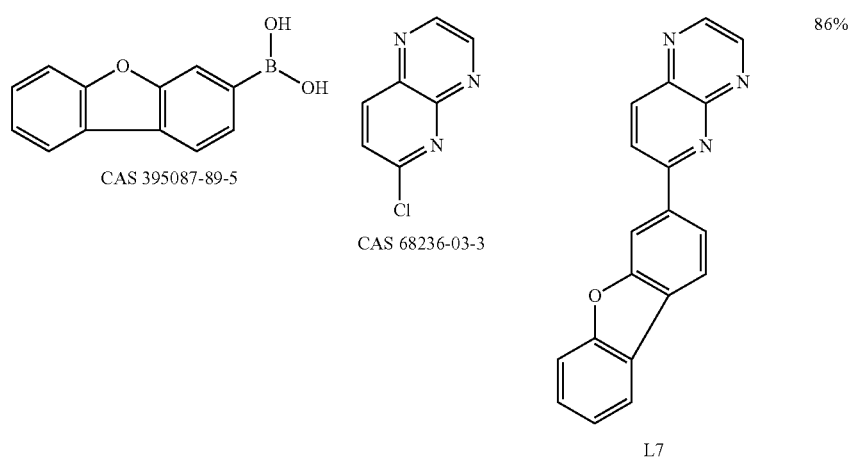 | | | 86% |
|  | | | 74% |

-continued
| Educt 1 | Educt 2 | Product | Yield |
|---|---|---|---|
| 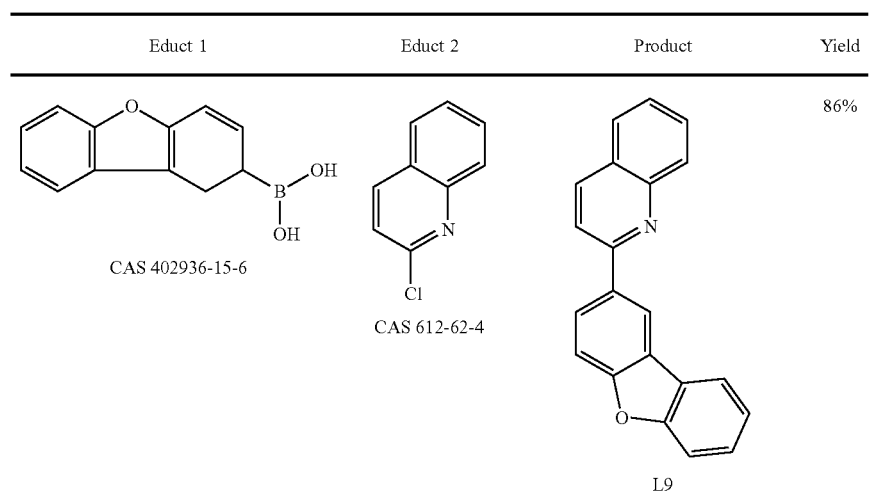 | | | |
L9 — 86%
L10 — 71%
L11 — 83%
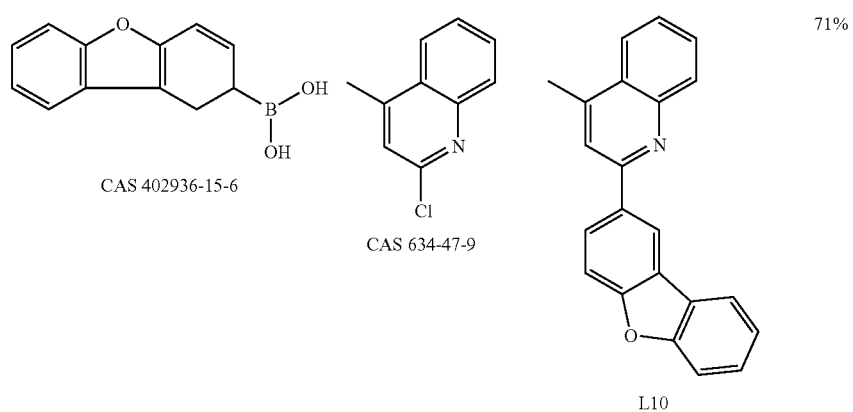
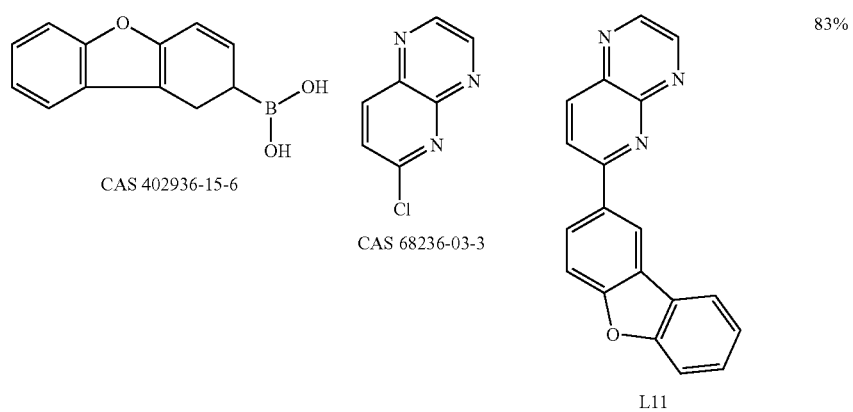

| Educt 1 | Educt 2 | Product | Yield |
|---|---|---|---|
| 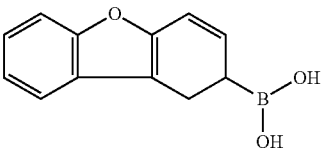 CAS 402936-15-6 | 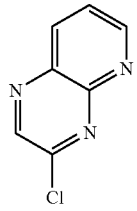 CAS 68236-03-3 | 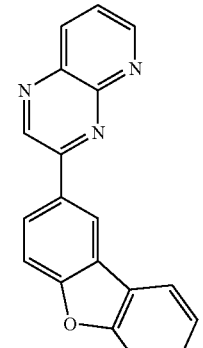 L12 | 82% |
| 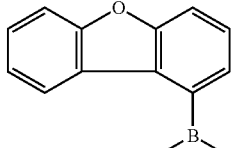 CAS 162607-19-4 | 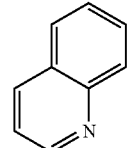 CAS 612-62-4 | 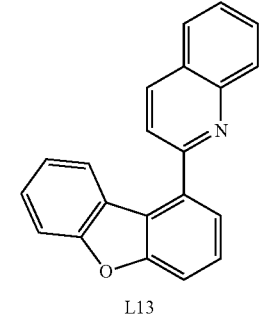 L13 | 78% |
| 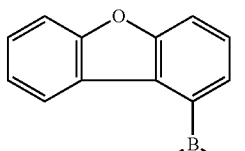 CAS 162607-19-4 | 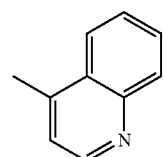 CAS 634-47-9 | 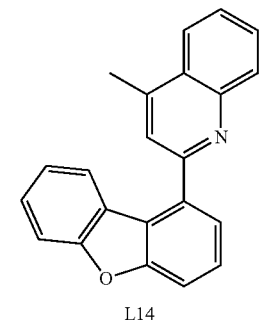 L14 | 79% |
| 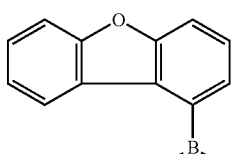 CAS 162607-19-4 | 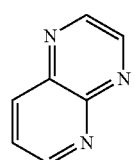 CAS 68236-03-3 | 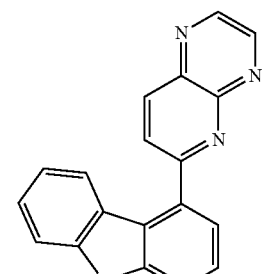 L15 | 85% |

| Educt 1 | Educt 2 | Product | Yield |
|---|---|---|---|
| 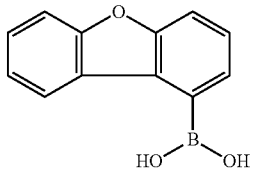<br>CAS 162607-19-4 | 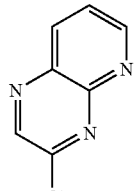<br>CAS 68236-03-3 | 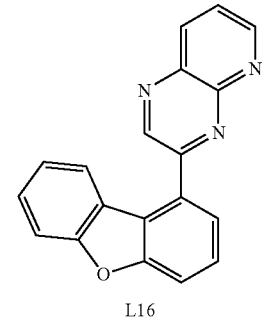 [SMILES: c1cnc2nc(-c3cccc4oc5ccccc5c34)cnc2c1]<br>L16 | 89% |
| 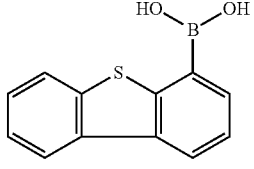<br>CAS 108847-20-7 | 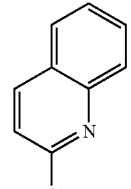<br>CAS 612-62-4 | 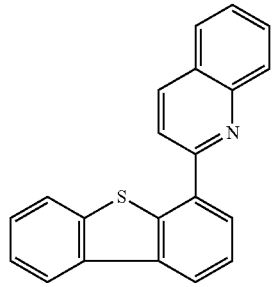<br>L17 | 76% |
| 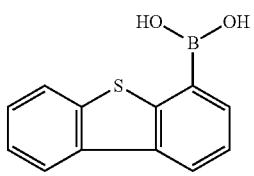<br>CAS 108847-20-7 | 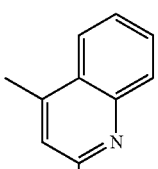<br>CAS 634-47-9 | 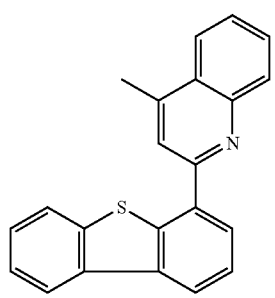<br>L18 | 90% |
| 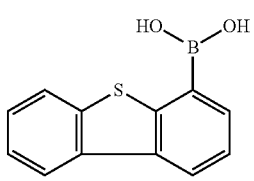<br>CAS 108847-20-7 | 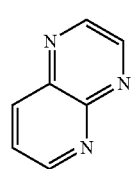<br>CAS 68236-03-3 | 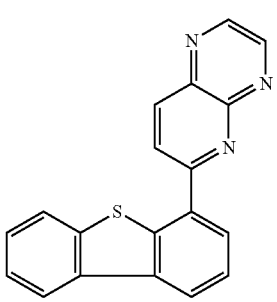<br>L19 | 95% |

-continued
| Educt 1 | Educt 2 | Product | Yield |
|---|---|---|---|
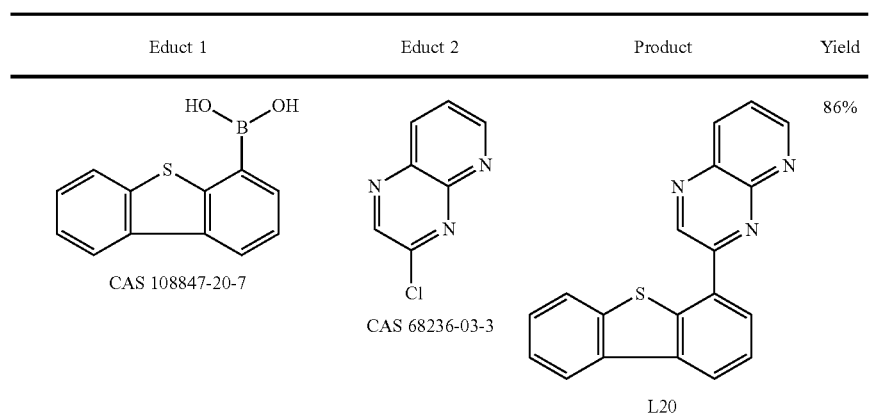
86%
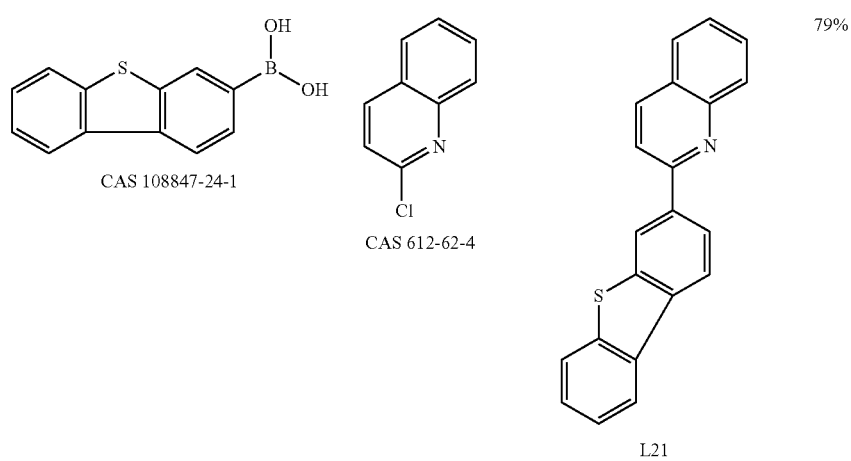
79%
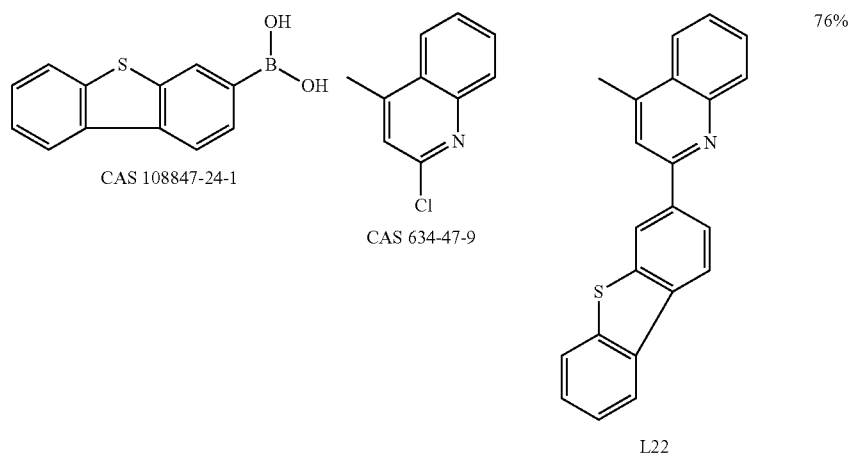
76%

-continued
| Educt 1 | Educt 2 | Product | Yield |
|---|---|---|---|
| 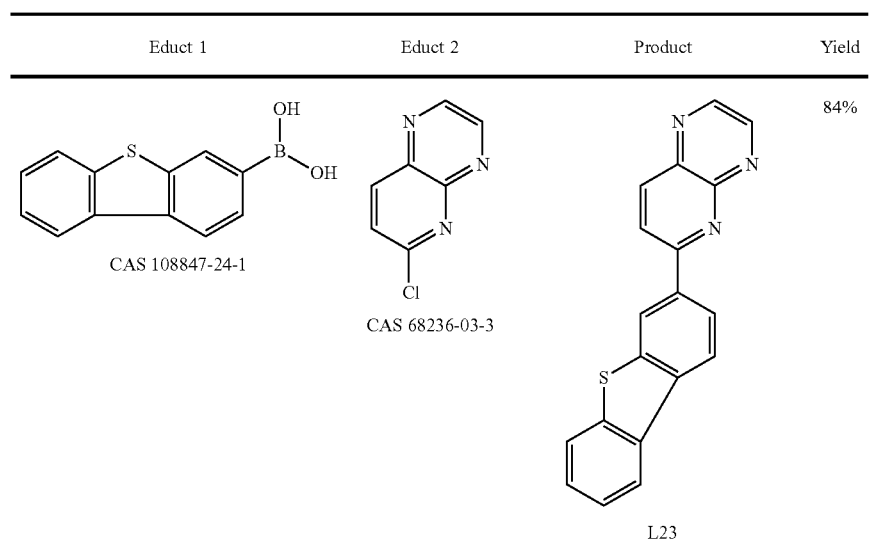 | | | 84% |
L23
| 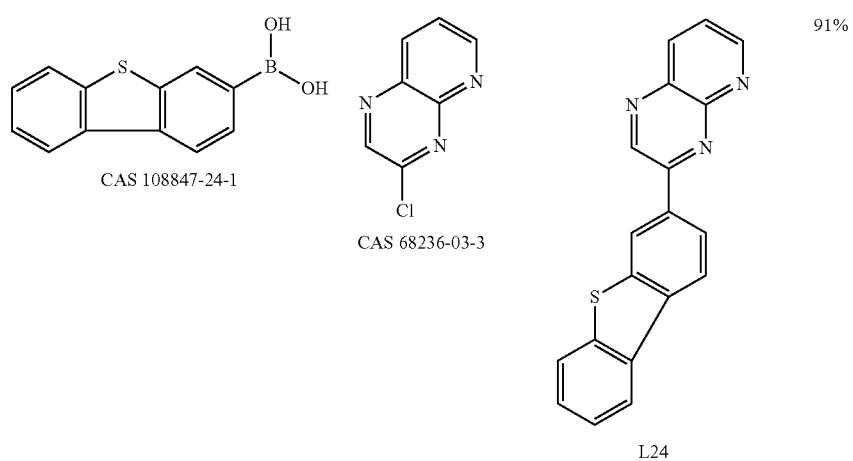 | | | 91% |
L24
| 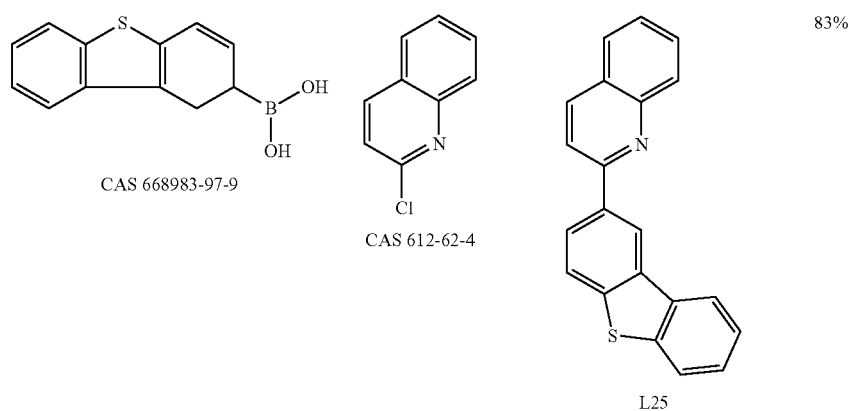 | | | 83% |
L25

| Educt 1 | Educt 2 | Product | Yield |
|---|---|---|---|
| CAS 668983-97-9 | CAS 634-47-9 | L26 | 77% |
| CAS 668983-97-9 | CAS 68236-03-3 | L27 | 76% |
| CAS 668983-97-9 | CAS 68236-03-3 | L28 | 85% |
| CAS 1245943-60-5 | CAS 612-62-4 | L29 | 71% |

-continued
| Educt 1 | Educt 2 | Product | Yield |
|---|---|---|---|
| 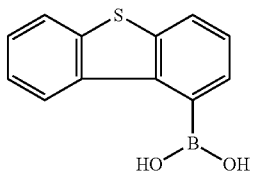 CAS 1245943-60-5 | 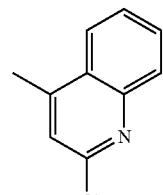 CAS 634-47-9 | 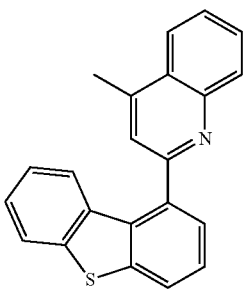 L30 | 80% |
| 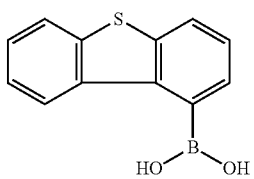 CAS 1245943-60-5 | 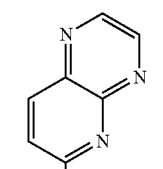 CAS 68236-03-3 | 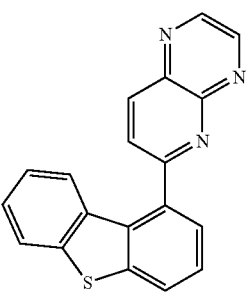 L31 | 83% |
| 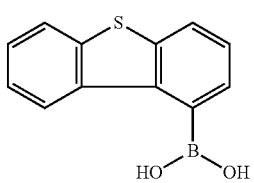 CAS 1245943-60-5 | 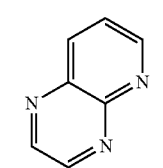 CAS 68236-03-3 | 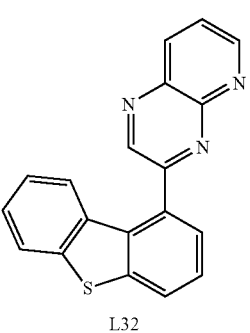 L32 | 78% |
| 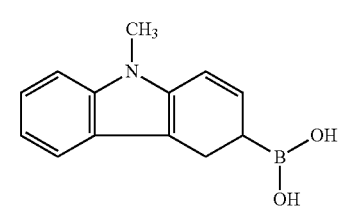 CAS 1039761-02-8 | 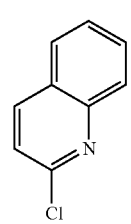 CAS 612-62-4 | 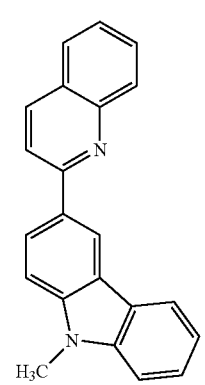 L33 | 72% |

-continued

| Educt 1 | Educt 2 | Product | Yield |
|---|---|---|---|
| CAS 1039761-02-8 | CAS 634-47-9 | L34 | 86% |
| CAS 1039761-02-8 | CAS 68236-03-3 | L35 | 81% |
| CAS 1039761-02-8 | CAS 68236-03-3 | L36 | 83% |

-continued
| Educt 1 | Educt 2 | Product | Yield |
|---|---|---|---|
| 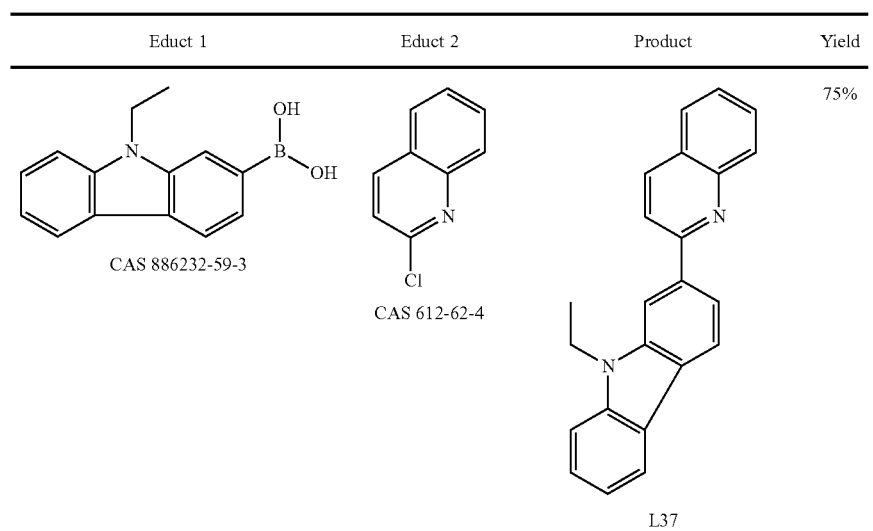 | | | |
L37 — 75%
L38 — 92%
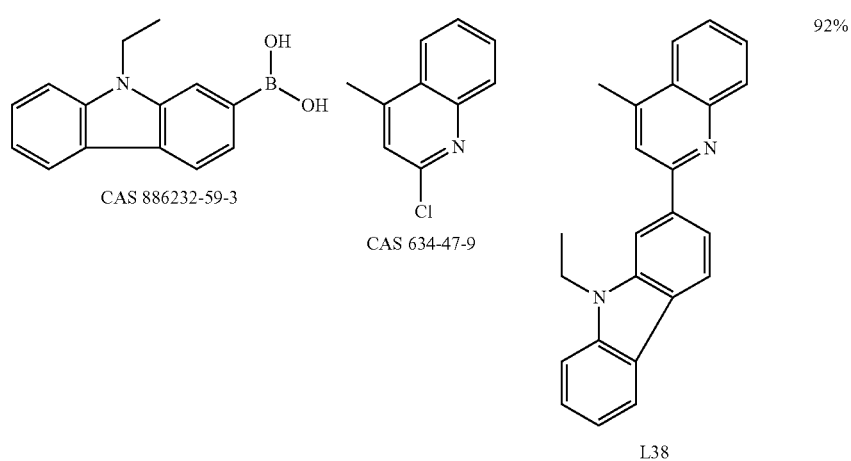
L39 — 77%
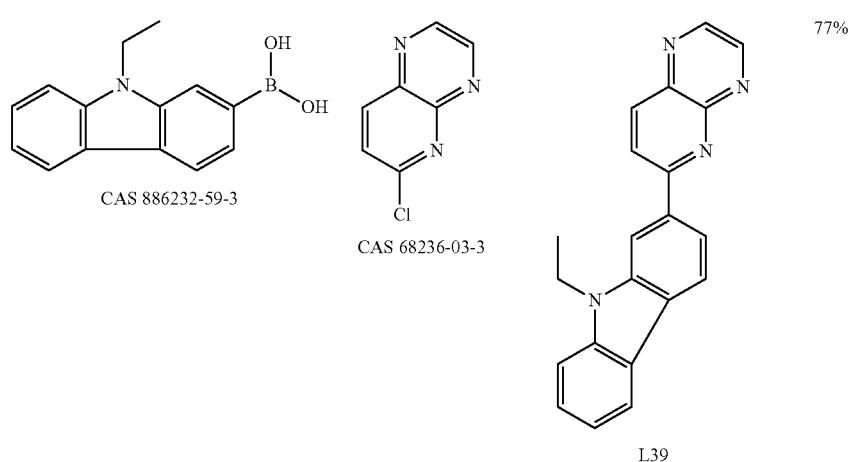

-continued
| Educt 1 | Educt 2 | Product | Yield |
|---|---|---|---|
| 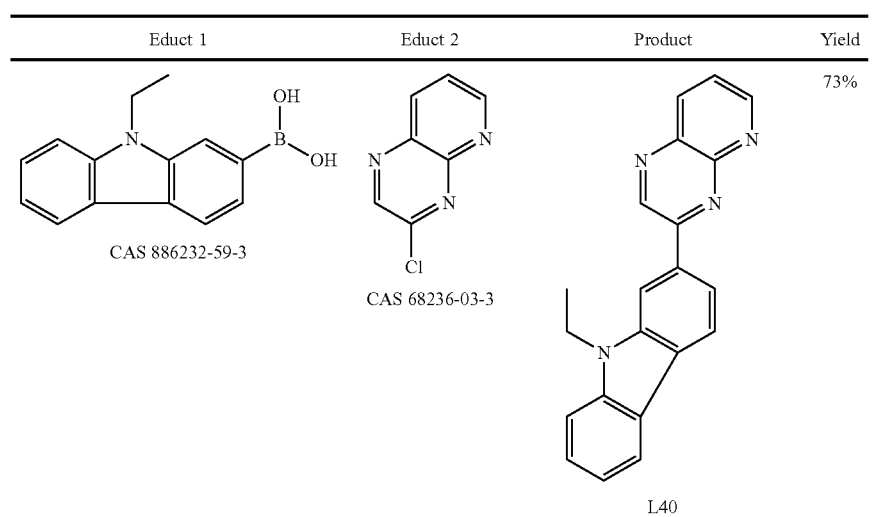 | | | 73% |
| 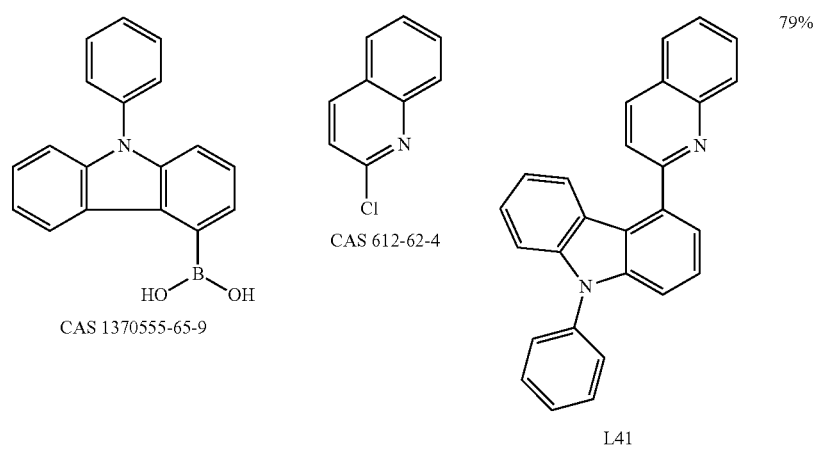 | | | 79% |
| 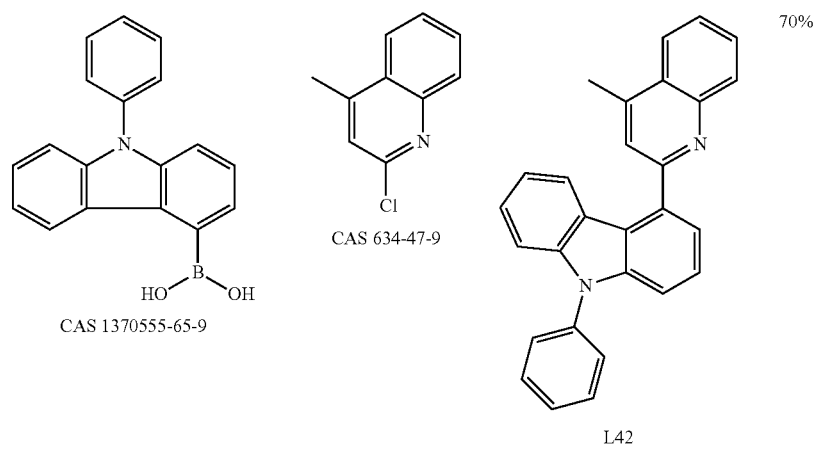 | | | 70% |

| Educt 1 | Educt 2 | Product | Yield |
|---|---|---|---|
| CAS 1370555-65-9 | CAS 68236-03-3 | L43 | 91% |
| CAS 1370555-65-9 | CAS 68236-03-3 | L44 | 85% |
Example 3
Synthesis of 2-(3-(trifluoromethyl)-1H-pyrazol-5-yl)pyridine (fppzH) and 2(3-(perfluorobutyl)-1H-pyrazol-5-yl)pyridine (hppzH)
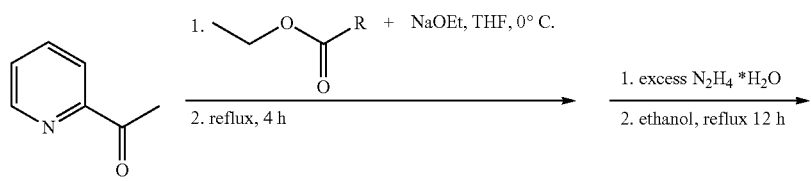
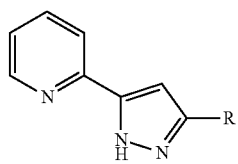
R = CF$_3$, fppzH
R = C$_4$F$_9$, hppzH Concentrations used in the reaction are provided for both fppzH and hppzH in the following description.

NaOEt (in case of fppzH: 1.82 g, 26.8 mmol; in case of hppzH: 1.23 g, 18.0 mmol) is dispersed in 50 mL of dry tetrahydrofuran (THF). To this solution either ethyl trifluoroacetate (3.2 mL, 26.8 mmol) for fppzH or nonafluoropentanoic acid ethyl ester (3.0 ml, 15.1 mmol) for hppzH is added slowly at 0° C. The mixture is stirred for 2 h followed by the addition of 2-acetylpyridine (in case of fppzH: 2.0 mL, 17.9 mmol; in case of hppzH: 1.87 mL, 16.7 mmol) at 0° C. The reaction is then heated to 50° C. for 4 h. Removal of the solvent renders a brown oily residue, which is dispersed in de-ionized water (50 mL). The mixture is neutralized with 2 N $HCl_{(aq)}$ (pH=4), followed by extraction with ethyl acetate (3×50 mL). The combined organic residue is dried over anhydrous $Na_2SO_4$. After filtration, a brown oil, the diketone, is obtained which is used without further purification. It is dissolved in 50 mL EtOH and treated with hydrazine monohydrate (in case of fppzH: 10 eq; in case of hppzH: 5 eq). The mixture is refluxed for 12 h. After cooling to room temperature, evaporation of the solvent at reduced pressure renders a brown residue, which is then dissolved in ethyl acetate. The organic phase is washed with water (20 mL×3), dried over $Na_2SO_4$, and then filtered. Removal of ethyl acetate gives a pale-yellow solid. Finally the solid is recrystallized from $CH_2Cl_2$/hexane. Compound fppzH is obtained with 62% yield (2.4 g, 11 mmol). Compound hppzH is obtained in 68% yield (3.7 g, 10.2 mmol).

Example 4

Synthesis of 2-(3-(trifluoromethyl)-1H-1,2,4-triazol-5-yl)pyridine (fptzH) and 2-(3-(perfluorobutyl)-1H-1,2,4-triazol-5-yl)pyridine (hptzH)

A mixture of 2-cyanopyridine (3.15 g, 30.3 mmol) and $NaOCH_3$ (0.16 g, 3 mmol) is prepared in 10 mL ethanol and stirred at RT for 4 h under inert atmosphere. After 4 h, $NH_4Cl$ (1.81 g, 33.8 mmol) is added to the solution. The mixture is refluxed for 6 hours, cooled down and filtered to remove excess salt. Ethanol is removed and a white solid of 2-pyridinecarboximidamidehydro-chloride (3.99 g, 25.2 mmol) is obtained.

In case of fptzH:

A solution of ethyl trifluoroacetate (3.52 g, 24.77 mmol) and hydrazine monohydrate (1.14 mL, 23.50 mmol) in 50 mL THF is refluxed for 1 h. Upon cooling to room temperature, 2-pyridinecarboximidamidehydro-chloride (3.99 g, 25.32 mmol) and NaOH (1.01 g, 25.32 mmol) are added to the solution. The mixture is refluxed for 6 h and cooled to room temperature. Afterwards a white solid is obtained by extraction with ethyl acetate. The product is purified via column chromatography and obtained with 56% yield (2.82 g, 13.16 mmol).

In case of hptzH:

A solution of nonafluoropentanoic acid ethyl ester (4.35 g, 14.9 mmol) and hydrazine monohydrate (0.73 mL, 15.8 mmol) in 50 mL THF is refluxed for 1 h. Upon cooling to room temperature, 2-pyridinecarboximidamide hydrochloride (2.49 g, 15.7 mmol) and NaOH (0.63 g, 15.8 mmol) are added to the solution. The mixture is refluxed for 6 h and cooled to room temperature. After the reaction is finished, a white solid is obtained by ethyl acetate extraction. The product is purified via column chromatography and is obtained in 62% yield (3.36 g, 9.23 mmol).

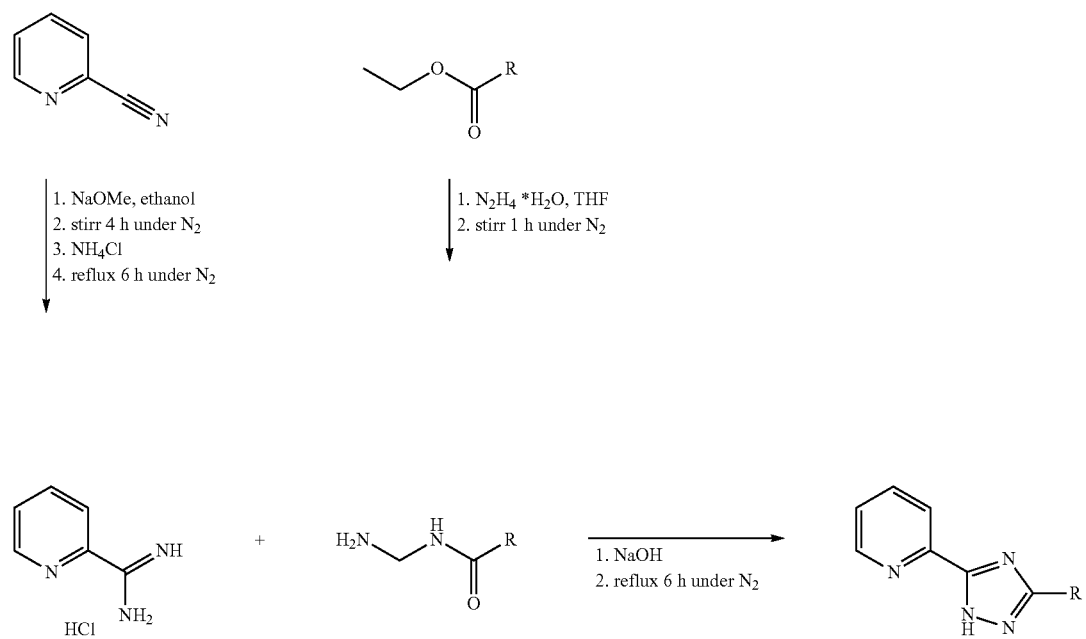

R = $CF_3$, fptzH
R = $C_4F_7$, hptzH

Example 5

Synthesis of 2-(3-(tert-butyl)-1H-1,2,4-triazol-5-yl)pyridine (tptzH)

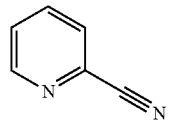

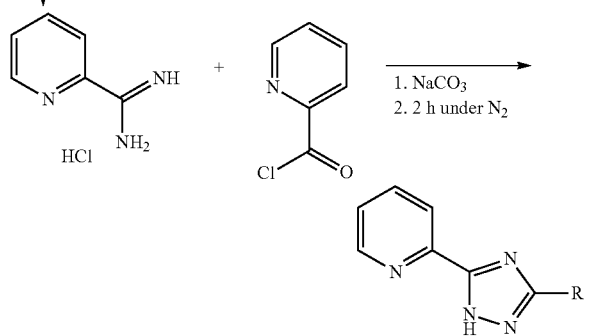

A mixture of 2-cyanopyridine (3.15 g, 30.3 mmol) and NaOCH₃ (0.16 g, 3 mmol) is prepared in 10 mL ethanol and stirred at RT for 4 h under inert atmosphere. After 4 h, NH₄Cl (1.81 g, 33.8 mmol) is added to the solution. The mixture is refluxed for 6 h, cooled down and filtered to remove excess salt. Ethanol is removed and a white solid of 2-pyridinecarboximidamidehydro-chloride (3.99 g, 25.2 mmol) is obtained.

A solution of pivalic acid chloride (3.54 g, 29.3 mmol) in 10 mL CH₂Cl₂ is added drop wise to 2-pyridinecarboximidamidehydrochloride (4 g, 29.3 mmol) and Na₂CO₃ (3.1 g, 29.3 mmol) in 100 mL H₂O. The reaction mixture is stirred at RT for 2 h, yielding a white precipitate. The precipitate is filtered, and the solid washed with water and ethanol. The solid then is suspended in 5 mL of ethylene glycol and heated to 200° C. for 2 h, yielding a pale yellow solution. Upon cooling to room temperature, a white solid is formed, filtered of and washed with de-ionized water. The solid is dried under vacuum and used without further purification (3.2 g, 15.8 mmol, 53.8%).

Example 6

Synthesis of 2-(3-trifluoromethyl)-1H-[1,2,4]triazol-4-yl)-4-methyl-5-pyridin iodide (ftmpiH)

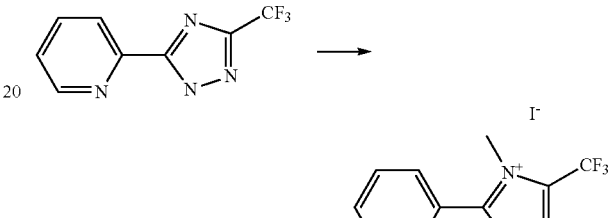

A mixture of ftptz (500 mg, 3.12 mmol) and methyl iodide (1 ml, 2.27 g, 16 mmol) is refluxed for 8 h, then anhydrous diethylether (100 ml) is added and the precipitate is filtered off. Recrystallisation from acetone renders a colorless product (424 mg, 1.40 mmol, 45% yield).

Example 7

Synthesis of (dbfq)₂Ir(μ-Cl)₂Ir(dbfq)₂ (I)

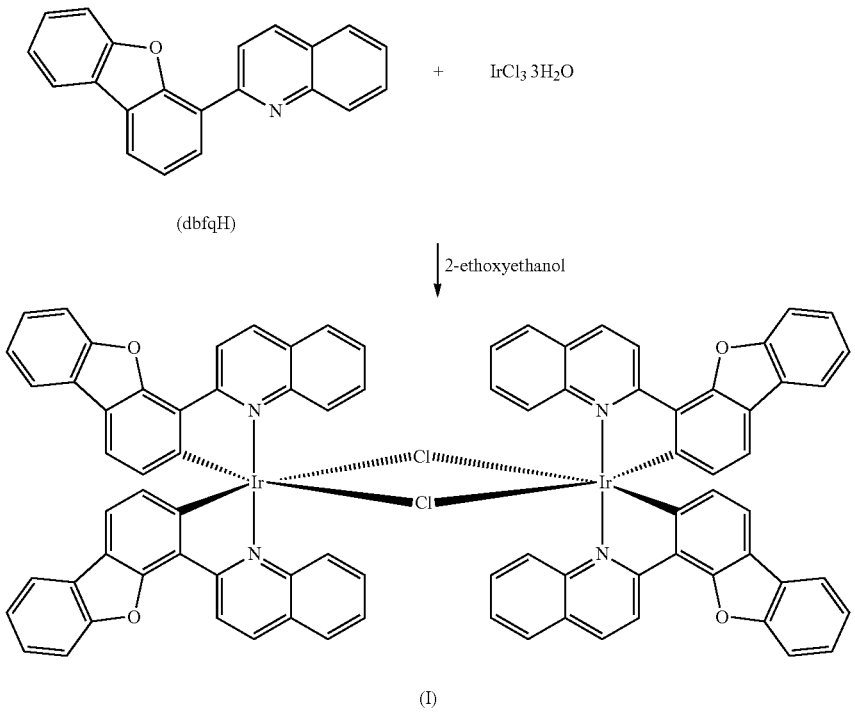

A solution of dbfq-H (0.34 g, 1.15 mmol) and IrCl$_3$·3H$_2$O (205 mg, 0.585 mmol) in 2-ethoxyethanol (15 mL) is refluxed for 24 h. After cooling, water (50 mL) is added and the precipitate is collected by filtration. The solid is washed with ethanol (20 mL) and hexane (20 mL) to obtain the titled compound (I) as a red powder (0.36 g, 0.23 mmol, 78% yield). This material is used without further purification.

Example 8

Synthesis of further chloro-gridged dimers

In analogy to the preparation of (dbfq)$_2$Ir(μ-Cl)$_2$Ir(dbfq)$_2$ (I) according to Example 7 further dimers can be produced. The general preparation method is as follows:

A solution of ligand (1 mmol) and IrCl$_3$·3H$_2$O (180 mg, 0.513 mmol) in 2-ethoxyethanol (15 mL) is refluxed for 24 h. After cooling, water (50 mL) is added and the precipitate is collected by filtration. The solid is washed with ethanol (20 mL) and hexane (20 mL) to obtain the chloro-bridged dimer as a powder. This material is used without further purification.

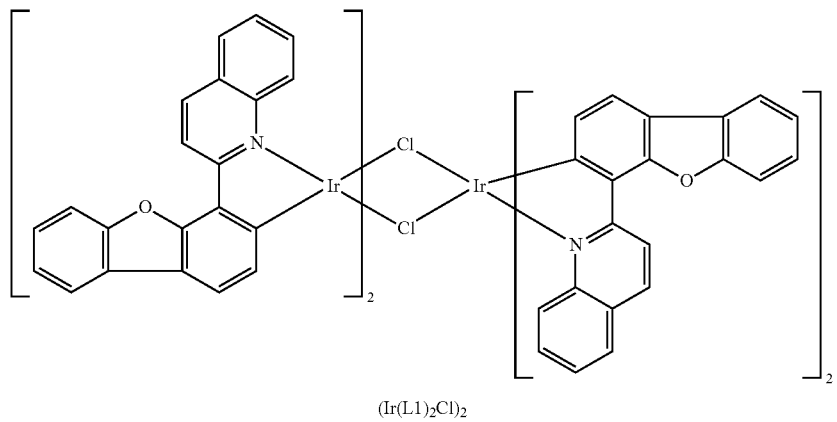

(Ir(L1)$_2$Cl)$_2$

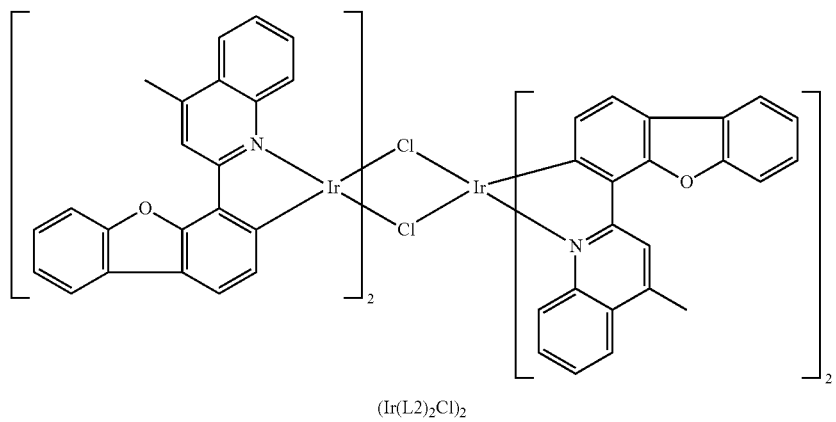

(Ir(L2)$_2$Cl)$_2$

-continued
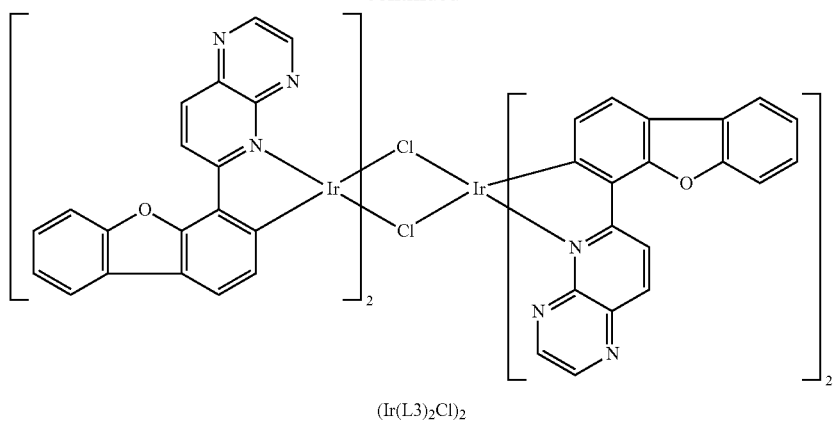
(Ir(L3)₂Cl)₂
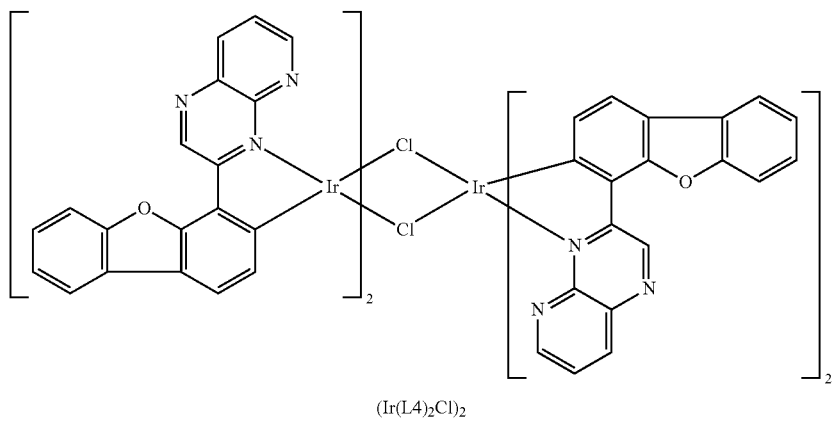
(Ir(L4)₂Cl)₂
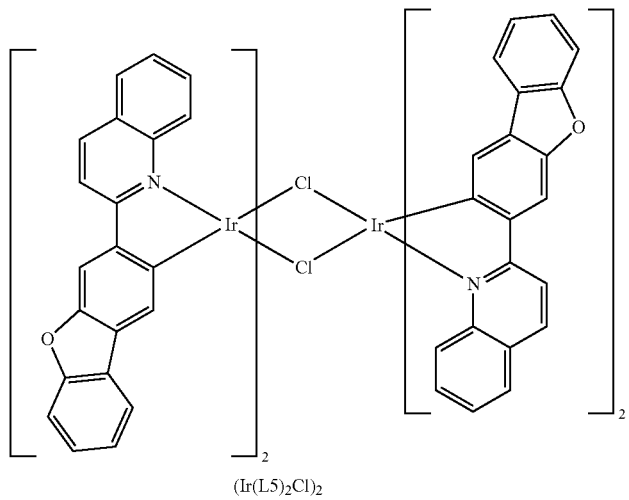
(Ir(L5)₂Cl)₂

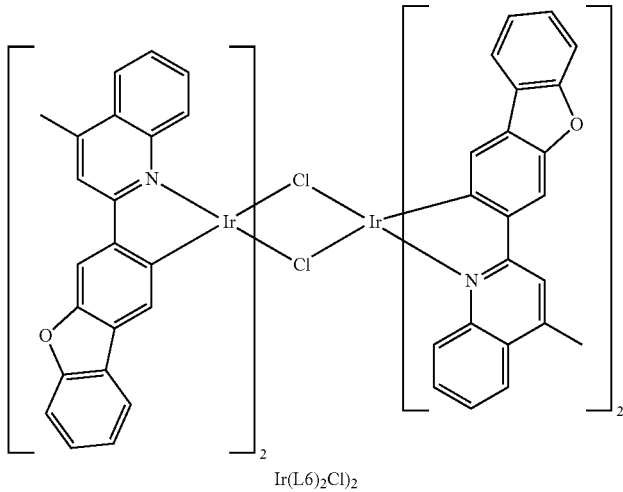
Ir(L6)₂Cl₂
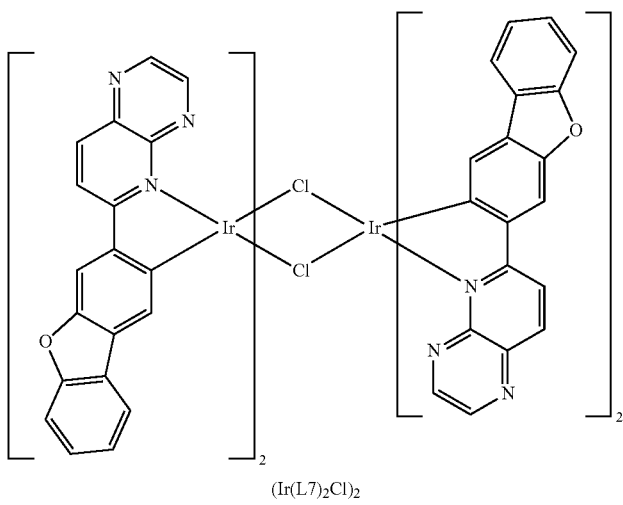
(Ir(L7)₂Cl₂
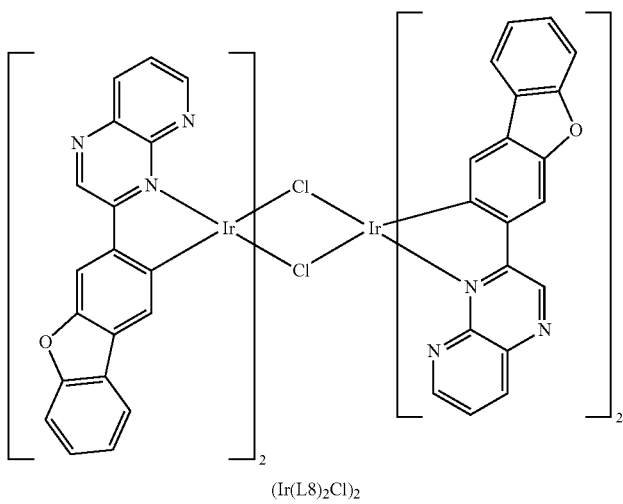
(Ir(L8)₂Cl₂

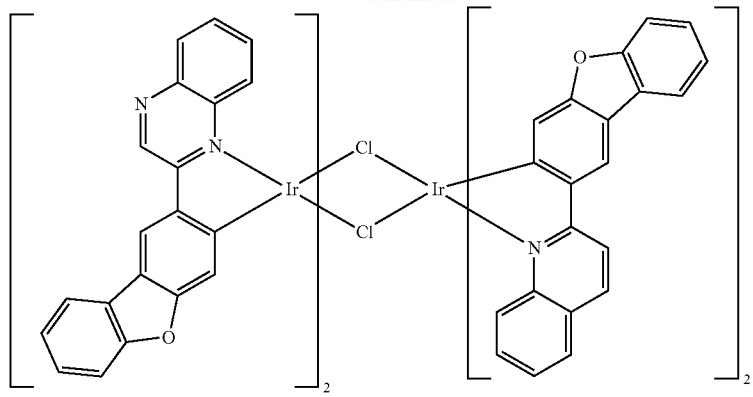
(Ir(L9)₂Cl)₂
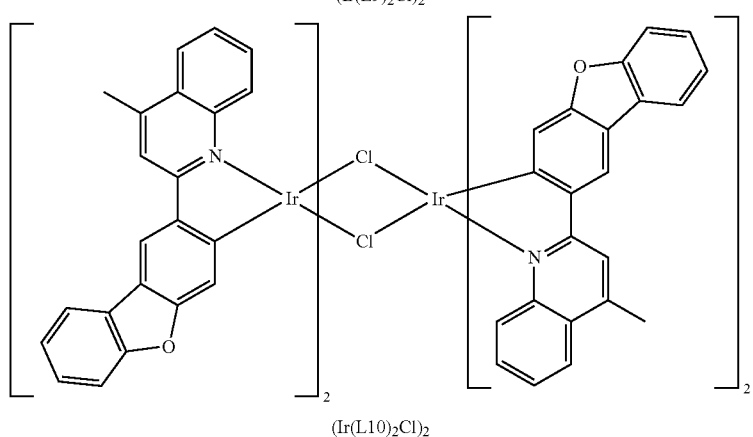
(Ir(L10)₂Cl)₂
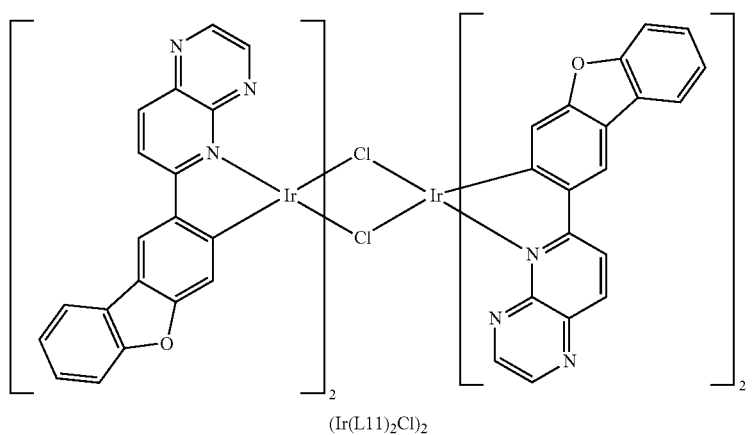
(Ir(L11)₂Cl)₂
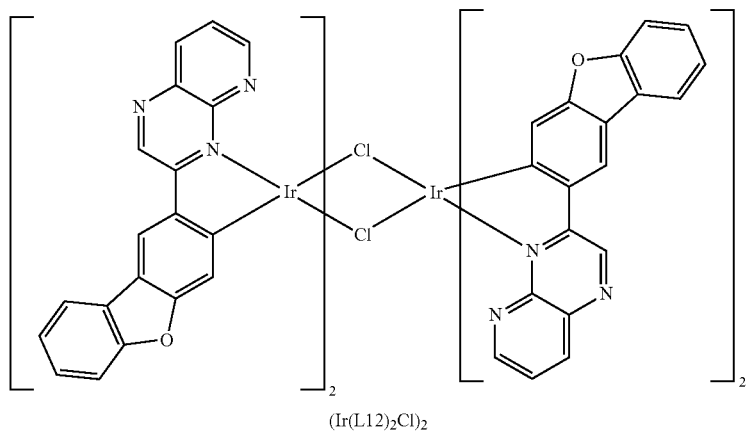
(Ir(L12)₂Cl)₂

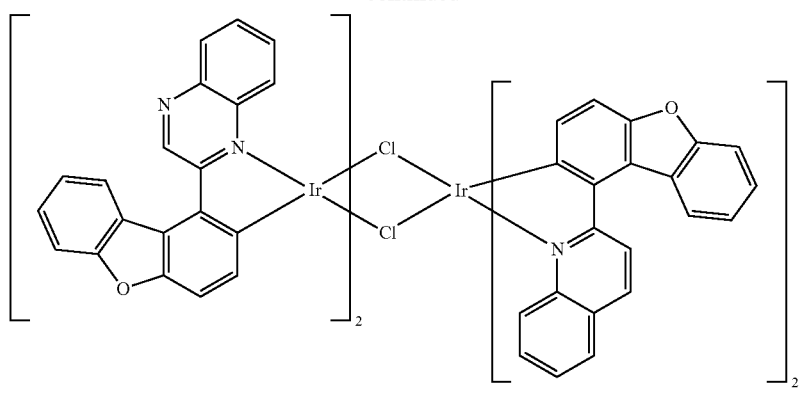
(Ir(L13)₂Cl)₂
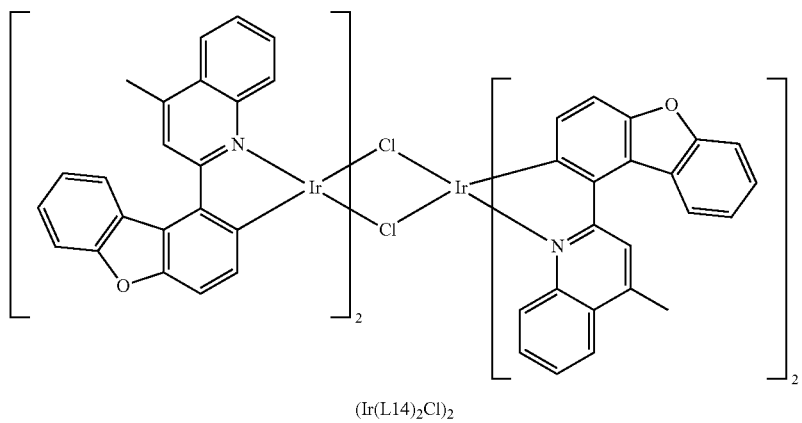
(Ir(L14)₂Cl)₂
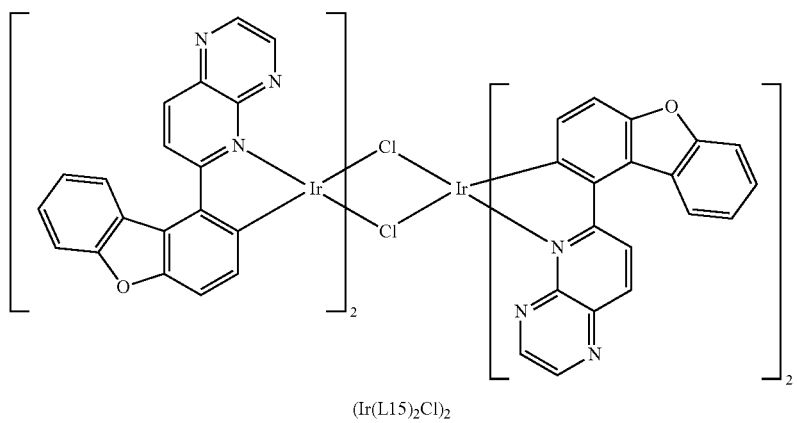
(Ir(L15)₂Cl)₂
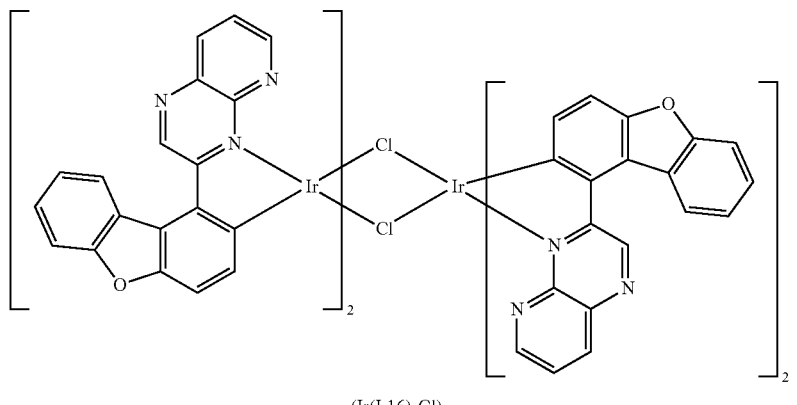
(Ir(L16)₂Cl)₂

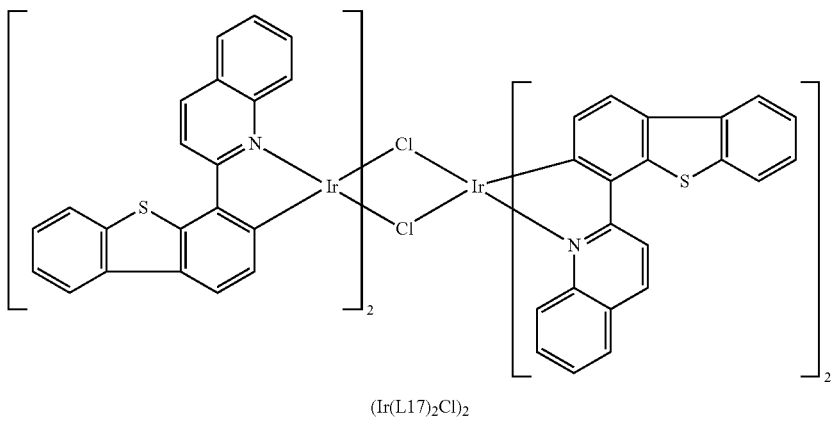
(Ir(L17)₂Cl)₂
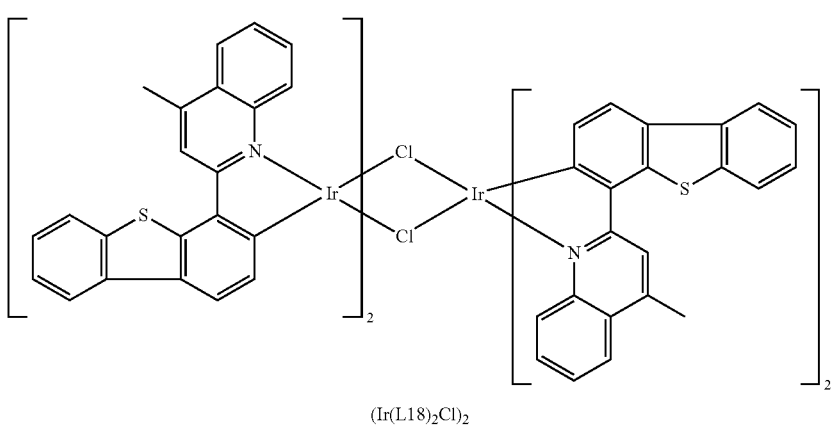
(Ir(L18)₂Cl)₂
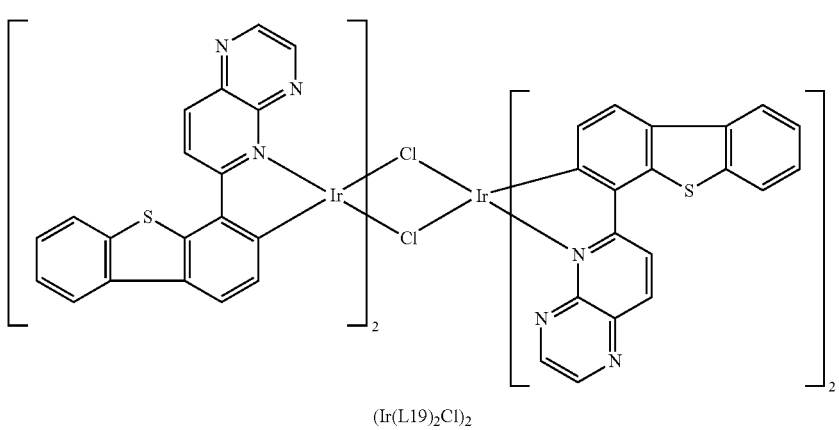
(Ir(L19)₂Cl)₂
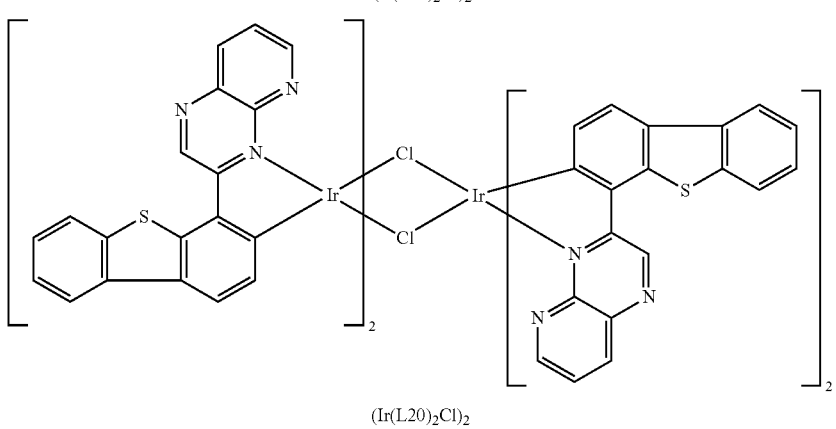
(Ir(L20)₂Cl)₂

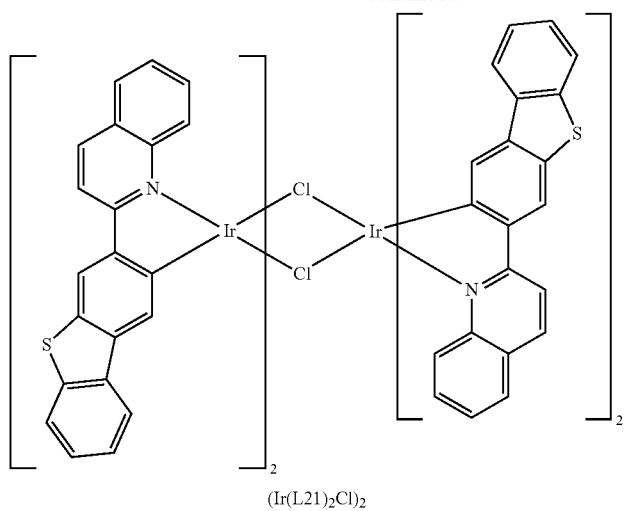
(Ir(L21)₂Cl)₂
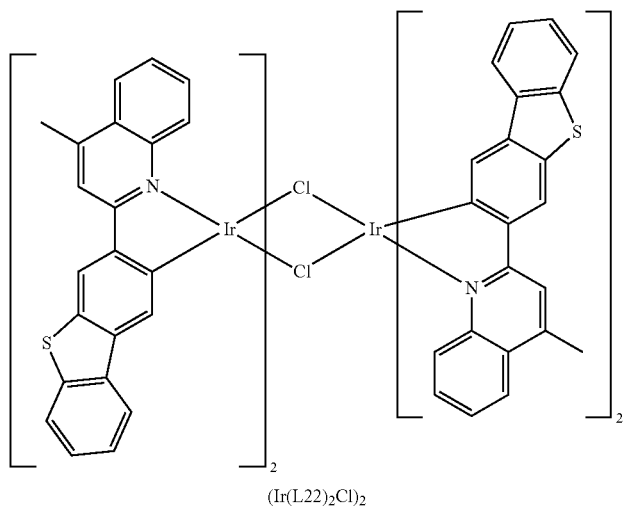
(Ir(L22)₂Cl)₂
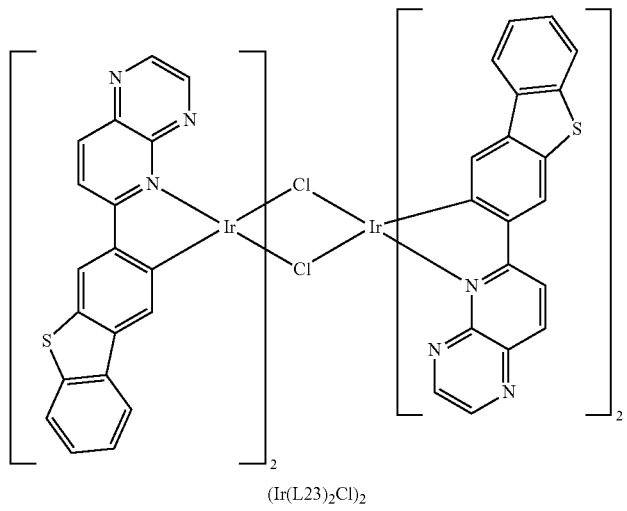
(Ir(L23)₂Cl)₂

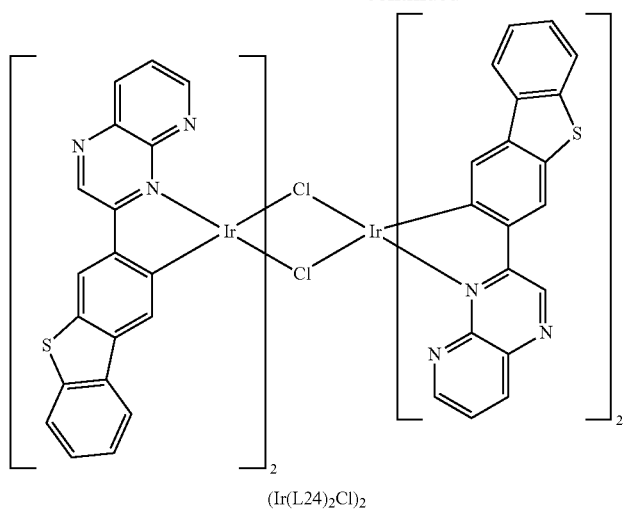
(Ir(L24)₂Cl)₂
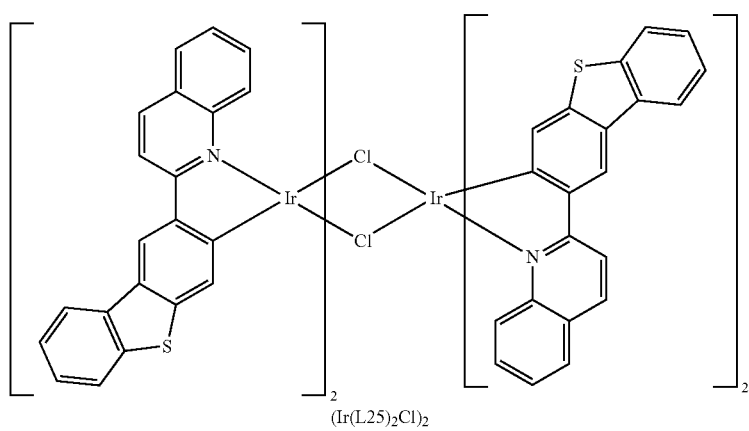
(Ir(L25)₂Cl)₂
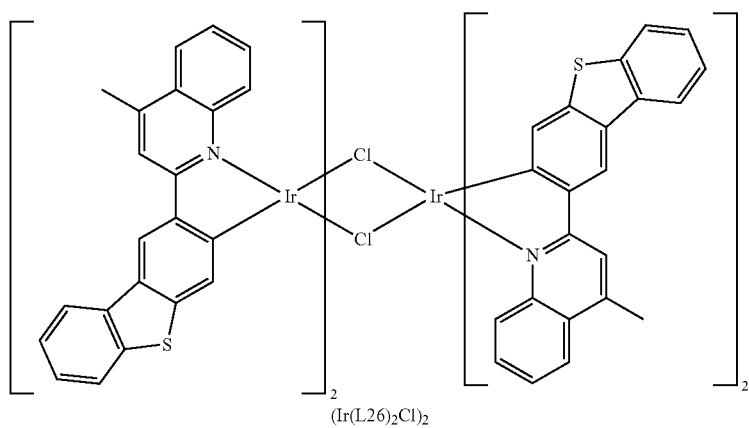
(Ir(L26)₂Cl)₂

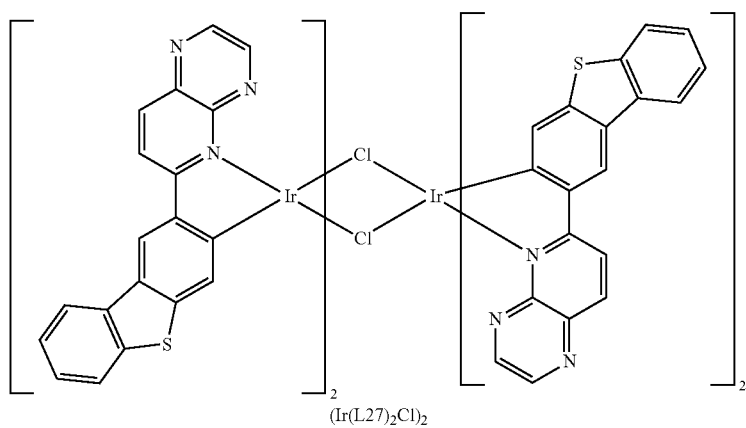
(Ir(L27)₂Cl)₂
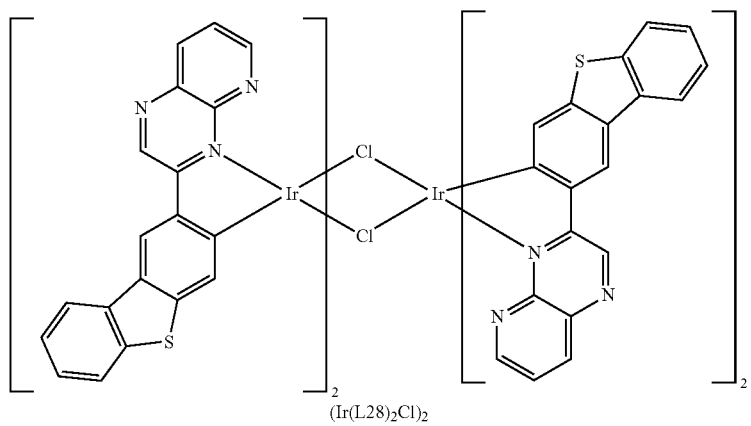
(Ir(L28)₂Cl)₂
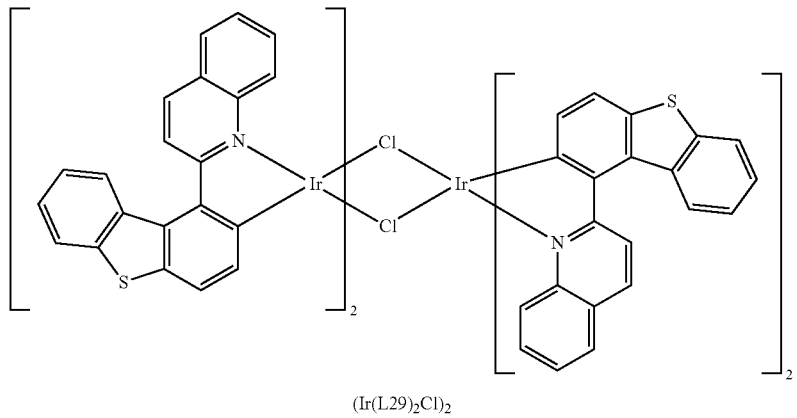
(Ir(L29)₂Cl)₂
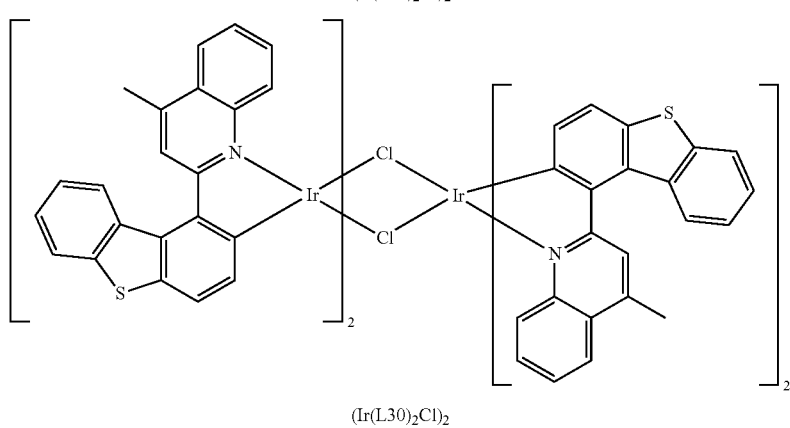
(Ir(L30)₂Cl)₂

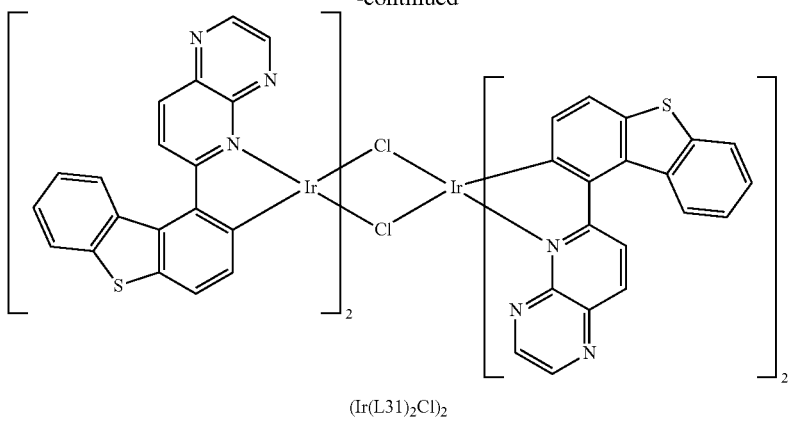
(Ir(L31)₂Cl)₂
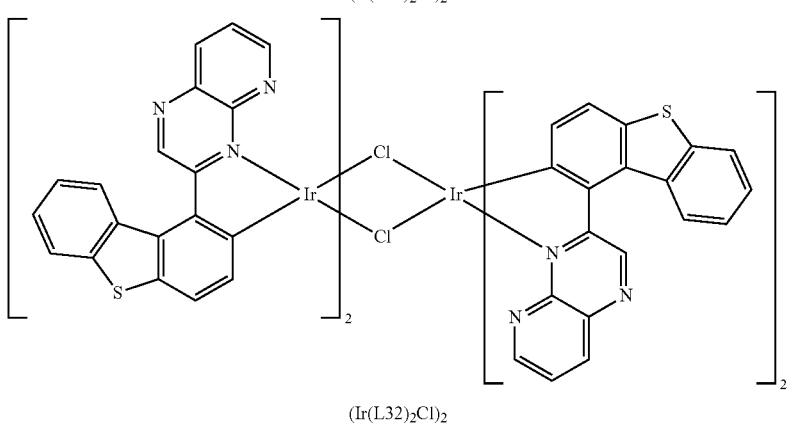
(Ir(L32)₂Cl)₂
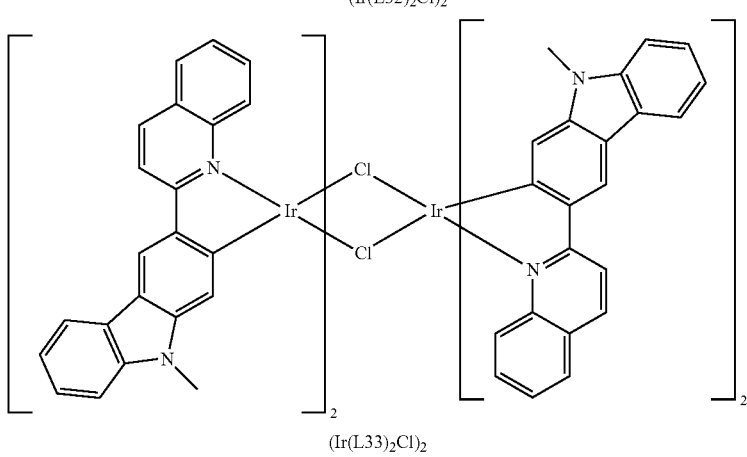
(Ir(L33)₂Cl)₂
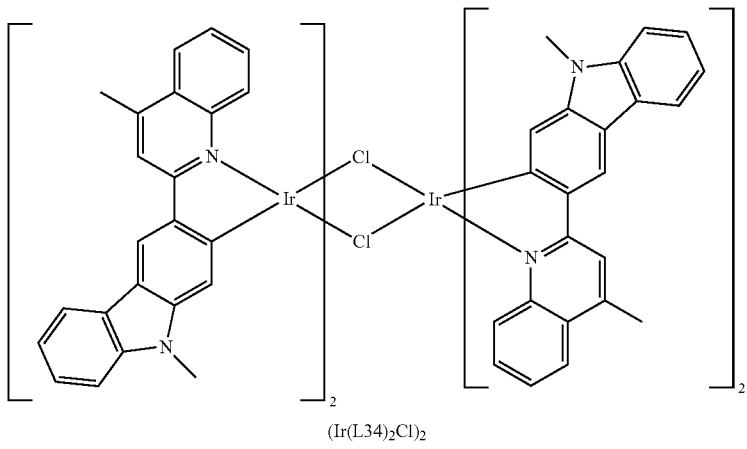
(Ir(L34)₂Cl)₂

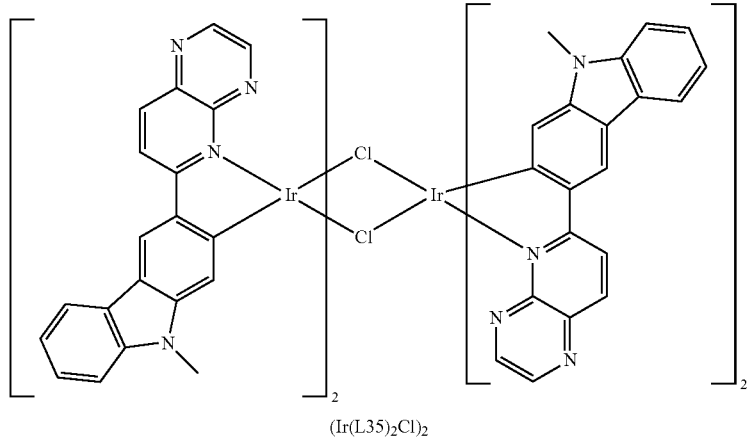
(Ir(L35)₂Cl)₂
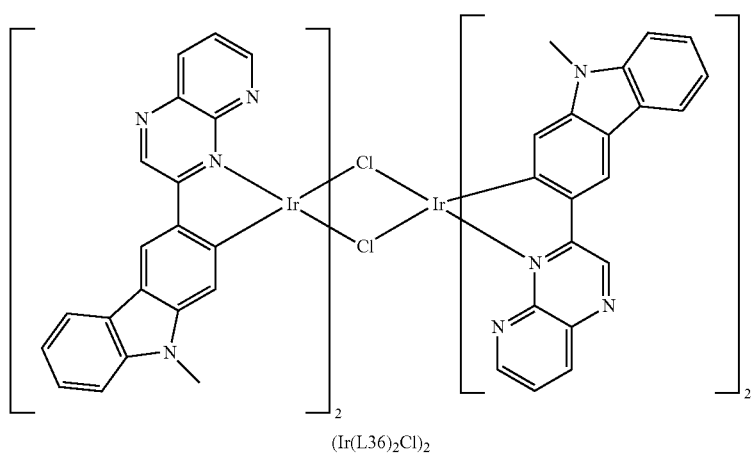
(Ir(L36)₂Cl)₂
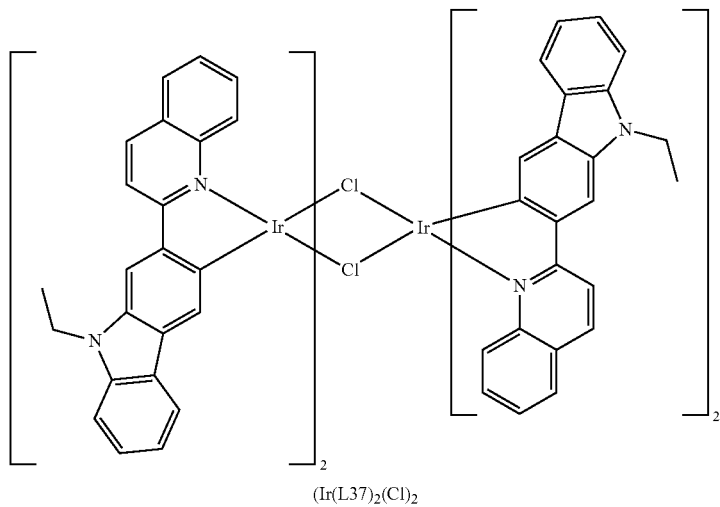
(Ir(L37)₂(Cl)₂

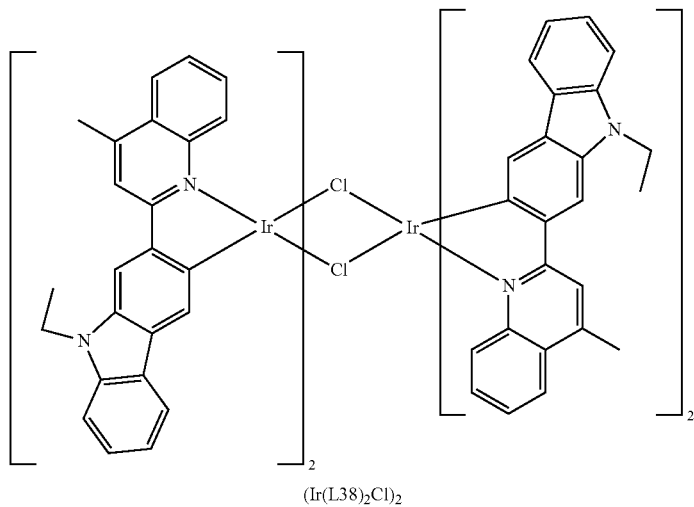
(Ir(L38)₂Cl)₂
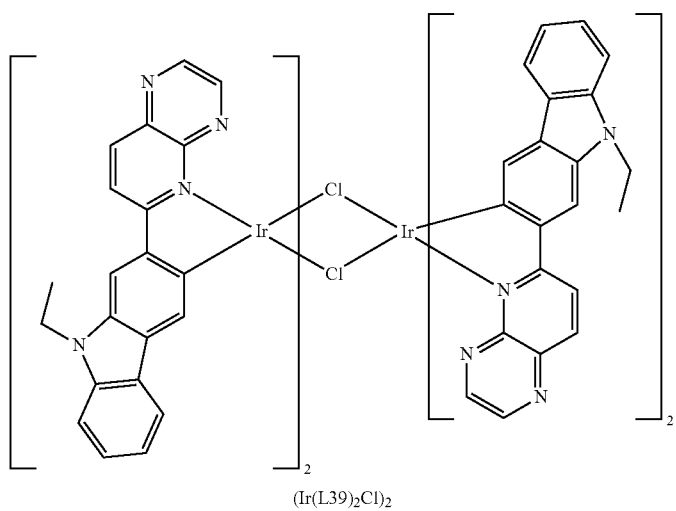
(Ir(L39)₂Cl)₂
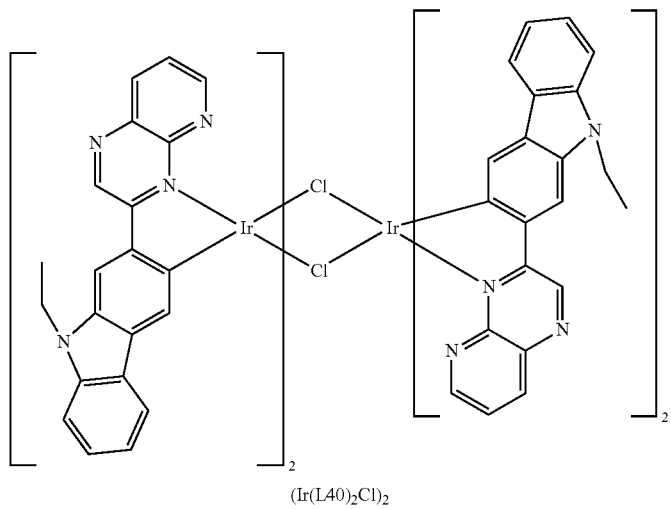
(Ir(L40)₂Cl)₂

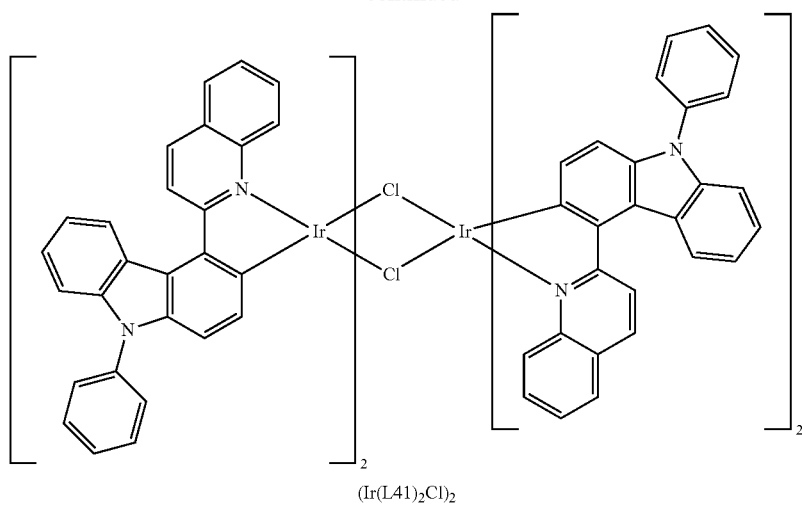
(Ir(L41)₂Cl)₂
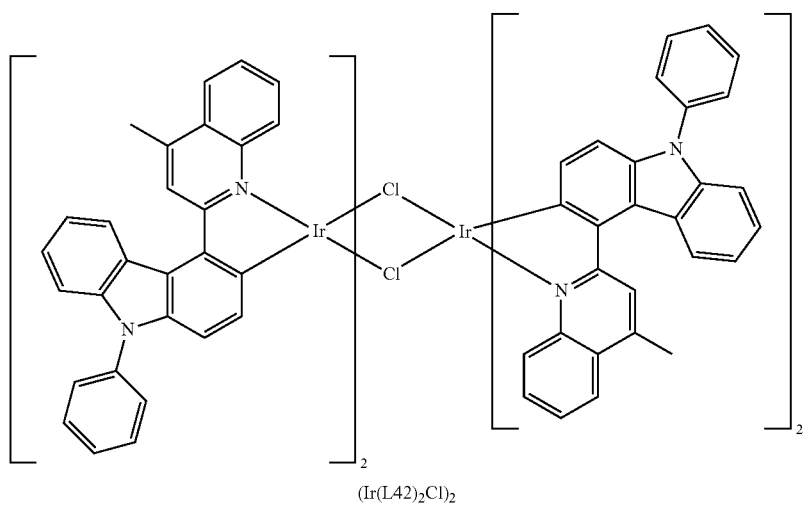
(Ir(L42)₂Cl)₂
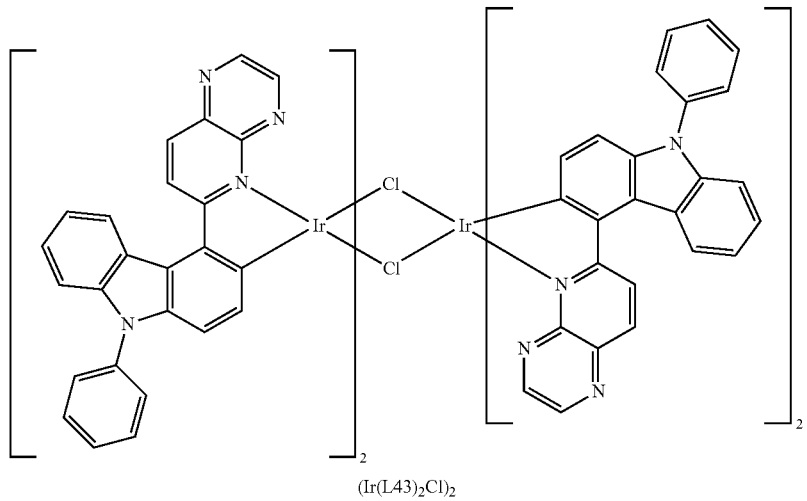
(Ir(L43)₂Cl)₂

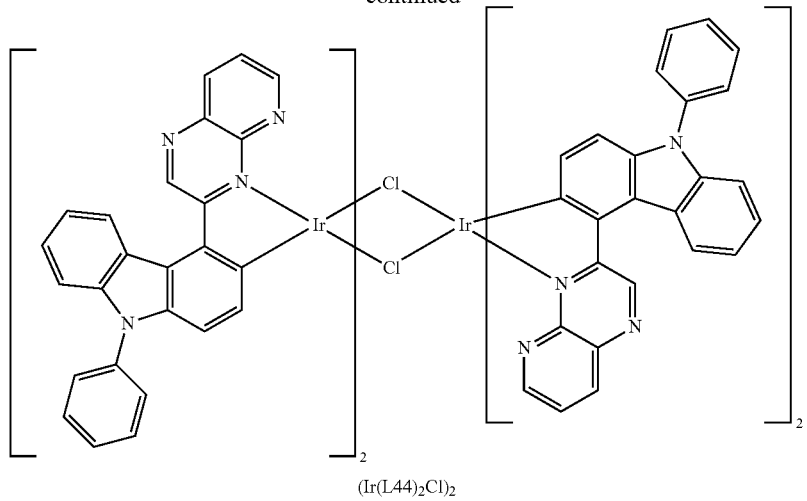
(Ir(L44)₂Cl)₂
Example 9
Synthesis of compound (Ir(L1)fppz) (III)
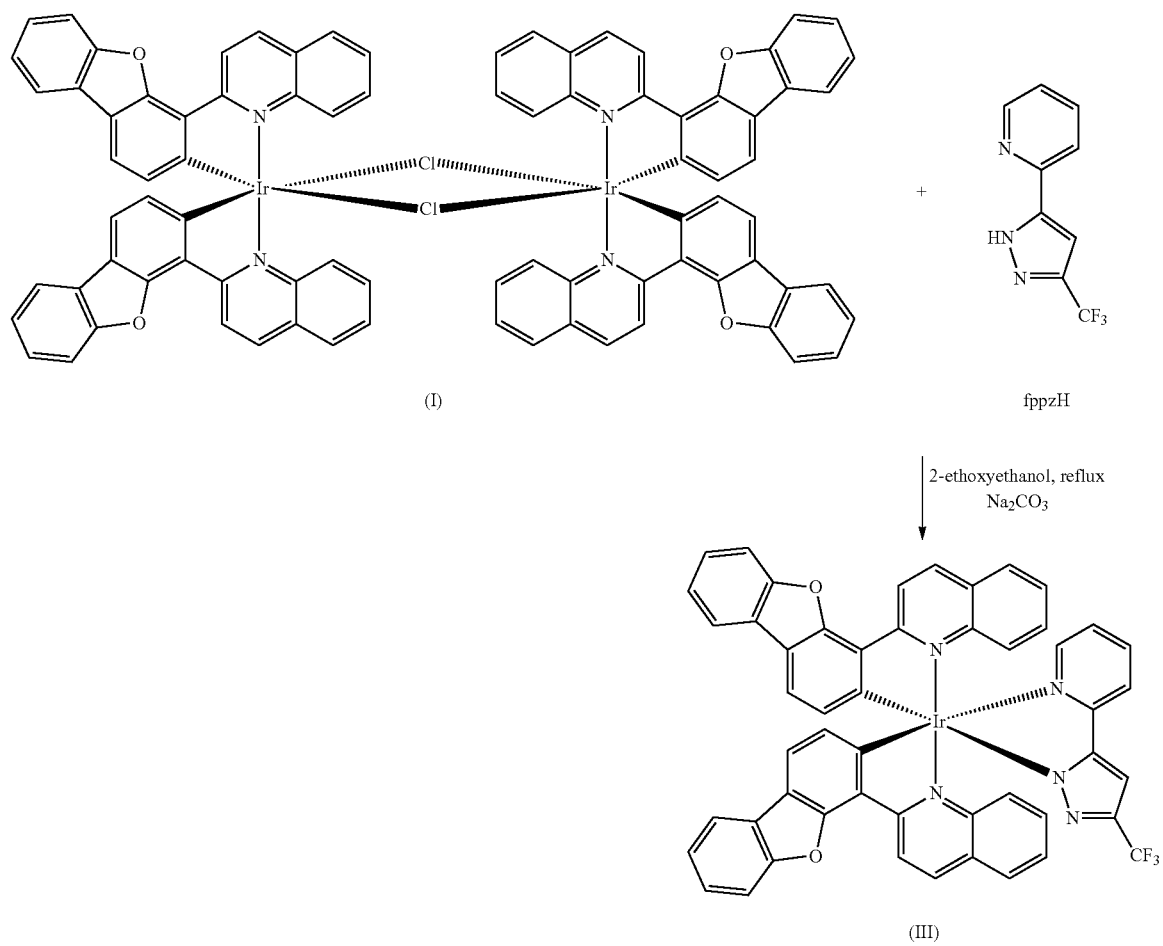
A mixture of (dbfq)₂Ir(μ-Cl)₂Ir(dbfq)₂ (I) (200 mg, 0.122 mmol), fppzH (53 mg, 0.248 mmol) and Na₂CO₃ (120 mg, 1.13 mmol) in ethoxyethanol (10 mL) is heated at 130° C. for 2 h under inert atmosphere. After cooling, the reaction mixture is poured into water (50 mL) and the precipitate is collected by filtration. The solid is purified via column chromatography using CH$_2$Cl$_2$ as eluent. Further purification is carried out by recrystallization from CH$_2$Cl$_2$/methanol to obtain compound (III) as a red powder (180 mg, 0.18 mmol, 74% yield).

Example 10

Synthesis of compound (XIII) [(dbfq)$_2$Ir(ftmpi)]

Example 11

Preparation of further complexes

In analogy to the preparation according to Example 10 further complexes can be produced. The general preparation method is as follows:

A mixture of the chloro-bridged dimer (Ir(Lxx)$_2$)Cl$_2$ (0.177 mmol) wherein Lxx is defined as being one of the ligands L1 to L44, the third ligand (fppz, fptz, mppz, bppz, hppz, hptz, pptz, mptz, tptz, or ftmpi) (0.365 mmol) and

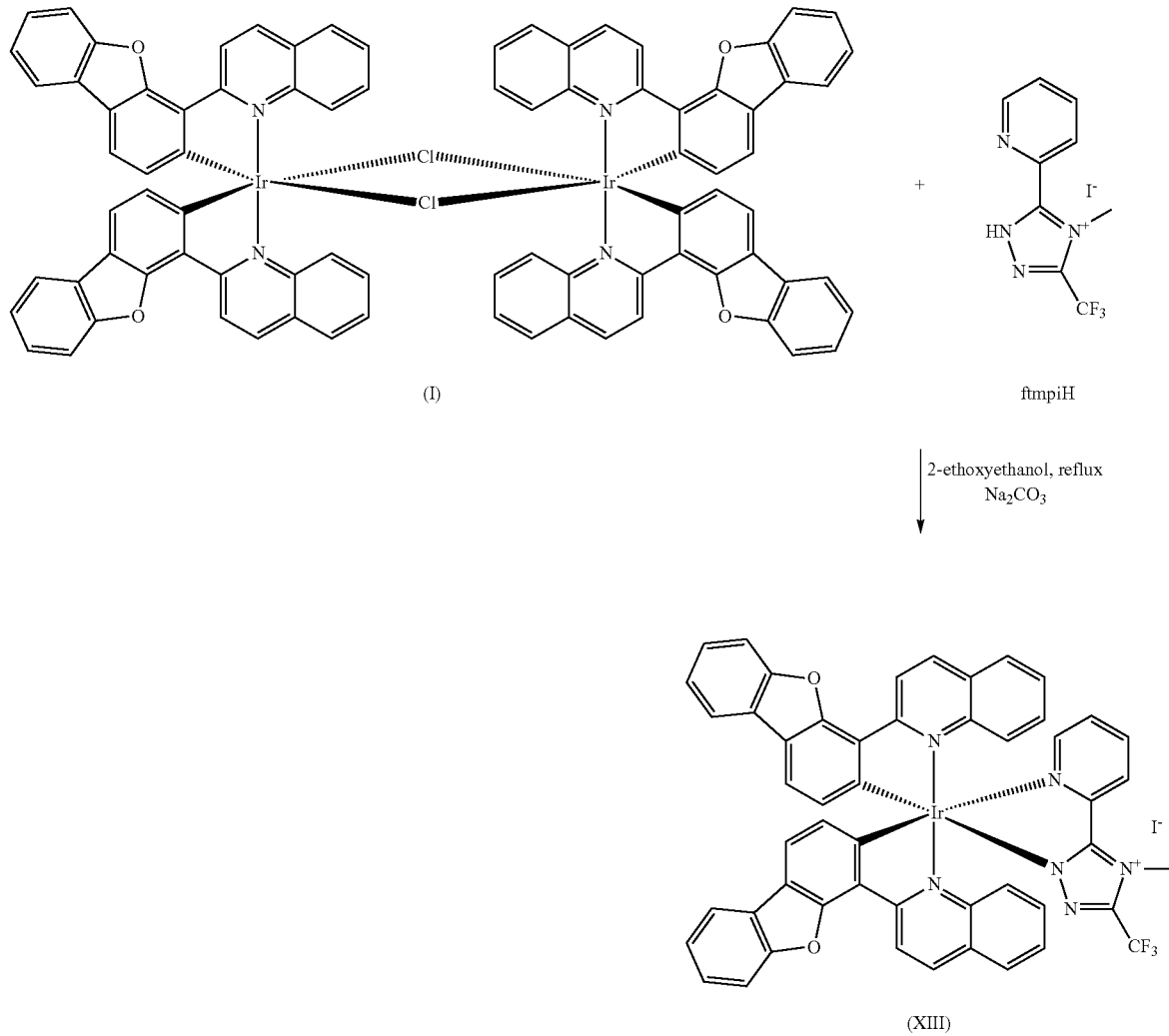

A mixture of (dbfq)$_2$Ir(μ-Cl)$_2$Ir(dbfq)$_2$ (I) (200 mg, 0.122 mmol), ftmpiH (89 mg, 0.250 mmol) and Na$_2$CO$_3$ (120 mg, 1.13 mmol) in ethoxyethanol (10 mL) is heated to 130° C. for 2 h in an inert atmosphere. After cooling, the reaction mixture is poured into water (50 mL) and the aqueous phase is extracted with dichloromethane. After removing the solvent, the product is purified via column chromatography using CH$_2$Cl$_2$ as eluent. Further purification is carried out by crystallization to obtain compound (XIII) as a red powder (185 mg, 0.17 mmol, 70% yield).

Na$_2$CO$_3$ (0.85 mmol) are solved in ethoxyethanol (10 mL) and the reaction mixture is heated at 130° C. for 5 h in an inert atmosphere. After cooling, the reaction mixture is poured into water (50 mL) and the precipitate is collected by filtration. The solid is purified via column chromatography using CH$_2$Cl$_2$ as eluent. Further purification is carried out by recrystallization from CH$_2$Cl$_2$/methanol to obtain the compound as a red powder.

The compounds given in the following table can be made according to the general procedure out of the chloro-bridged-dimers (Ir(L1)$_2$Cl)$_2$ to (Ir(L44)$_2$Cl)$_2$ and the third ligands ligand (fppz, fptz, mppz, bppz, hppz, hptz, pptz, mptz, tptz, or ftmpi). The over-all yield for each reaction is between 43% and 78%.

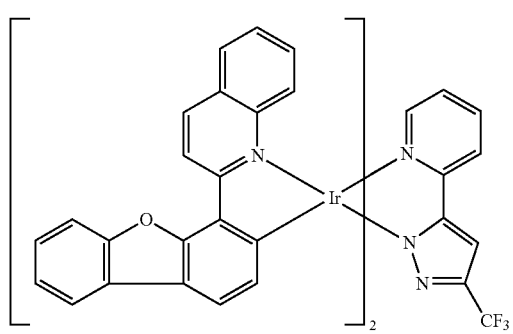
Ir(L1)₂fppz
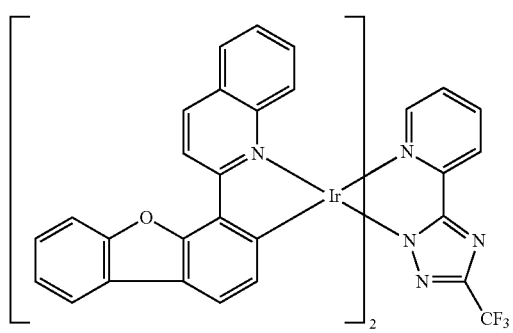
Ir(L1)₂fptz
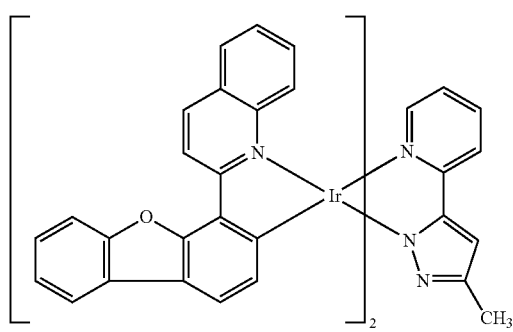
Ir(L1)₂mppz
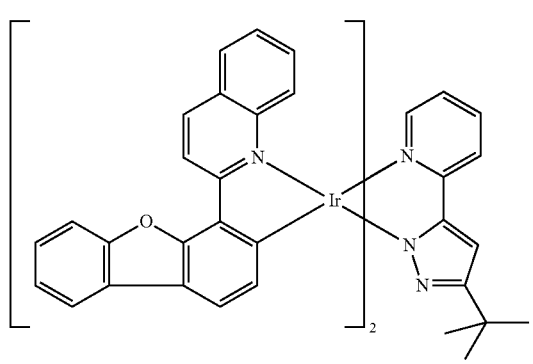
Ir(L1)₂bppz
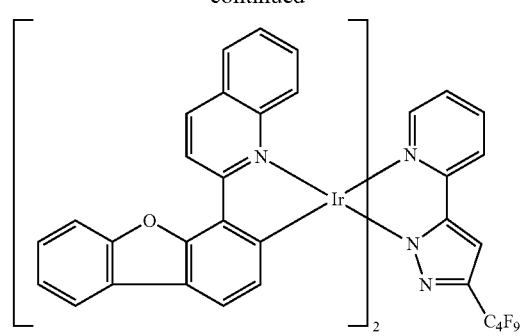
Ir(L1)₂hppz
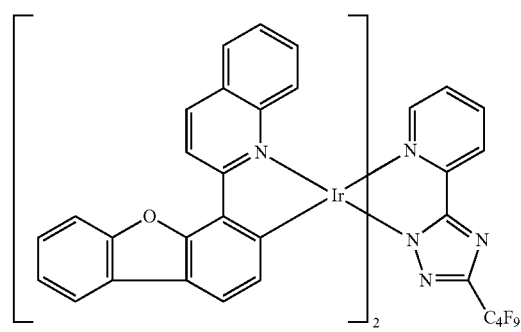
Ir(L1)₂hptz
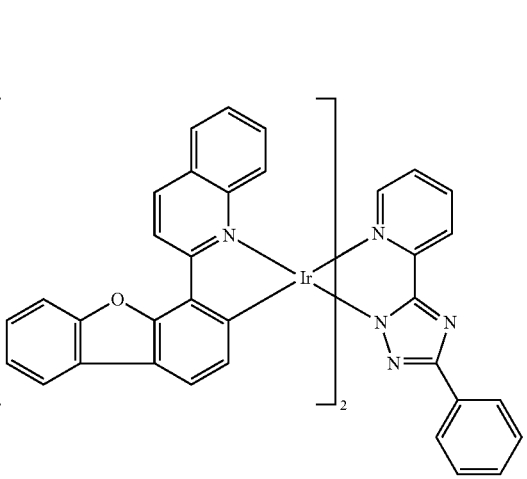
Ir(L1)pptz
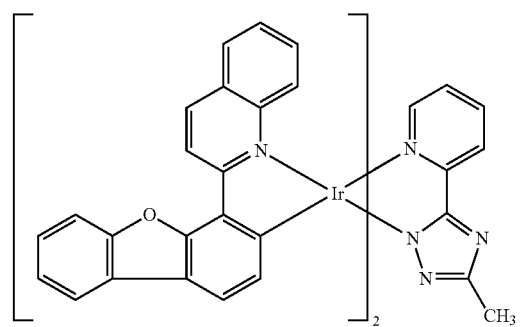
Ir(L1)mptz

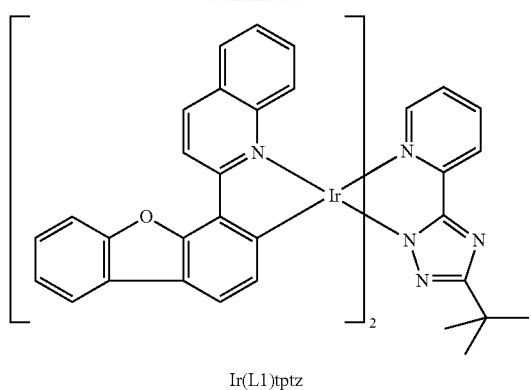
Ir(L1)tptz
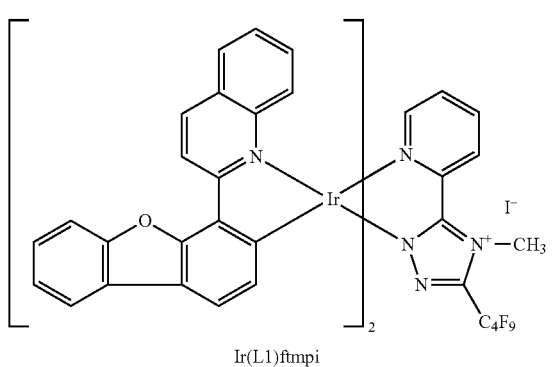
Ir(L1)ftmpi
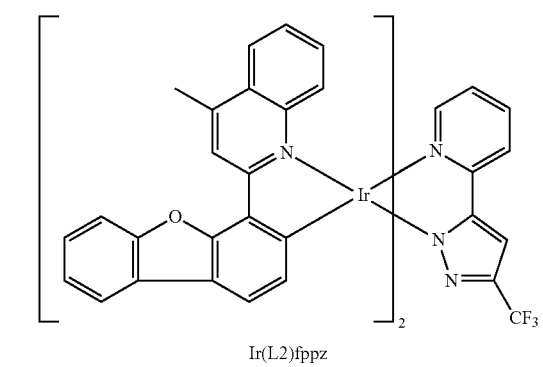
Ir(L2)fppz
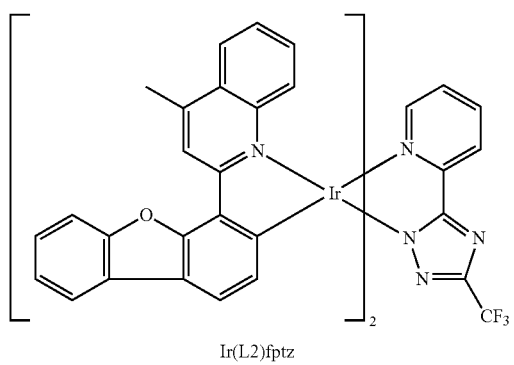
Ir(L2)fptz
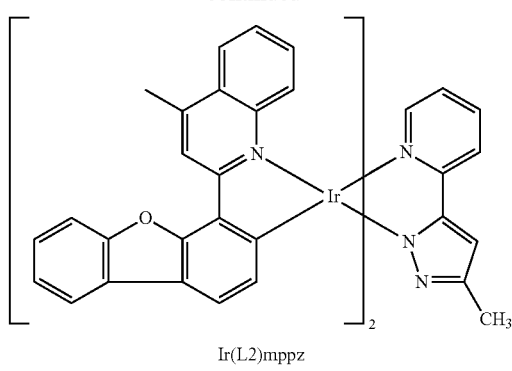
Ir(L2)mppz
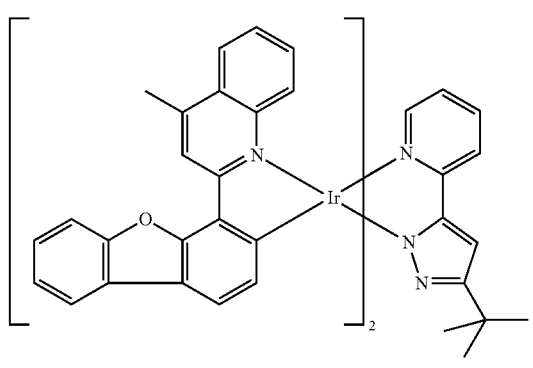
Ir(L2)bppz
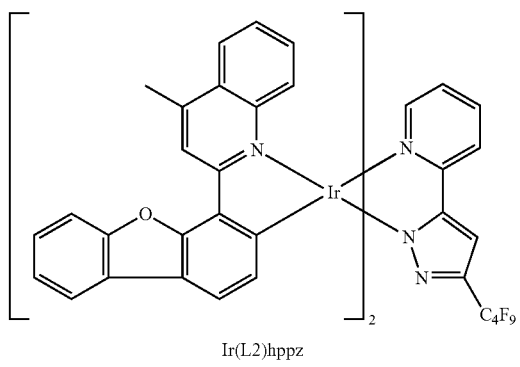
Ir(L2)hppz
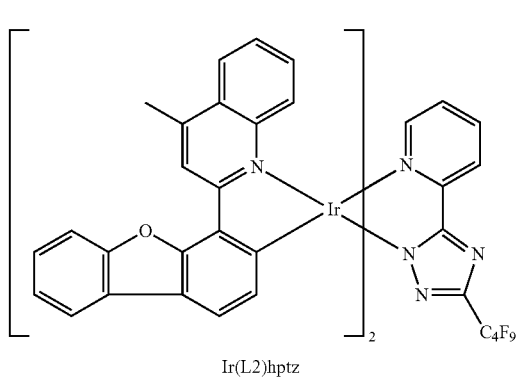
Ir(L2)hptz -continued
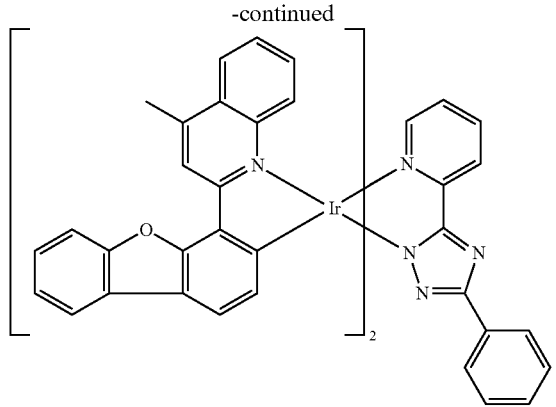
Ir(L2)pptz
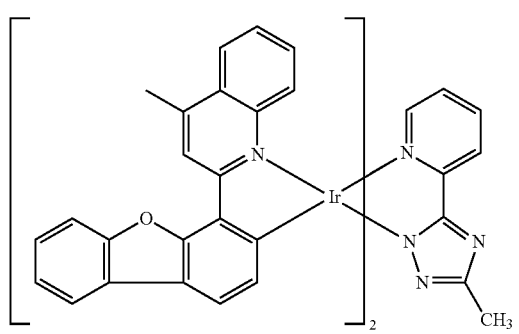
Ir(L2)mptz
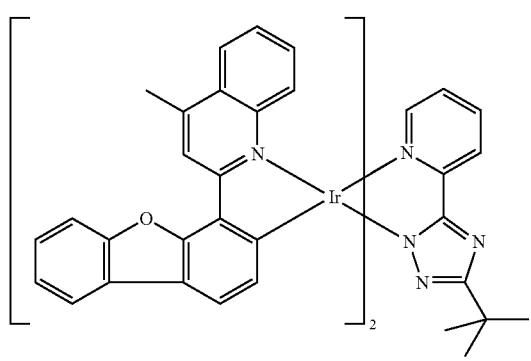
Ir(L2)tptz
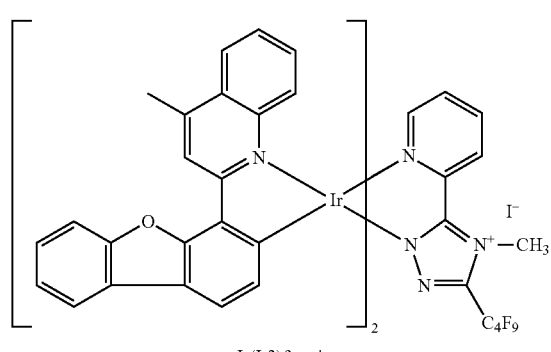
Ir(L2)ftmpi
-continued
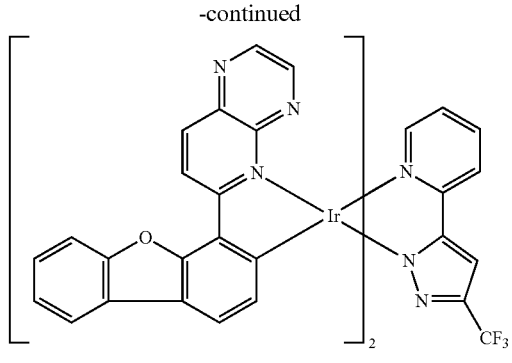
Ir(L3)fppz
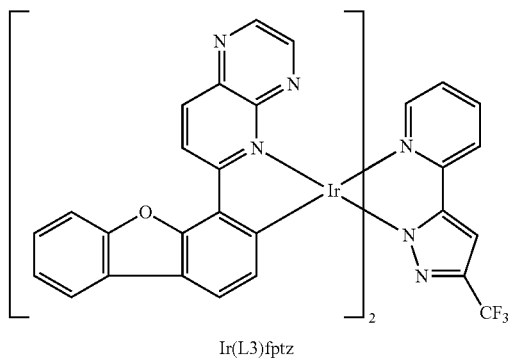
Ir(L3)fptz
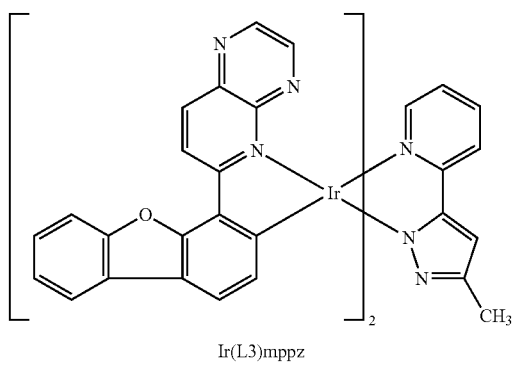
Ir(L3)mppz
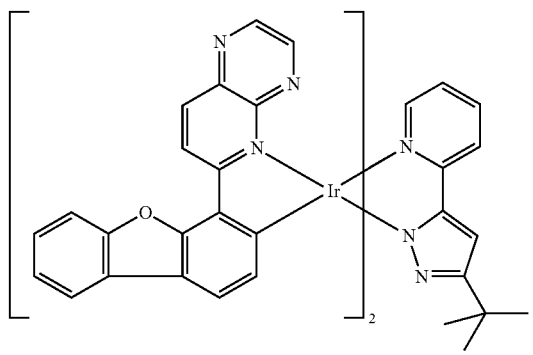
Ir(L3)bppz 163
-continued
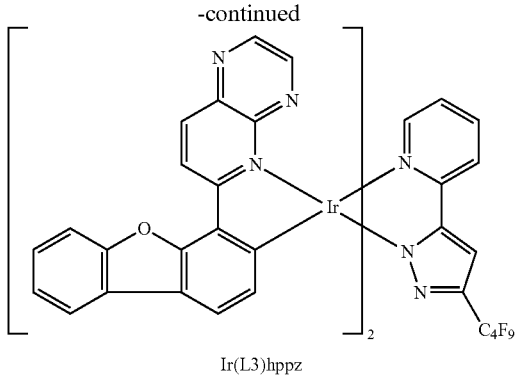
Ir(L3)hppz
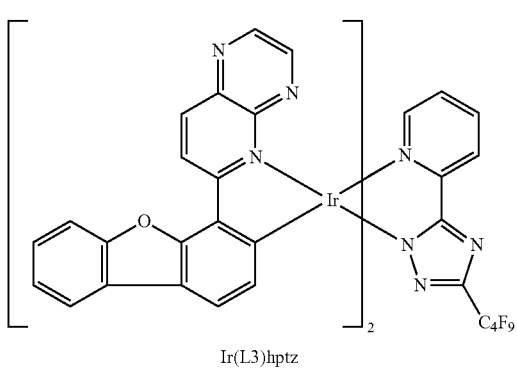
Ir(L3)hptz
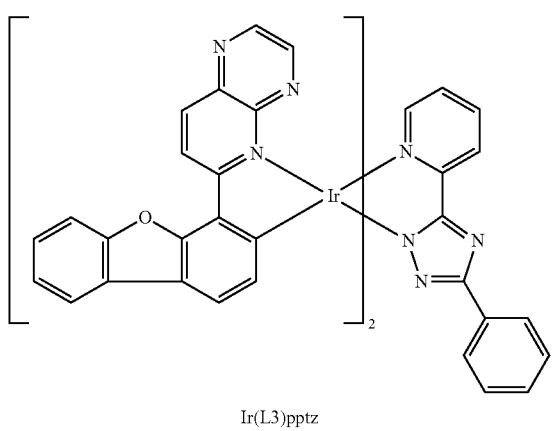
Ir(L3)pptz
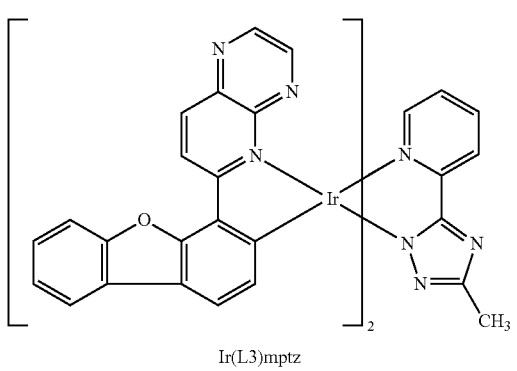
Ir(L3)mptz
164
-continued
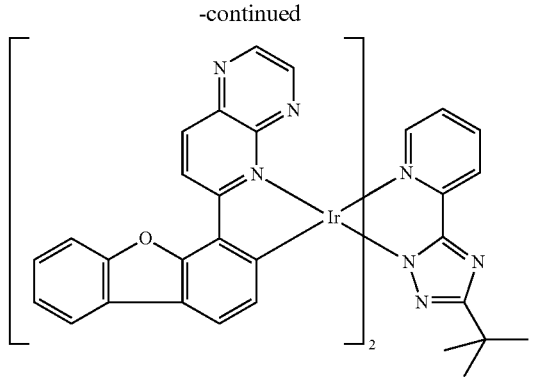
Ir(L3)tptz
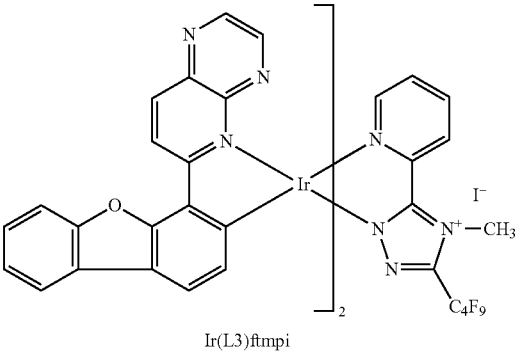
Ir(L3)ftmpi
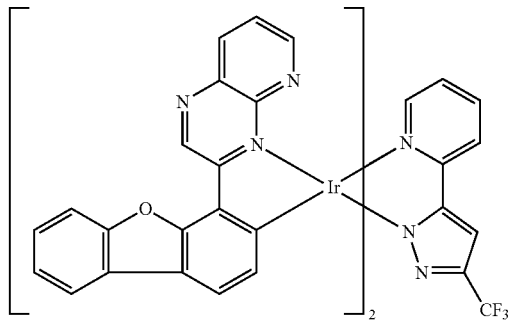
Ir(L4)fppz
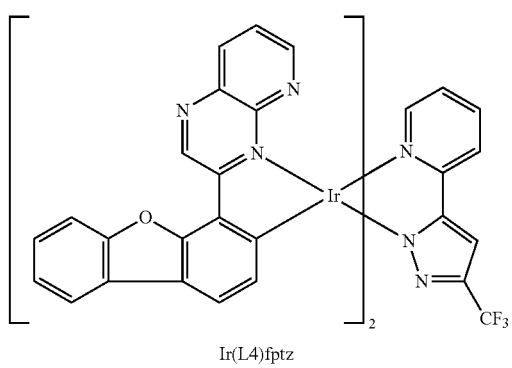
Ir(L4)fptz

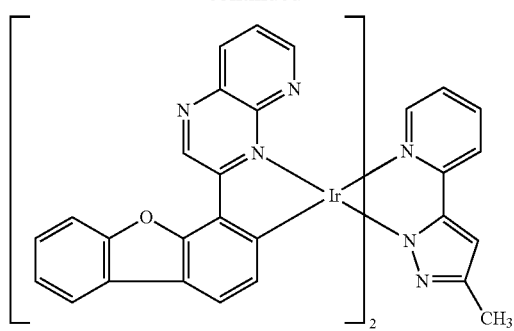
Ir(L4)mppz
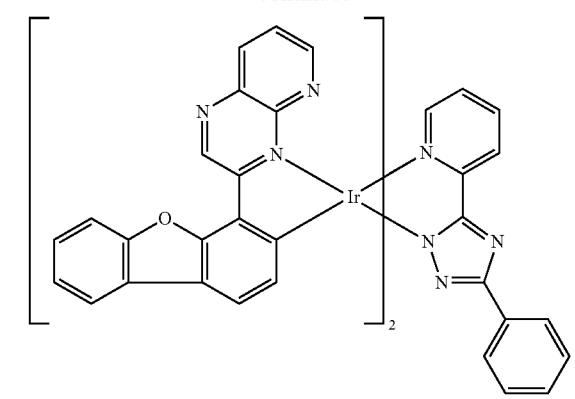
Ir(L4)pptz
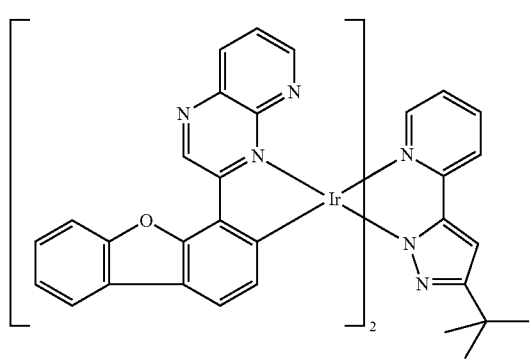
Ir(L4)bppz
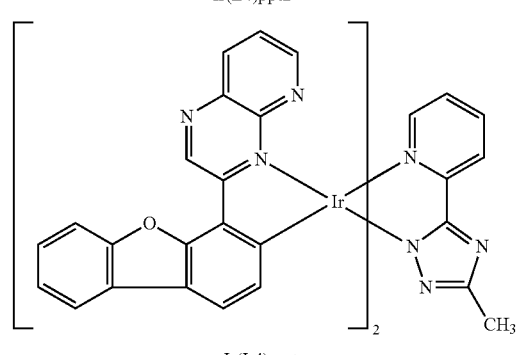
Ir(L4)mptz
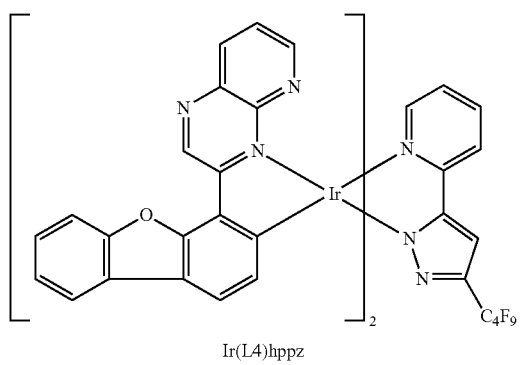
Ir(L4)hppz
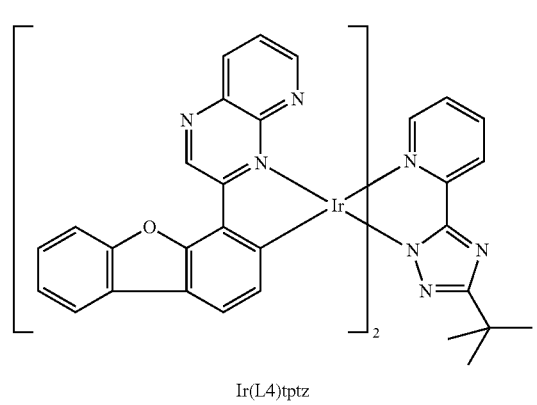
Ir(L4)tptz
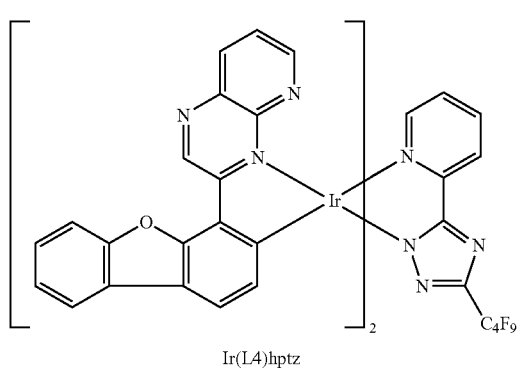
Ir(L4)hptz
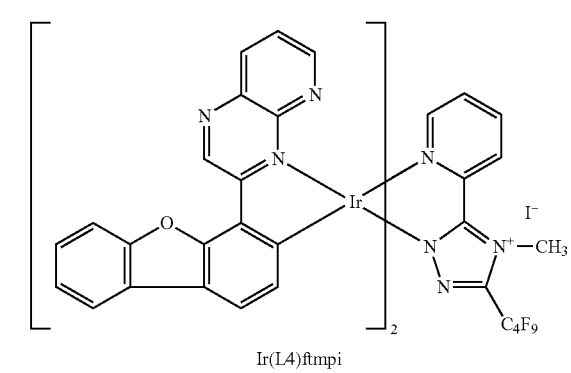
Ir(L4)ftmpi

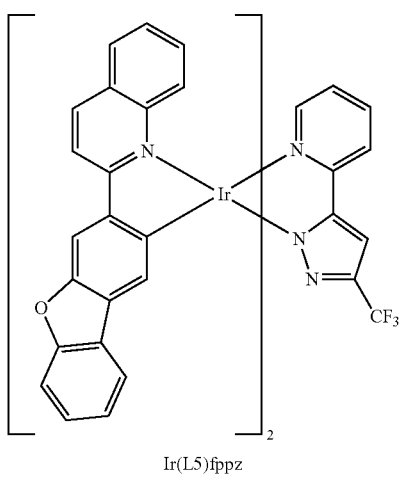
Ir(L5)fppz
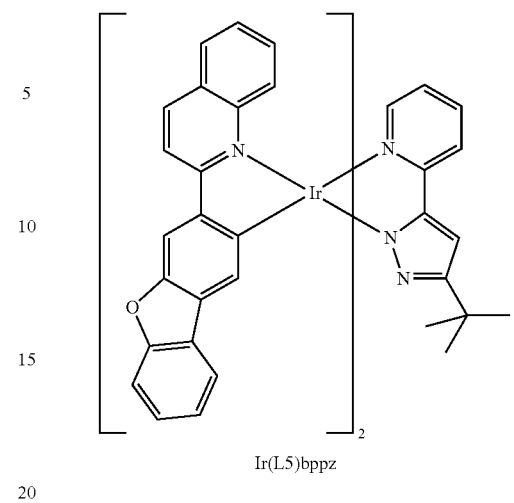
Ir(L5)bppz
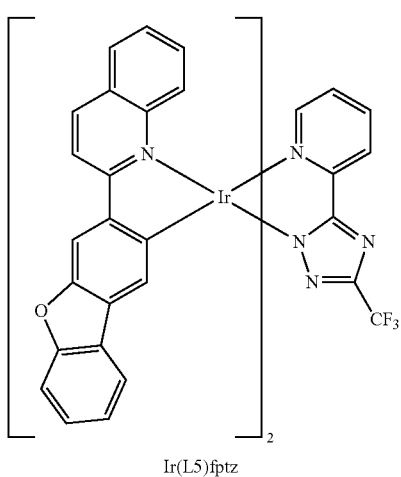
Ir(L5)fptz
Ir(L5)hppz
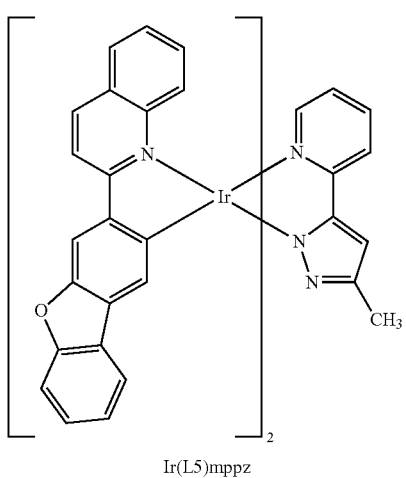
Ir(L5)mppz
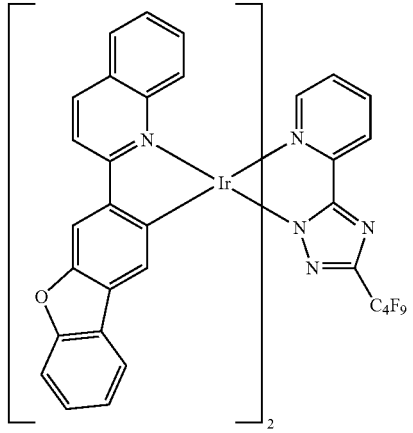
Ir(L5)hptz

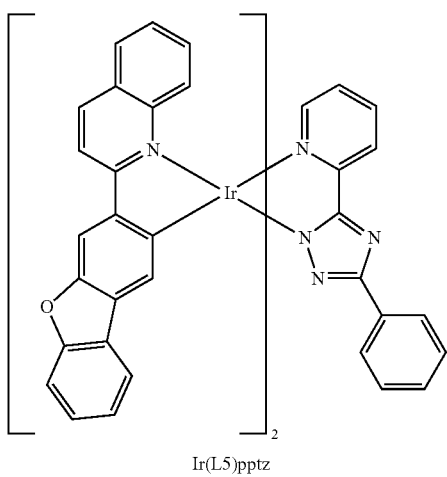
Ir(L5)pptz
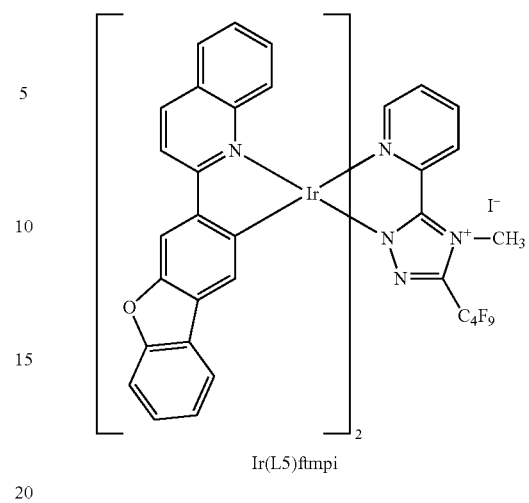
Ir(L5)ftmpi
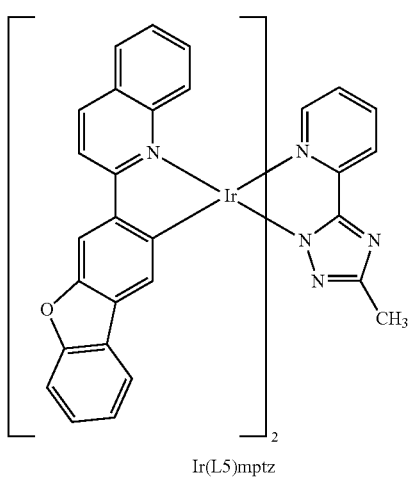
Ir(L5)mptz
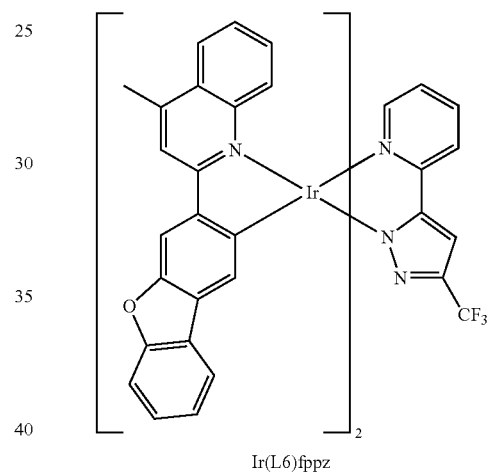
Ir(L6)fppz
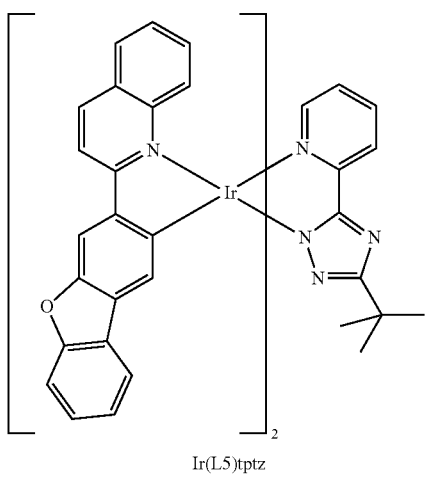
Ir(L5)tptz
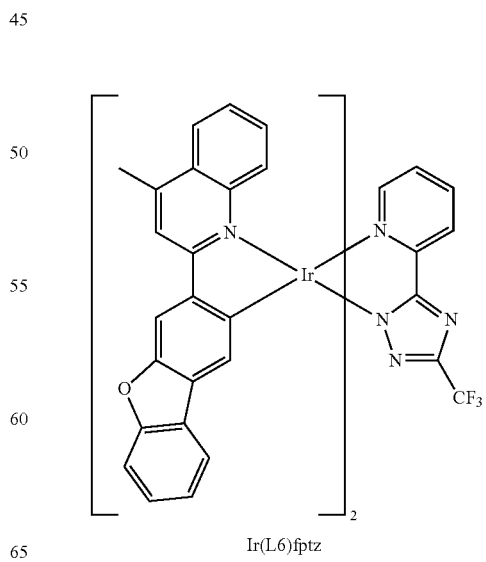
Ir(L6)fptz

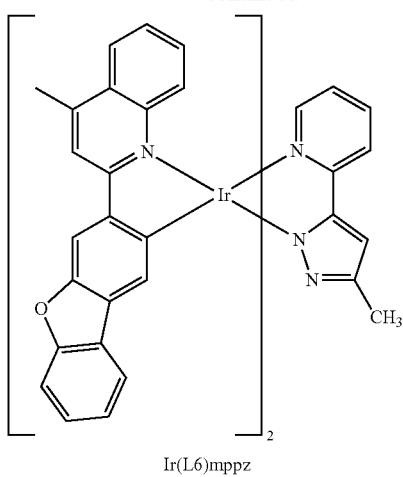
Ir(L6)mppz
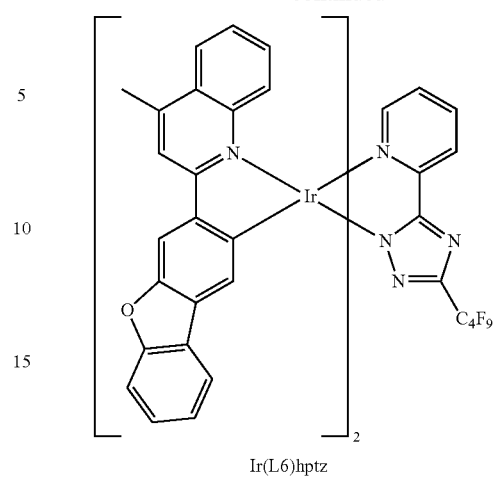
Ir(L6)hptz
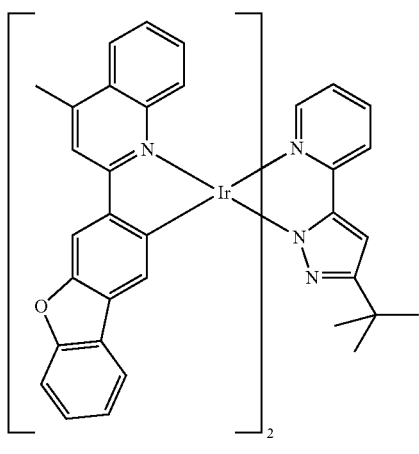
Ir(L6)bppz
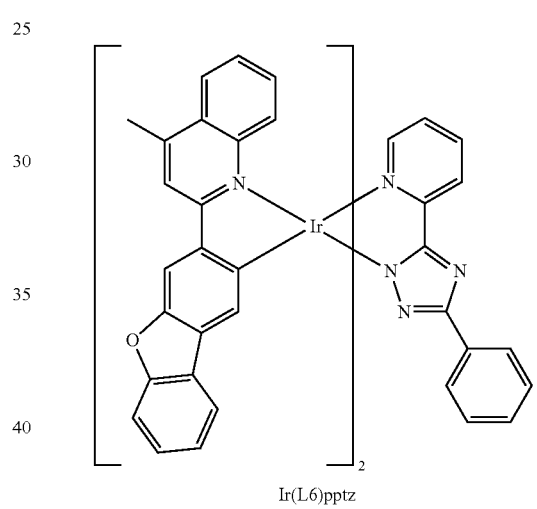
Ir(L6)pptz
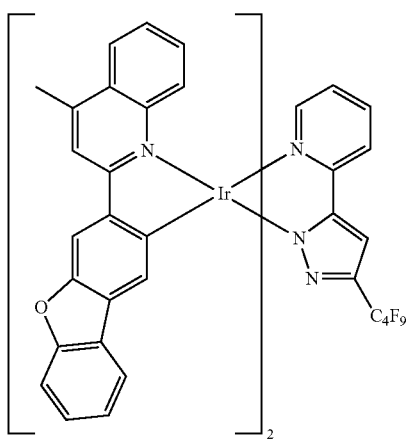
Ir(L6)hppz
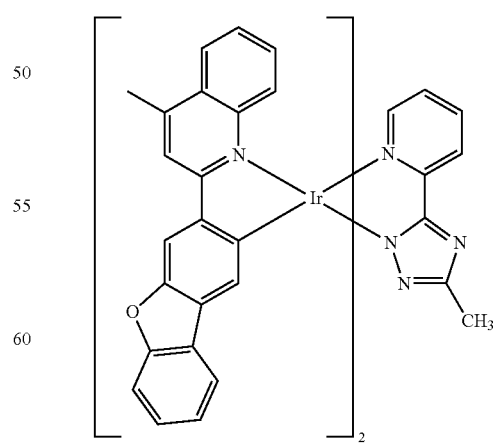
Ir(L6)mptz

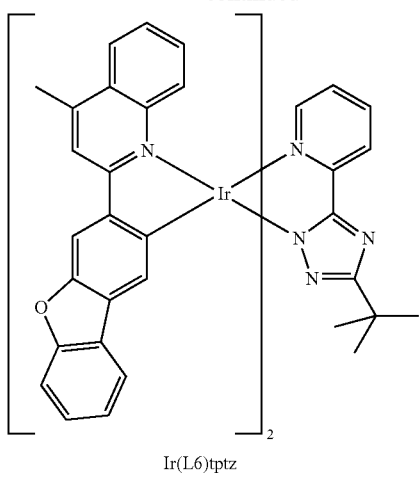
Ir(L6)tptz
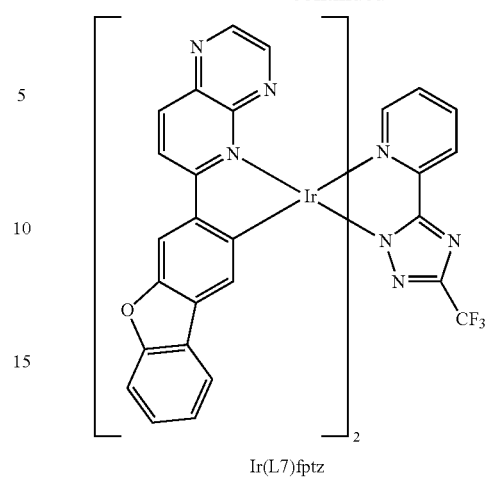
Ir(L7)fptz
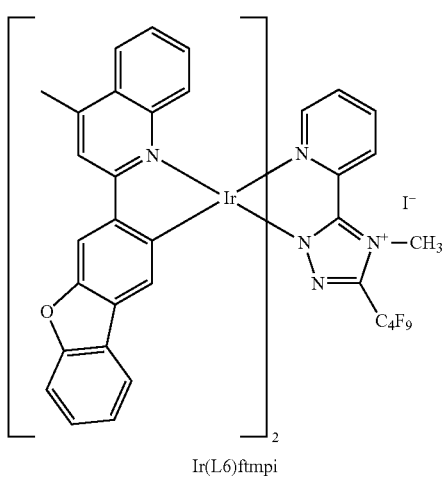
Ir(L6)ftmpi
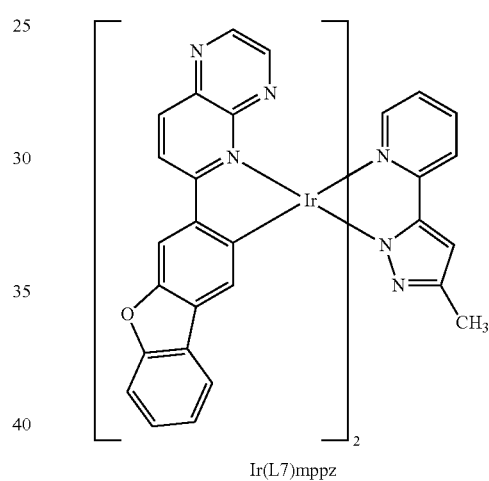
Ir(L7)mppz
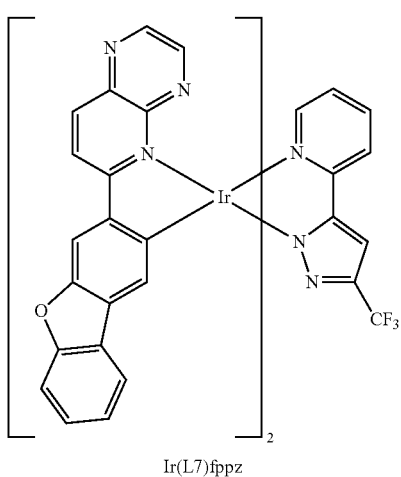
Ir(L7)fppz
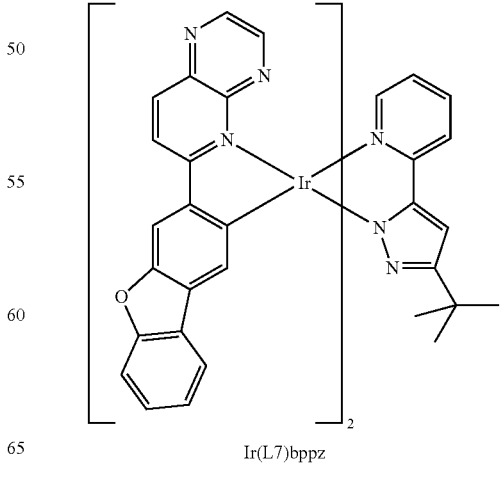
Ir(L7)bppz

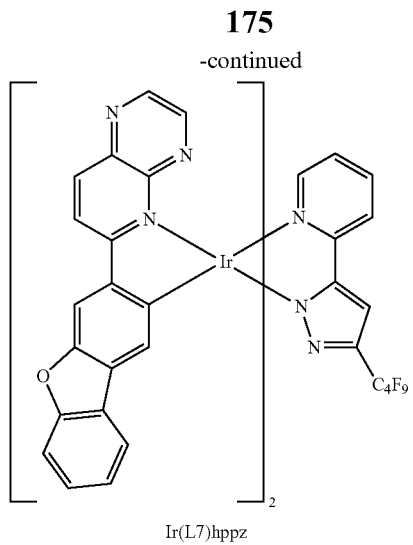
Ir(L7)hppz
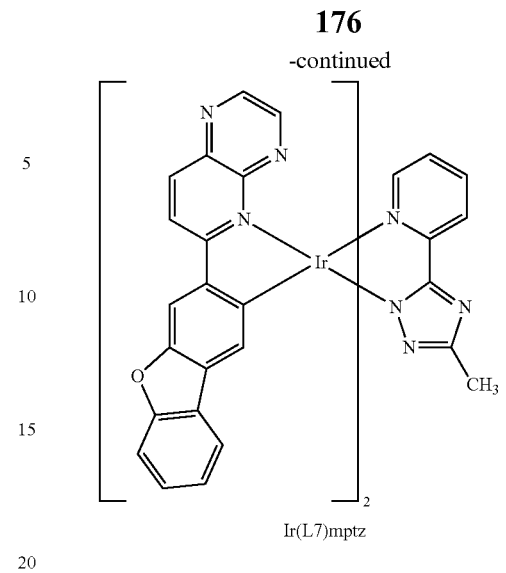
Ir(L7)mptz
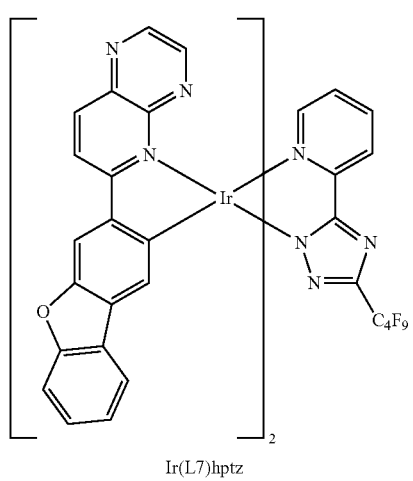
Ir(L7)hptz
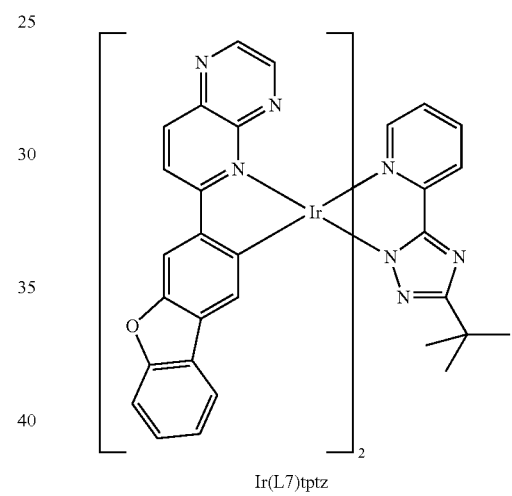
Ir(L7)tptz
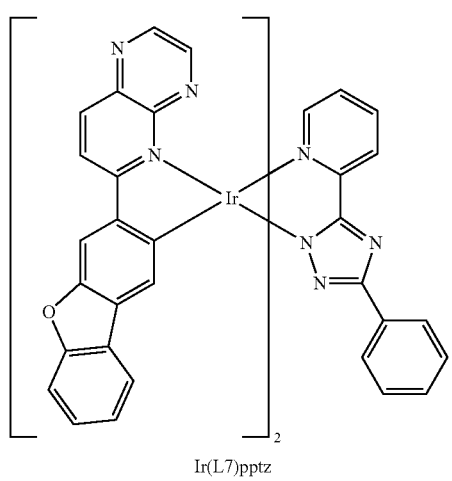
Ir(L7)pptz
Ir(L7)ftmpi

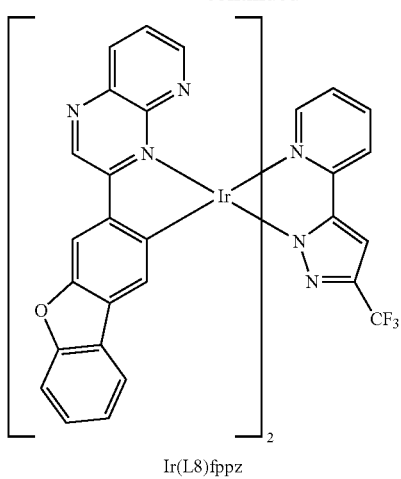
Ir(L8)fppz
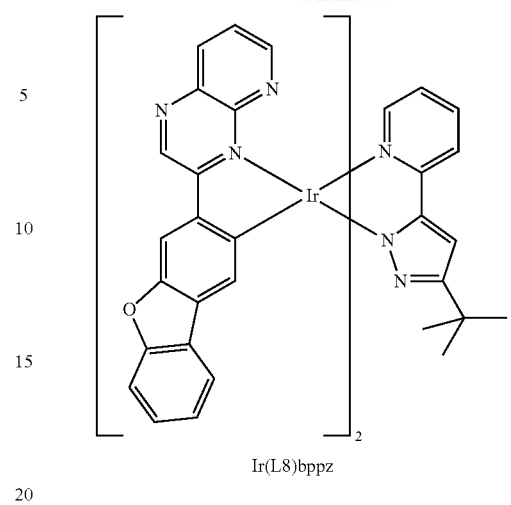
Ir(L8)bppz
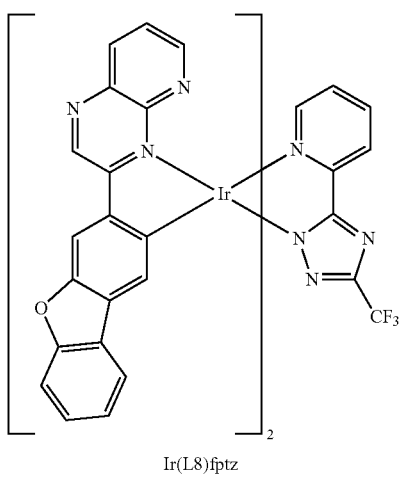
Ir(L8)fptz
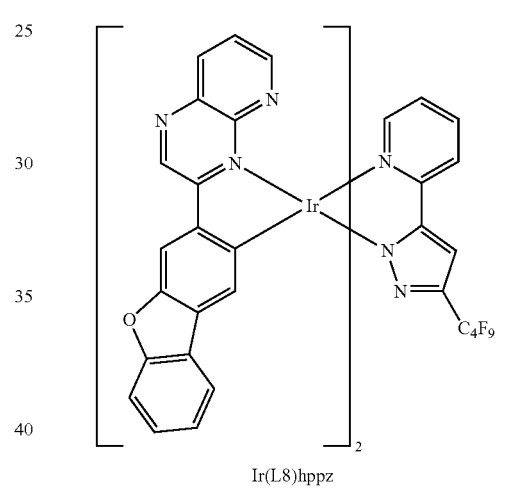
Ir(L8)hppz
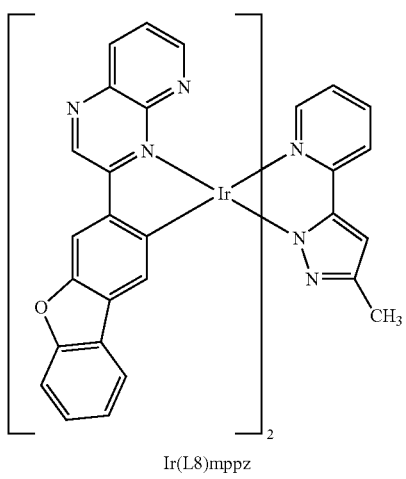
Ir(L8)mppz
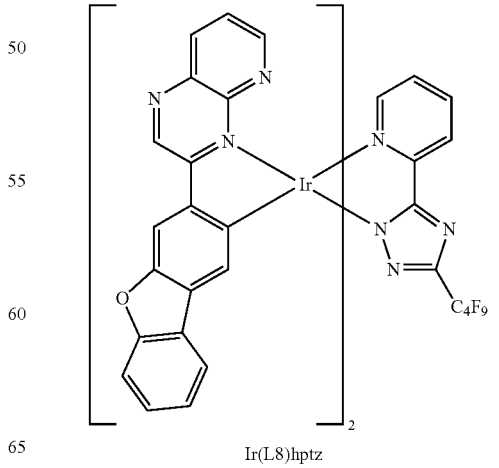
Ir(L8)hptz 179
-continued
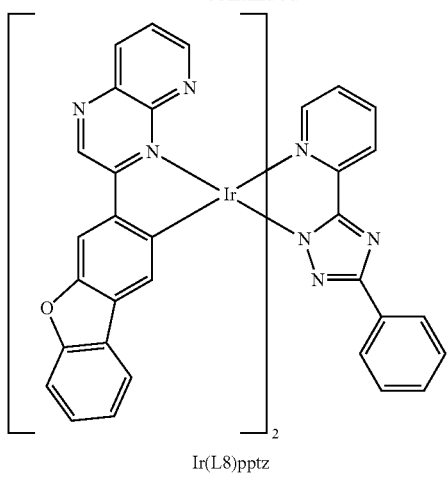
Ir(L8)pptz
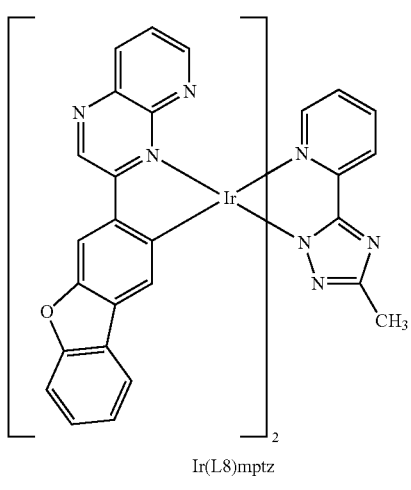
Ir(L8)mptz
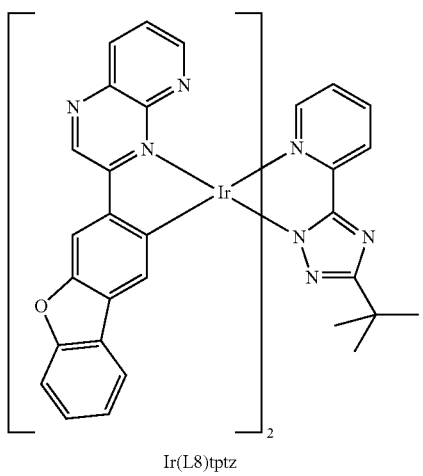
Ir(L8)tptz
180
-continued
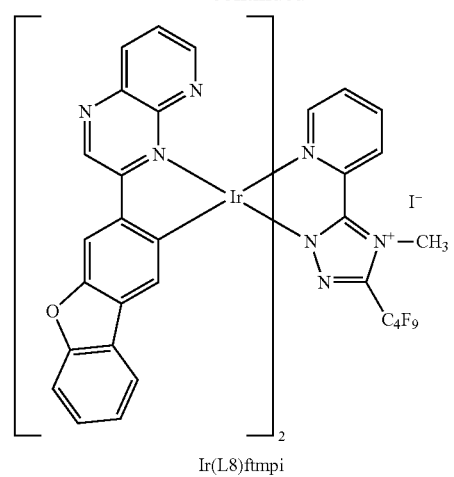
Ir(L8)ftmpi
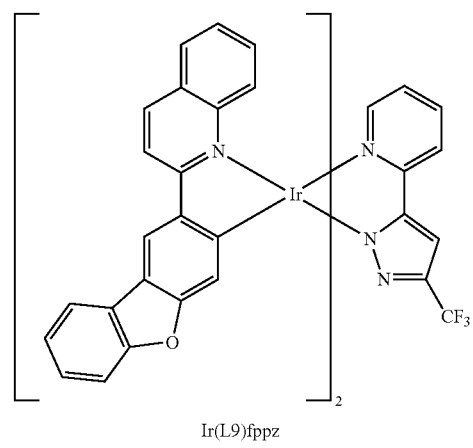
Ir(L9)fppz
Ir(L9)fptz

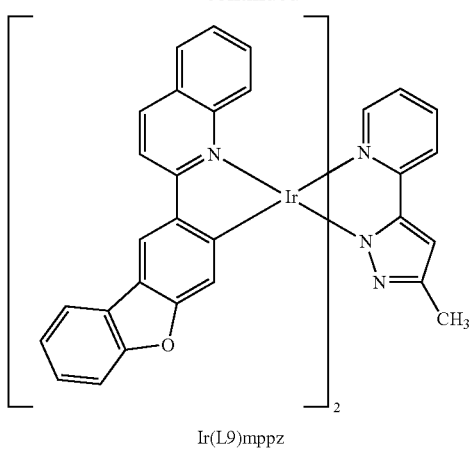
Ir(L9)mppz
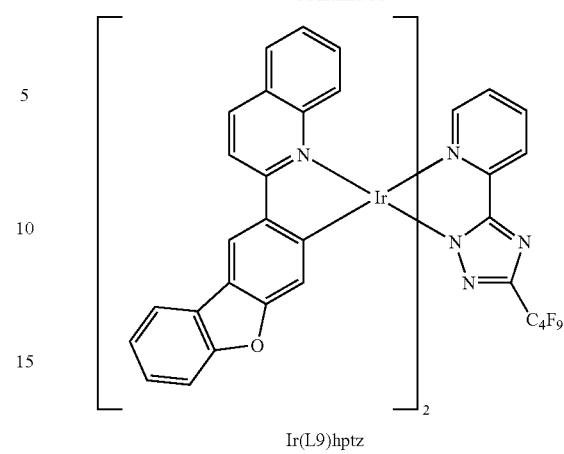
Ir(L9)hptz
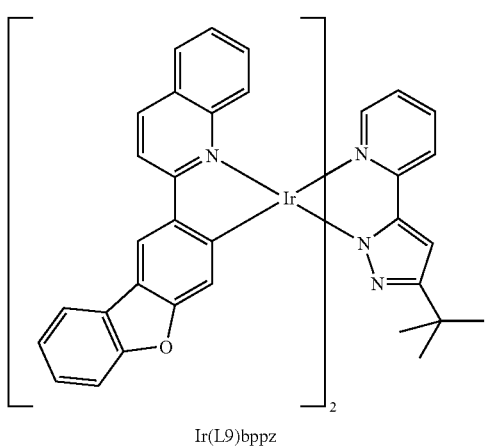
Ir(L9)bppz
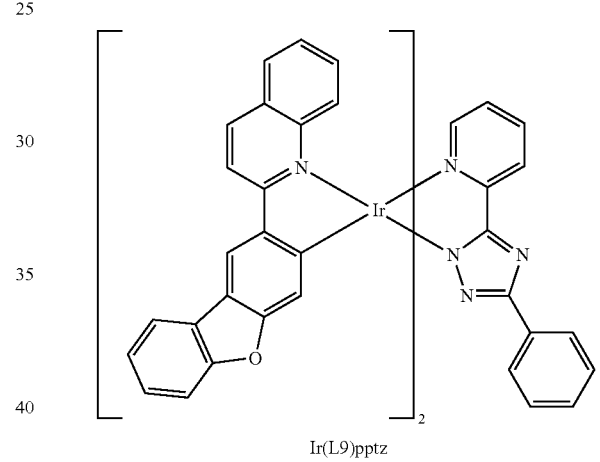
Ir(L9)pptz
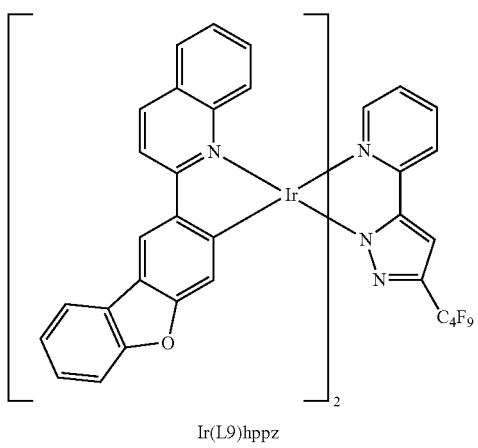
Ir(L9)hppz
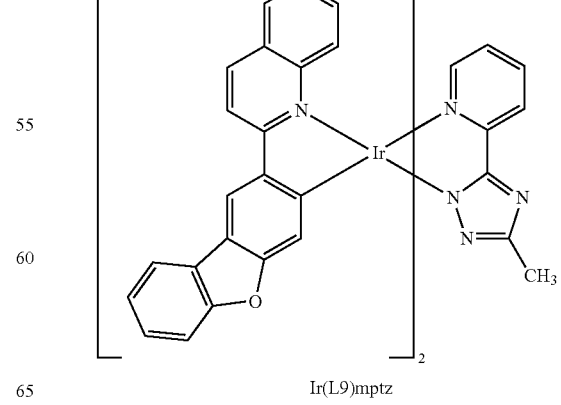
Ir(L9)mptz

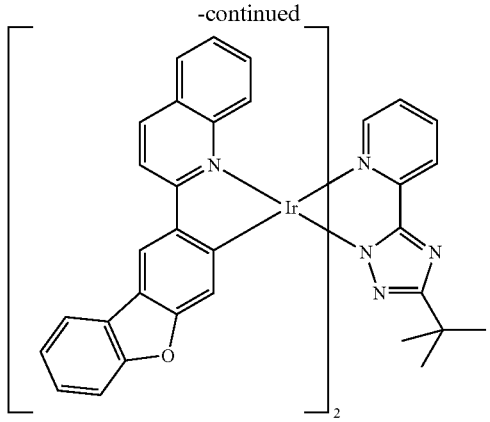
Ir(L9)tptz
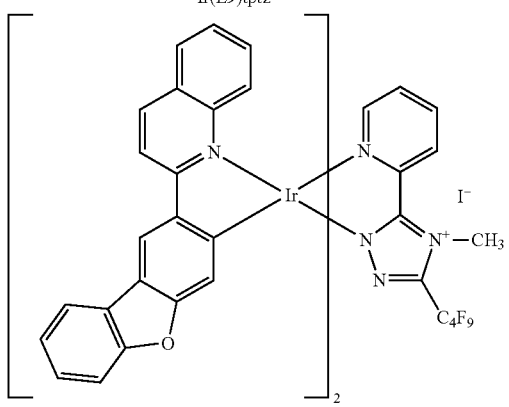
Ir(L9)ftmpi
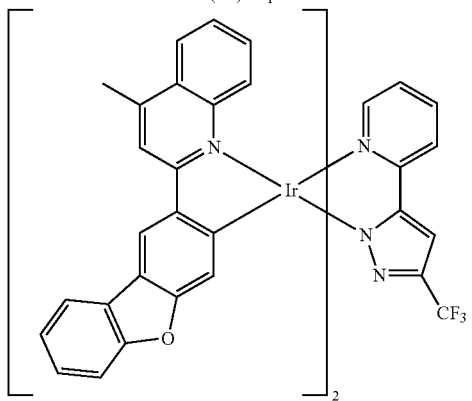
Ir(L10)fppz
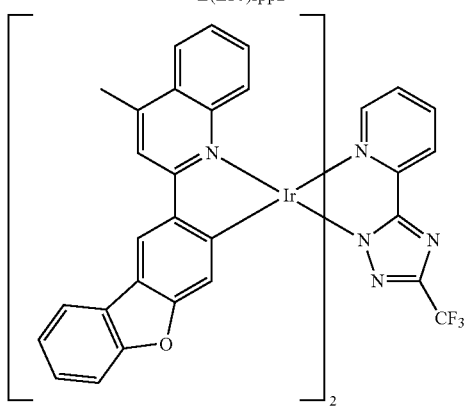
Ir(L10)fptz
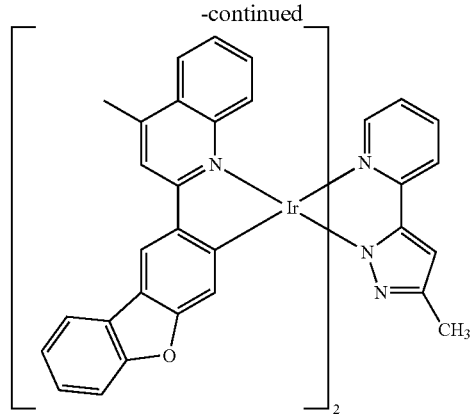
Ir(L10)mppz
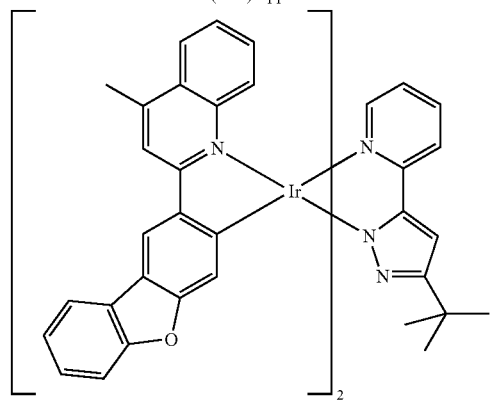
Ir(L10)bppz
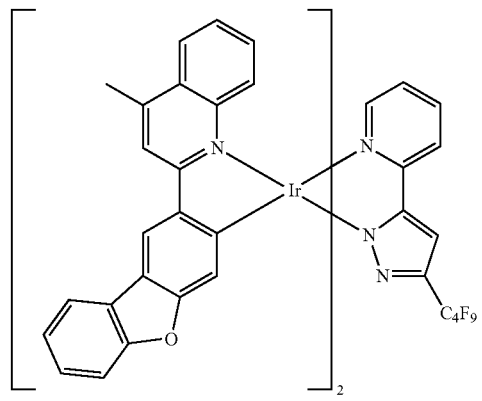
Ir(L10)hppz
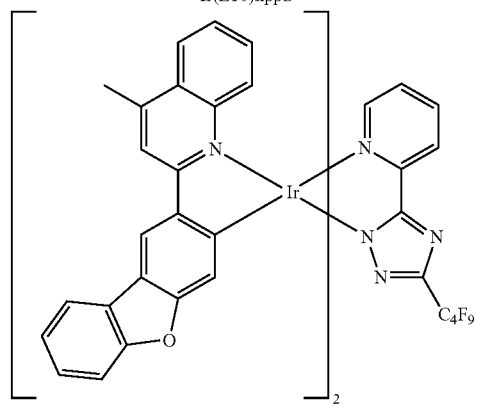
Ir(L10)hptz

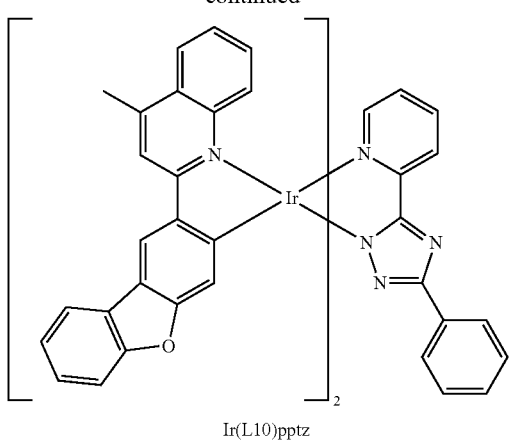
Ir(L10)pptz
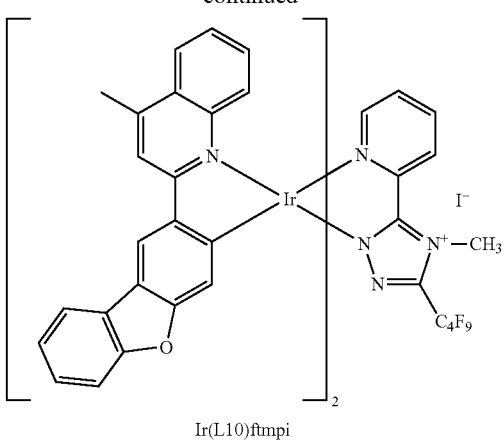
Ir(L10)ftmpi
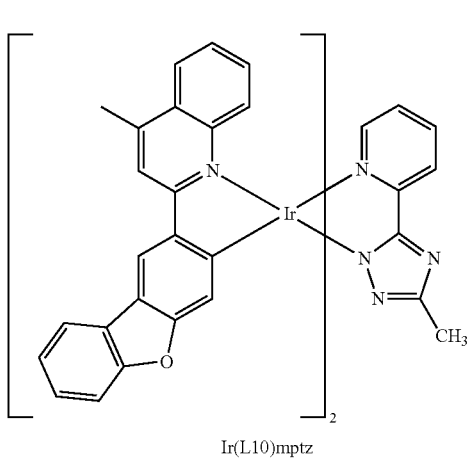
Ir(L10)mptz
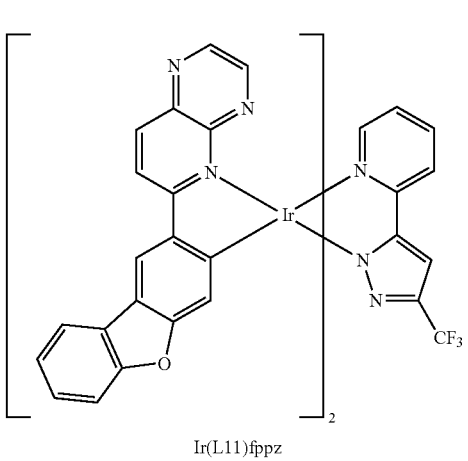
Ir(L11)fppz
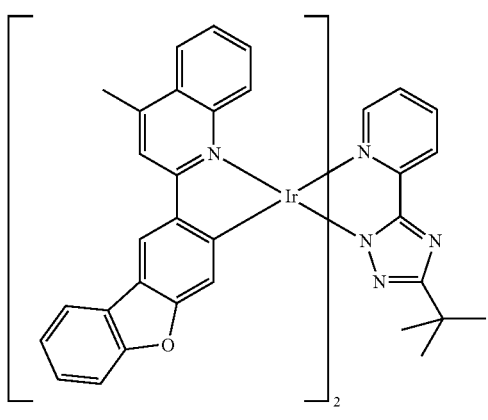
Ir(L10)tptz
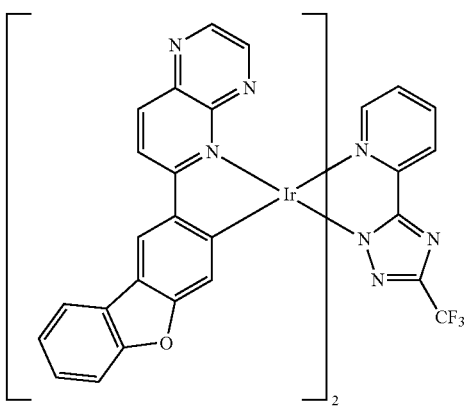
Ir(L11)fptz

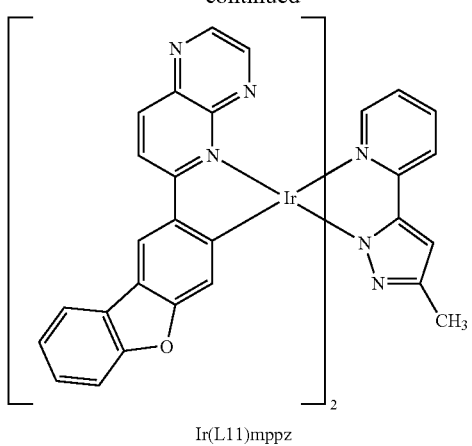
Ir(L11)mppz
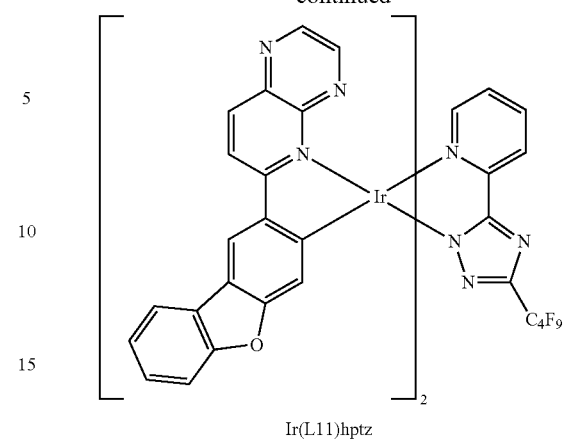
Ir(L11)hptz
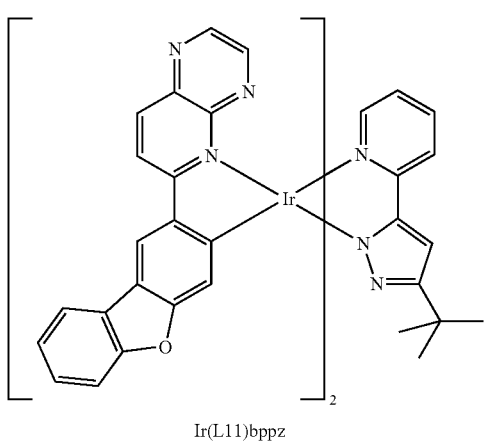
Ir(L11)bppz
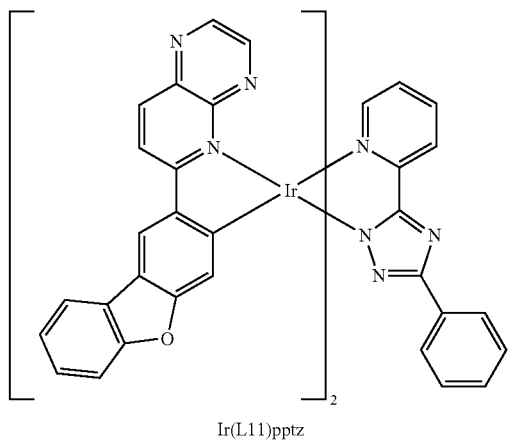
Ir(L11)pptz
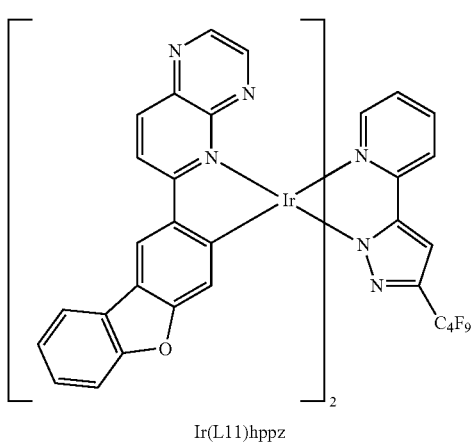
Ir(L11)hppz
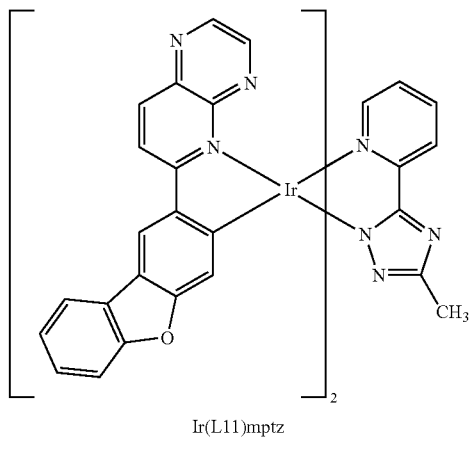
Ir(L11)mptz

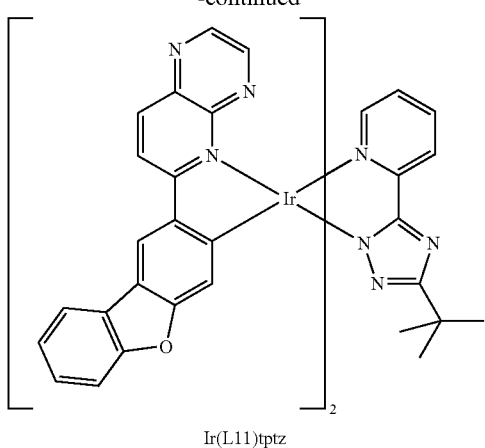
Ir(L11)tptz
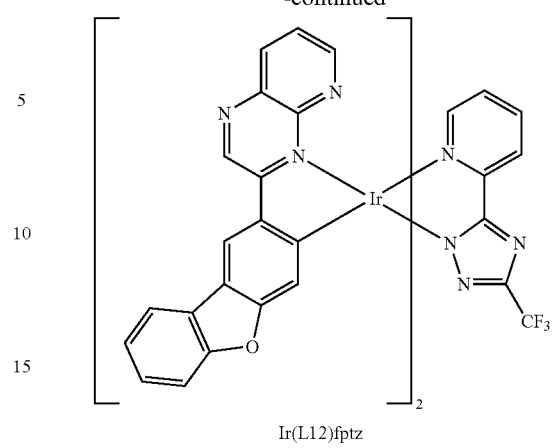
Ir(L12)fptz
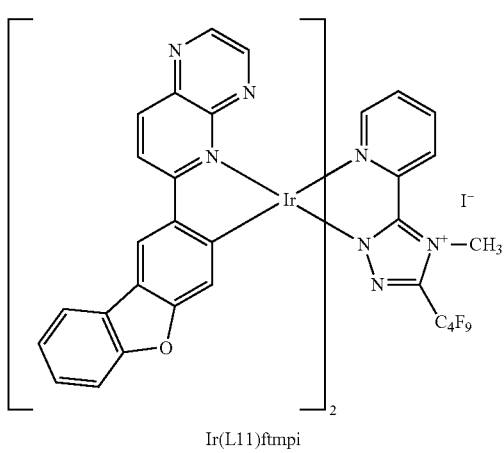
Ir(L11)ftmpi
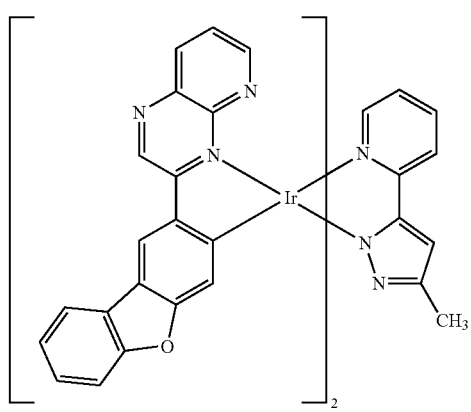
Ir(L12)mppz
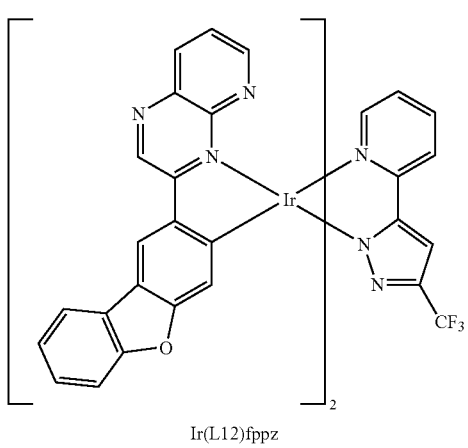
Ir(L12)fppz
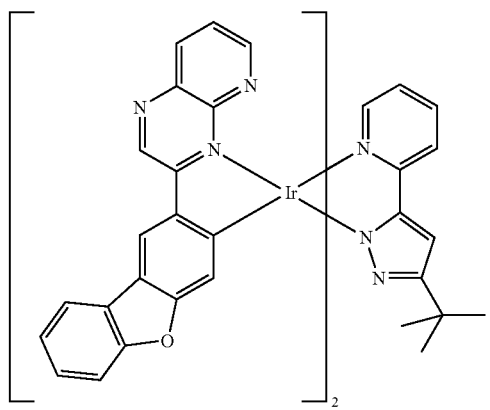
Ir(L12)bppz

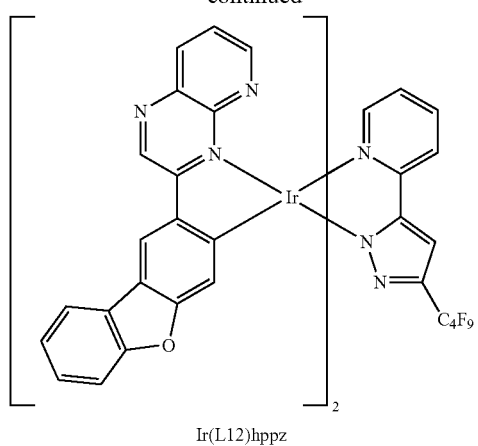
Ir(L12)hppz
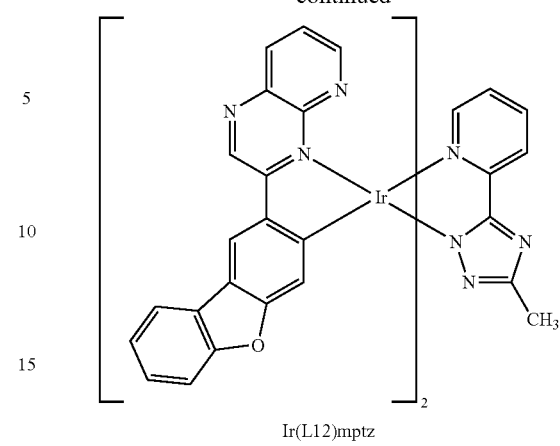
Ir(L12)mptz
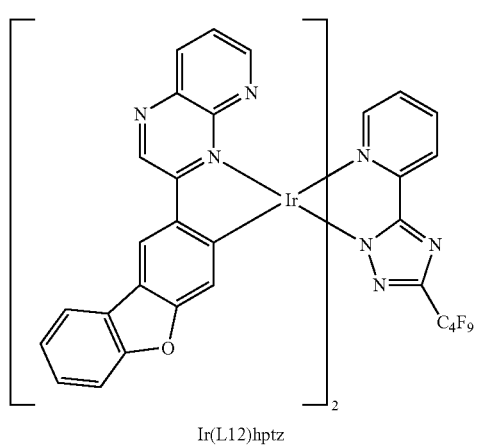
Ir(L12)hptz
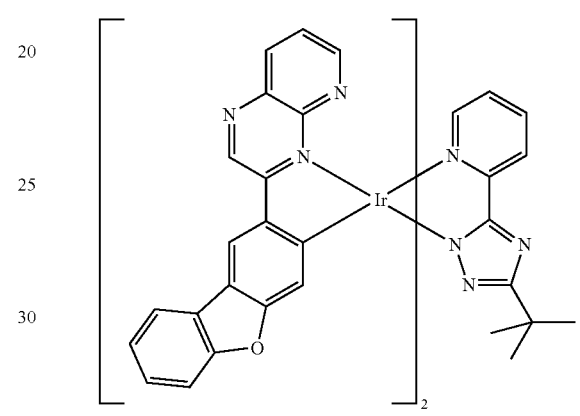
Ir(L12)tptz
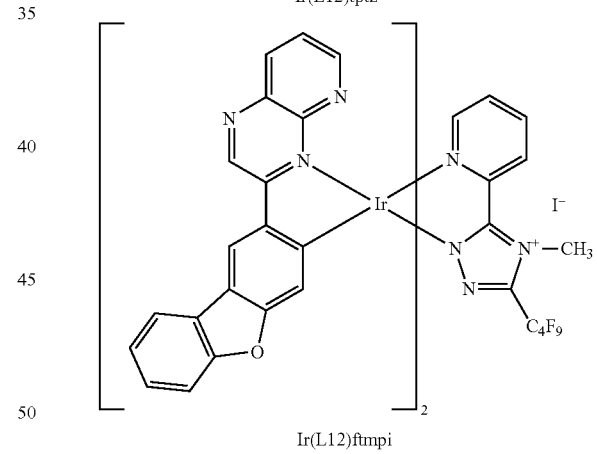
Ir(L12)ftmpi
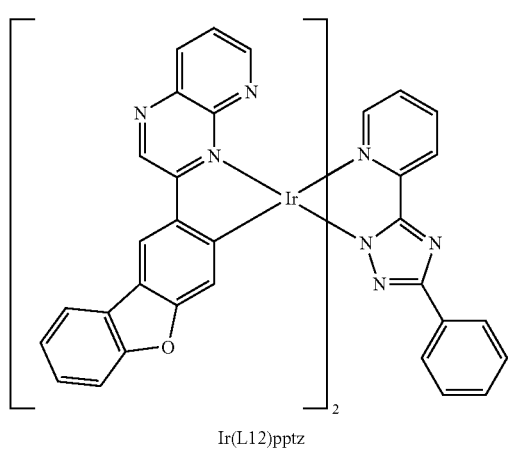
Ir(L12)pptz
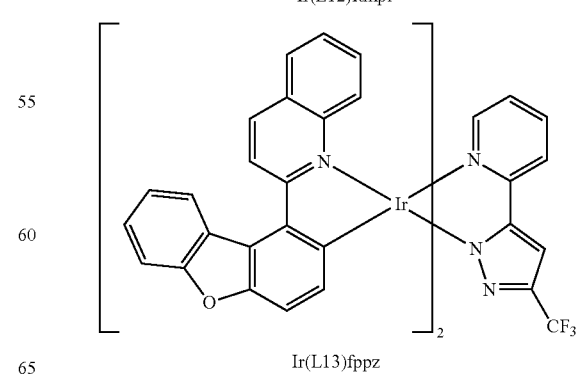
Ir(L13)fppz

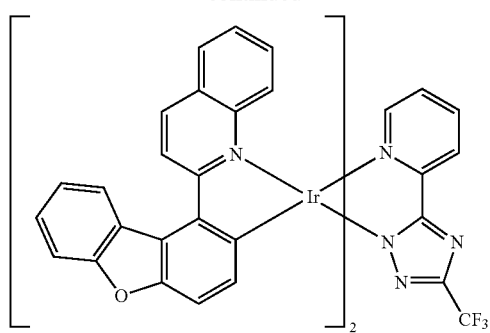
Ir(L13)fptz
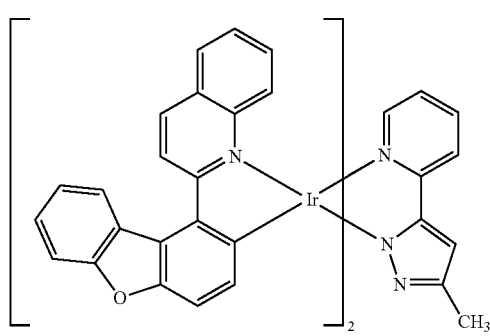
Ir(L13)mppz
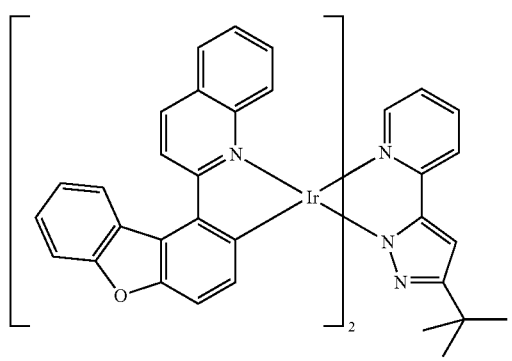
Ir(L13)bppz
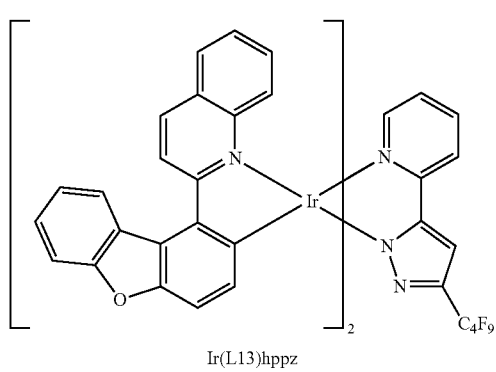
Ir(L13)hppz
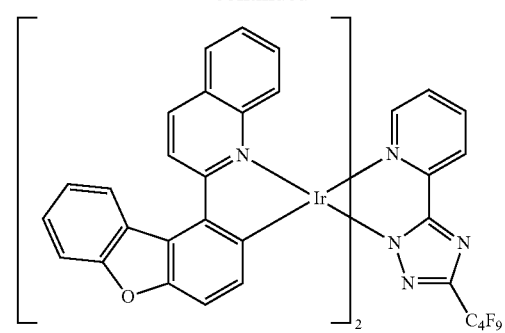
Ir(L13)hptz
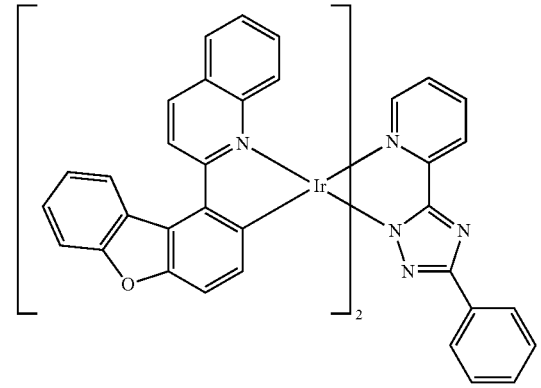
Ir(L13)pptz
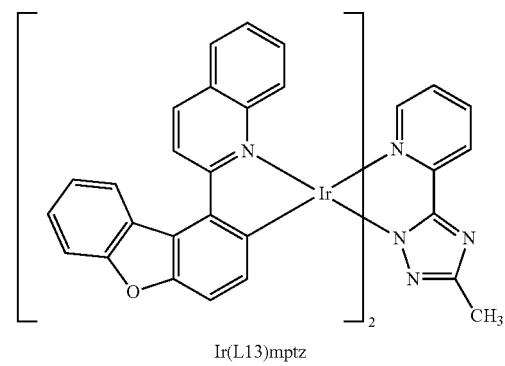
Ir(L13)mptz
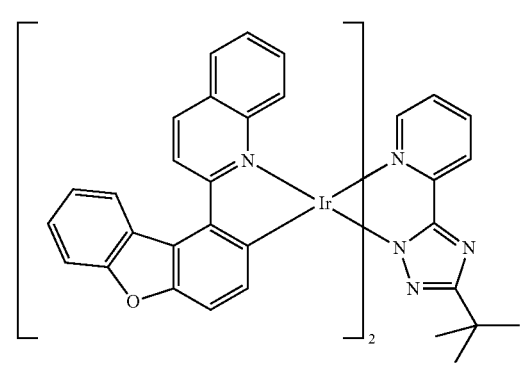
Ir(L13)tptz

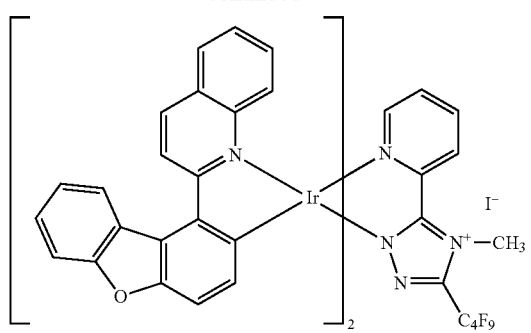
Ir(L13)ftmpi
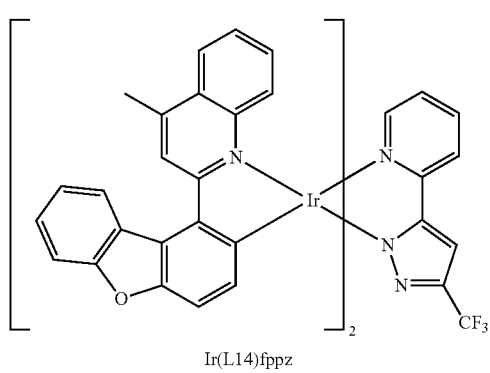
Ir(L14)fppz
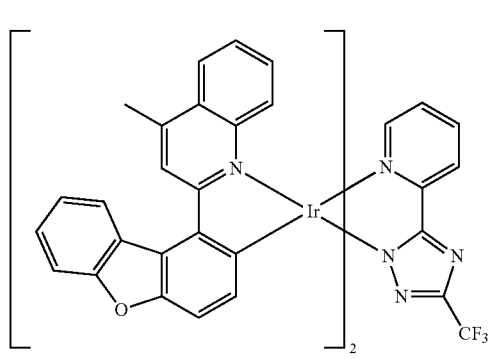
Ir(L14)fptz
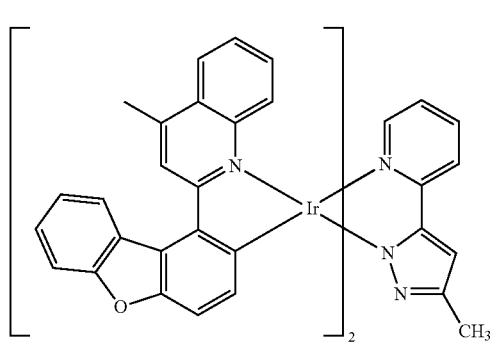
Ir(L14)mppz
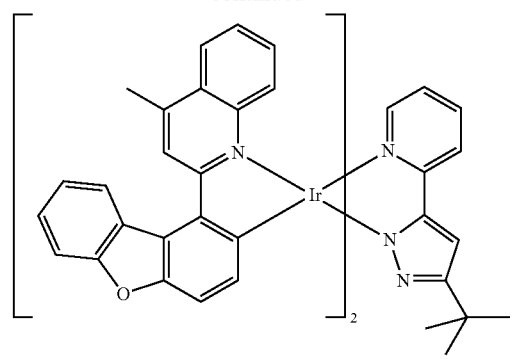
Ir(L14)bppz
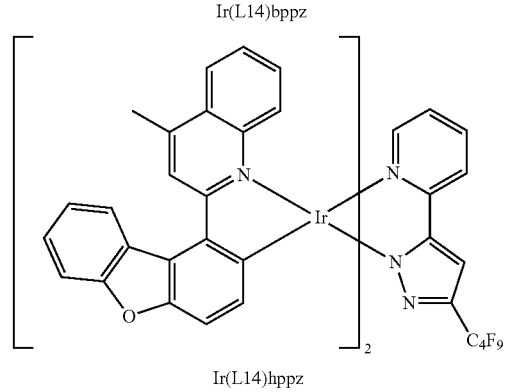
Ir(L14)hppz
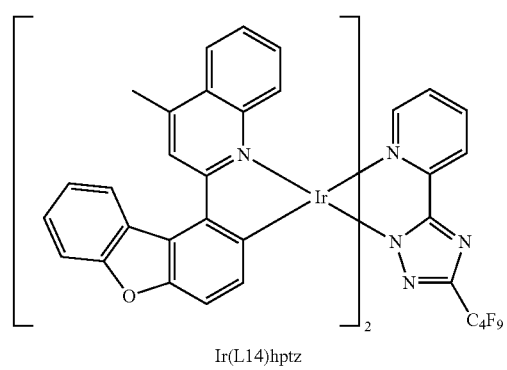
Ir(L14)hptz
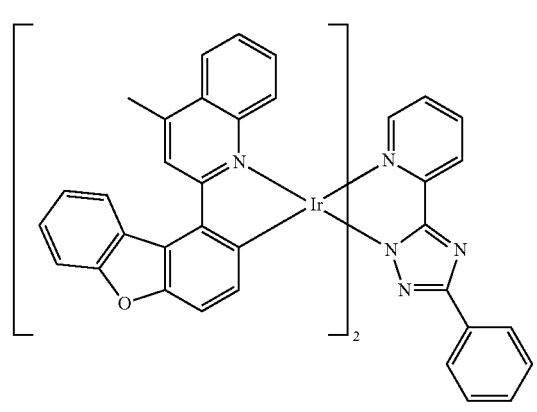
Ir(L14)pptz

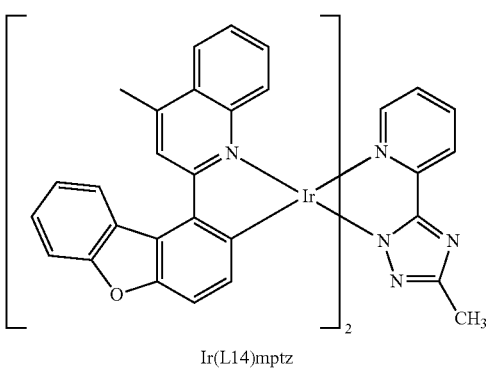
Ir(L14)mptz
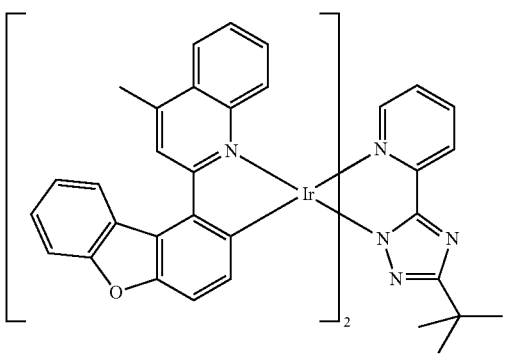
Ir(L14)tptz
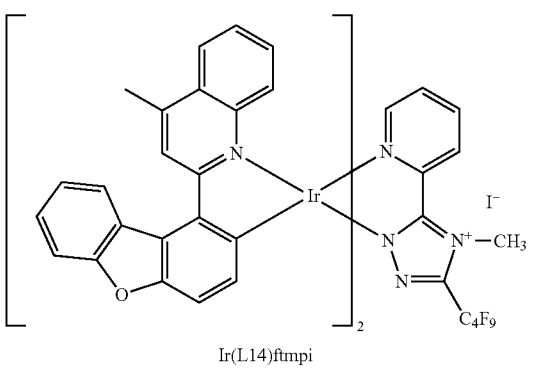
Ir(L14)ftmpi
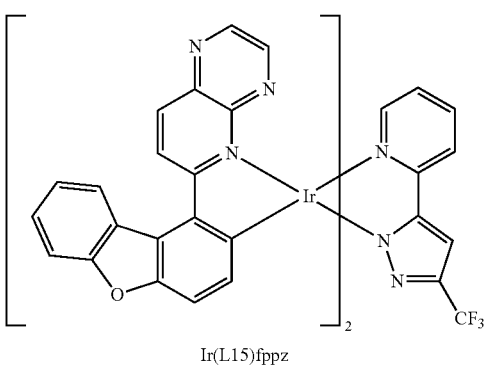
Ir(L15)fppz
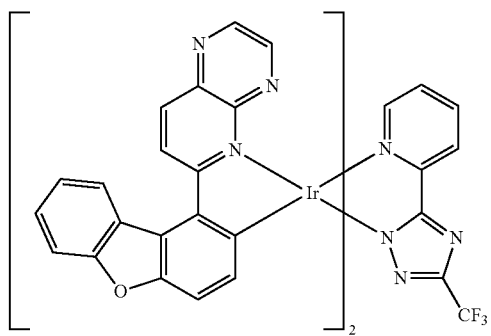
Ir(L15)fptz
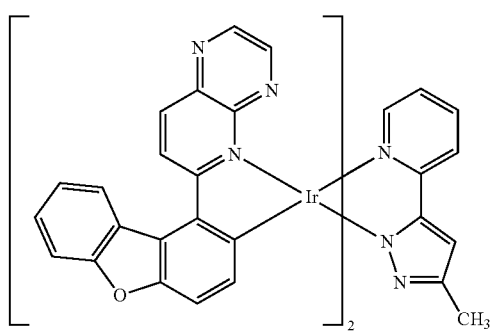
Ir(L15)mppz
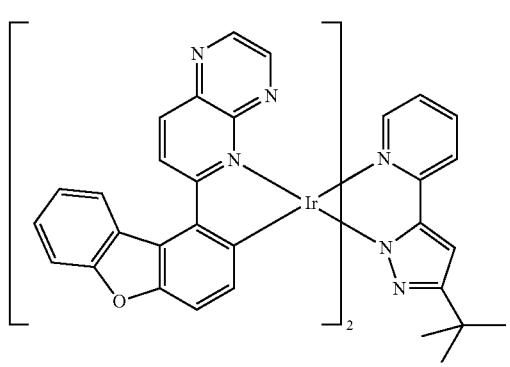
Ir(L15)bppz
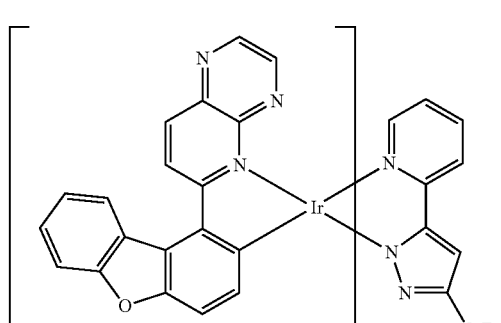
Ir(L15)hppz 199
-continued
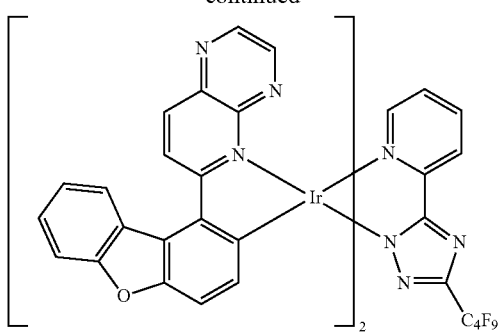
Ir(L15)hptz
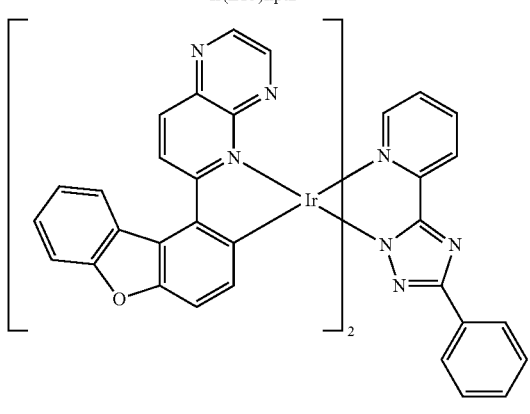
Ir(L15)pptz
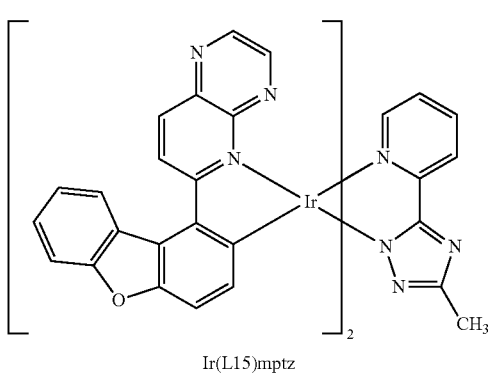
Ir(L15)mptz
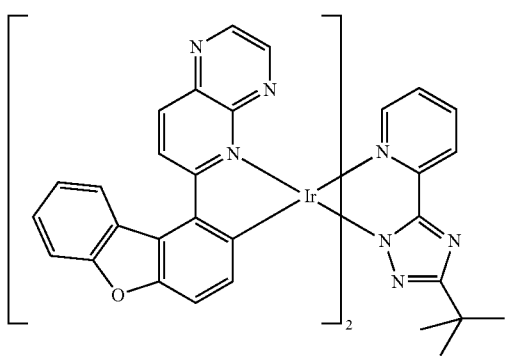
Ir(L15)tptz
200
-continued
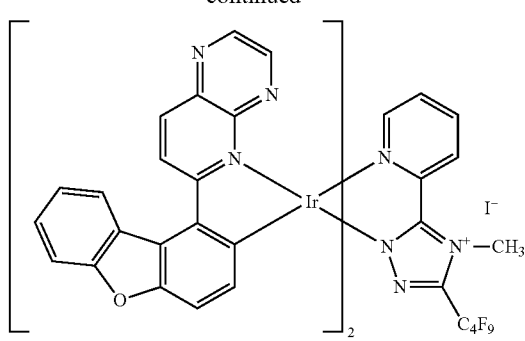
Ir(L15)ftmpi
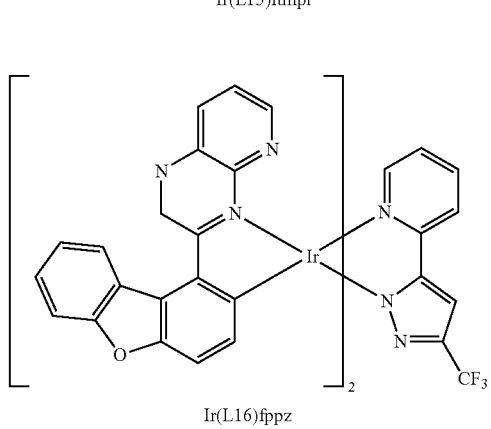
Ir(L16)fppz
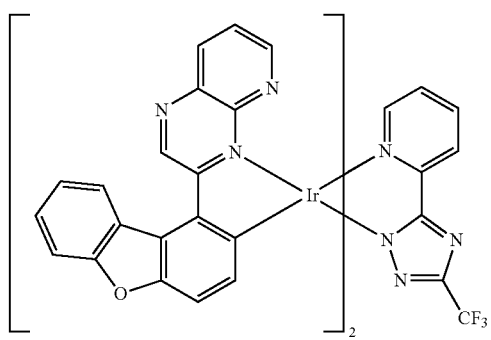
Ir(L16)fptz
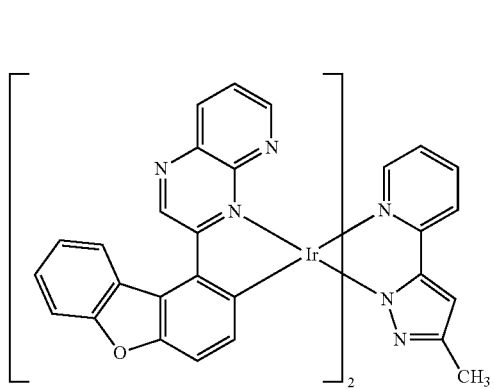
Ir(L16)mppz

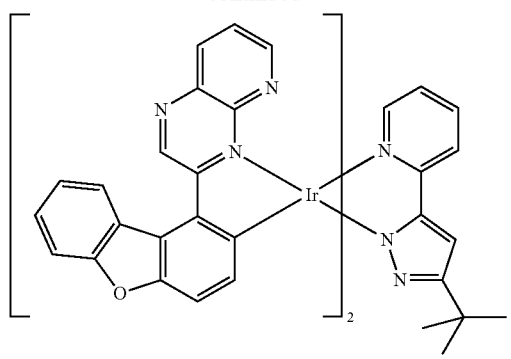
Ir(L16)bppz
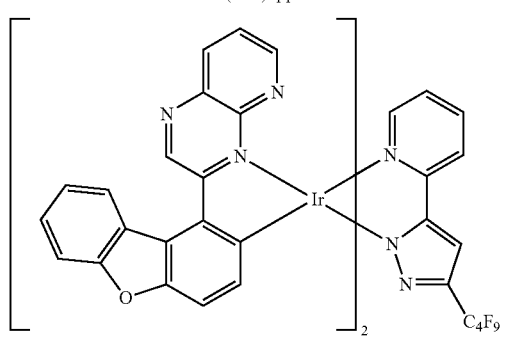
Ir(L16)hppz
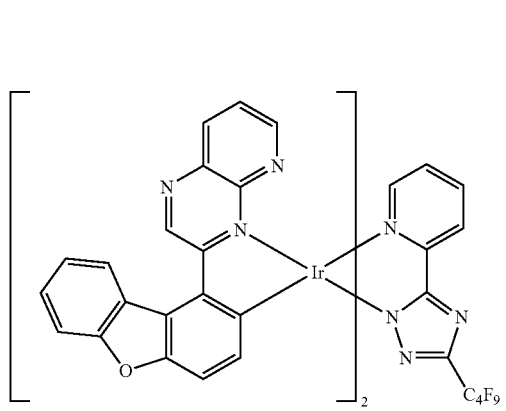
Ir(L16)hptz
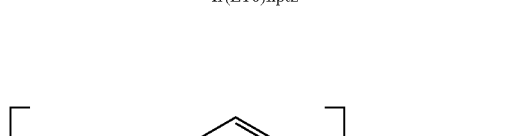
Ir(L16)pptz
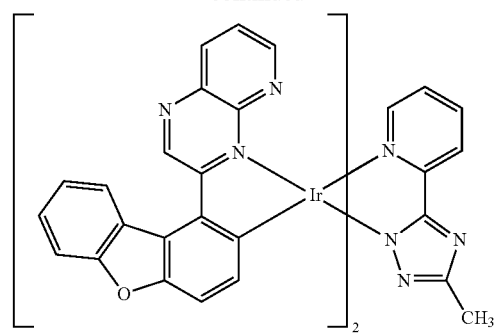
Ir(L16)mptz
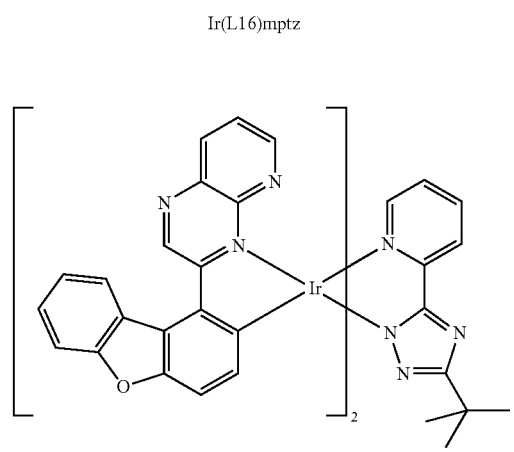
Ir(L16)tptz
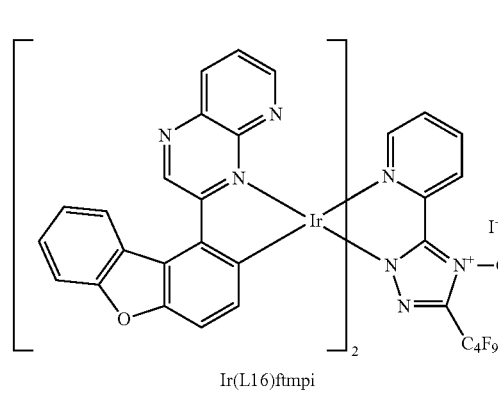
Ir(L16)ftmpi
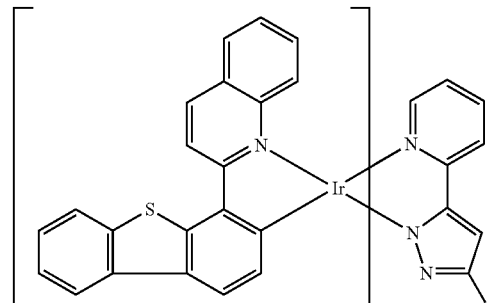
Ir(L17)fppz

203
-continued
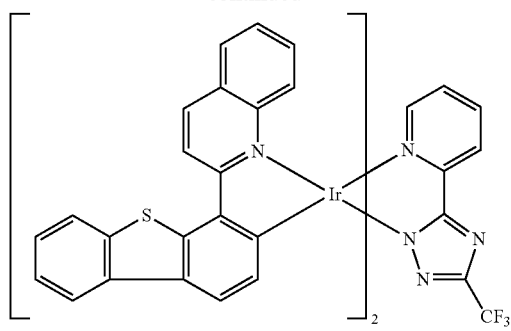
Ir(L17)fptz
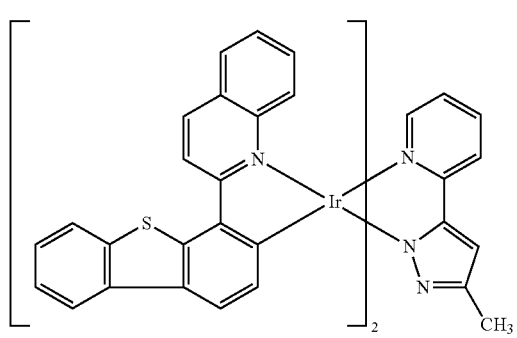
Ir(L17)mppz
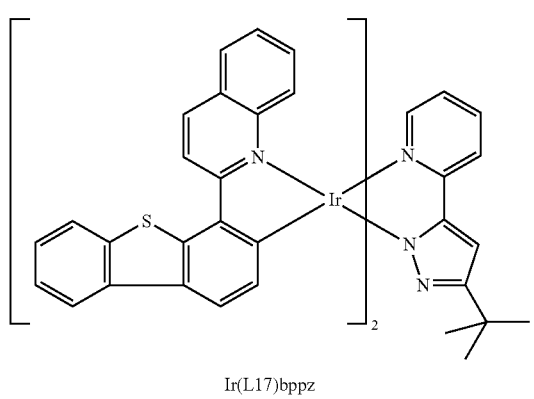
Ir(L17)bppz
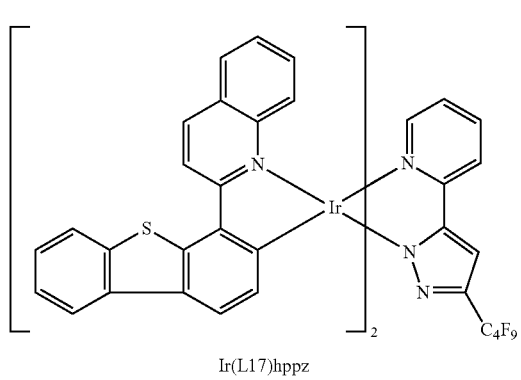
Ir(L17)hppz
204
-continued
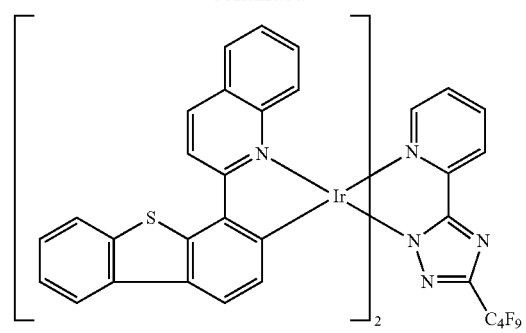
Ir(L17)hptz
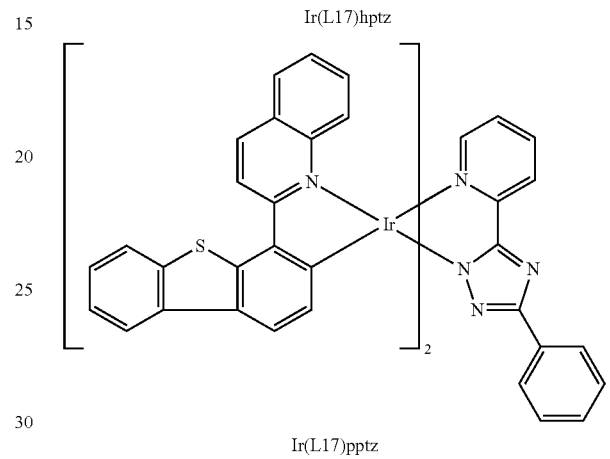
Ir(L17)pptz
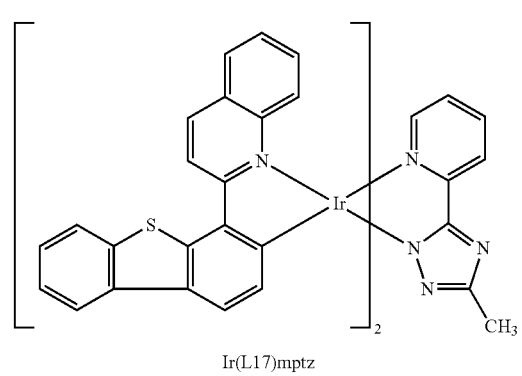
Ir(L17)mptz
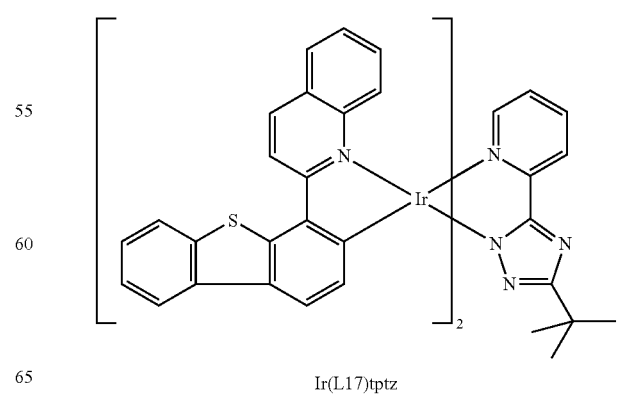
Ir(L17)tptz 205
-continued
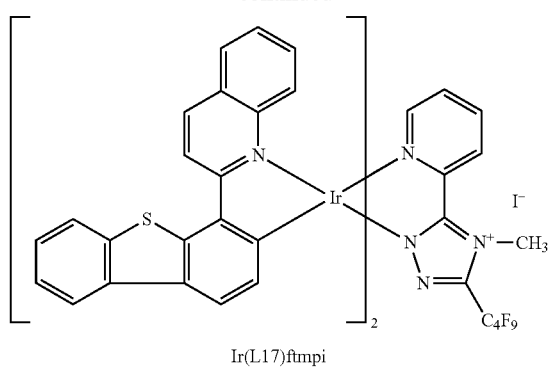
Ir(L17)ftmpi
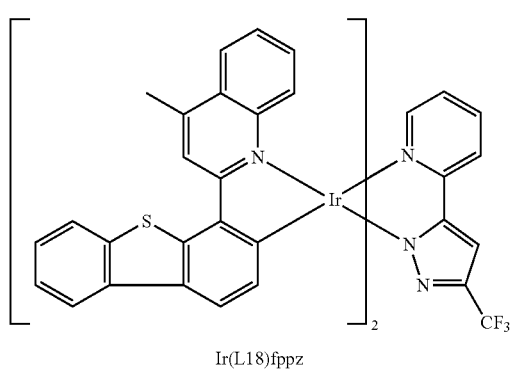
Ir(L18)fppz
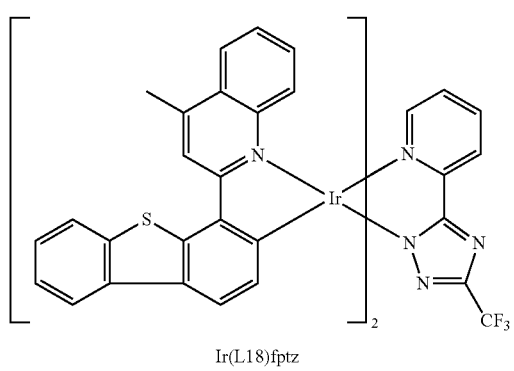
Ir(L18)fptz
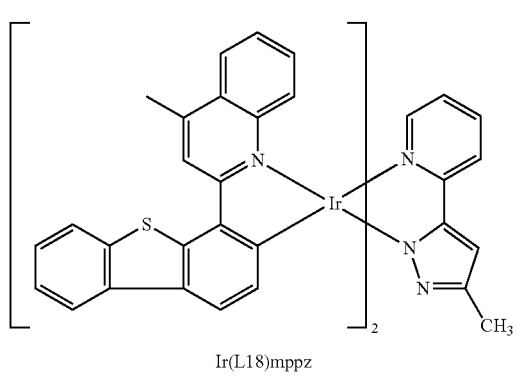
Ir(L18)mppz
206
-continued
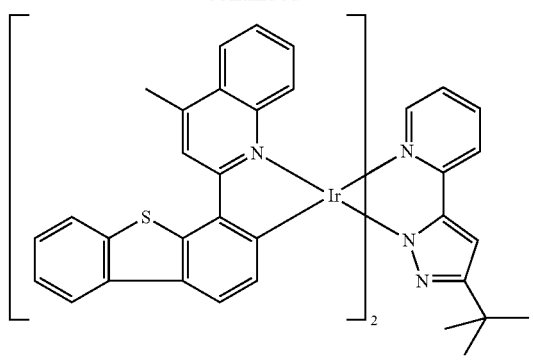
Ir(L18)bppz
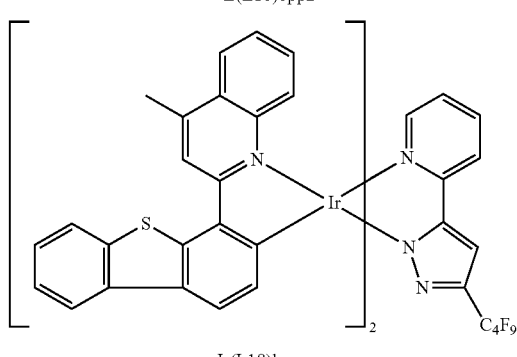
Ir(L18)hppz
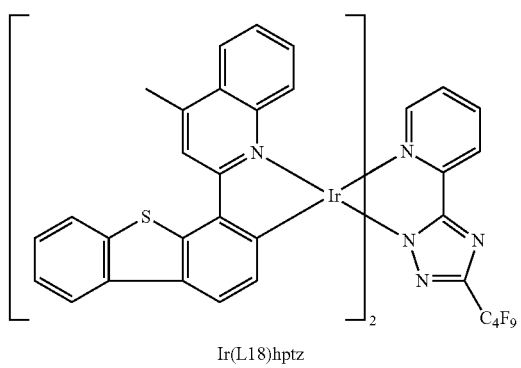
Ir(L18)hptz
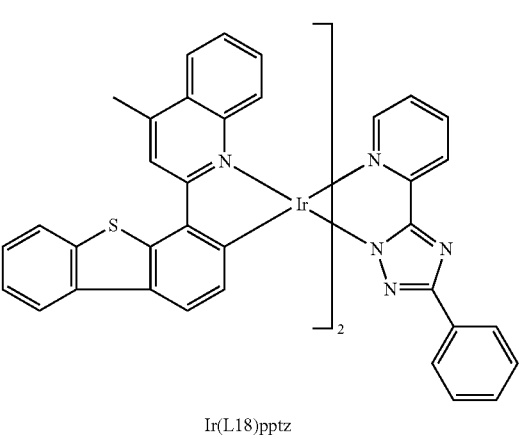
Ir(L18)pptz

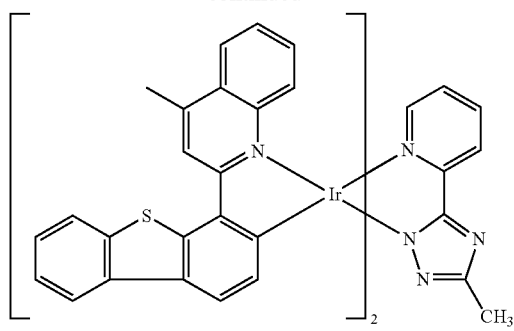
Ir(L18)mptz
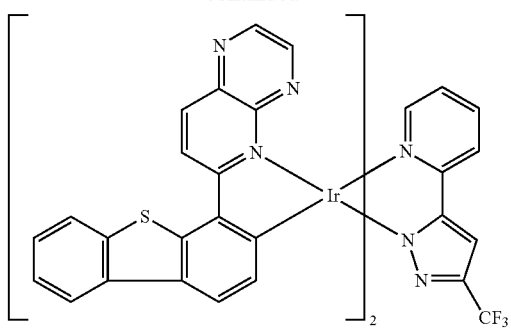
Ir(L19)fptz
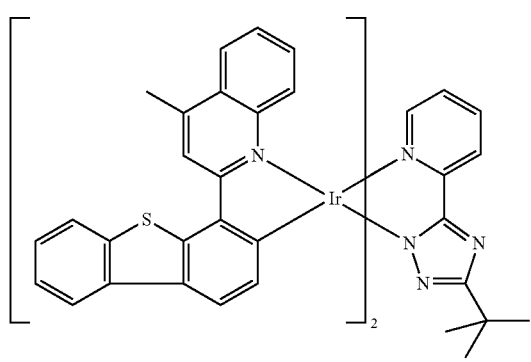
Ir(L18)tptz
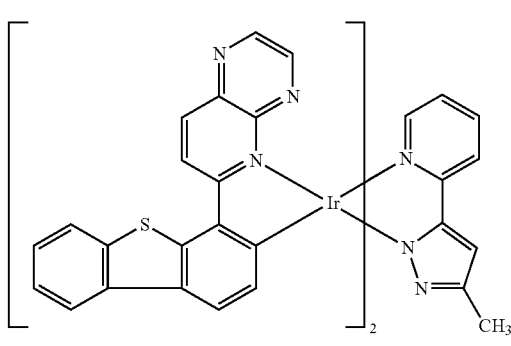
Ir(L19)mppz
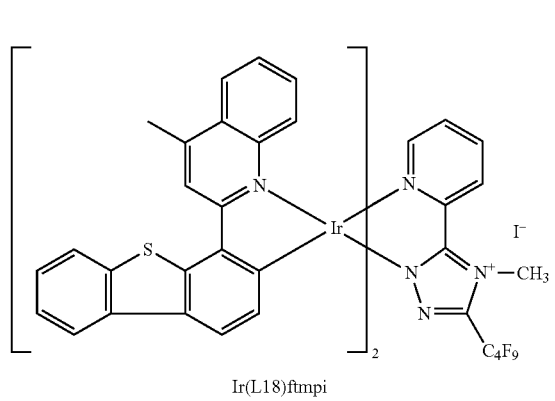
Ir(L18)ftmpi
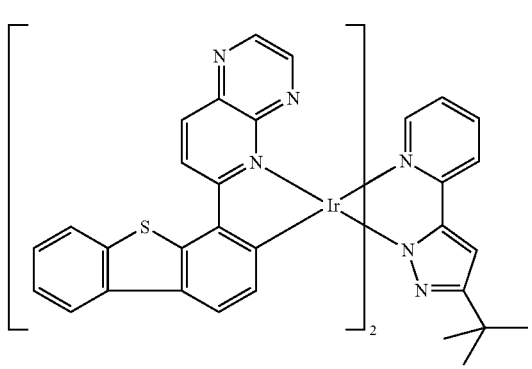
Ir(L19)bppz
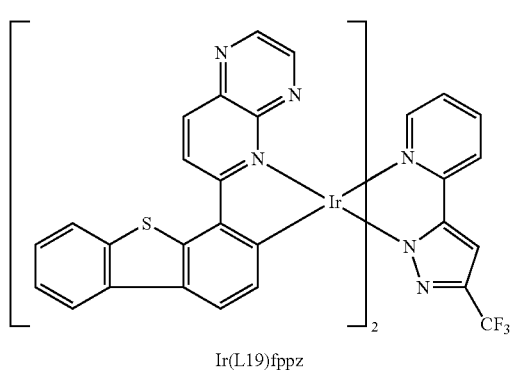
Ir(L19)fppz
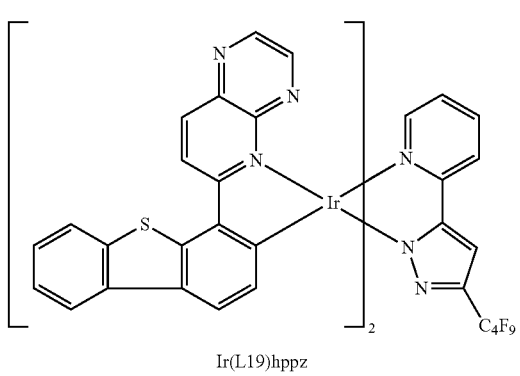
Ir(L19)hppz -continued
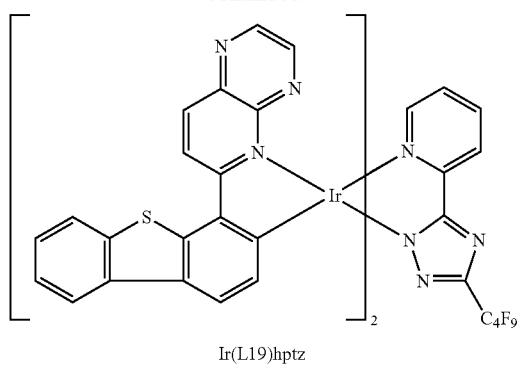
Ir(L19)hptz
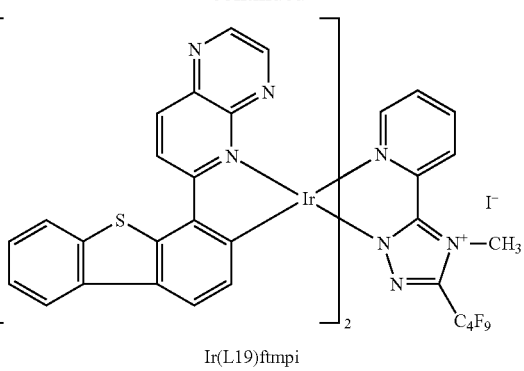
Ir(L19)ftmpi
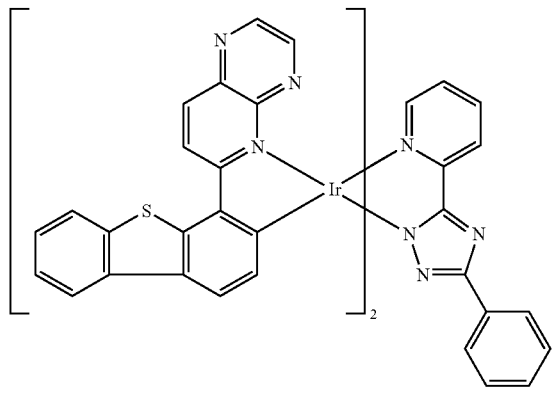
Ir(L19)pptz
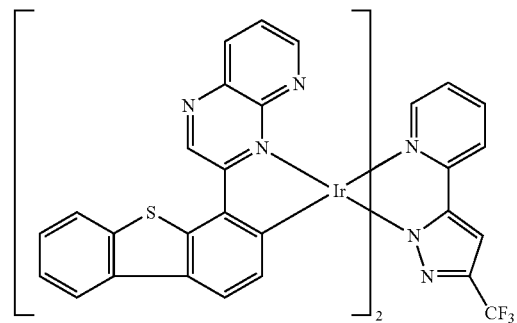
Ir(L20)fppz
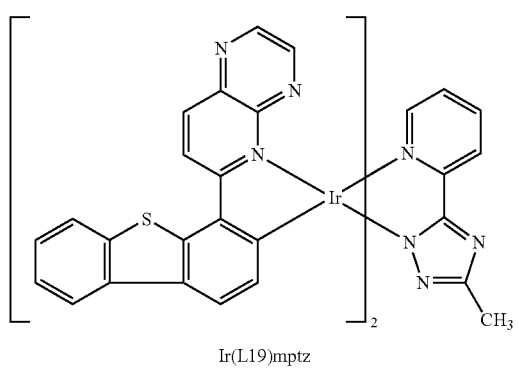
Ir(L19)mptz
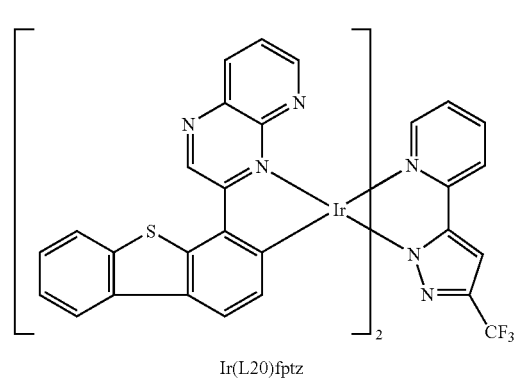
Ir(L20)fptz
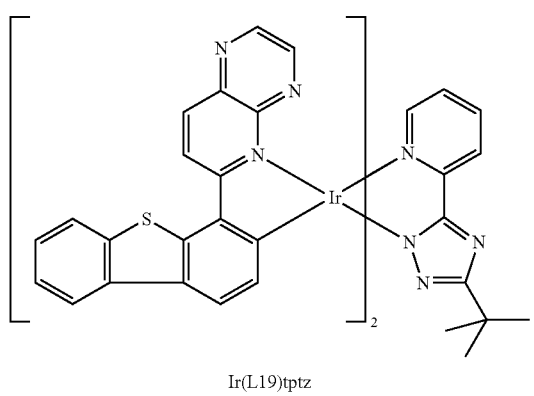
Ir(L19)tptz
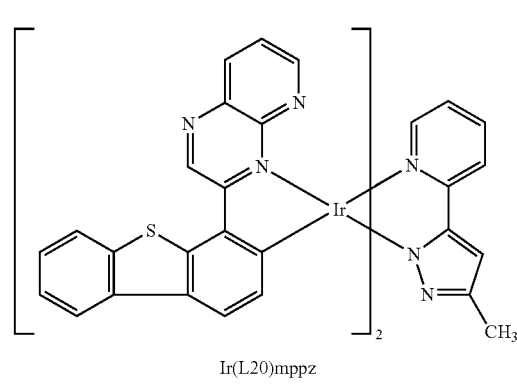
Ir(L20)mppz

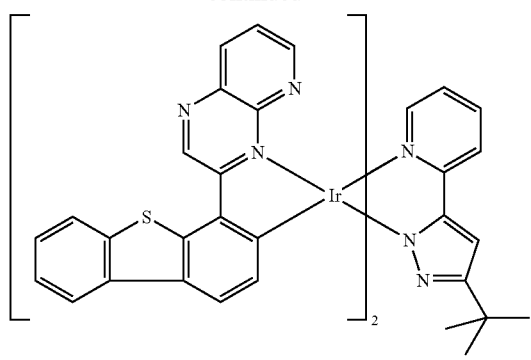
Ir(L20)bppz
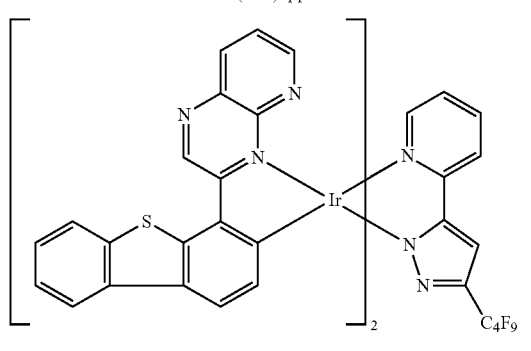
Ir(L20)hppz
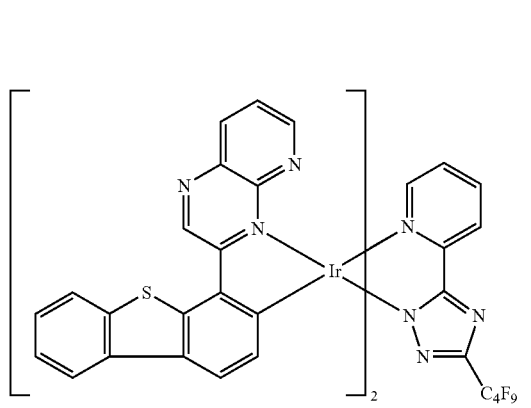
Ir(L20)hptz
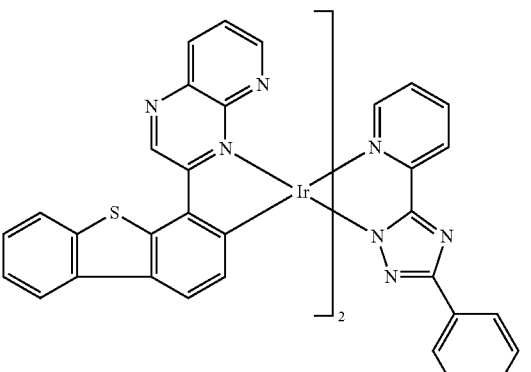
Ir(L20)pptz
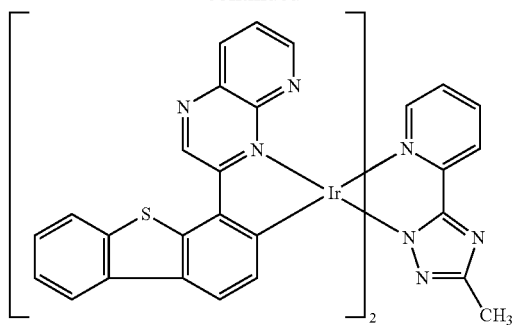
Ir(L20)mptz
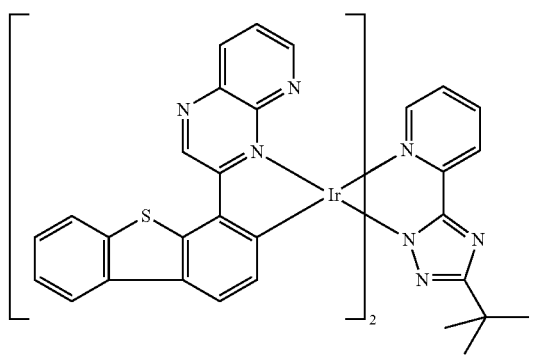
Ir(L20)tptz
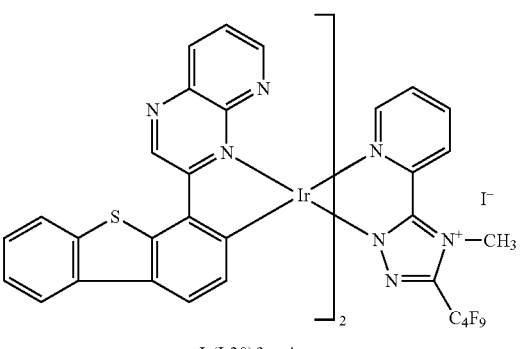
Ir(L20)ftmpi
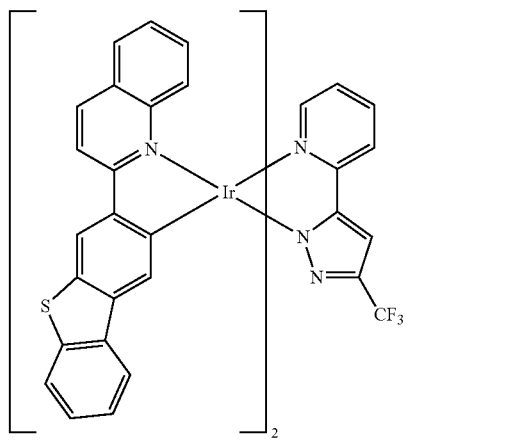
Ir(L21)fppz

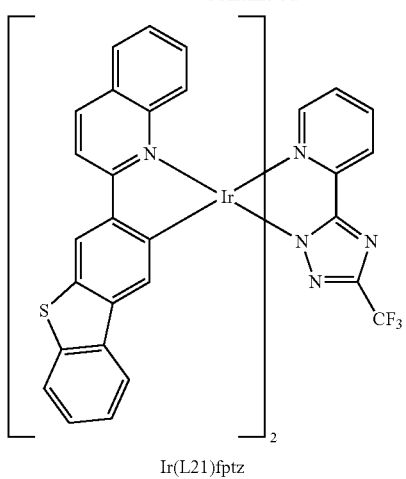
Ir(L21)fptz
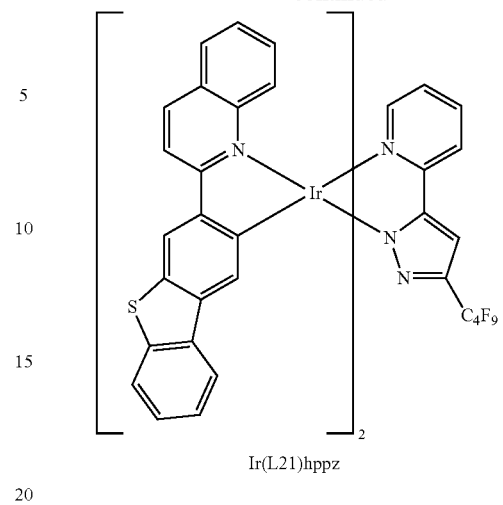
Ir(L21)hppz
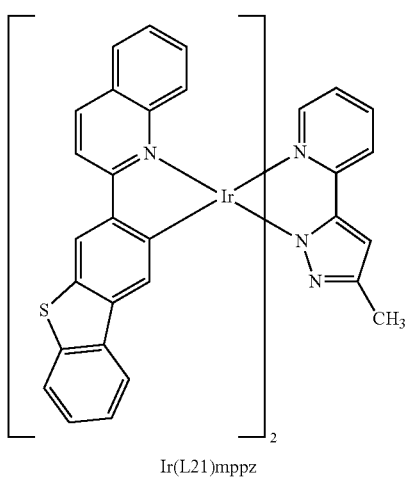
Ir(L21)mppz
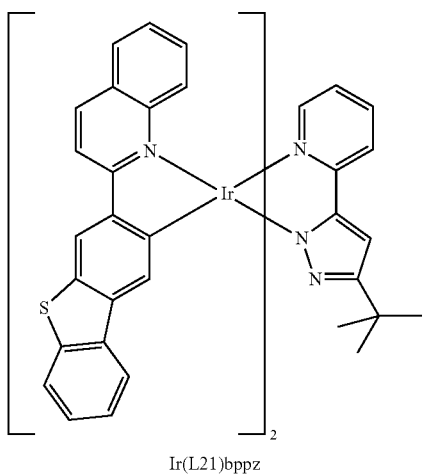
Ir(L21)bppz
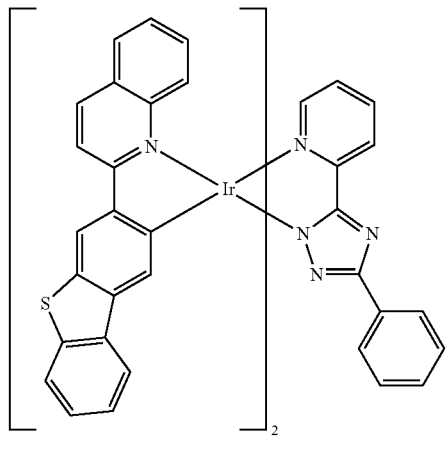
Ir(L21)hptz
Ir(L21)pptz 215
-continued
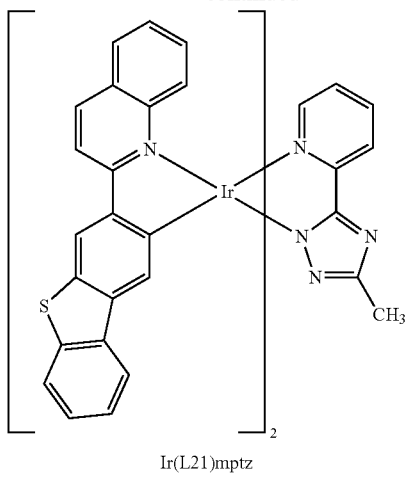
Ir(L21)mptz
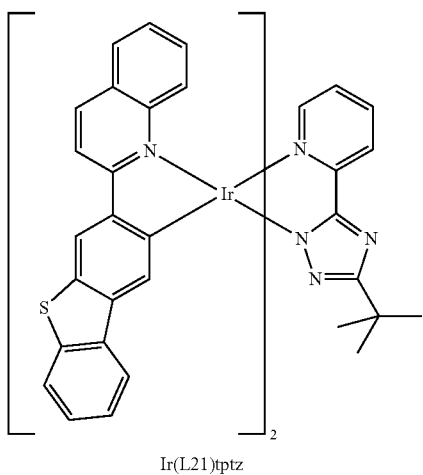
Ir(L21)tptz
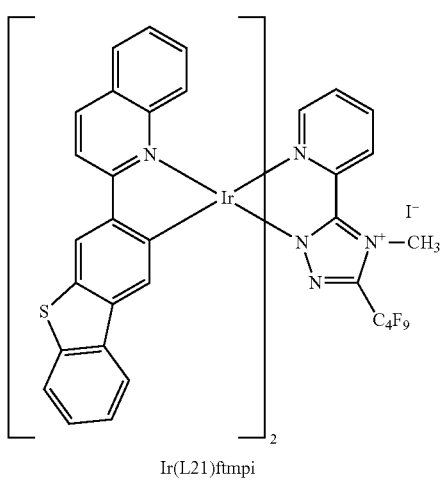
Ir(L21)ftmpi
216
-continued
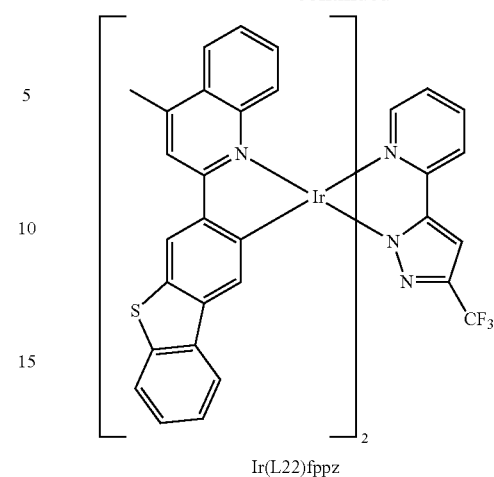
Ir(L22)fppz
Ir(L22)fptz
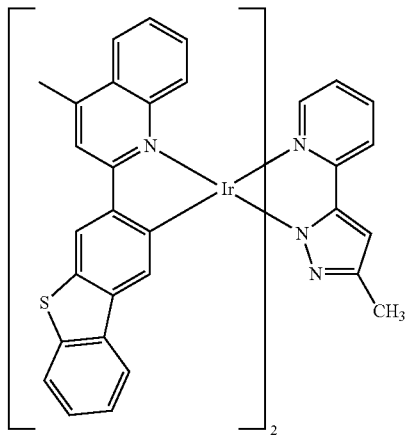
Ir(L22)mppz

217
-continued
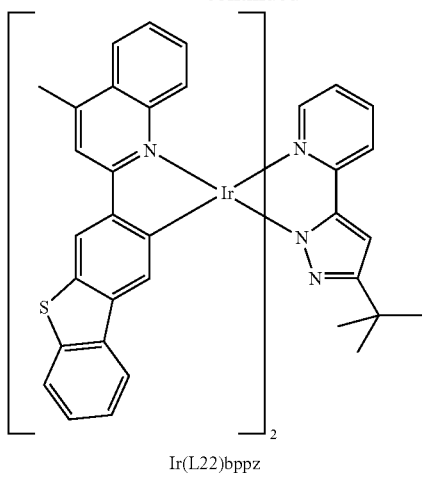
Ir(L22)bppz
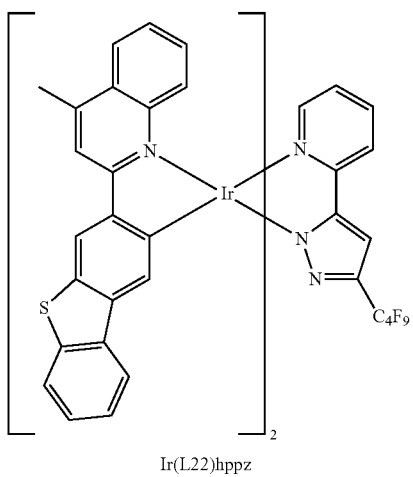
Ir(L22)hppz
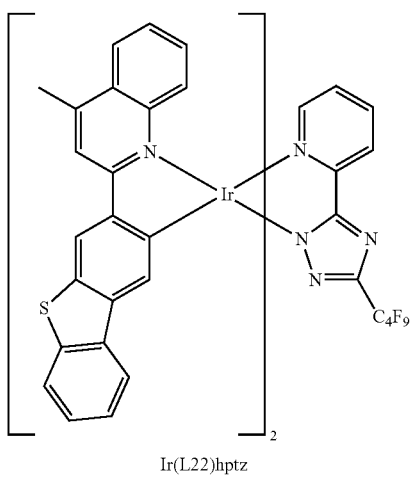
Ir(L22)hptz
218
-continued
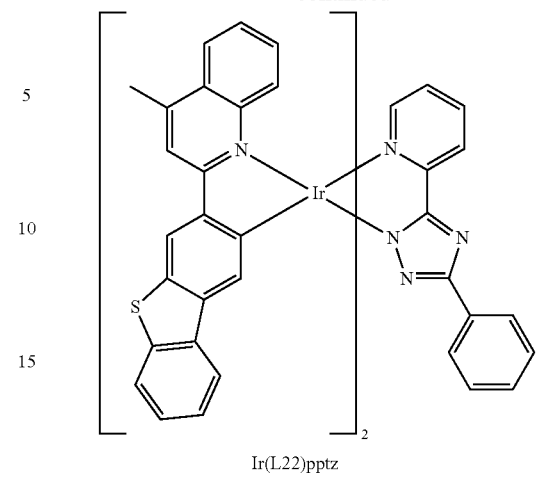
Ir(L22)pptz
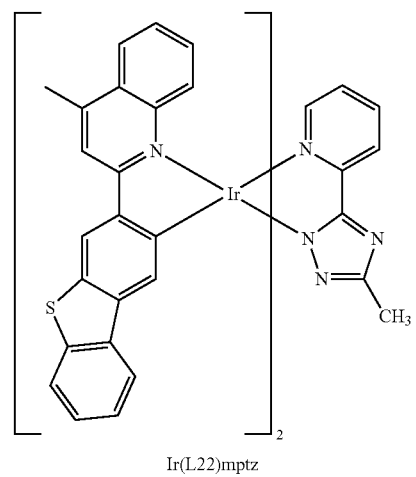
Ir(L22)mptz
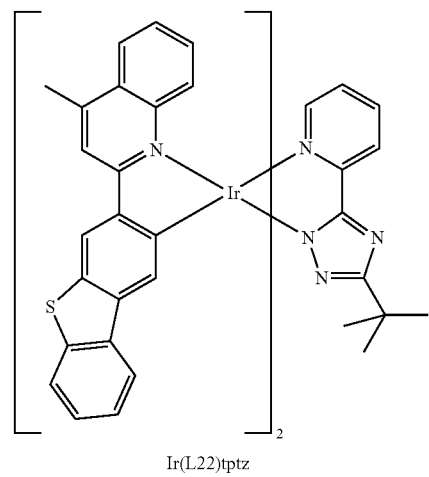
Ir(L22)tptz

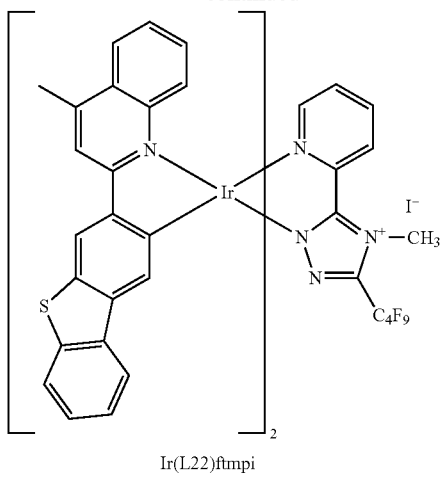
Ir(L22)ftmpi
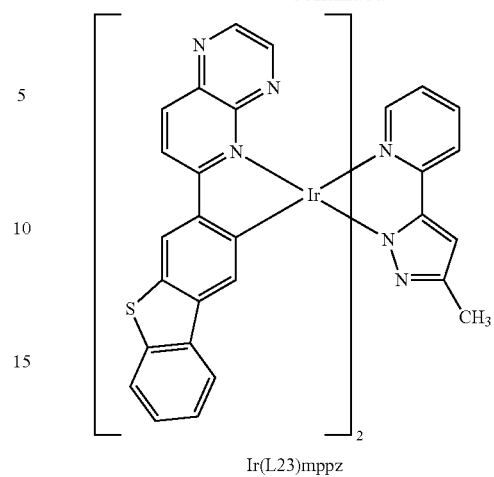
Ir(L23)mppz
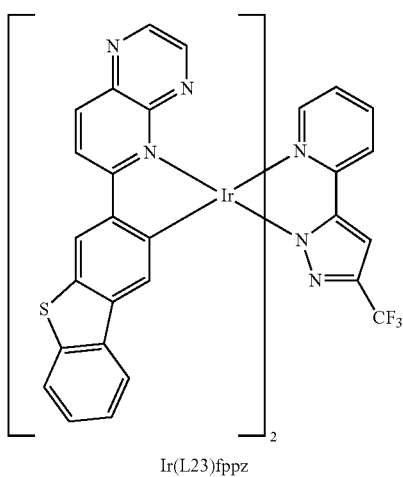
Ir(L23)fppz
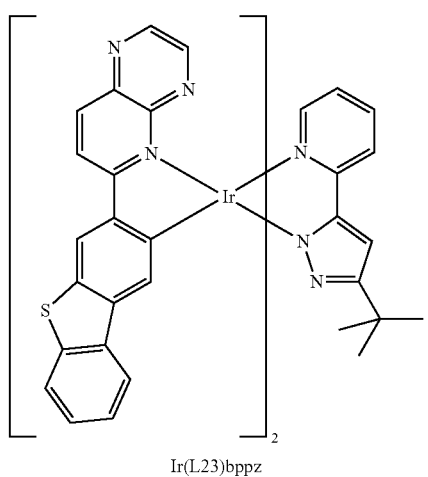
Ir(L23)bppz
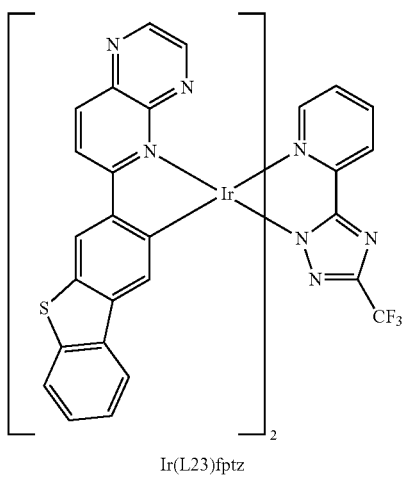
Ir(L23)fptz
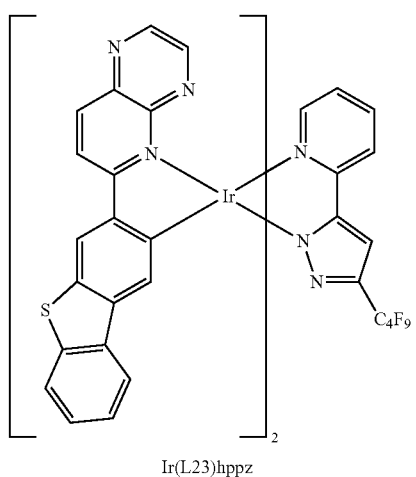
Ir(L23)hppz -continued
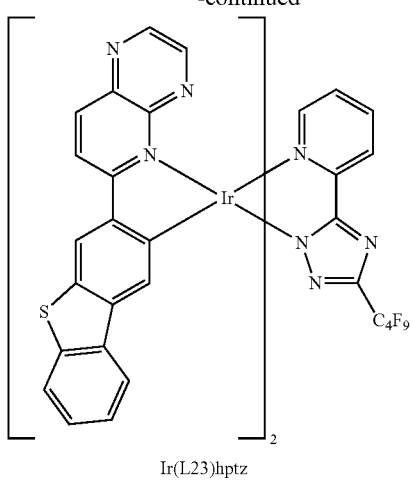
Ir(L23)hptz
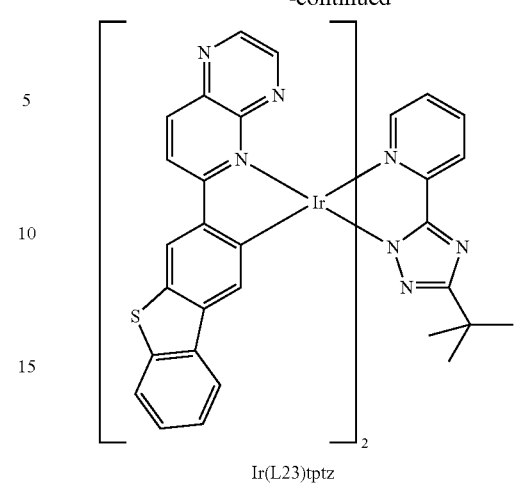
Ir(L23)tptz
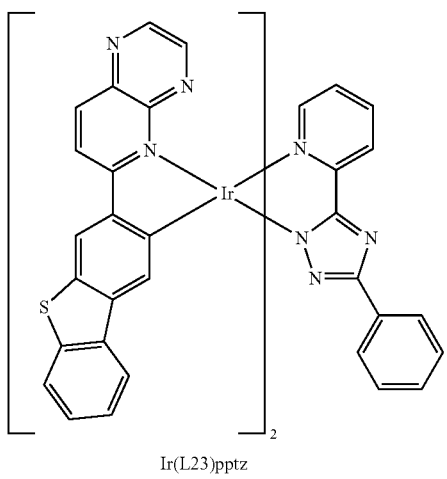
Ir(L23)pptz
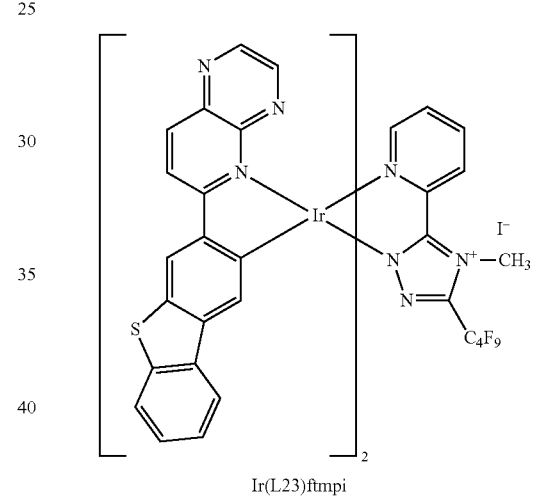
Ir(L23)ftmpi
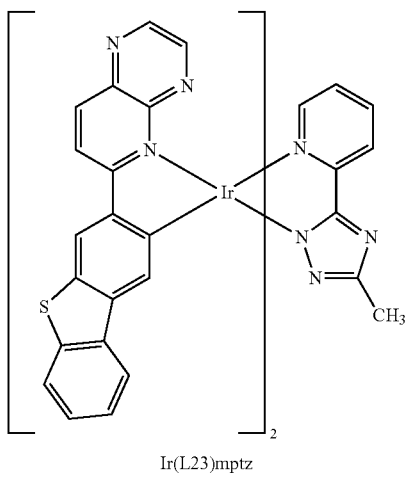
Ir(L23)mptz
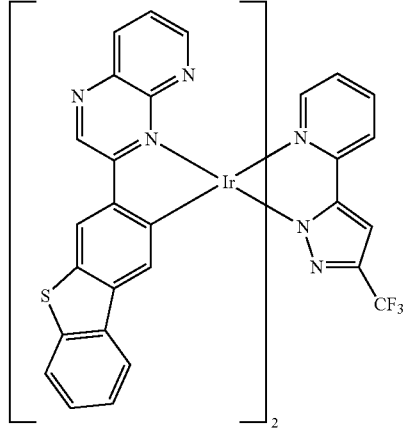
Ir(L24)fppz

223
-continued
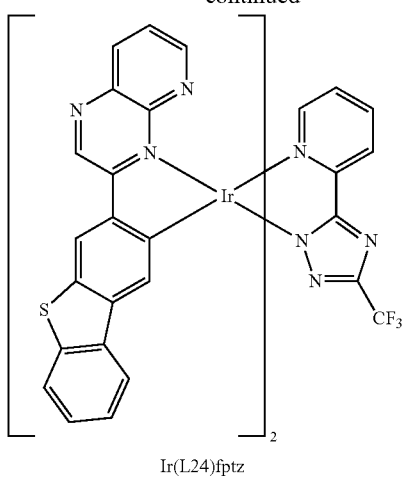
Ir(L24)fptz
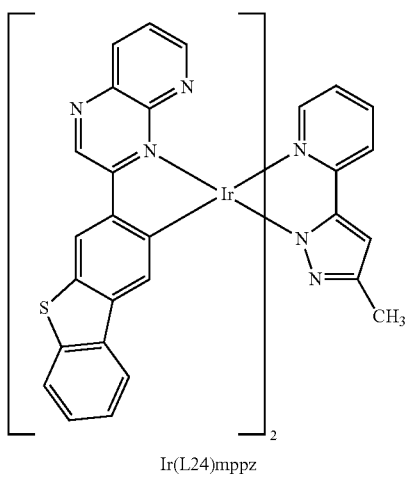
Ir(L24)mppz
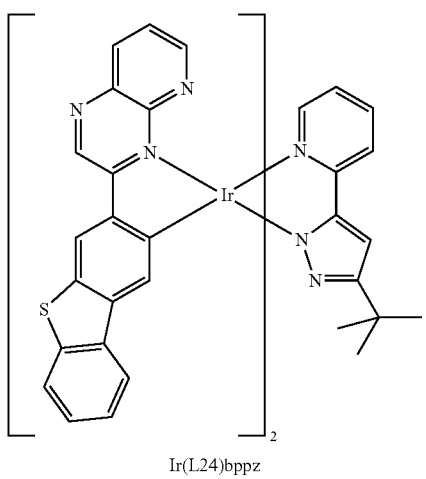
Ir(L24)bppz
224
-continued
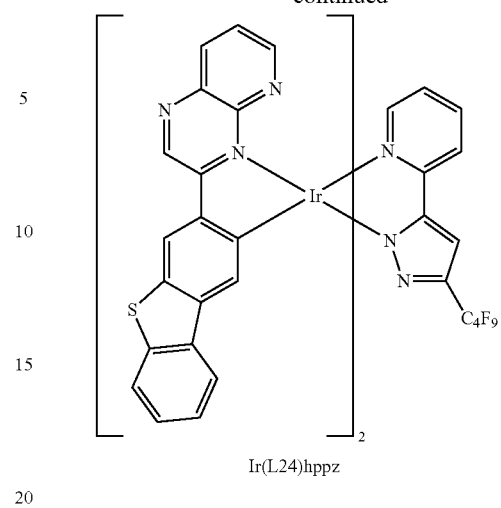
Ir(L24)hppz
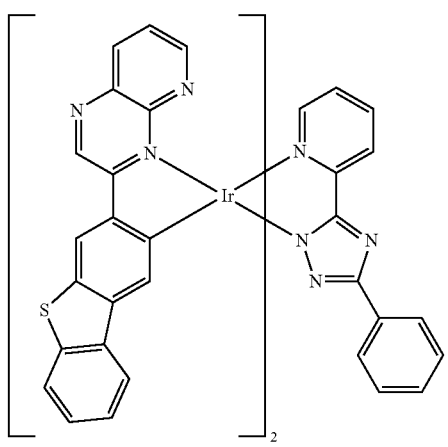
Ir(L24)hptz
Ir(L24)pptz

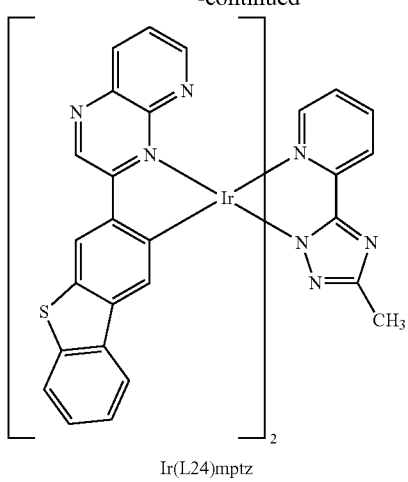
Ir(L24)mptz
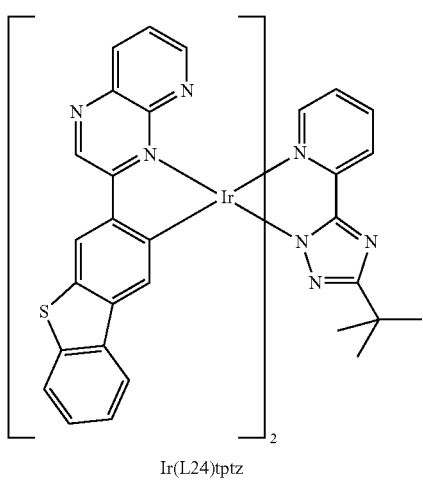
Ir(L24)tptz
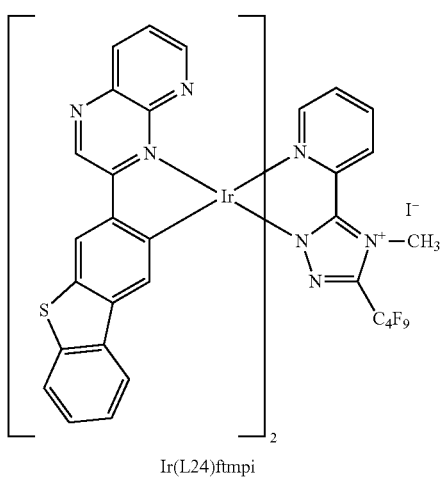
Ir(L24)ftmpi
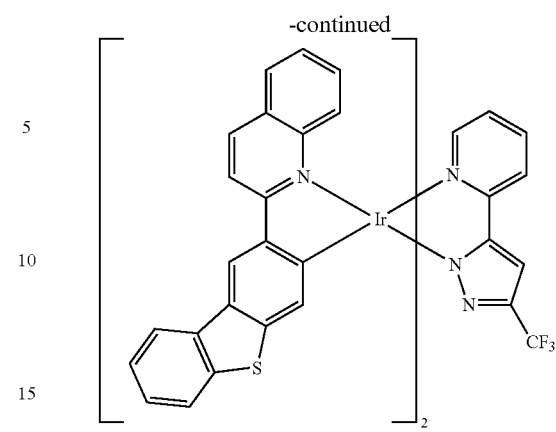
Ir(L25)fppz
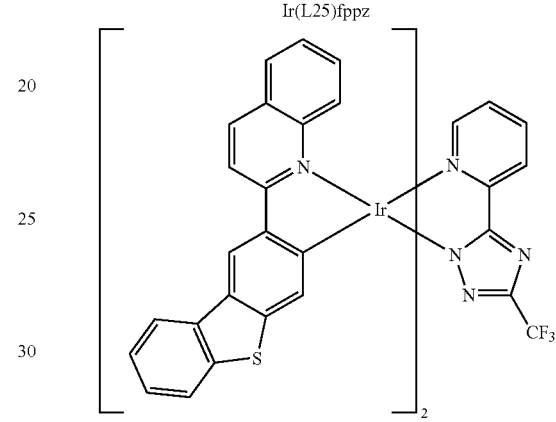
Ir(L25)fptz
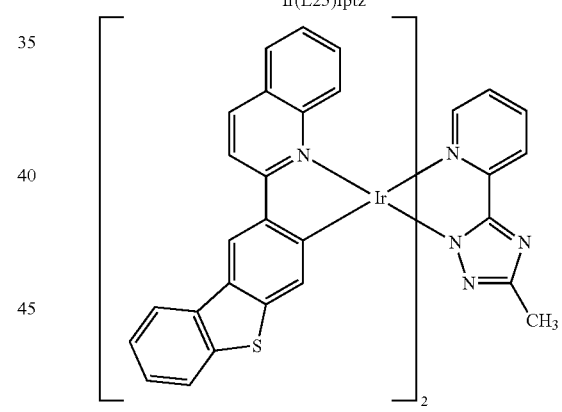
Ir(L25)mppz
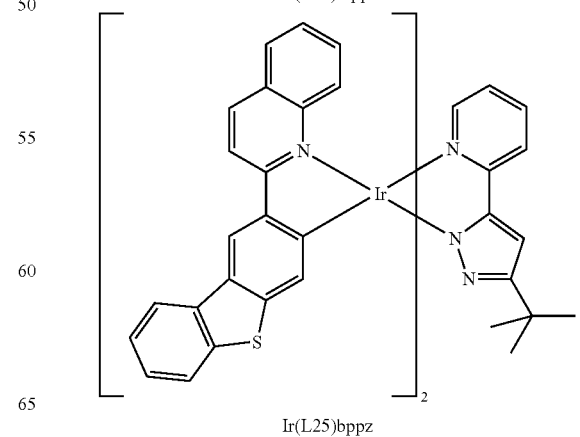
Ir(L25)bppz

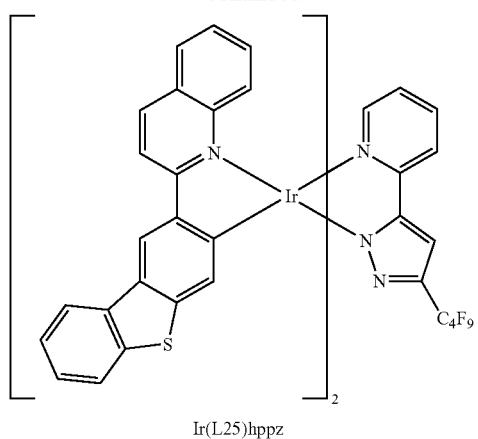
Ir(L25)hppz
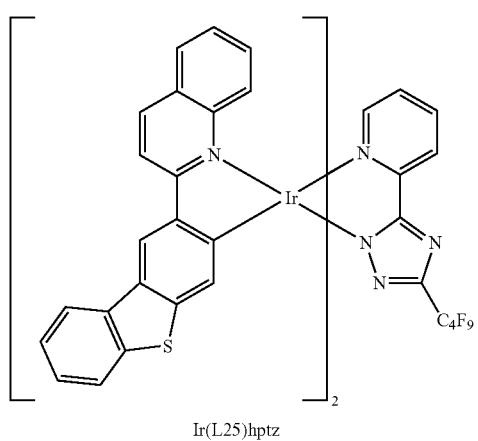
Ir(L25)hptz
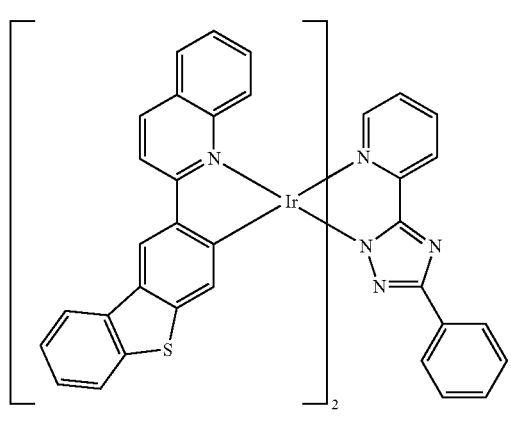
Ir(L25)pptz
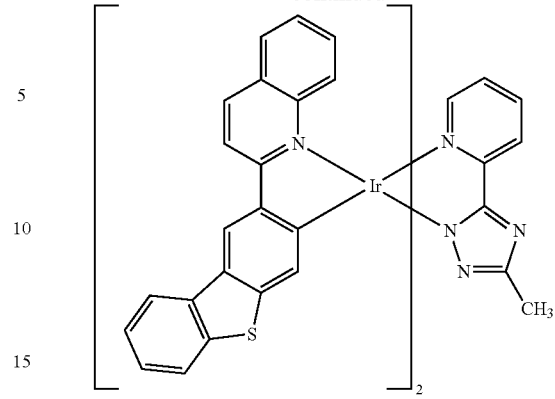
Ir(L25)mptz
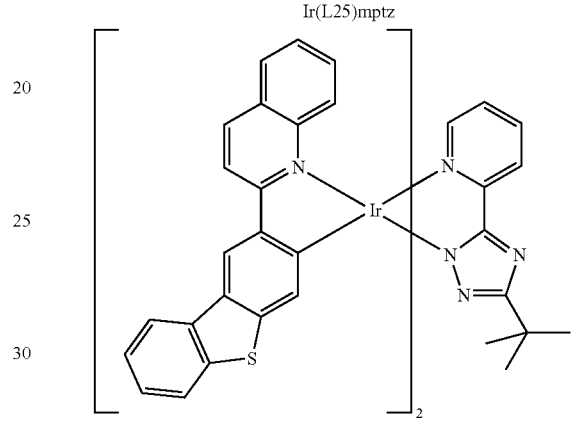
Ir(L25)tptz
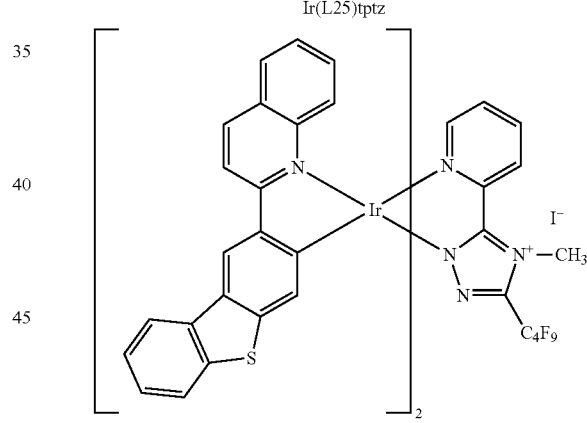
Ir(L25)ftmpi
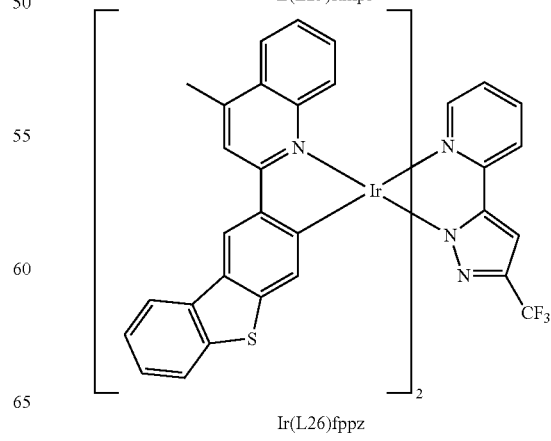
Ir(L26)fppz

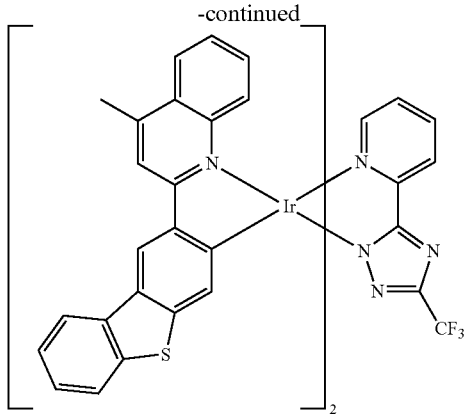
Ir(L26)fptz
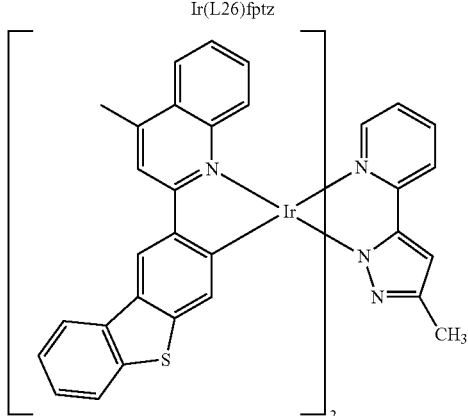
Ir(L26)mppz
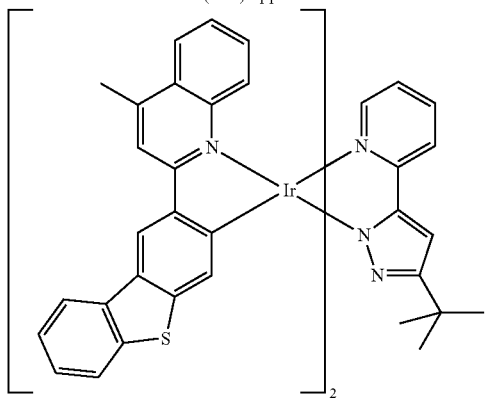
Ir(L26)bppz
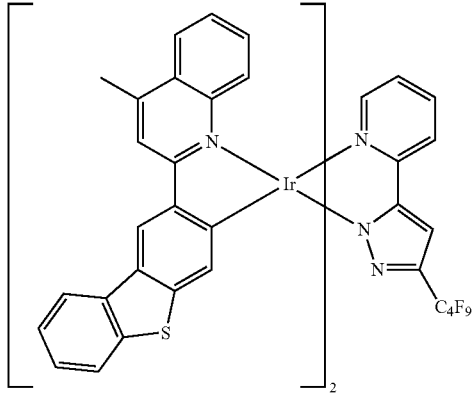
Ir(L26)hppz
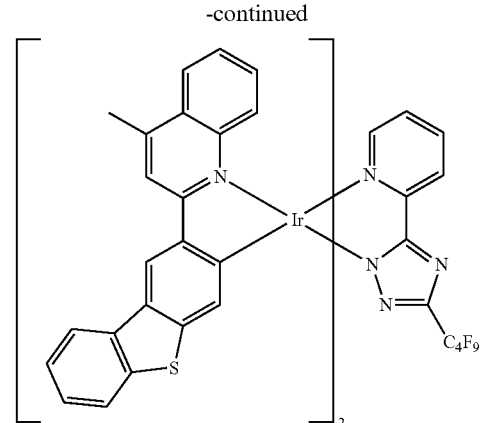
Ir(L26)hptz
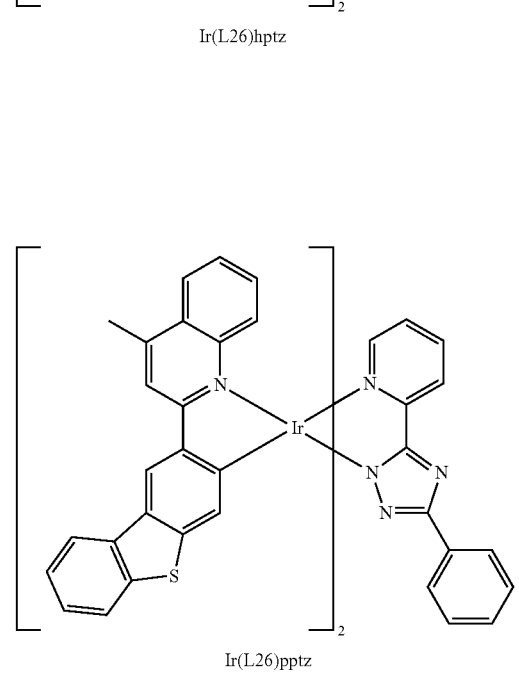
Ir(L26)pptz
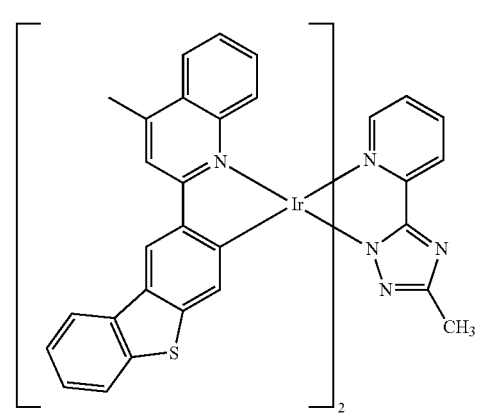
Ir(L26)mptz

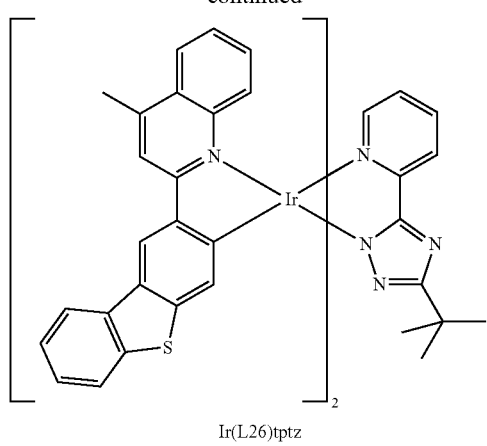
Ir(L26)tptz
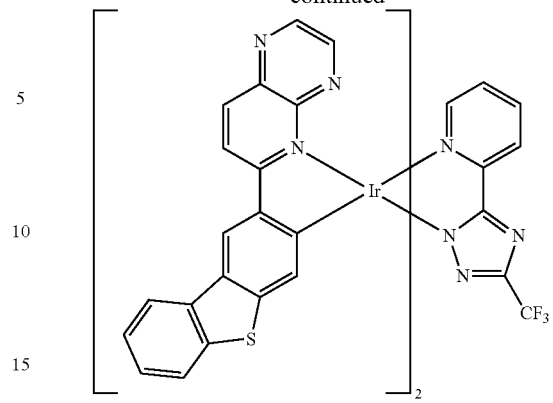
Ir(L27)fptz
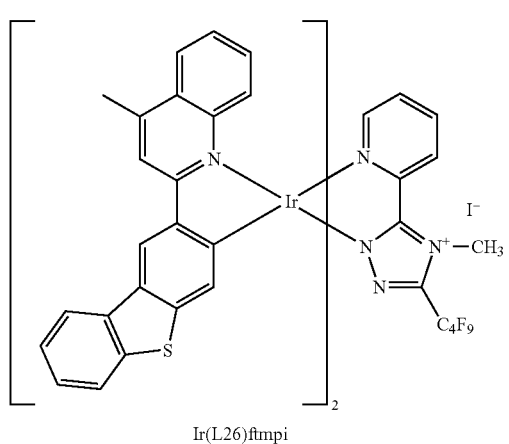
Ir(L26)ftmpi
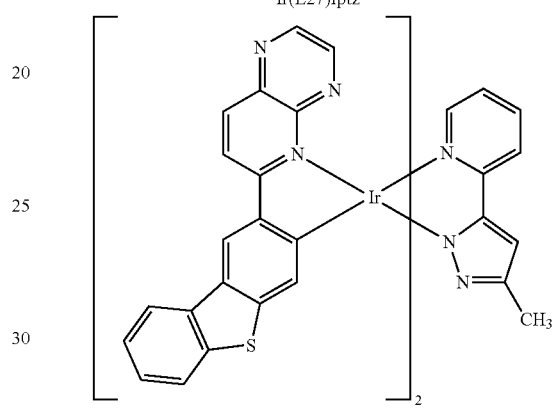
Ir(L27)mppz
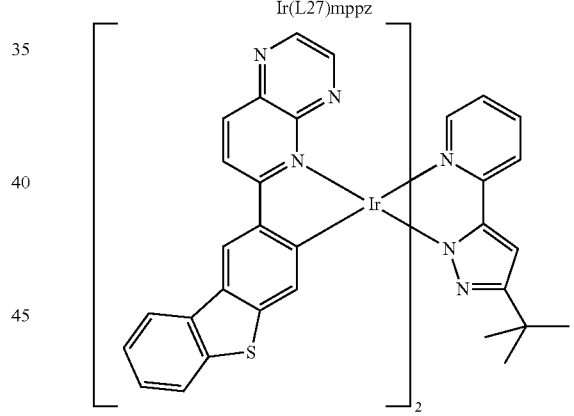
Ir(L27)bppz
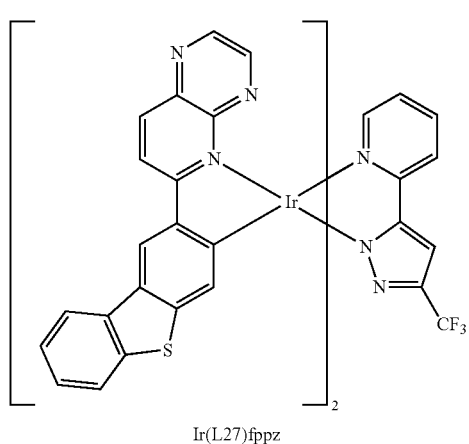
Ir(L27)fppz
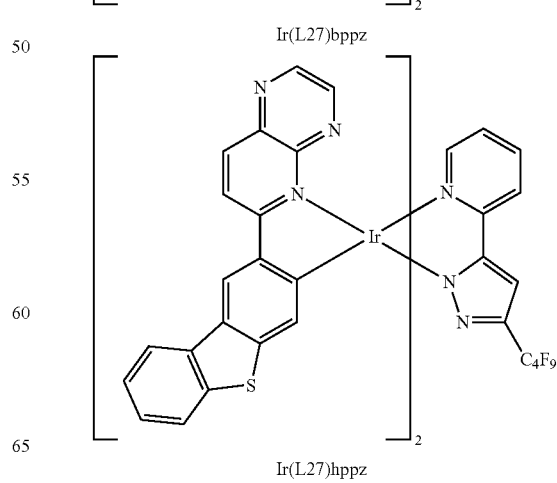
Ir(L27)hppz -continued
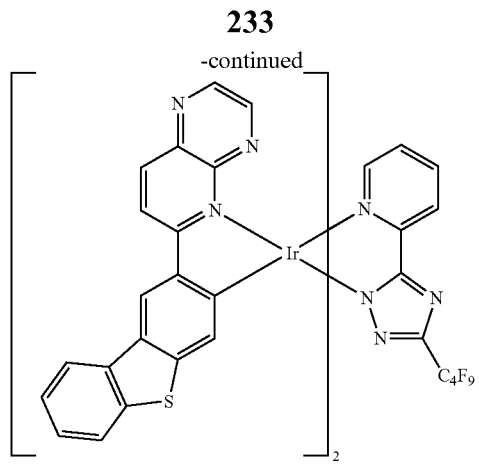
Ir(L27)hptz
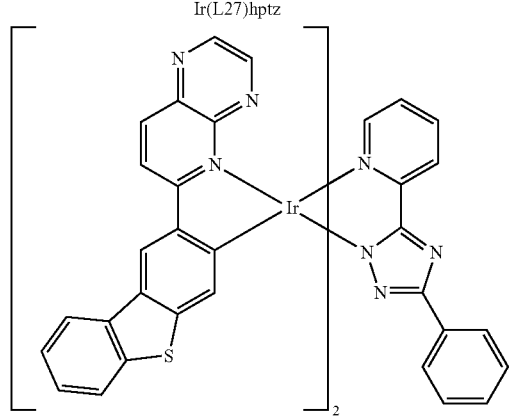
Ir(L27)pptz
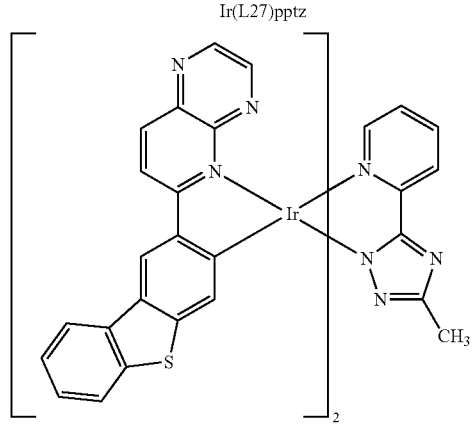
Ir(L27)mptz
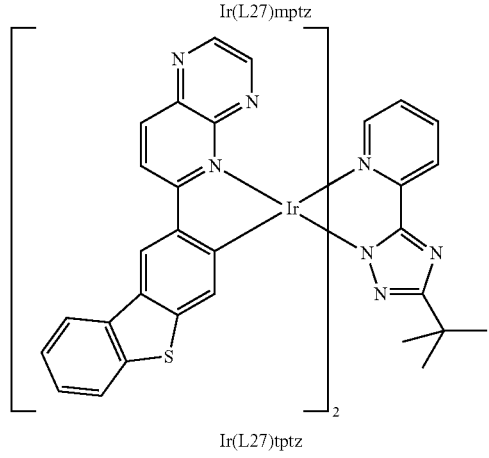
Ir(L27)tptz
-continued
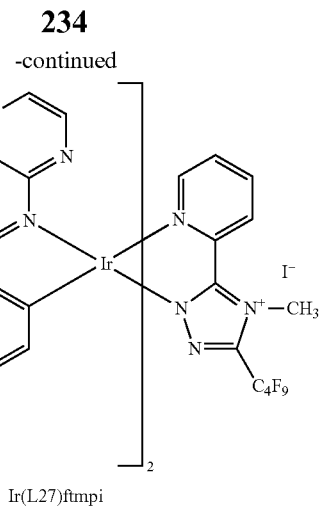
Ir(L27)ftmpi
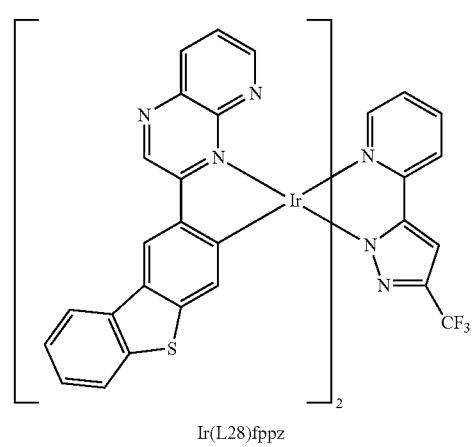
Ir(L28)fppz
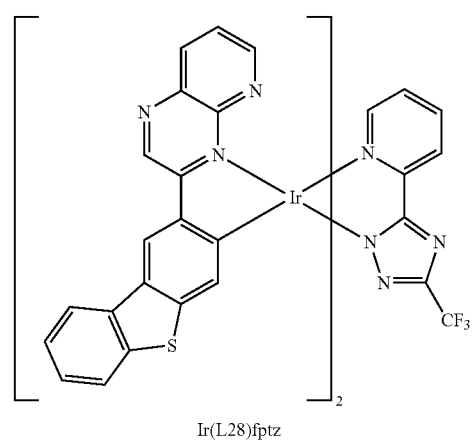
Ir(L28)fptz -continued
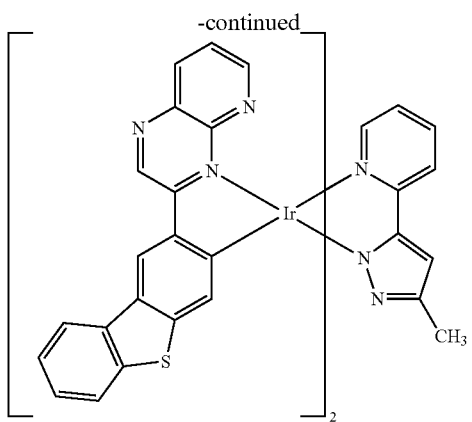
Ir(L28)mppz
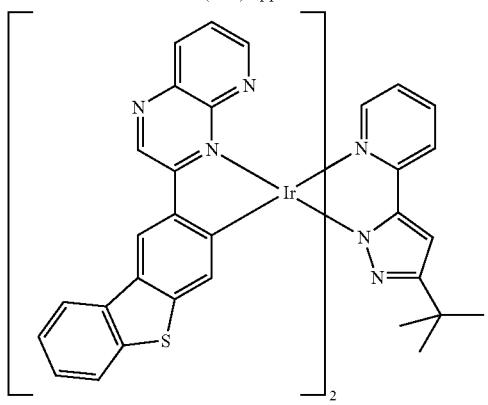
Ir(L28)bppz
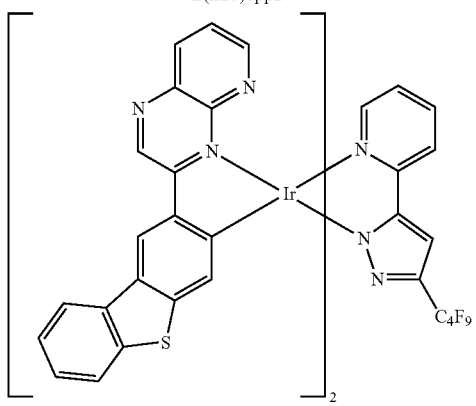
Ir(L28)hppz
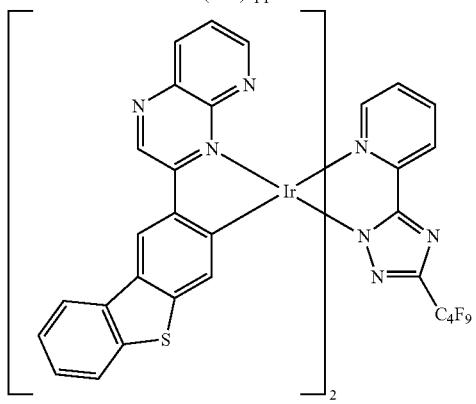
Ir(L28)hptz
-continued
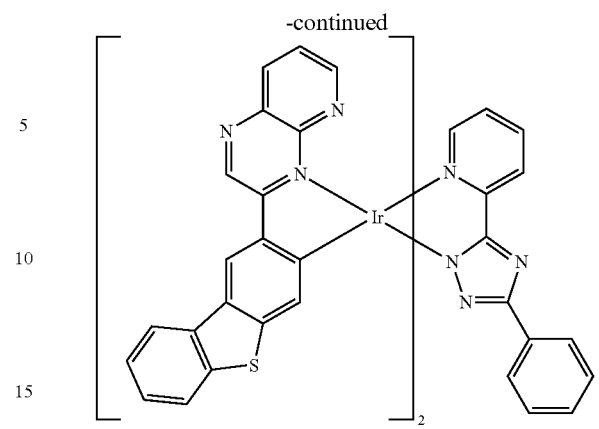
Ir(L28)pptz
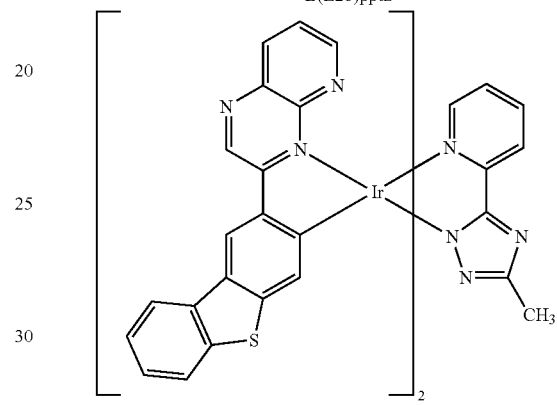
Ir(L28)mptz
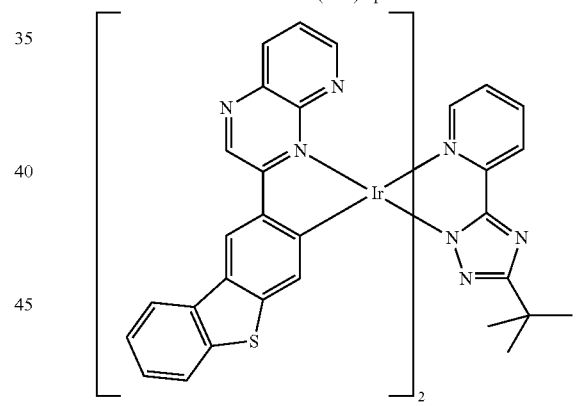
Ir(L28)tptz
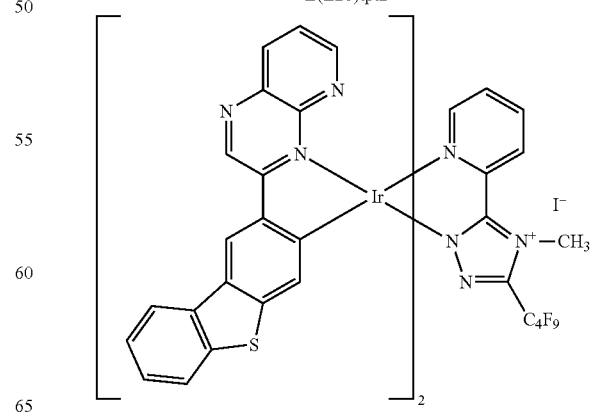
Ir(L28)ftmpi -continued
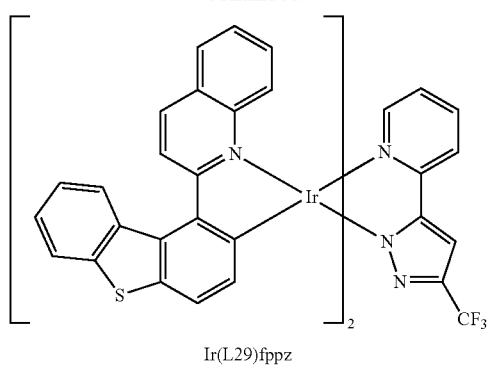
Ir(L29)fppz
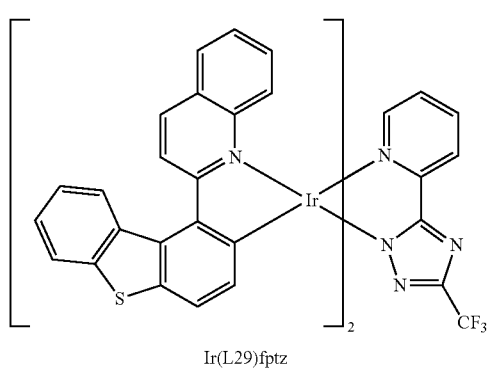
Ir(L29)fptz
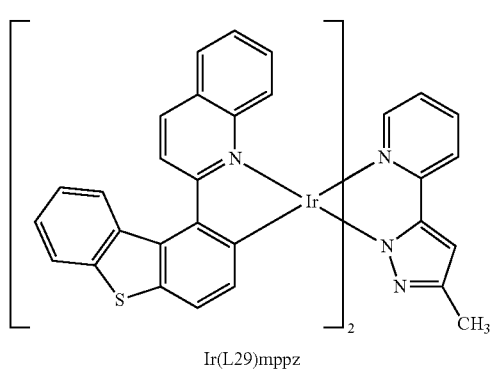
Ir(L29)mppz
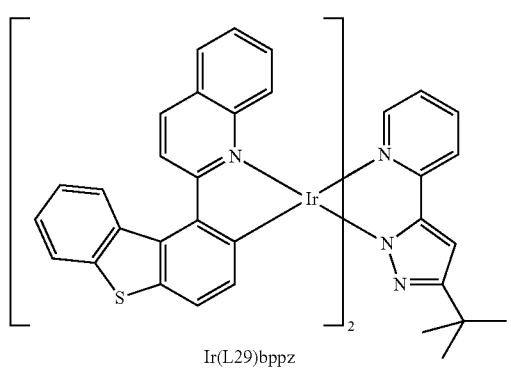
Ir(L29)bppz
-continued
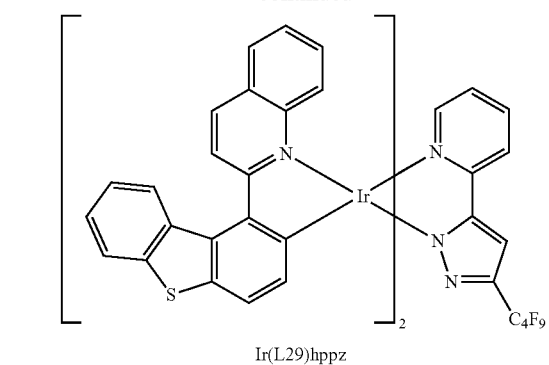
Ir(L29)hppz
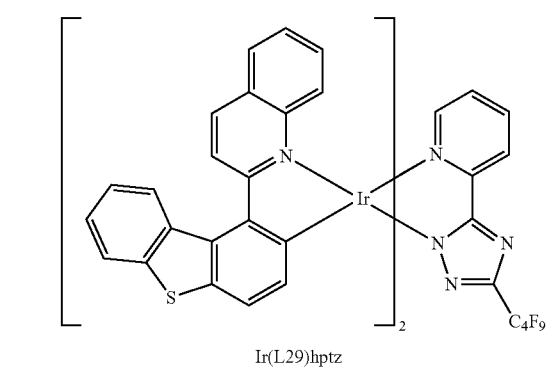
Ir(L29)hptz
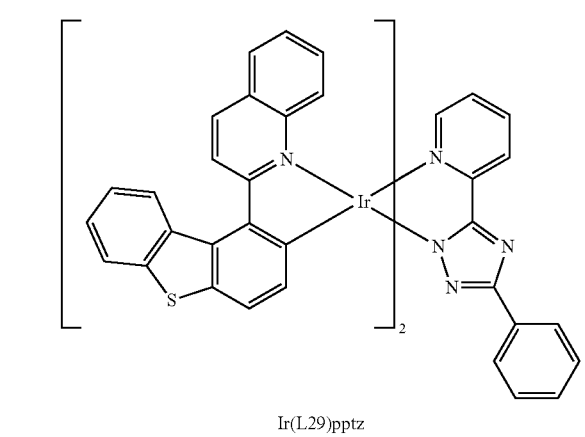
Ir(L29)pptz
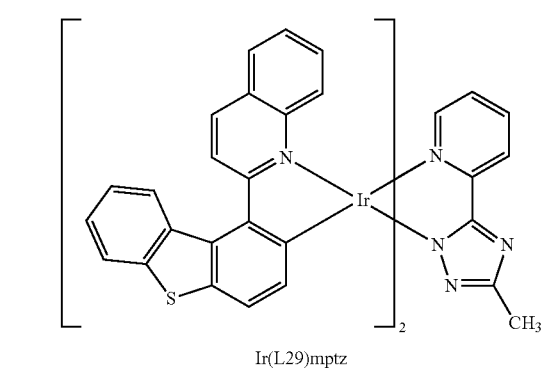
Ir(L29)mptz

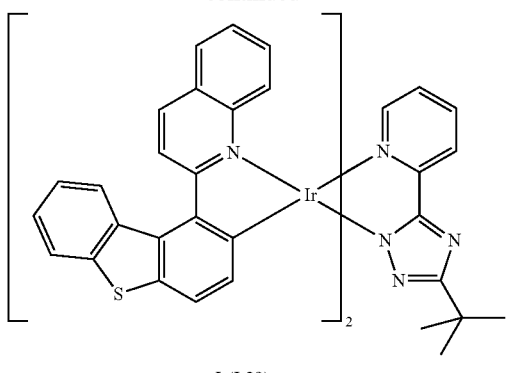
Ir(L29)tptz
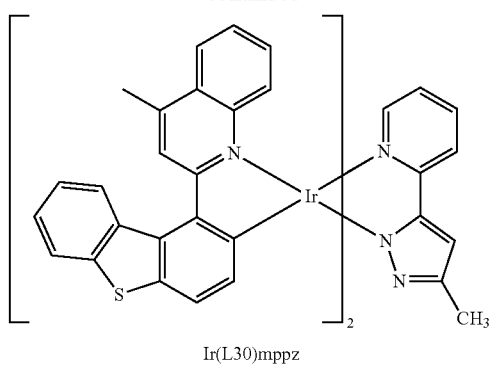
Ir(L30)mppz
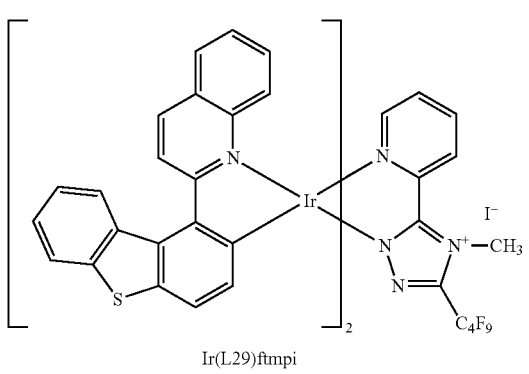
Ir(L29)ftmpi
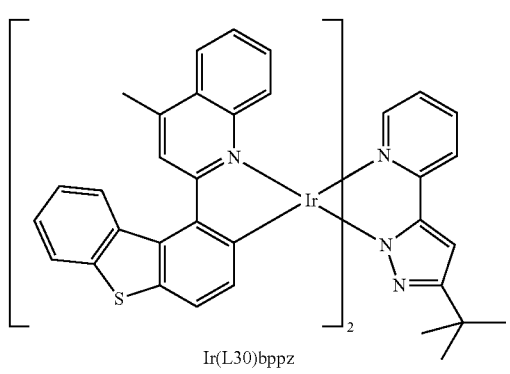
Ir(L30)bppz
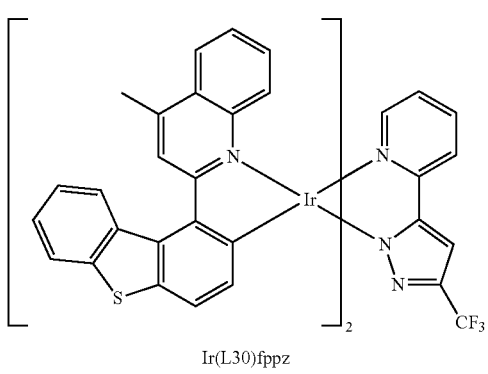
Ir(L30)fppz
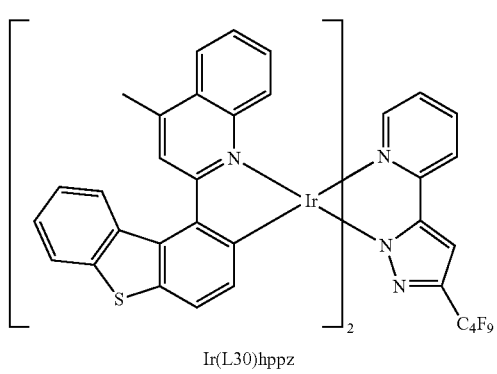
Ir(L30)hppz
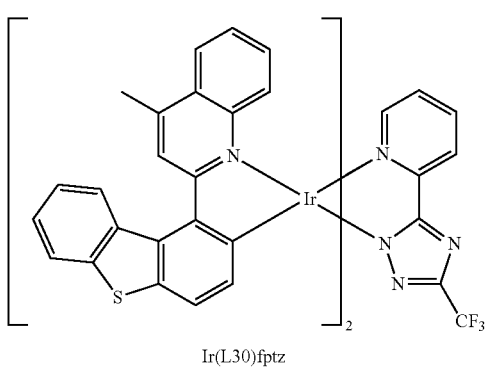
Ir(L30)fptz
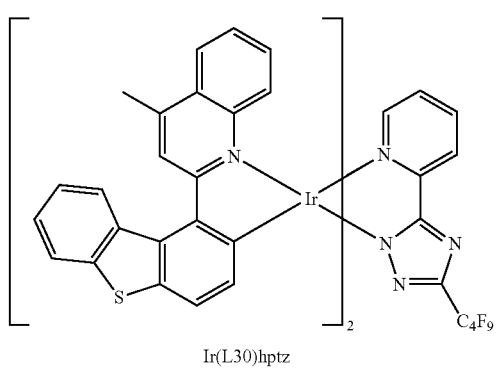
Ir(L30)hptz

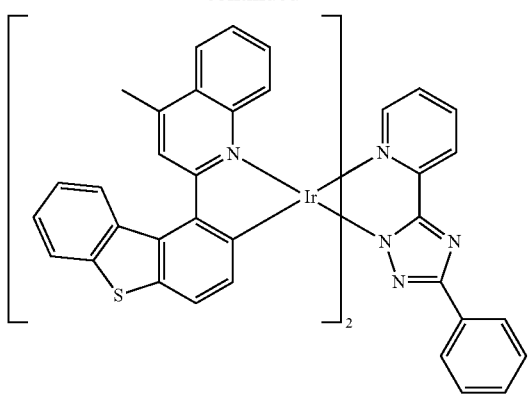
Ir(L30)pptz
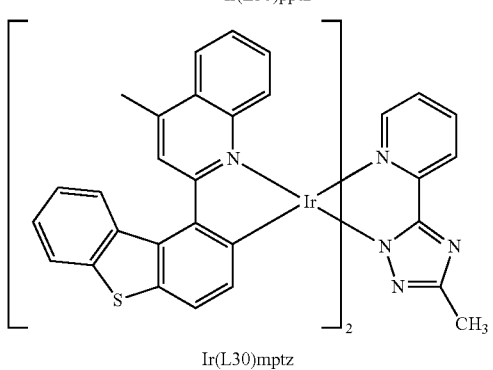
Ir(L30)mptz
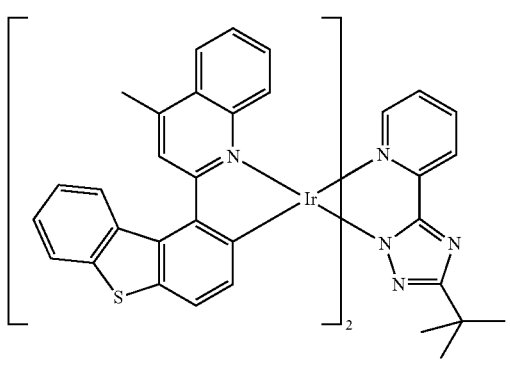
Ir(L30)tptz
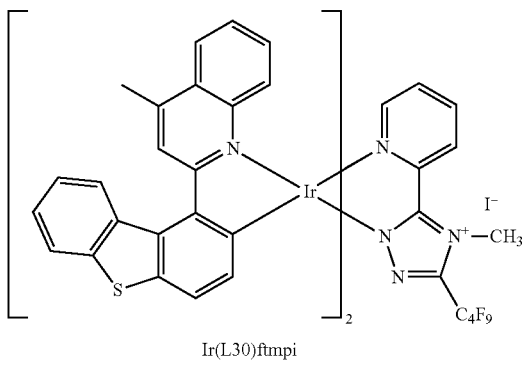
Ir(L30)ftmpi
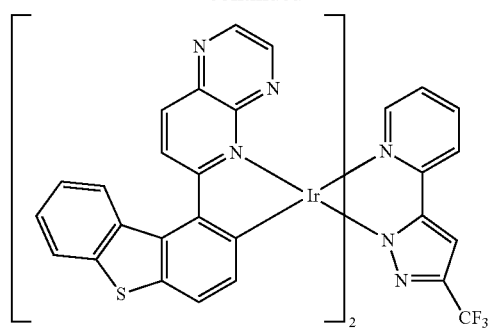
Ir(L31)fppz
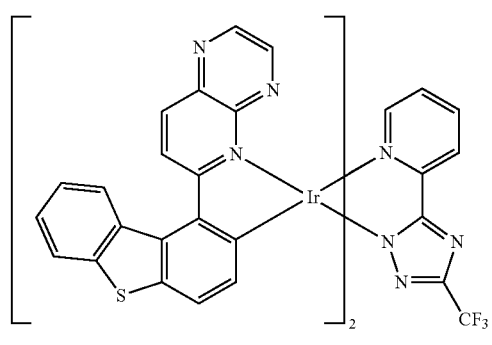
Ir(L31)fptz
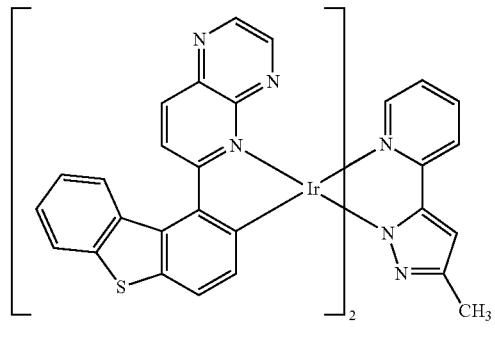
Ir(L31)mppz
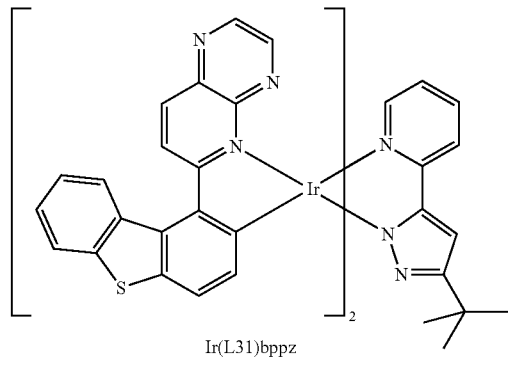
Ir(L31)bppz -continued
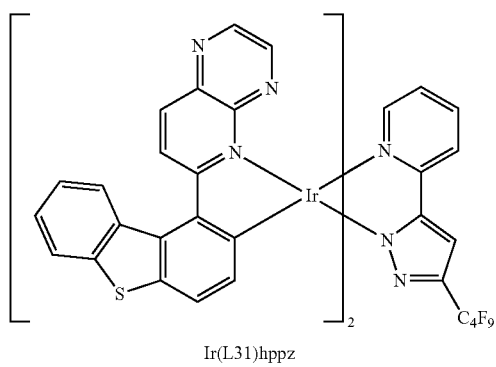
Ir(L31)hppz
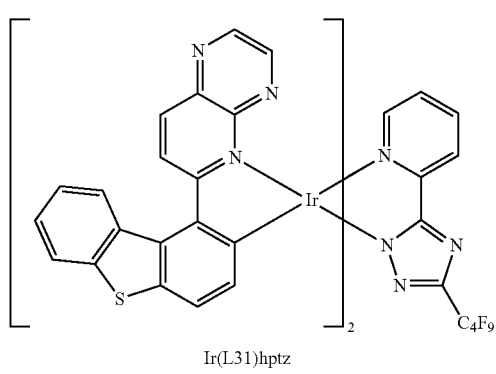
Ir(L31)hptz
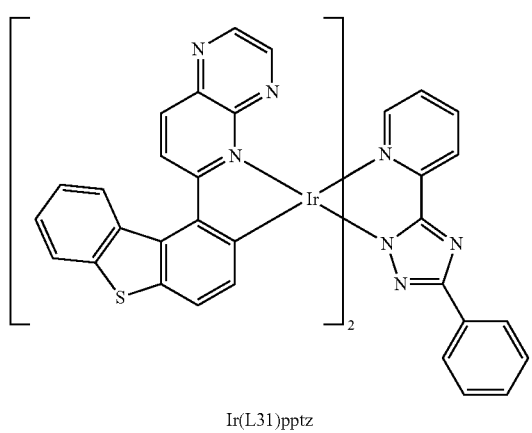
Ir(L31)pptz
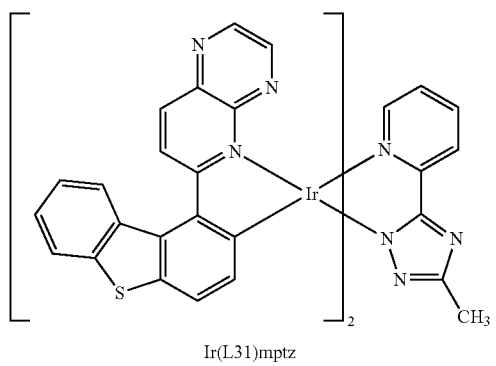
Ir(L31)mptz
-continued
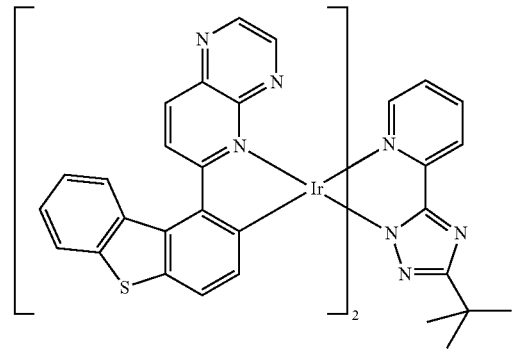
Ir(L31)tptz
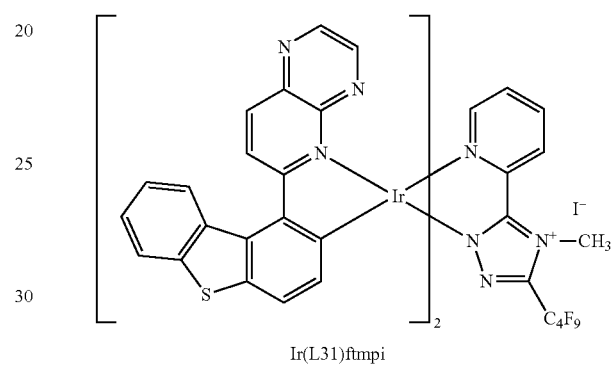
Ir(L31)ftmpi
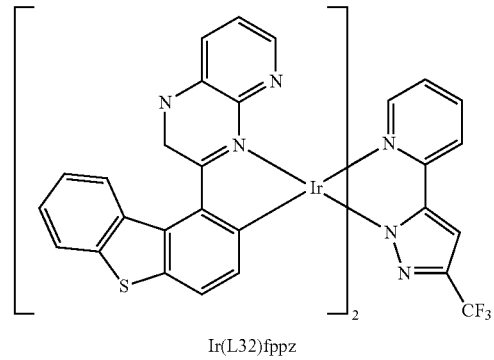
Ir(L32)fppz
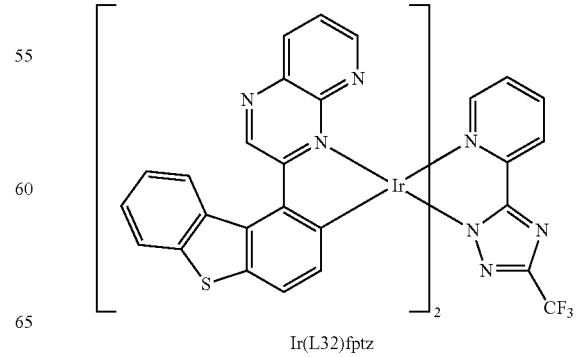
Ir(L32)fptz

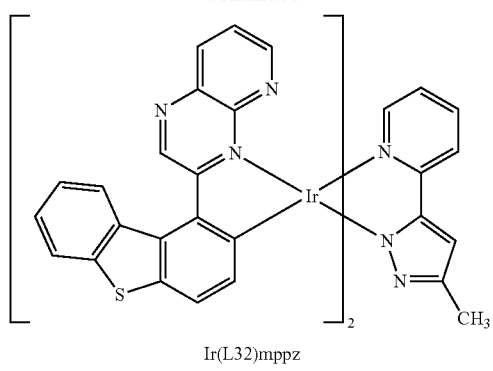
Ir(L32)mppz
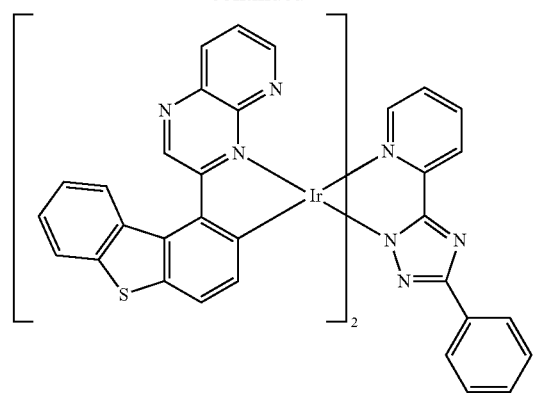
Ir(L32)pptz
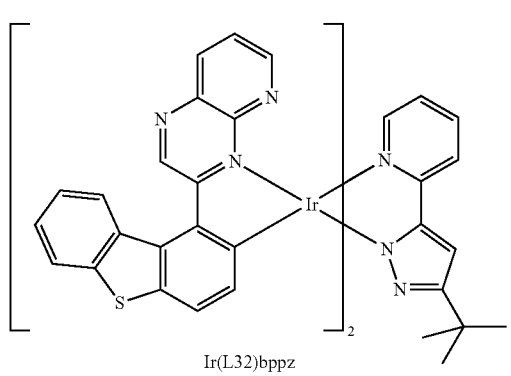
Ir(L32)bppz
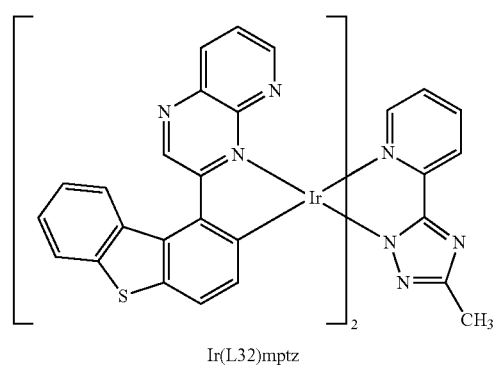
Ir(L32)mptz
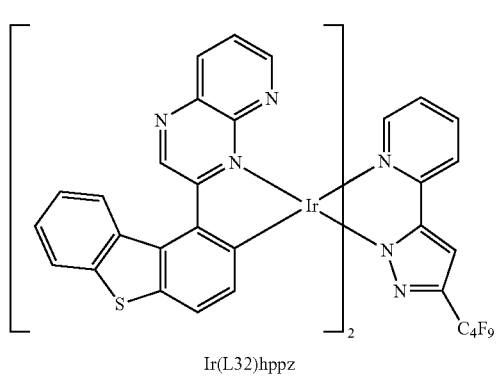
Ir(L32)hppz
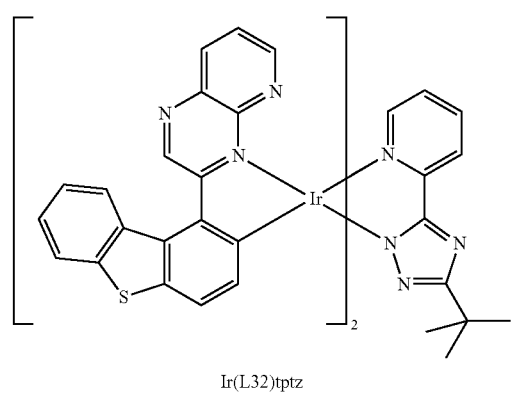
Ir(L32)tptz
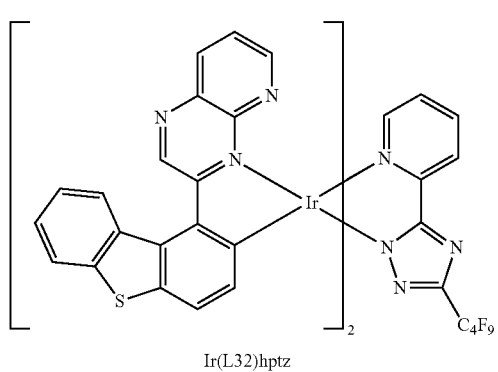
Ir(L32)hptz
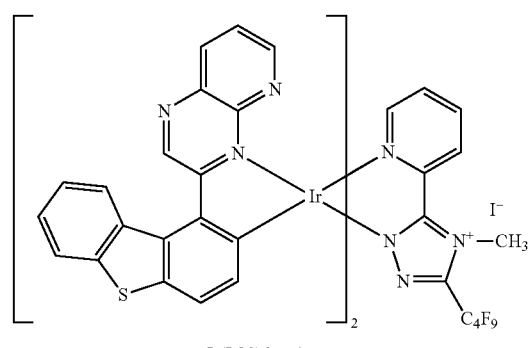
Ir(L32)ftmpi -continued
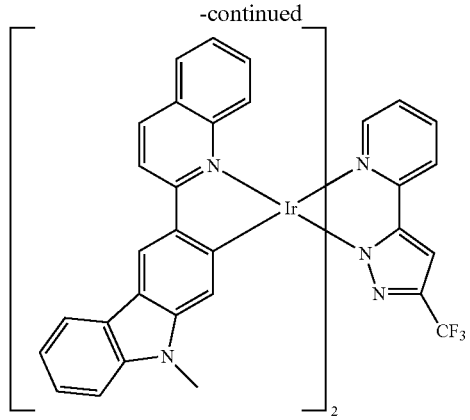
Ir(L33)fppz
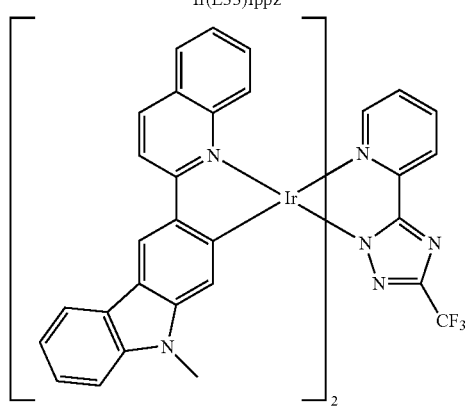
Ir(L33)fptz
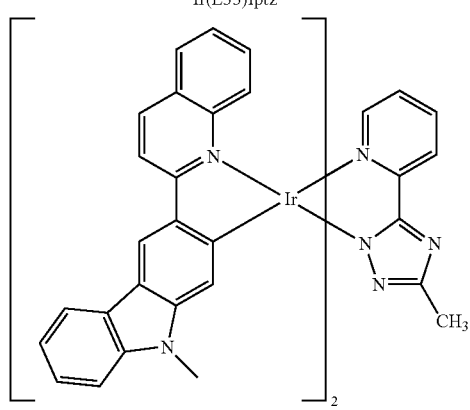
Ir(L33)mppz
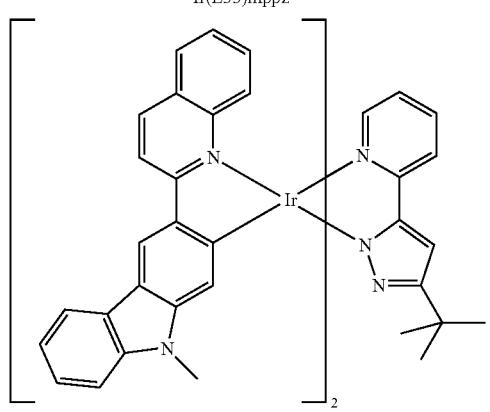
Ir(L33)bppz
-continued
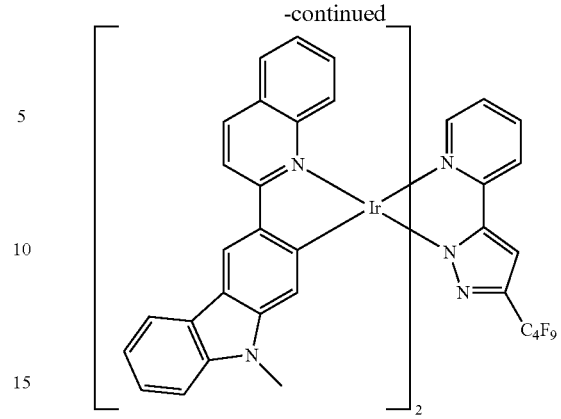
Ir(L33)hppz
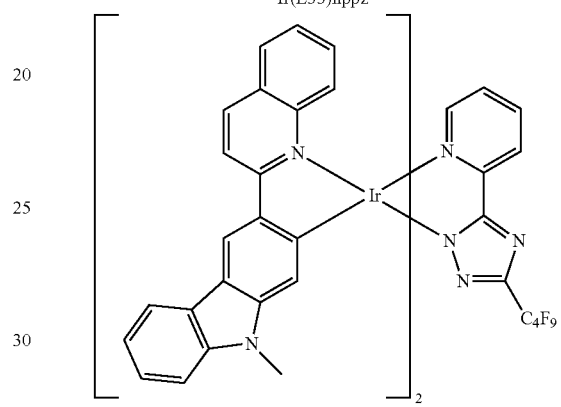
Ir(L33)hptz
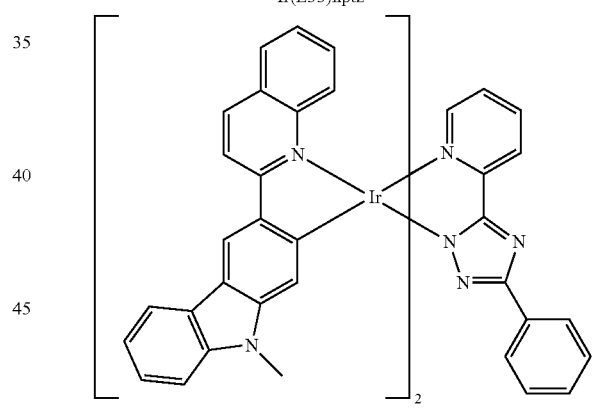
Ir(L33)pptz
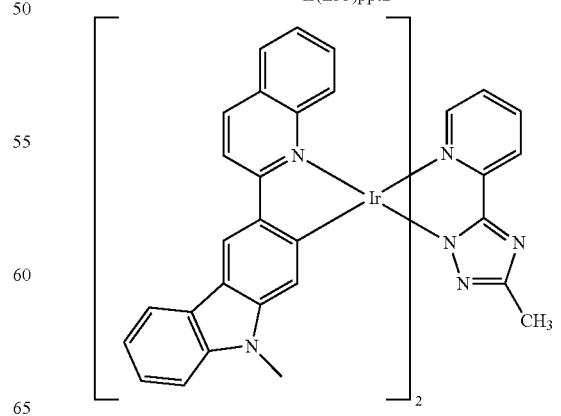
Ir(L33)mptz -continued
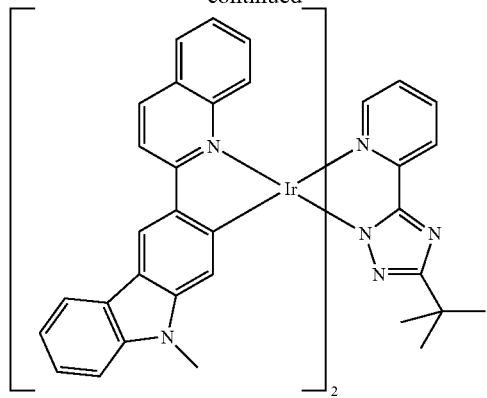
Ir(L33)tptz
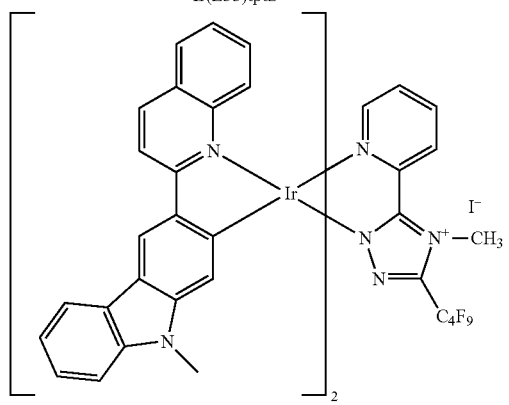
Ir(L33)ftmpi
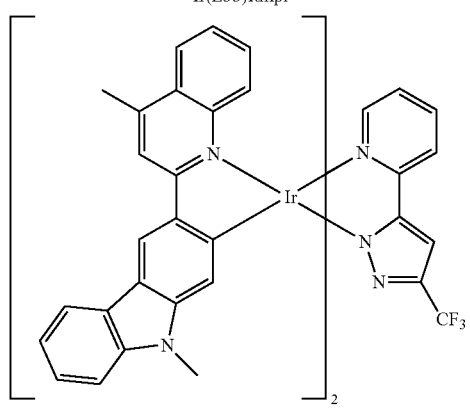
Ir(L34)fppz
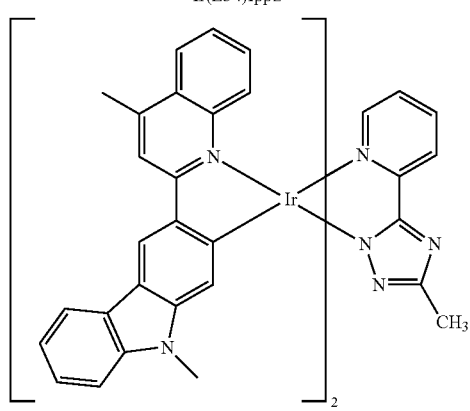
Ir(L34)mppz
-continued
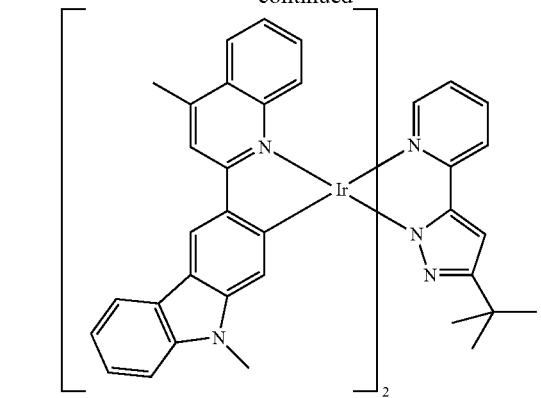
Ir(L34)bppz
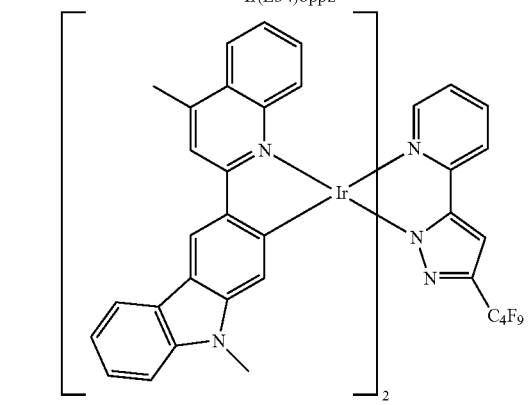
Ir(L34)hppz
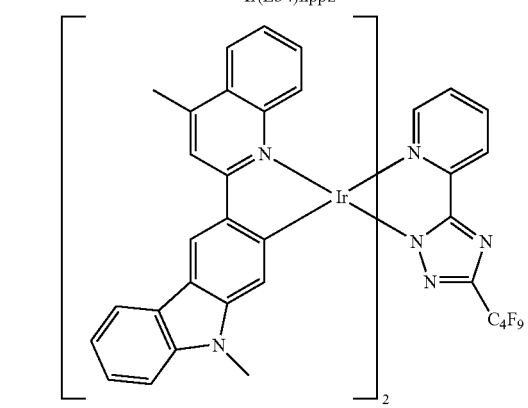
Ir(L34)hptz
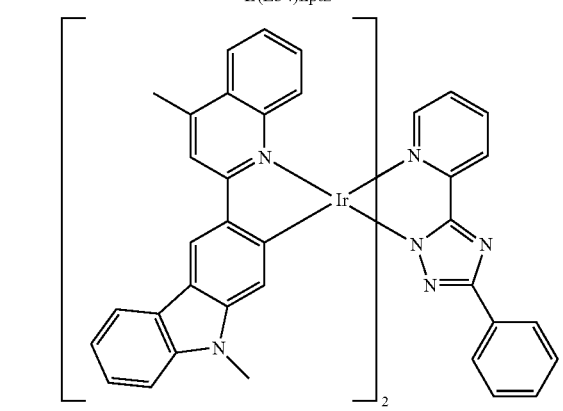
Ir(L34)pptz

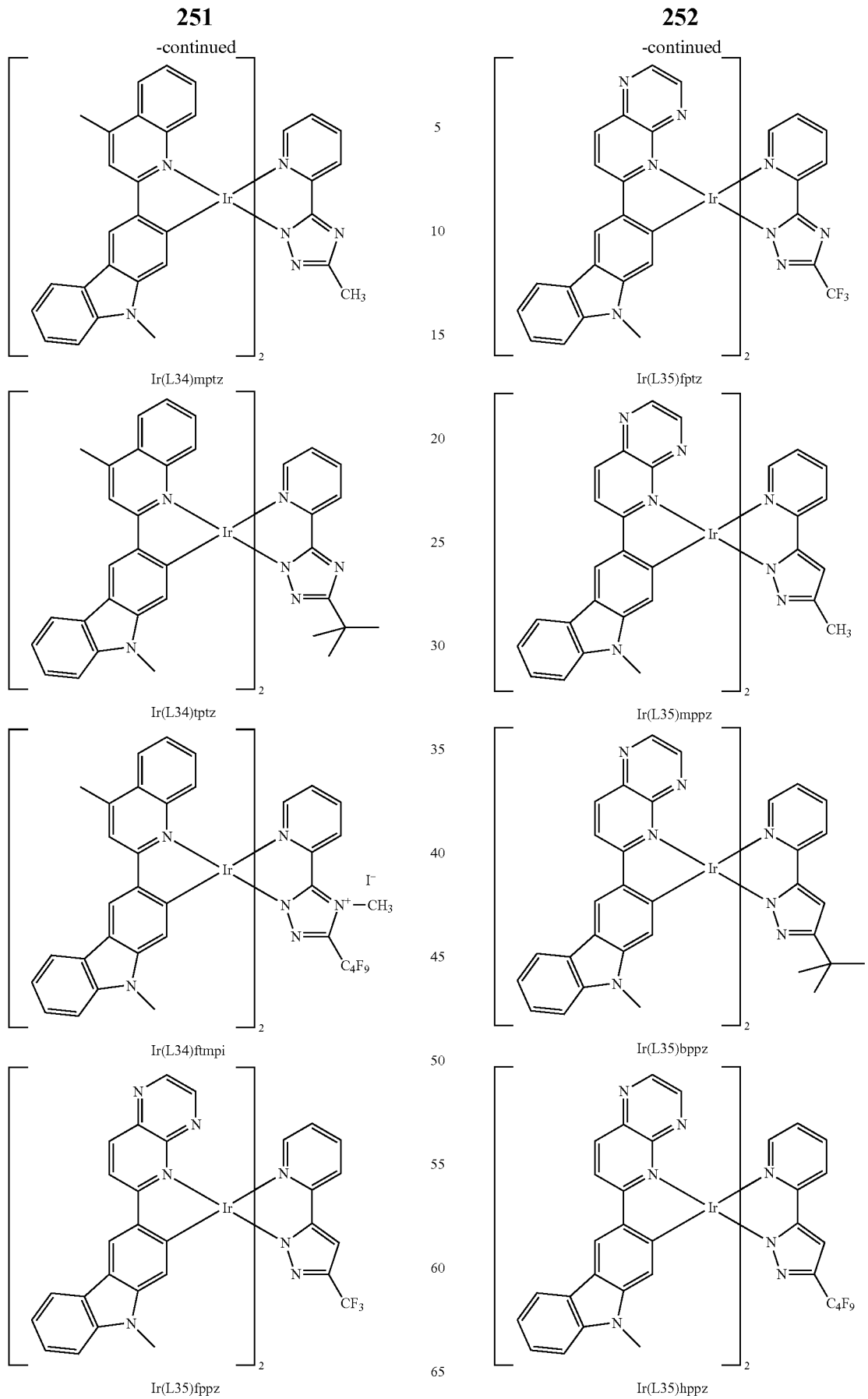

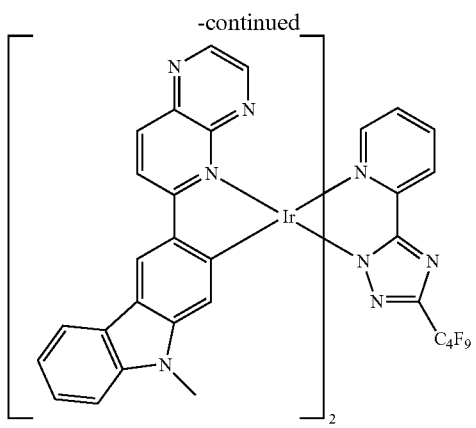
Ir(L35)hptz
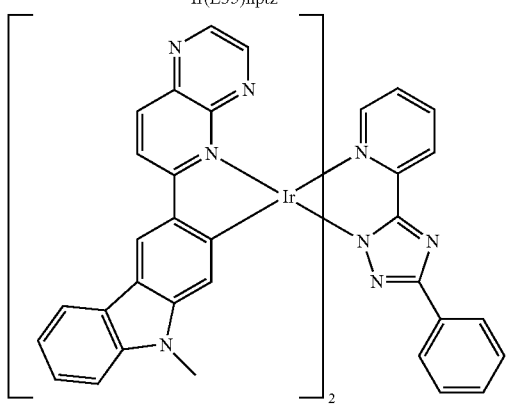
Ir(L35)pptz
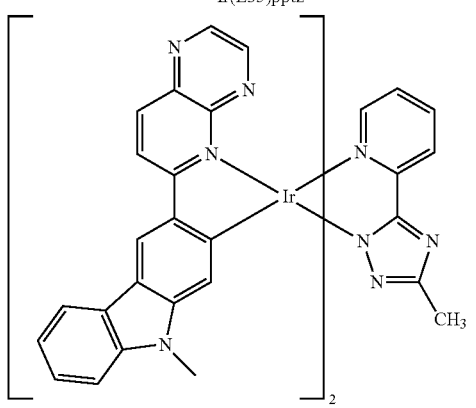
Ir(L35)mptz
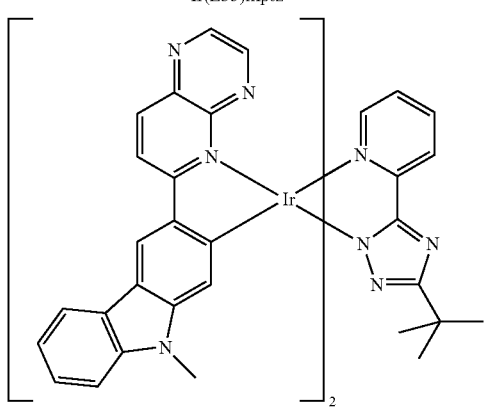
Ir(L35)tptz
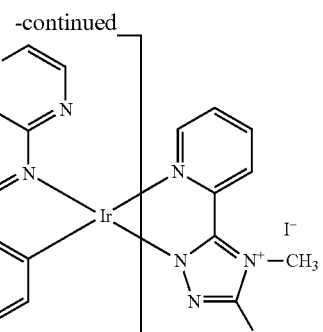
Ir(L35)ftmpi
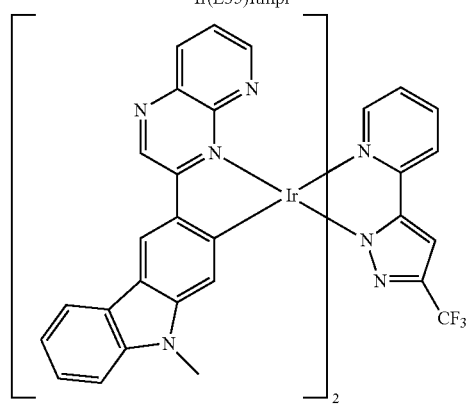
Ir(L36)fppz
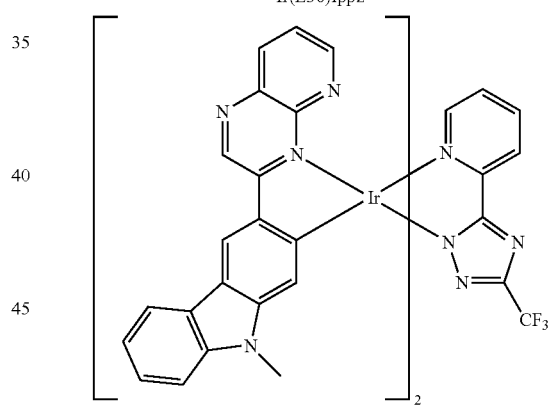
Ir(L36)fptz
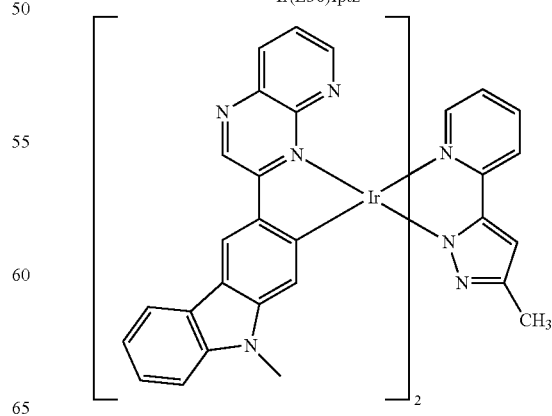
Ir(L36)mppz -continued
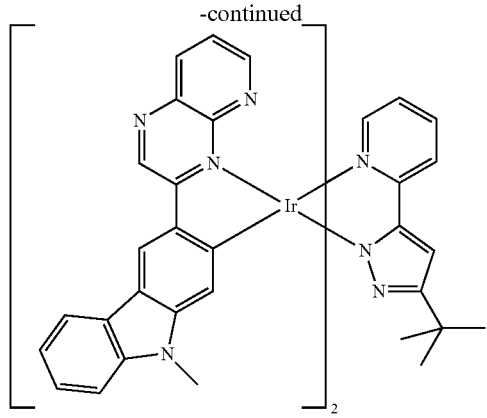
Ir(L36)bppz
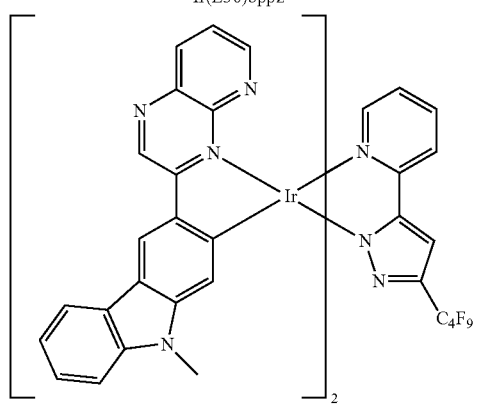
Ir(L36)hppz
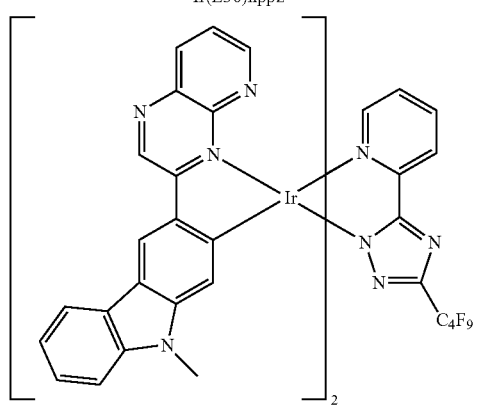
Ir(L36)hptz
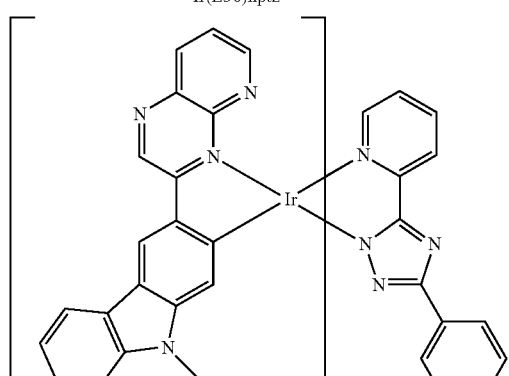
Ir(L36)pptz
-continued
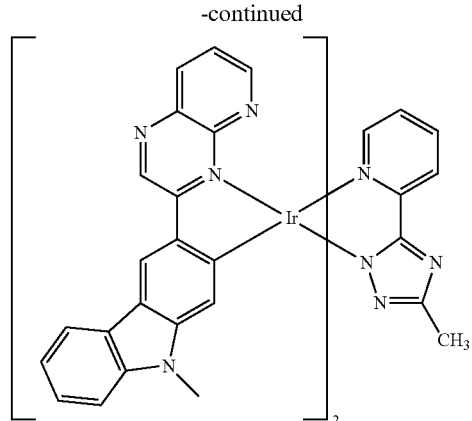
Ir(L36)mptz
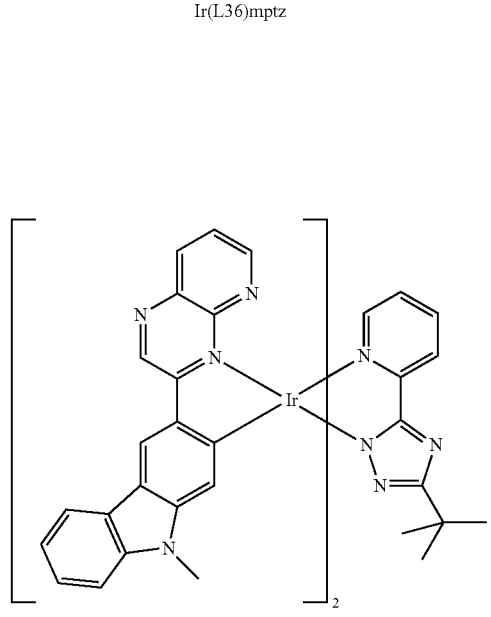
Ir(L36)tptz
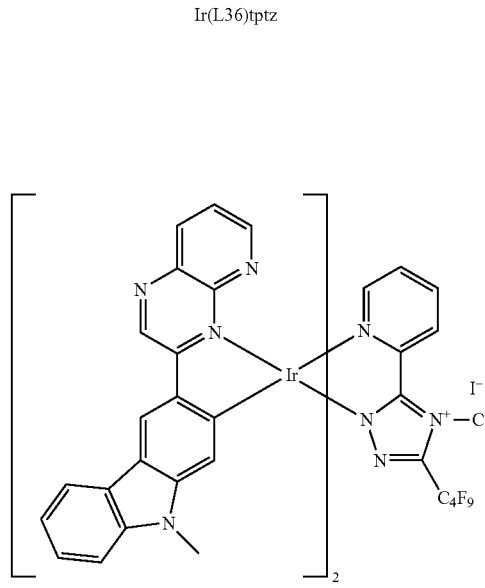
Ir(L36)ftmpi

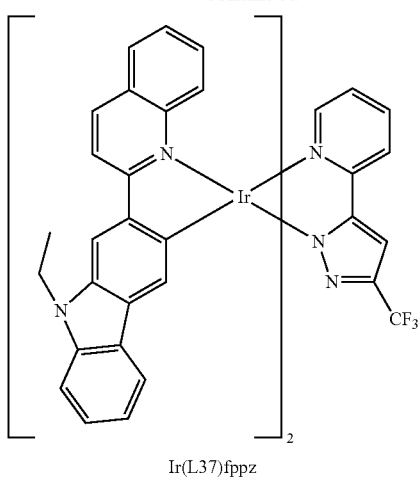
Ir(L37)fppz
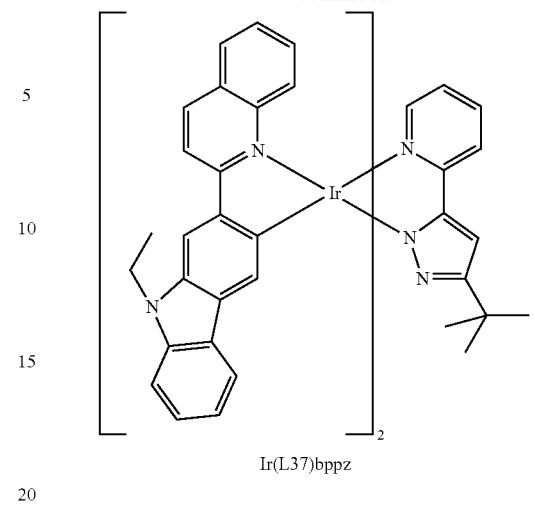
Ir(L37)bppz
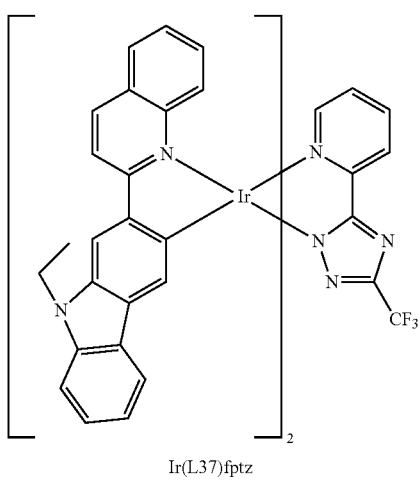
Ir(L37)fptz
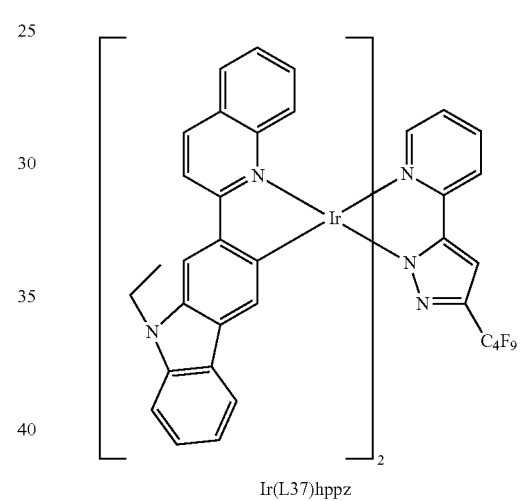
Ir(L37)hppz
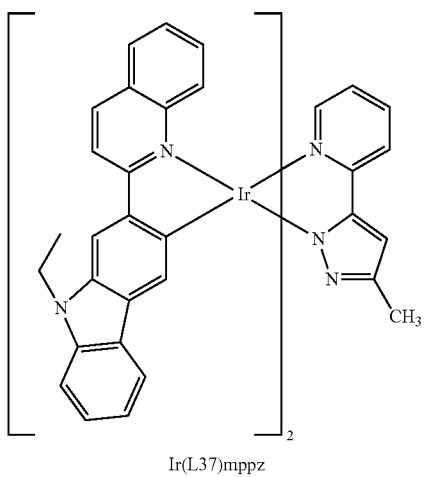
Ir(L37)mppz
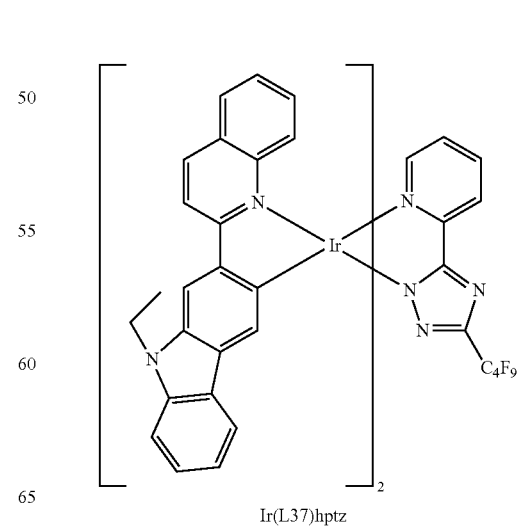
Ir(L37)hptz

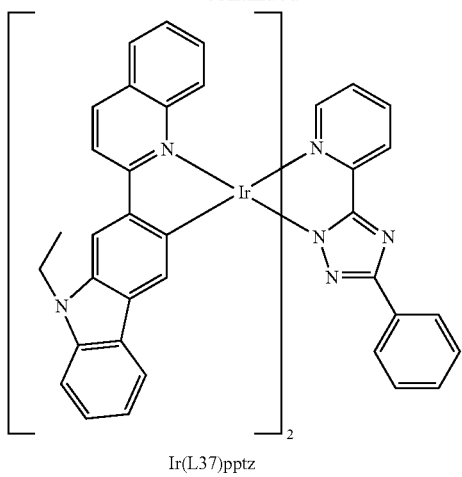
Ir(L37)pptz
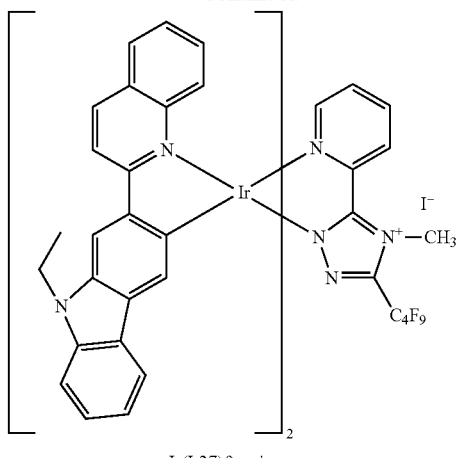
Ir(L37)ftmpi
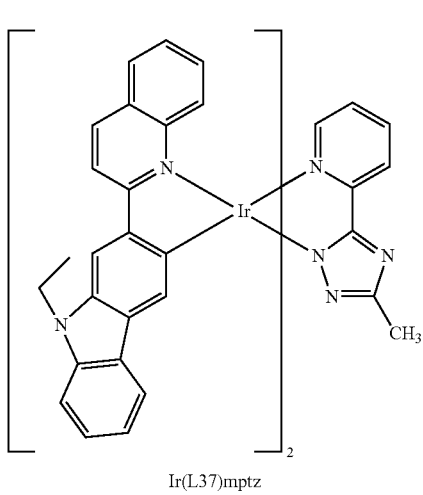
Ir(L37)mptz
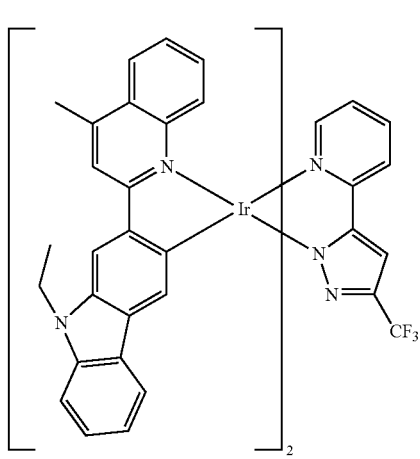
Ir(L38)fppz
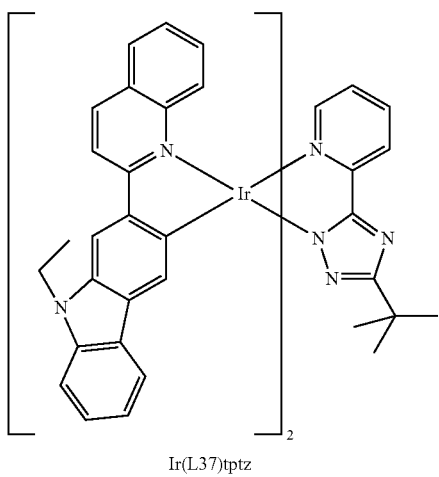
Ir(L37)tptz
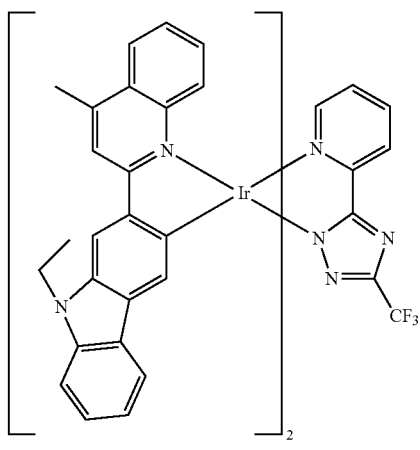
Ir(L38)fptz -continued
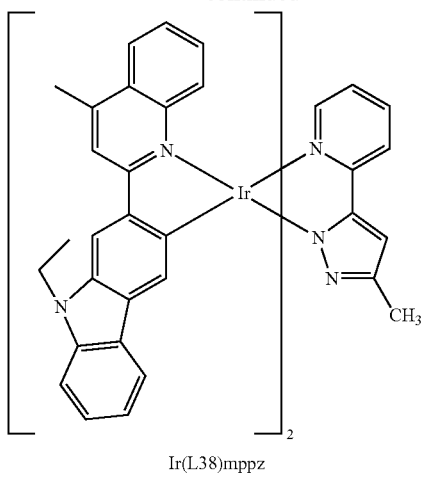
Ir(L38)mppz
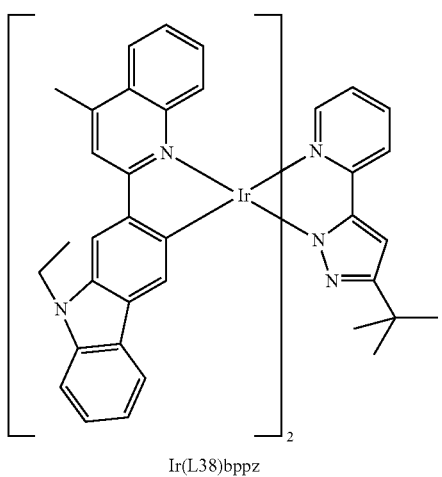
Ir(L38)bppz
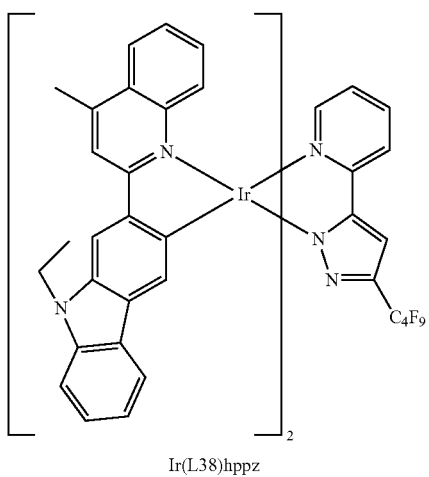
Ir(L38)hppz
-continued
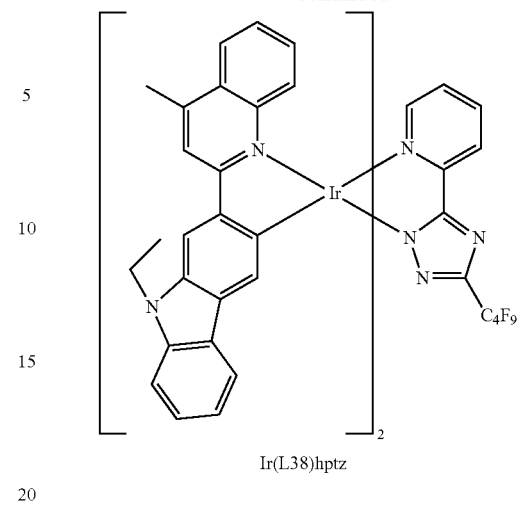
Ir(L38)hptz
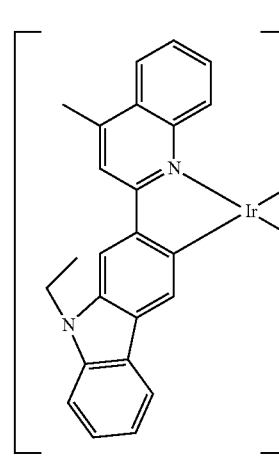
Ir(L38)pptz
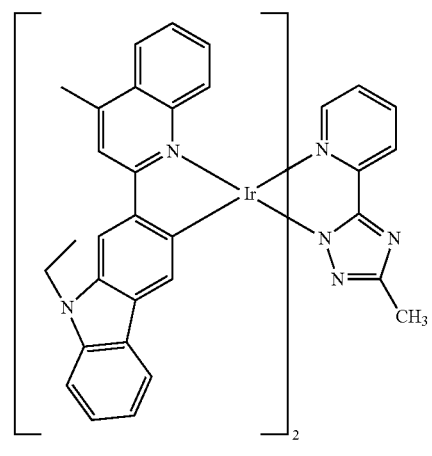
Ir(L38)mptz

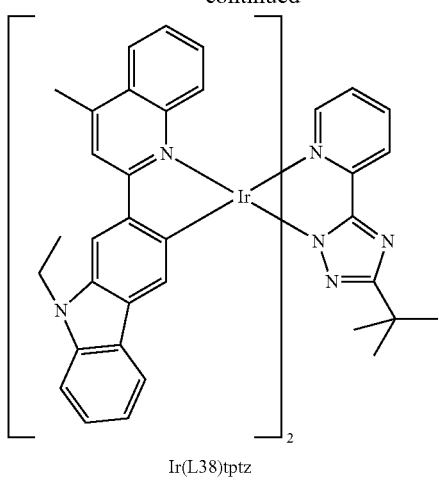
Ir(L38)tptz
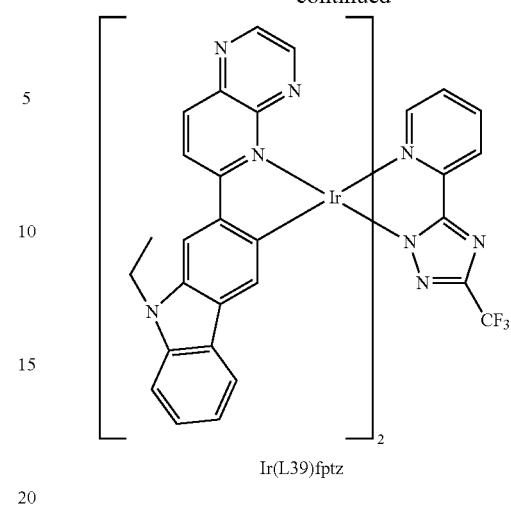
Ir(L39)fptz
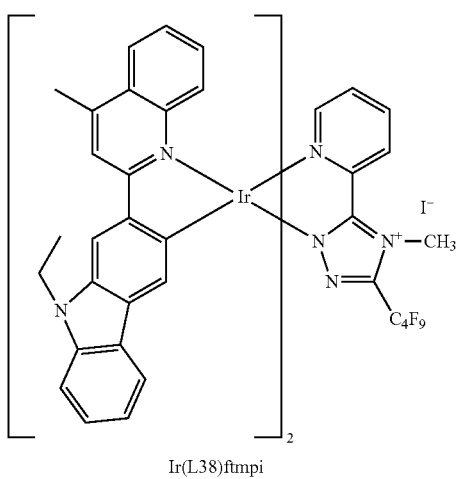
Ir(L38)ftmpi
Ir(L39)mppz
Ir(L39)fppz
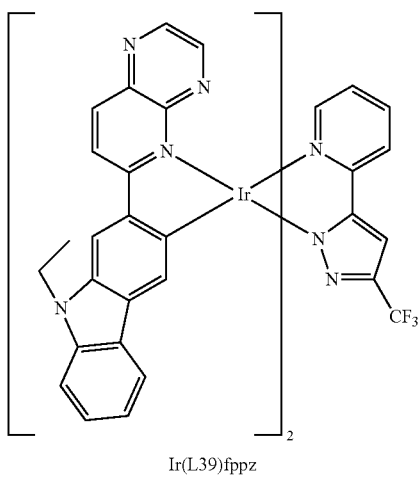
Ir(L39)bppz 265
-continued
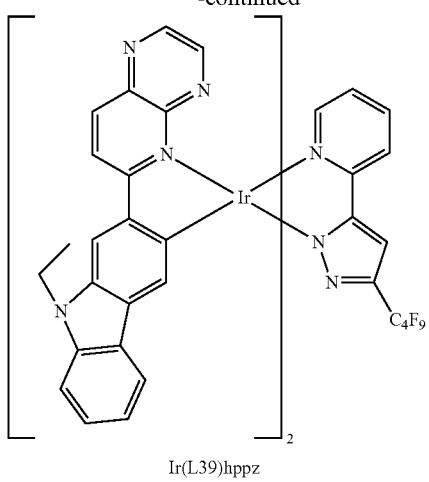
Ir(L39)hppz
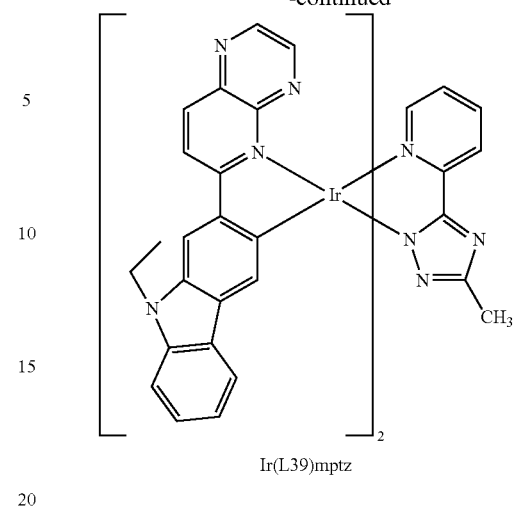
Ir(L39)mptz
266
-continued
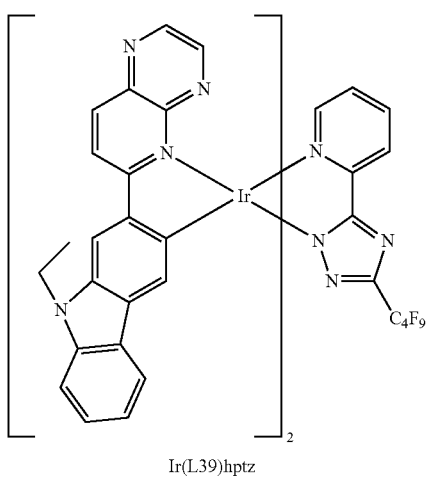
Ir(L39)hptz
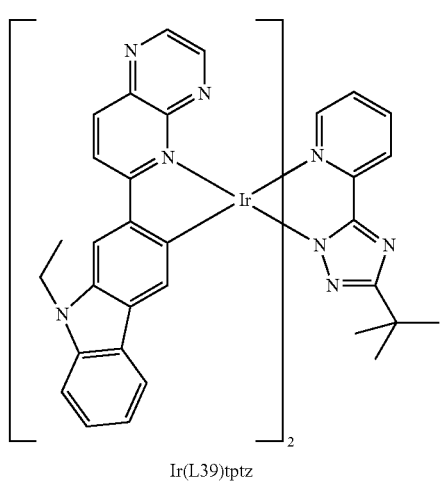
Ir(L39)tptz
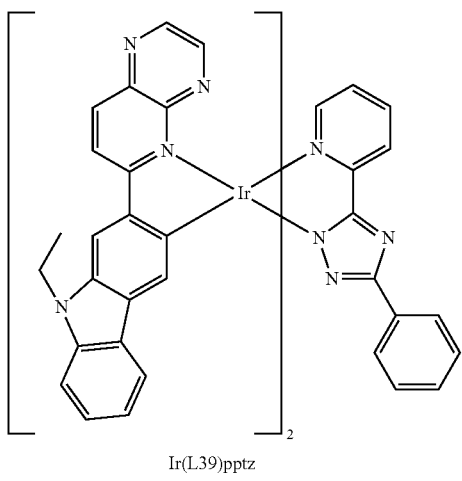
Ir(L39)pptz
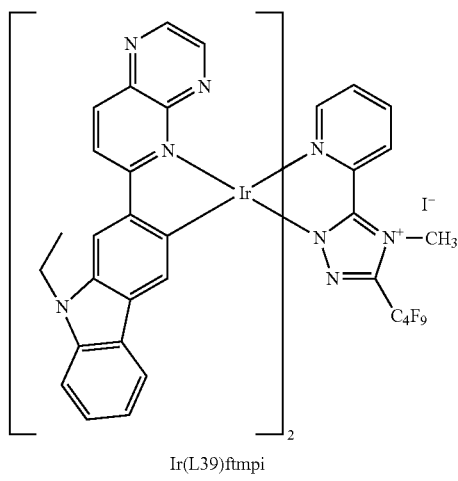
Ir(L39)ftmpi 267
-continued
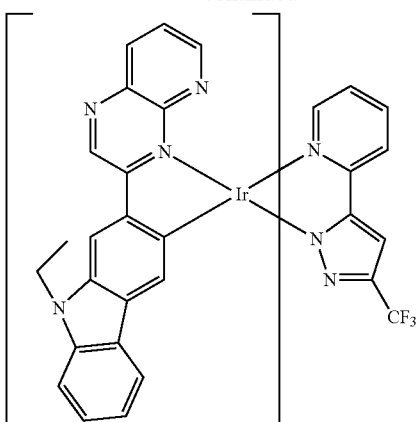
Ir(L40)fppz
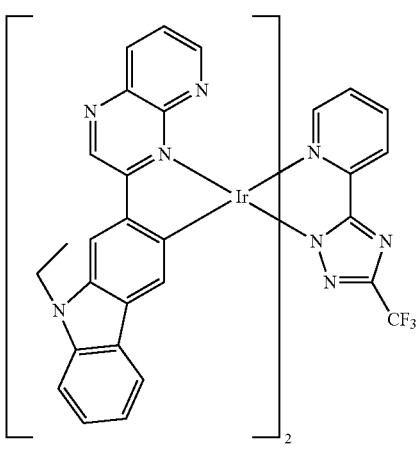
Ir(L40)fptz
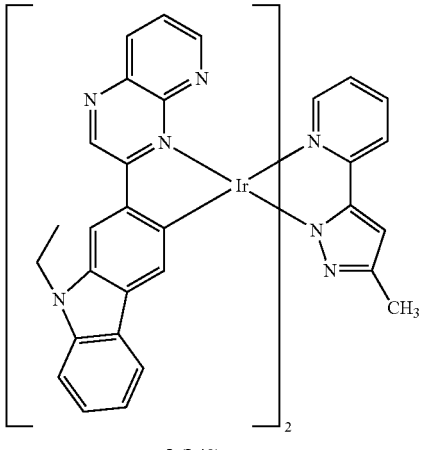
Ir(L40)mppz
268
-continued
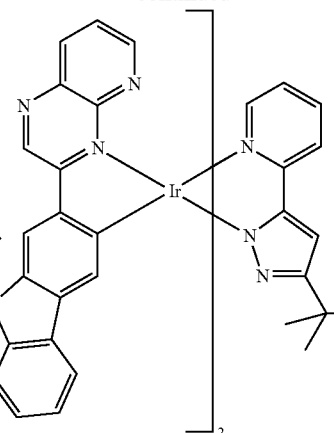
Ir(L40)bppz
Ir(L40)hppz
Ir(L40)hptz 269
-continued
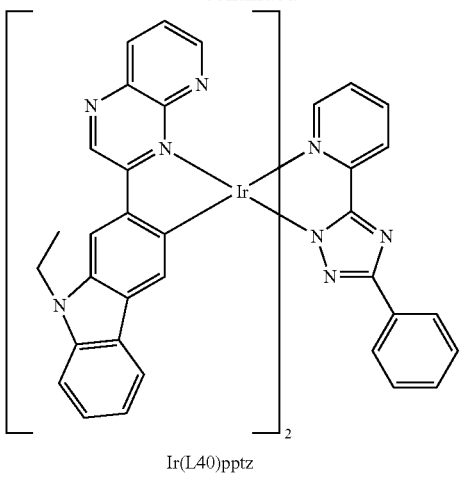
Ir(L40)pptz
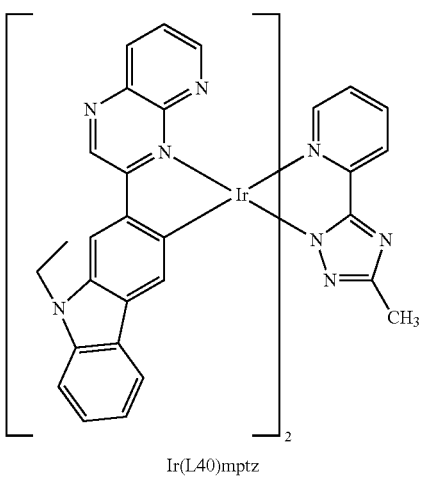
Ir(L40)mptz
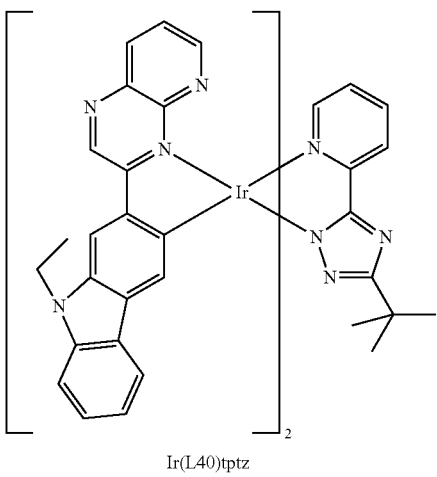
Ir(L40)tptz
270
-continued
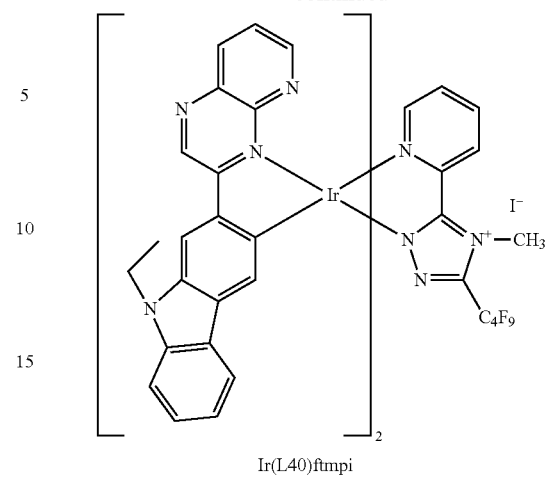
Ir(L40)ftmpi
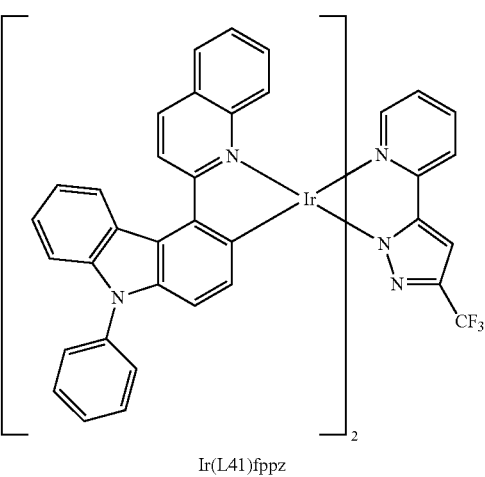
Ir(L41)fppz
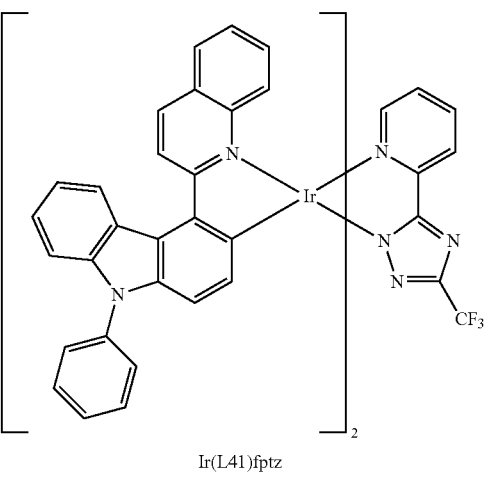
Ir(L41)fptz

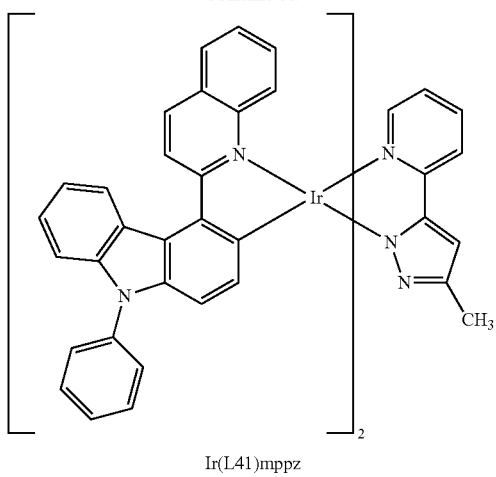
Ir(L41)mppz
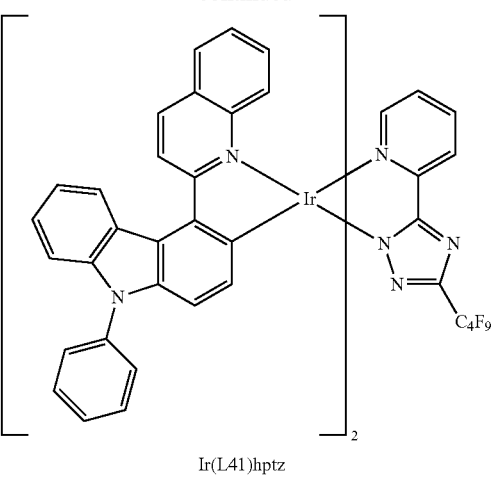
Ir(L41)hptz
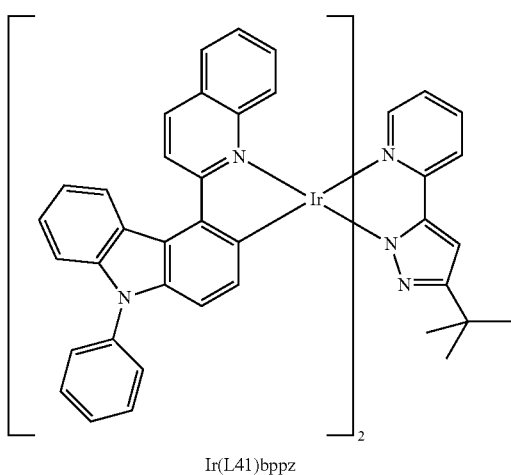
Ir(L41)bppz
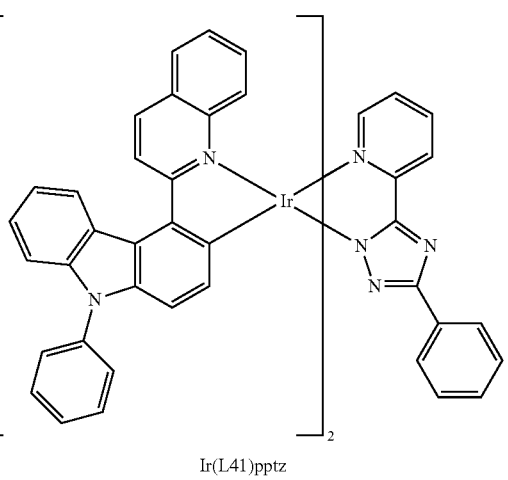
Ir(L41)pptz
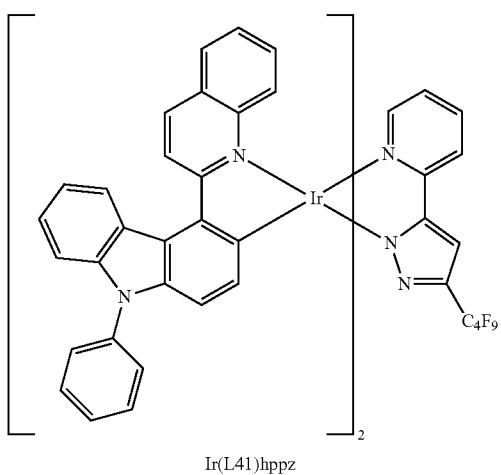
Ir(L41)hppz
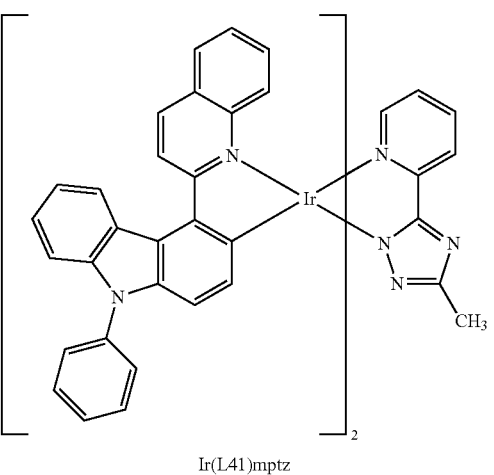
Ir(L41)mptz

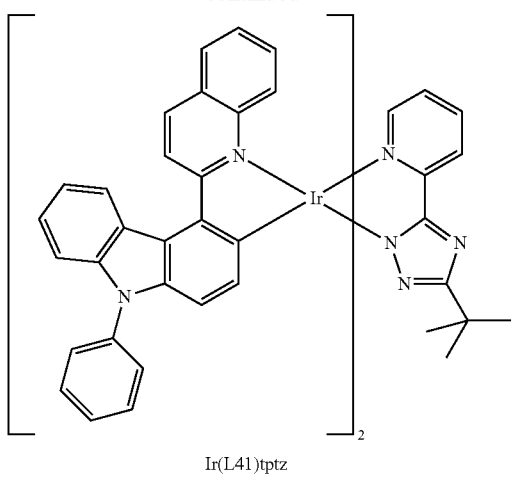
Ir(L41)tptz
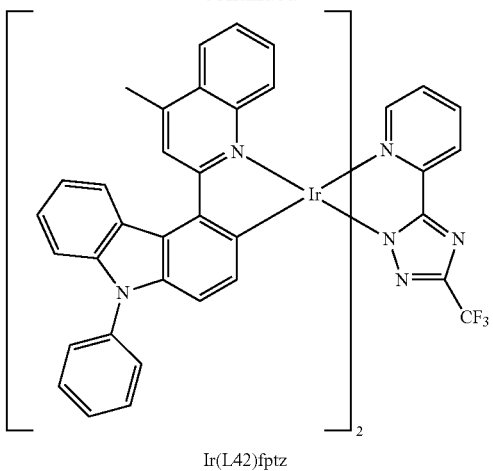
Ir(L42)fptz
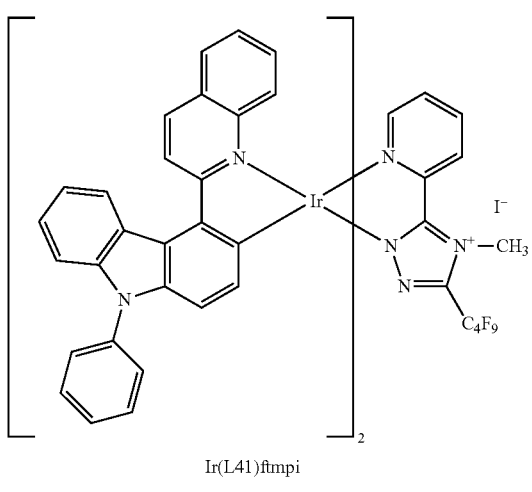
Ir(L41)ftmpi
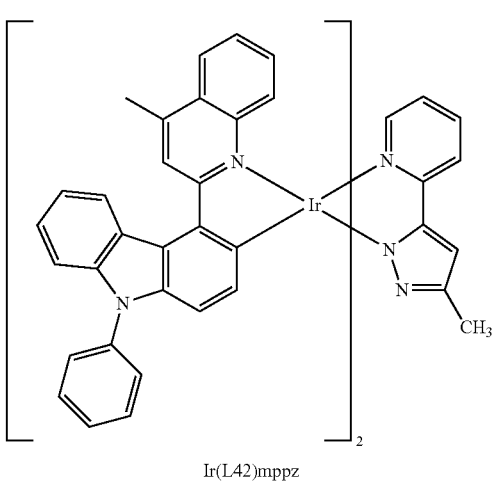
Ir(L42)mppz
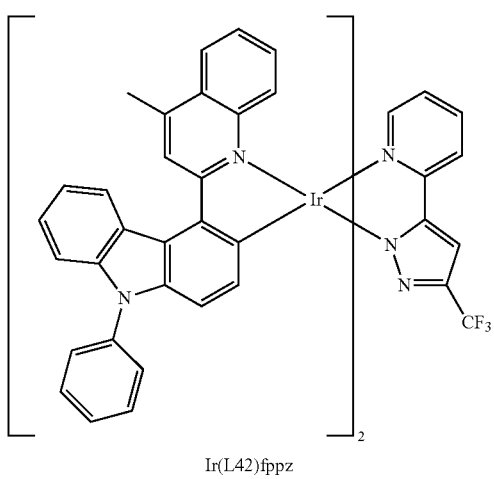
Ir(L42)fppz
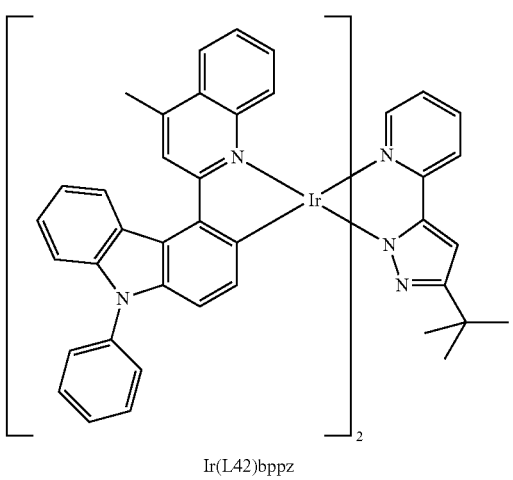
Ir(L42)bppz

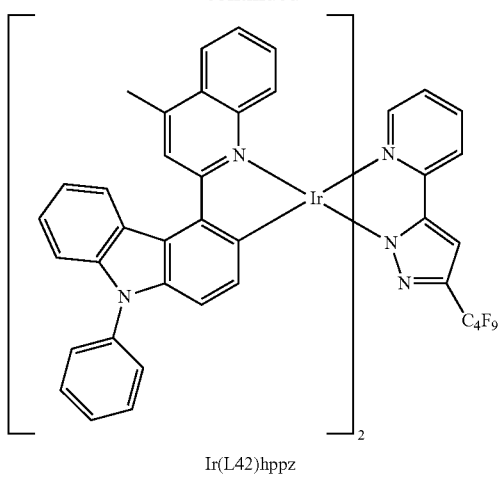
Ir(L42)hppz
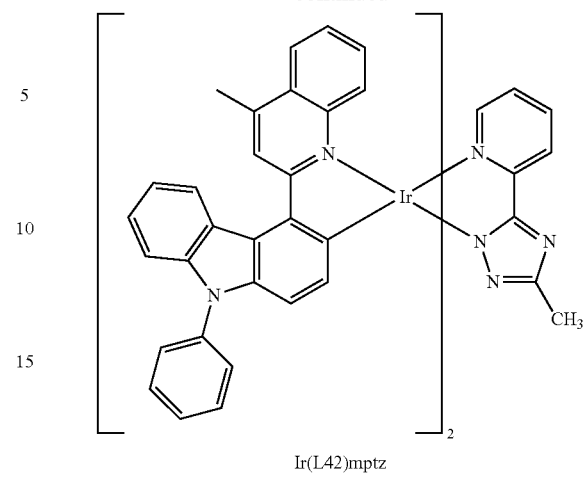
Ir(L42)mptz
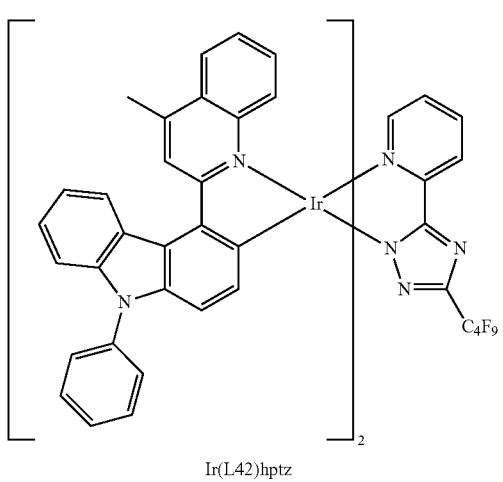
Ir(L42)hptz
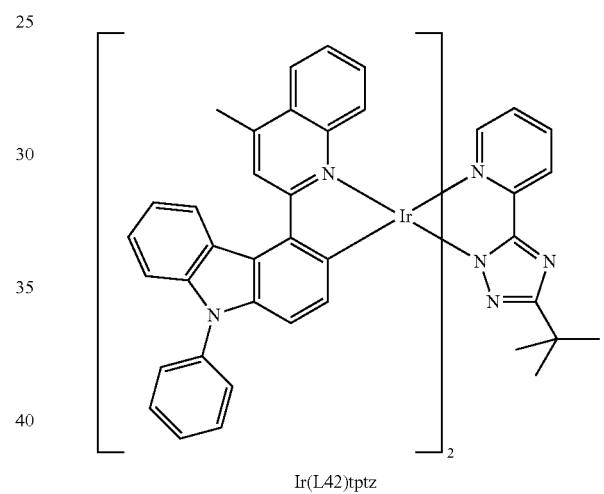
Ir(L42)tptz
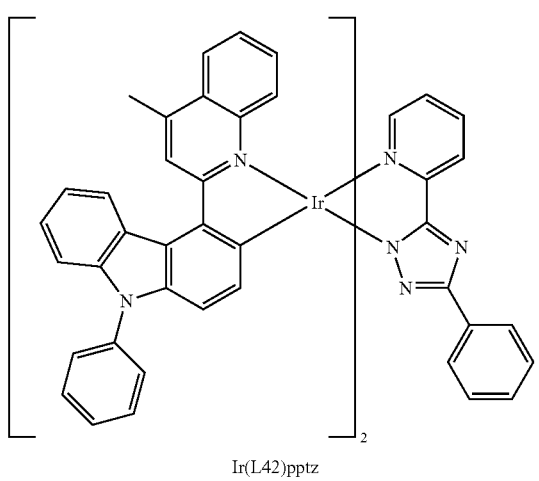
Ir(L42)pptz
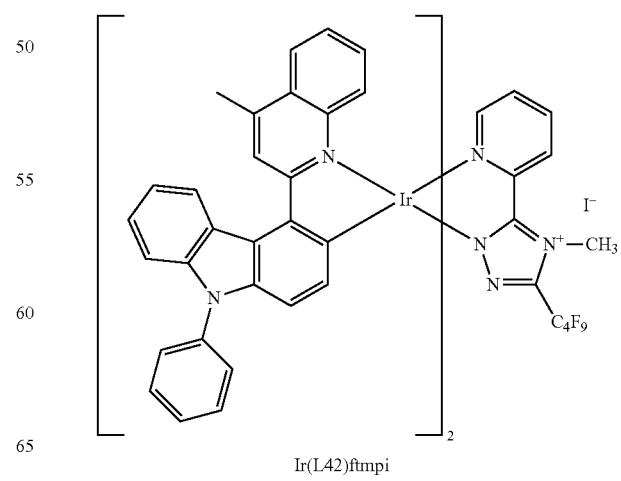
Ir(L42)ftmpi

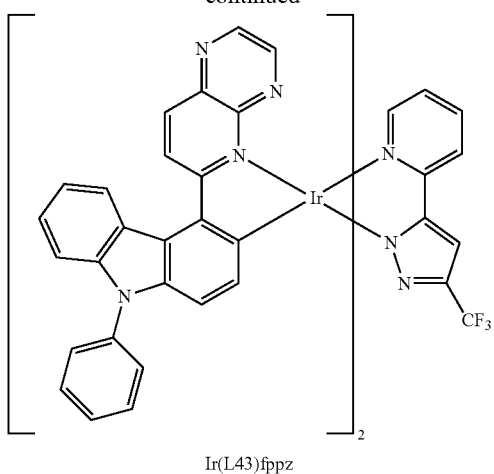
Ir(L43)fppz
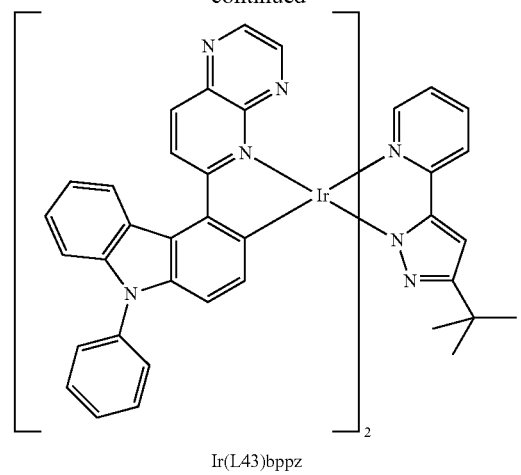
Ir(L43)bppz
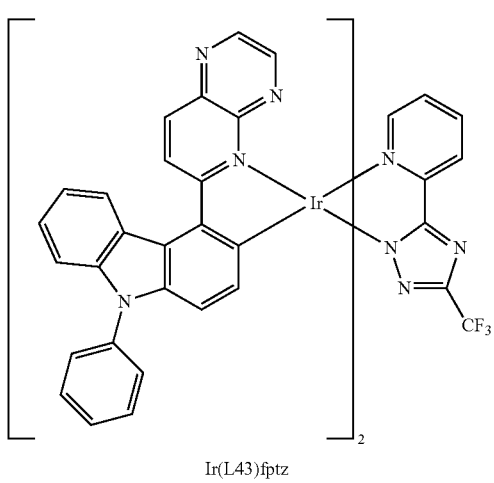
Ir(L43)fptz
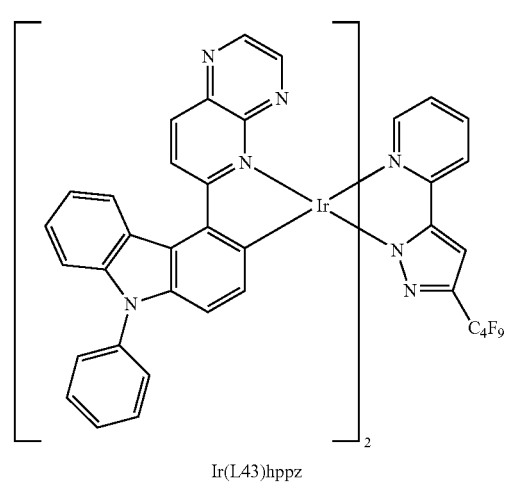
Ir(L43)hppz
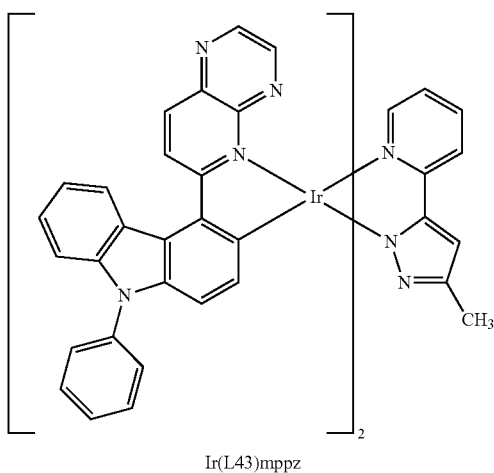
Ir(L43)mppz
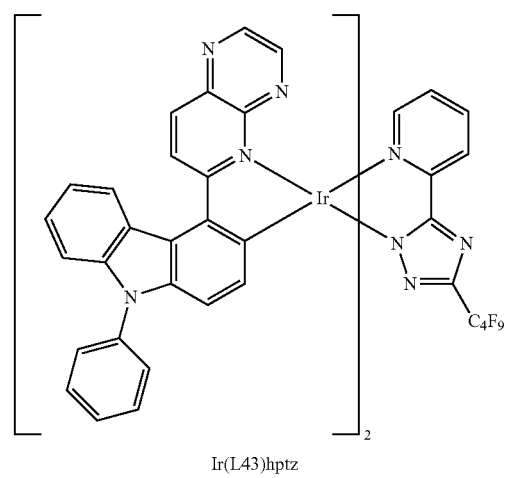
Ir(L43)hptz

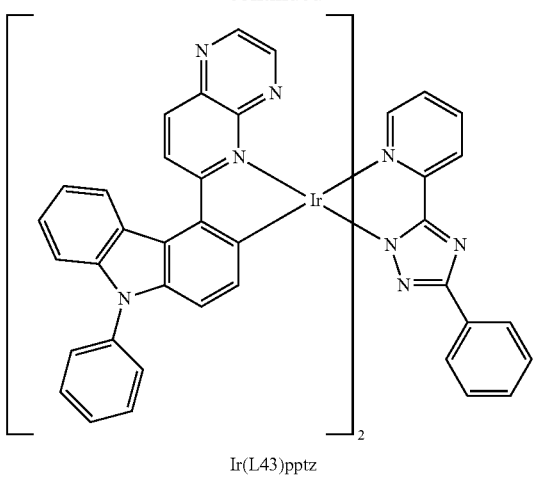
Ir(L43)pptz
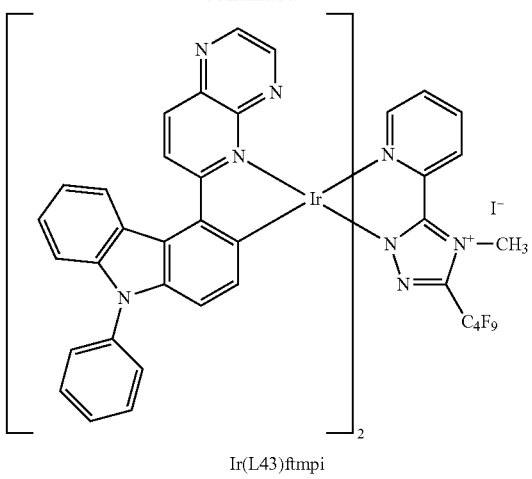
Ir(L43)ftmpi
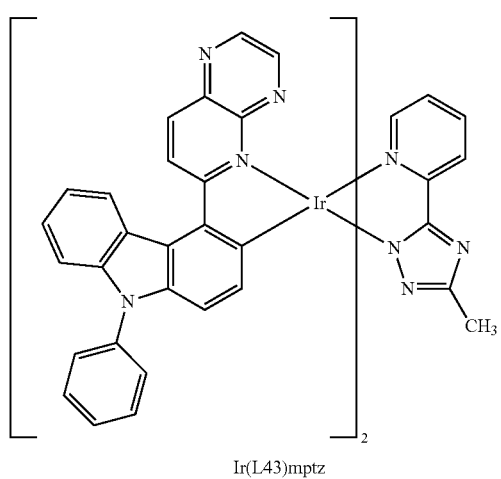
Ir(L43)mptz
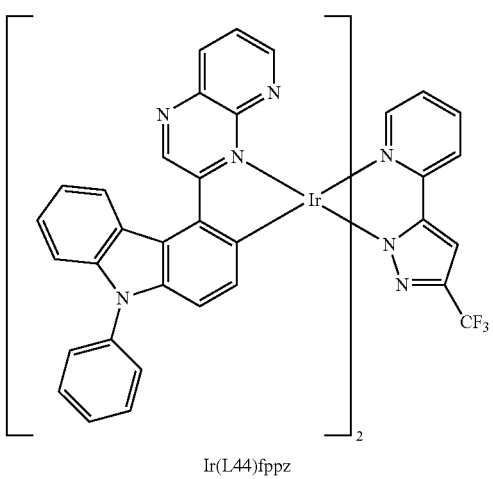
Ir(L44)fppz
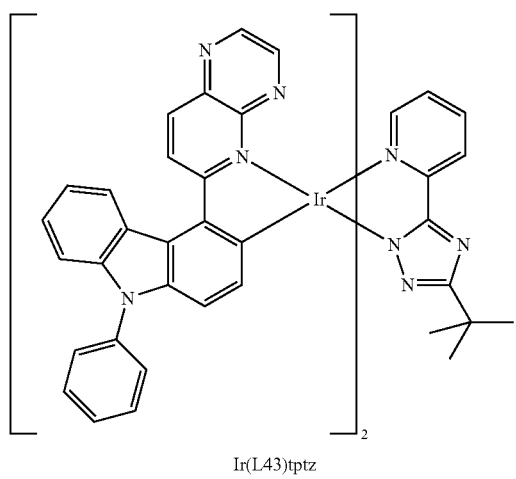
Ir(L43)tptz
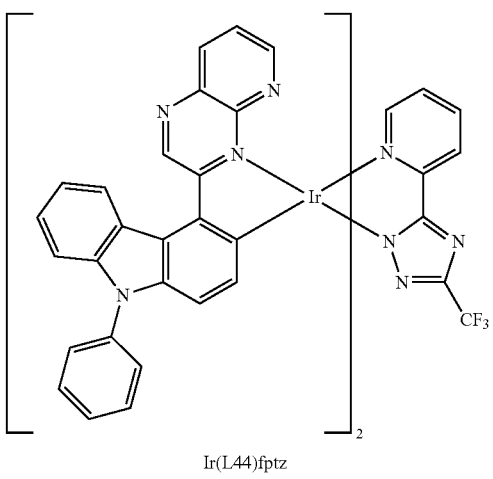
Ir(L44)fptz -continued
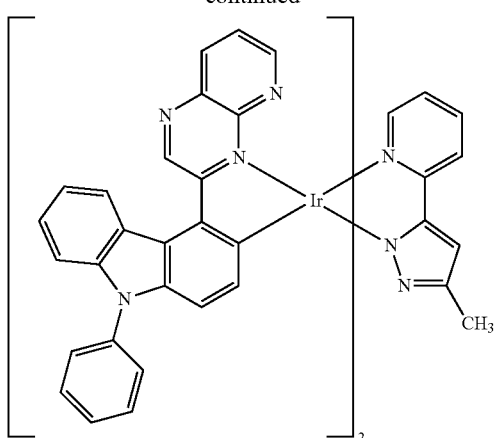
Ir(L44)mppz
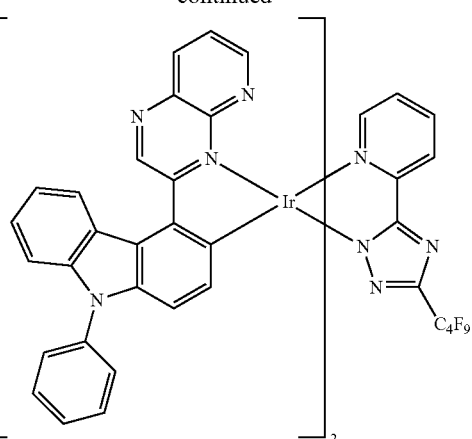
Ir(L44)hptz
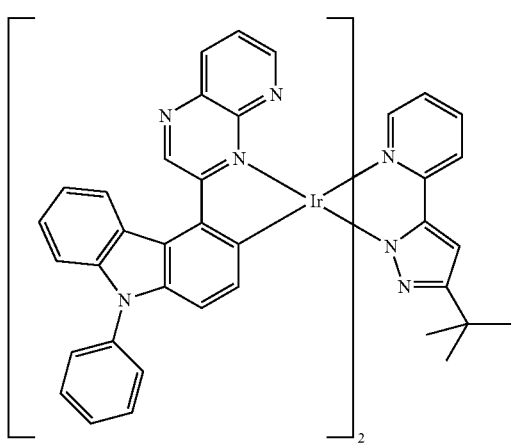
Ir(L44)bppz
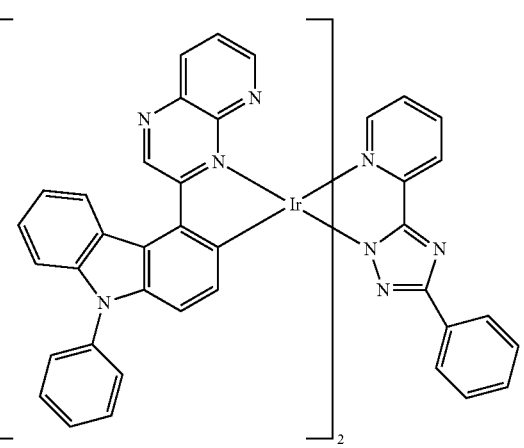
Ir(L44)pptz
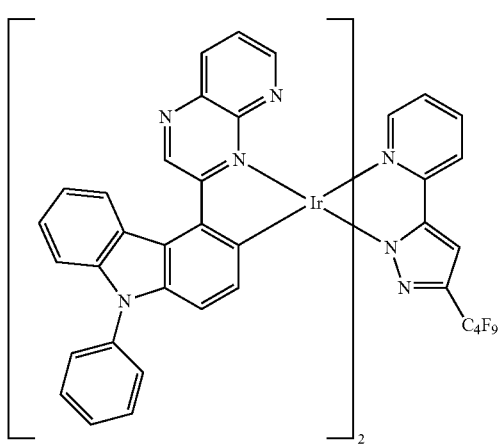
Ir(L44)hppz
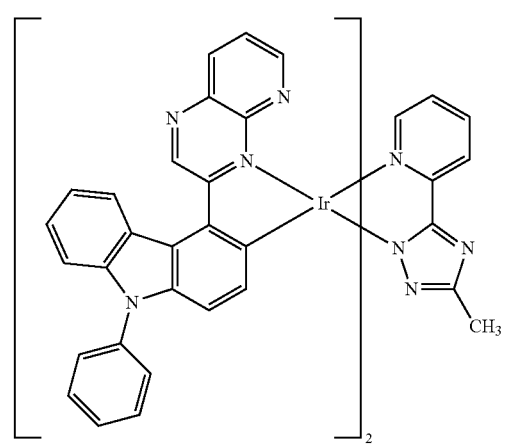
Ir(L44)mptz -continued

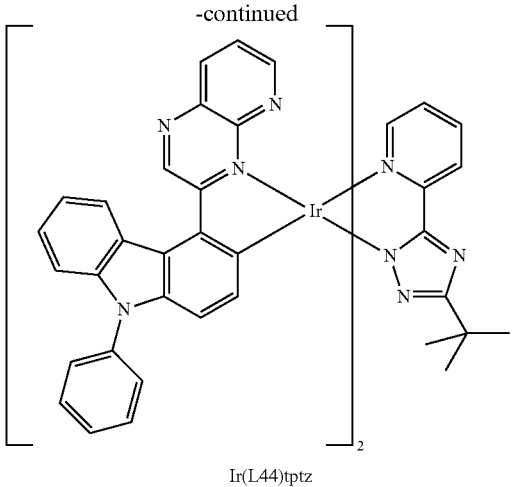

Ir(L44)tptz

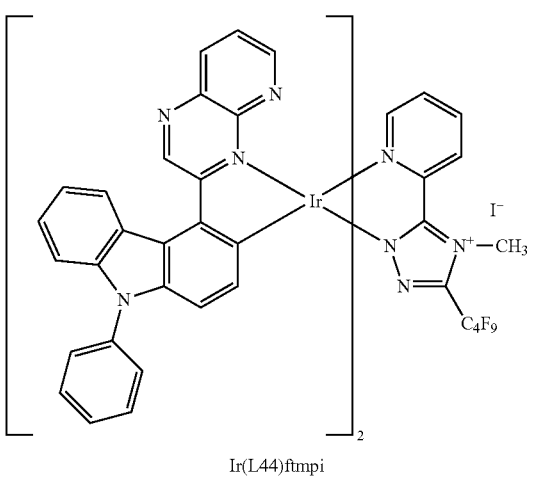

Ir(L44)ftmpi

Example 12

Synthesis of compound (XIV) [(dbfq)₂Ir(ftmpp)]

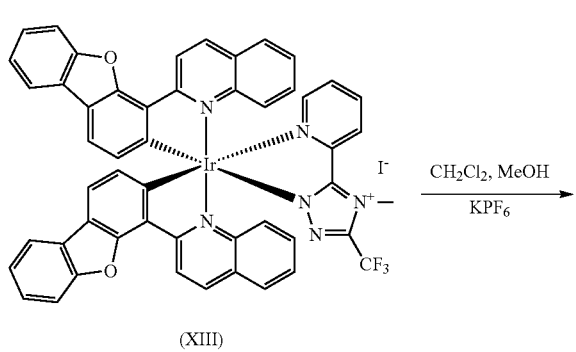

(XIII)

-continued

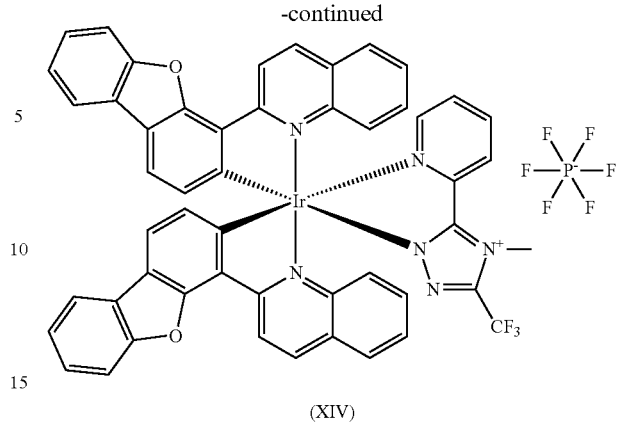

(XIV)

Compound (XIII) (500 mg, 0.46 mmol) is dissolved in a mixture of CH₂Cl₂ and MeOH (2:1, 30 mL) and KPF₆ in MeOH (5 mL) is added. After stirring for 12 h at room temperature, the solvent is removed in vacuu and the residue is washed with de-ionized water (50 mL), Recrystallization yields in a red powder of compound (XIV) (395 mg, 0,36 mmol, 78% yield).

Example 13

Preparation of further complexes

In analogy to the preparation according to Example 12 further complexes can be produced. The general preparation method is as follows:

Compound (Ir(Lxx)ftmpi) (0.5 mmol) is dissolved in a mixture of CH₂Cl₂ and MeOH (2:1, 30 mL) and KPF₆ in MeOH (5 mL) is added, wherein Lxx is defined as being one of the ligands L1 to L44. After stirring for 12 h at room temperature, the solvent is removed in vacuu and the residue is washed with de-ionized water (50 mL). Recrystallization yields in a powder of the hexafluorophosphate compound (Ir(Lxx)ftmpp).

The following table shows all ftmpi-based emitter compounds which can be converted to the ftmpp compounds according to this procedure with yields between 67% to 83%.

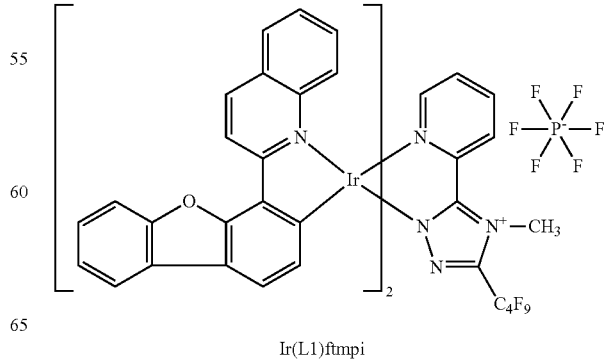

Ir(L1)ftmpi

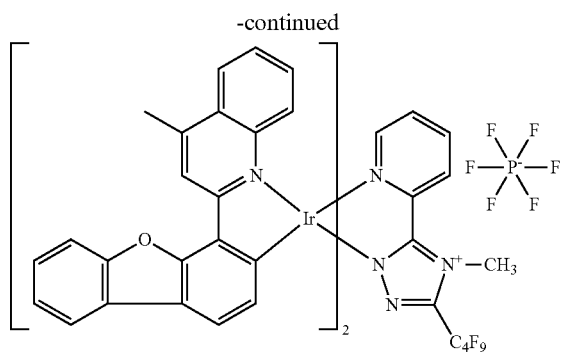
Ir(L2)ftmpi
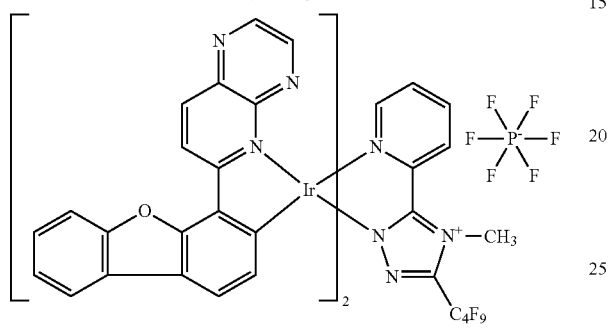
Ir(L3)ftmpi
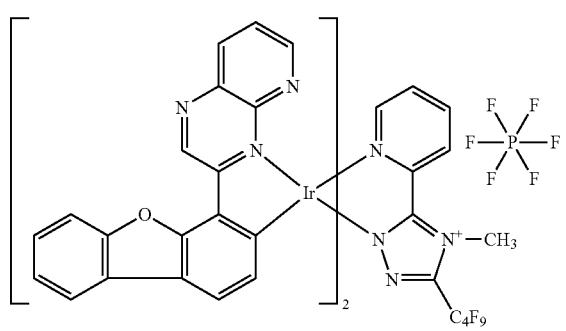
Ir(L4)ftmpi
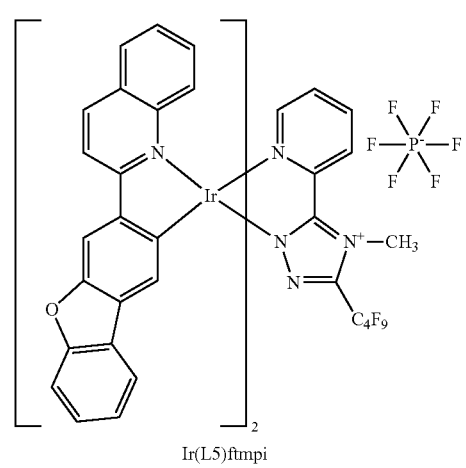
Ir(L5)ftmpi
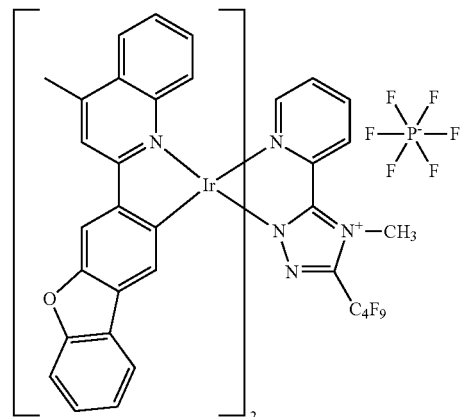
Ir(L6)ftmpi
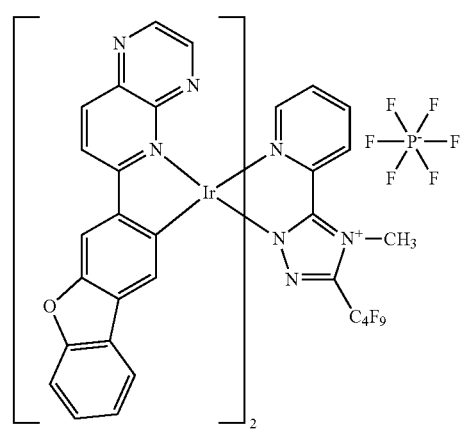
Ir(L7)ftmpi
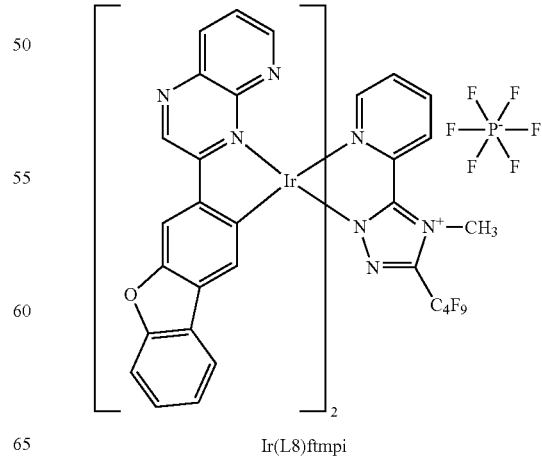
Ir(L8)ftmpi -continued
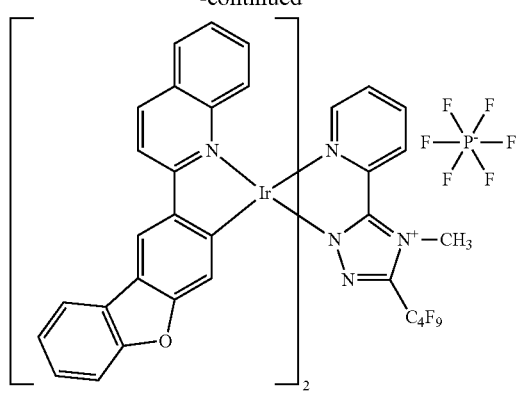
Ir(L9)ftmpi
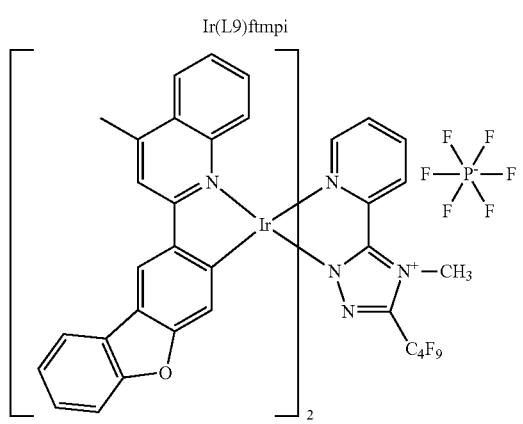
Ir(L10)ftmpi
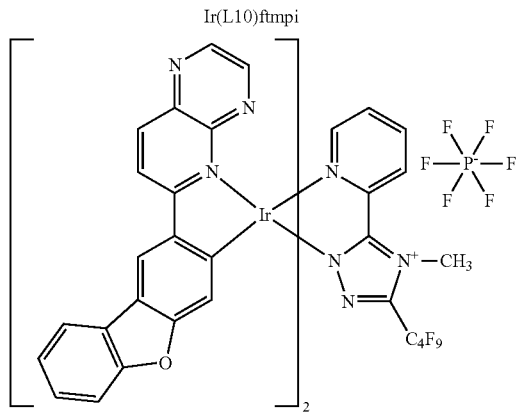
Ir(L11)ftmpi
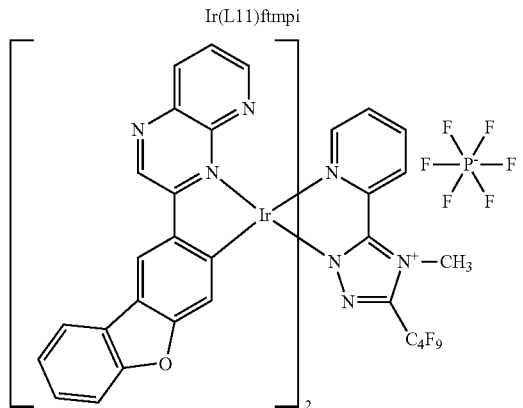
Ir(L12)ftmpi
-continued
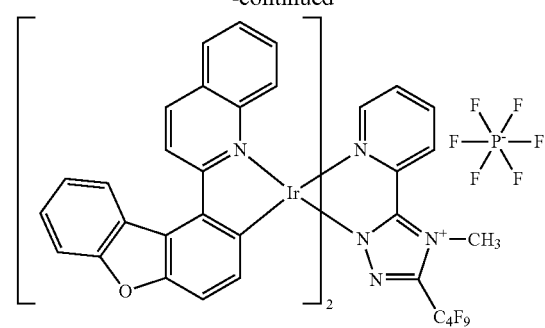
Ir(13)ftmpi
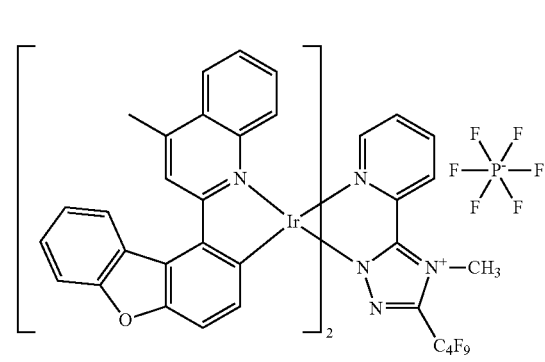
Ir(14)ftmpi
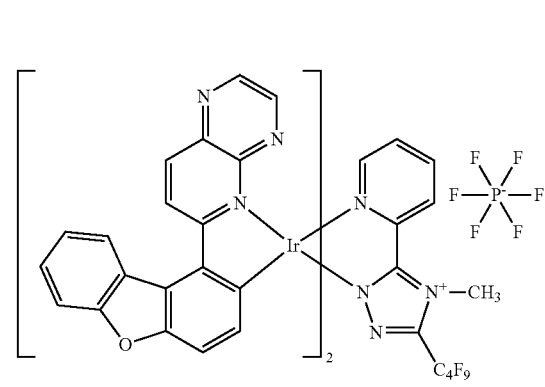
Ir(15)ftmpi
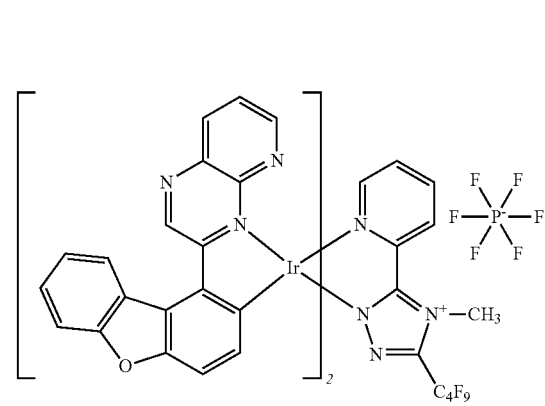
Ir(16)ftmpi -continued
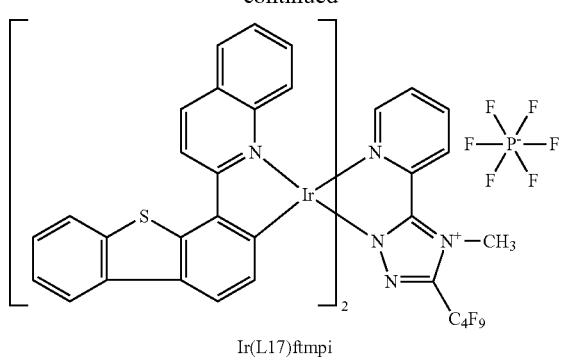
Ir(L17)ftmpi
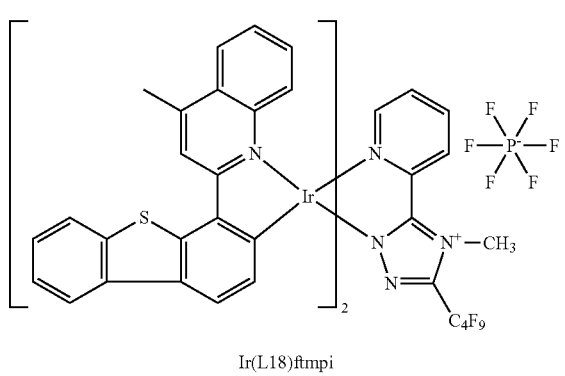
Ir(L18)ftmpi
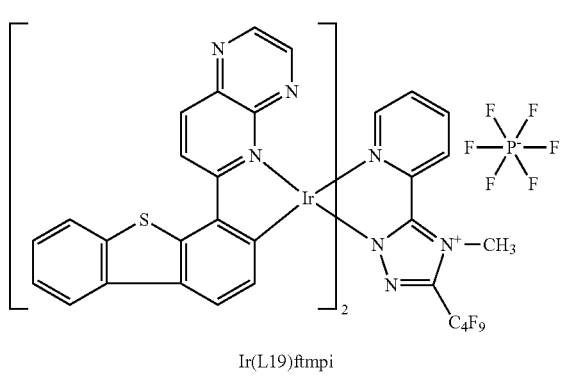
Ir(L19)ftmpi
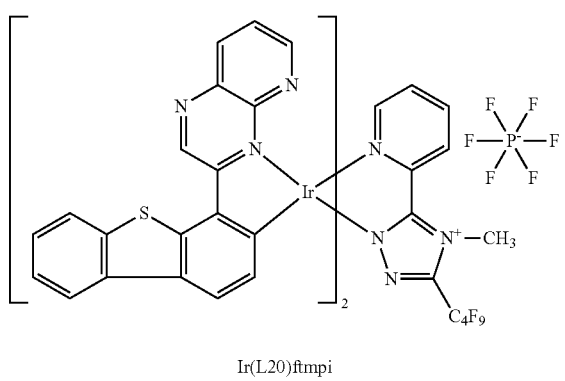
Ir(L20)ftmpi
-continued
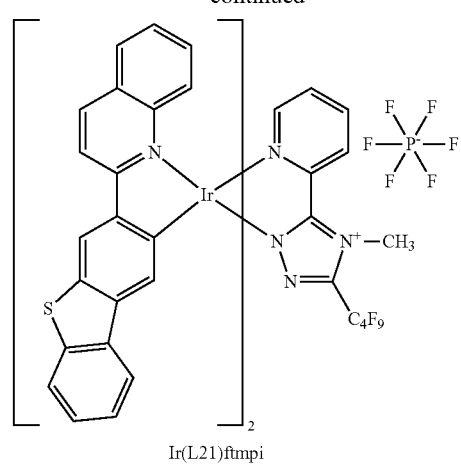
Ir(L21)ftmpi
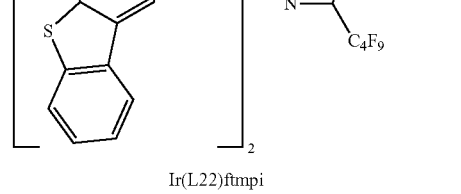
Ir(L22)ftmpi
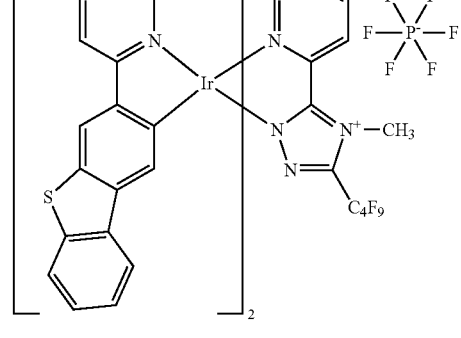
Ir(L21)ftmpi -continued
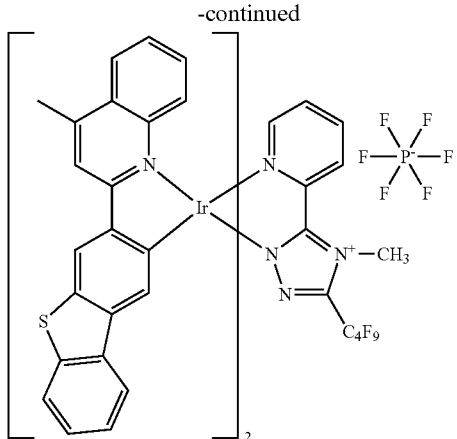
Ir(L22)ftmpi
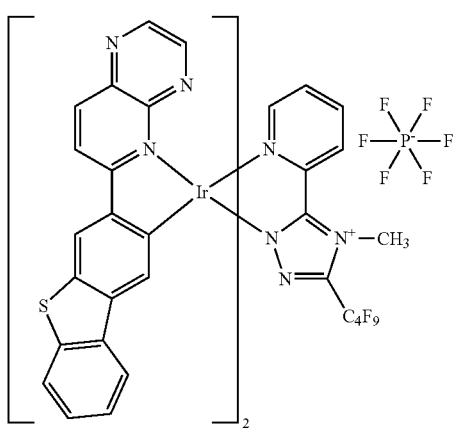
Ir(L23)ftmpi
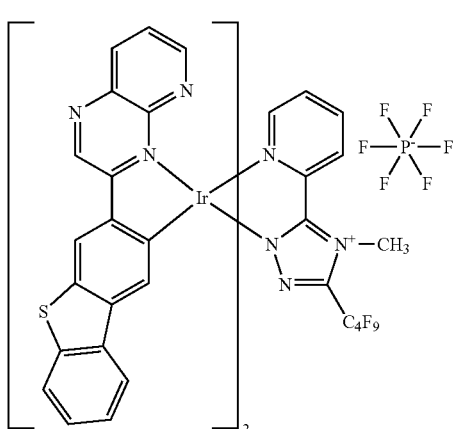
Ir(L24)ftmpi
-continued
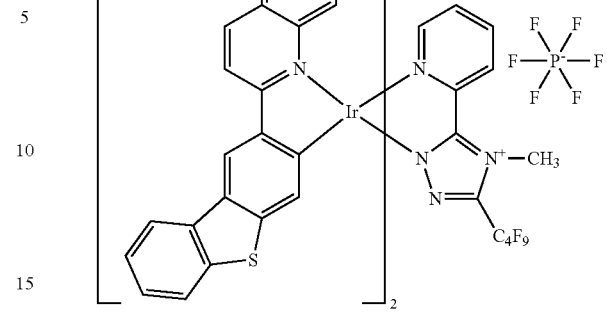
Ir(L25)ftmpi
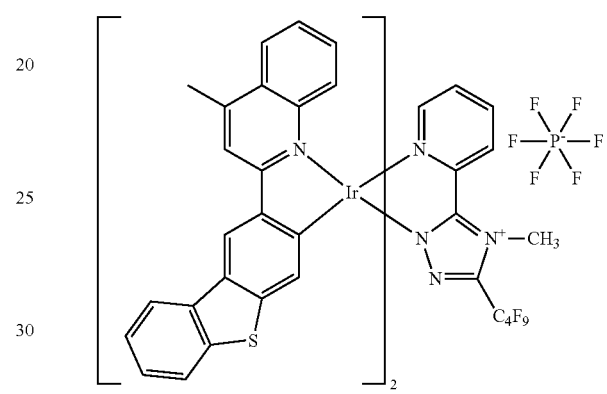
Ir(L26)ftmpi
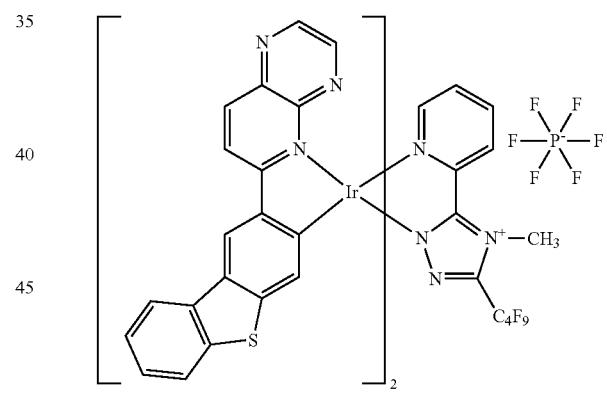
Ir(L27)ftmpi
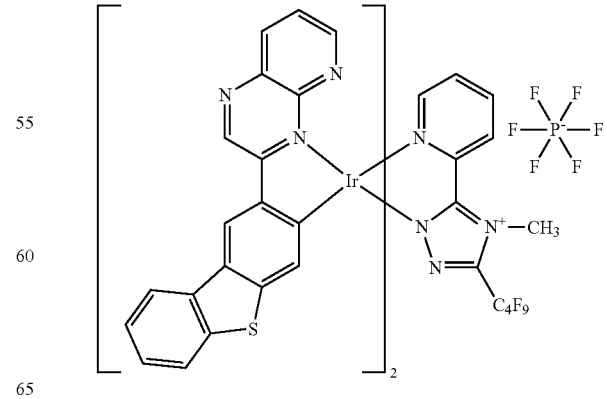
Ir(L28)ftmpi

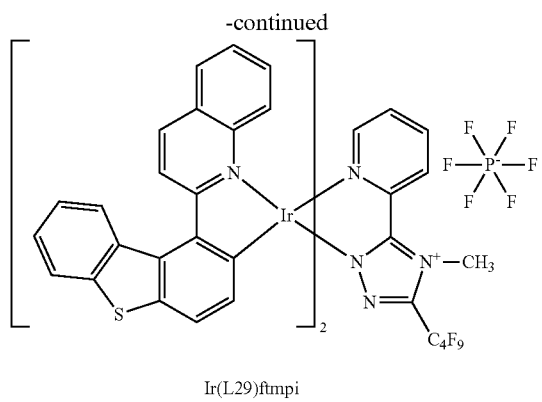
Ir(L29)ftmpi
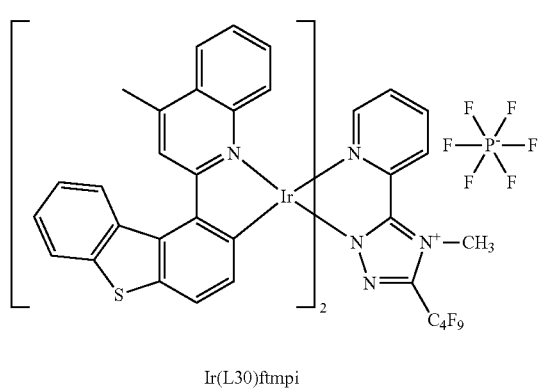
Ir(L30)ftmpi
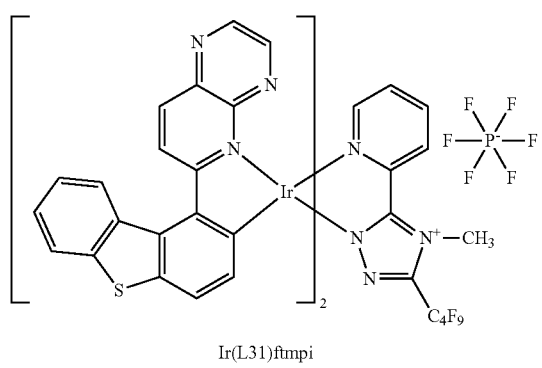
Ir(L31)ftmpi
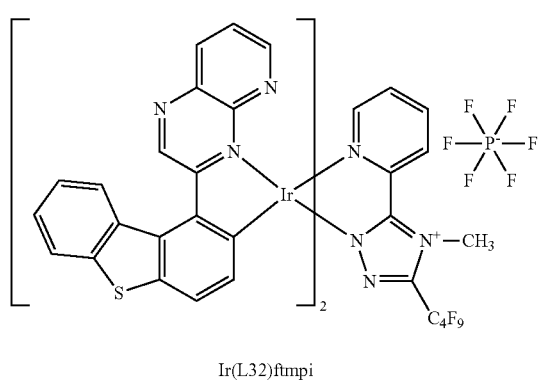
Ir(L32)ftmpi
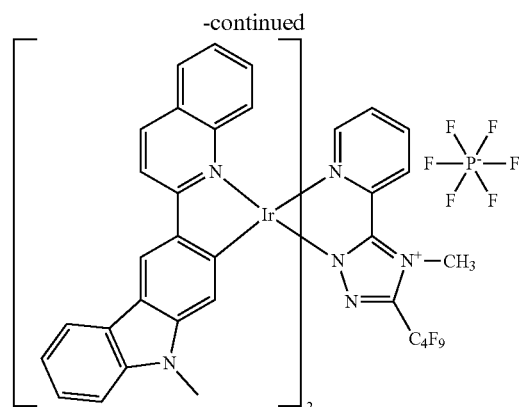
Ir(L33)ftmpi
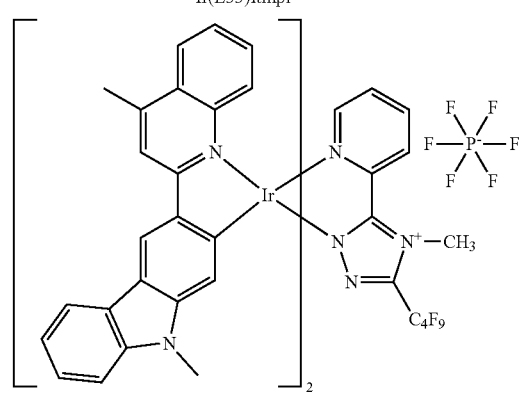
Ir(L34)ftmpi
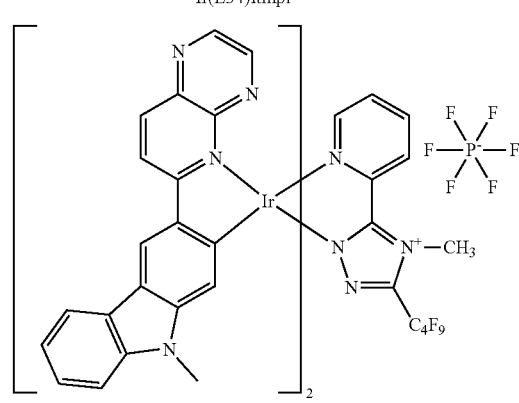
Ir(L35)ftmpi
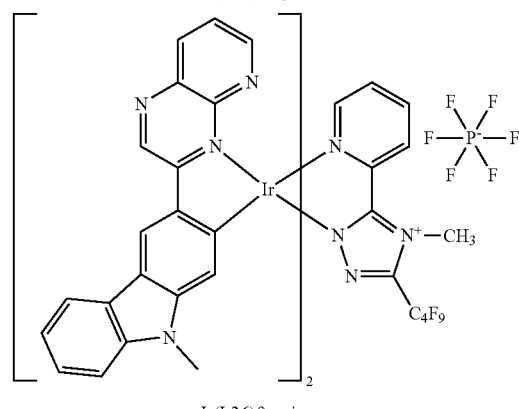
Ir(L36)ftmpi

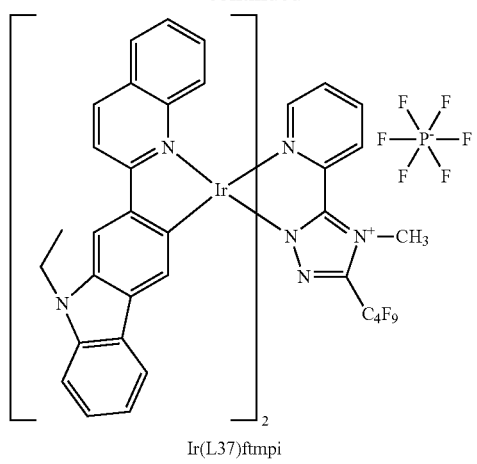
Ir(L37)ftmpi
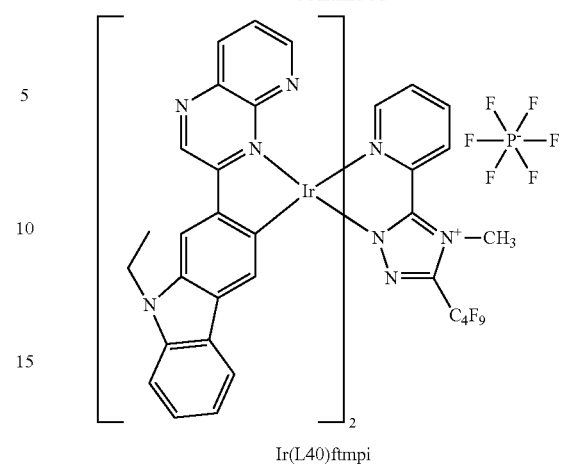
Ir(L40)ftmpi
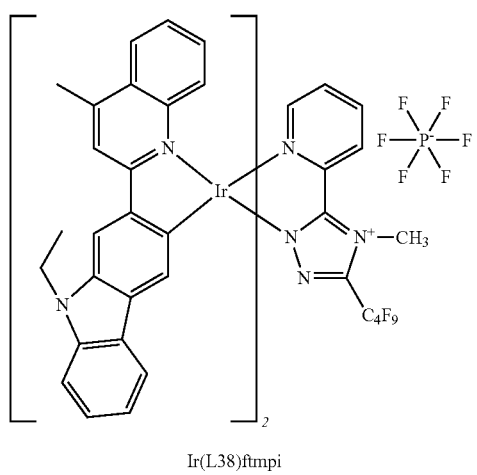
Ir(L38)ftmpi
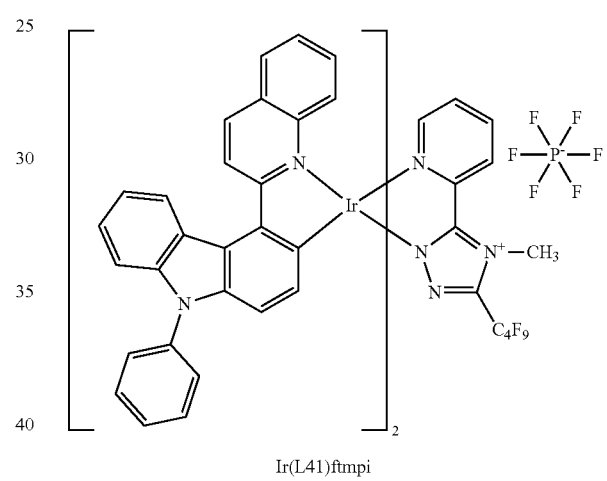
Ir(L41)ftmpi
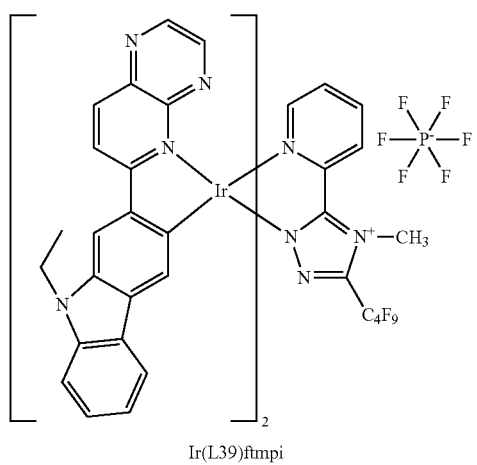
Ir(L39)ftmpi
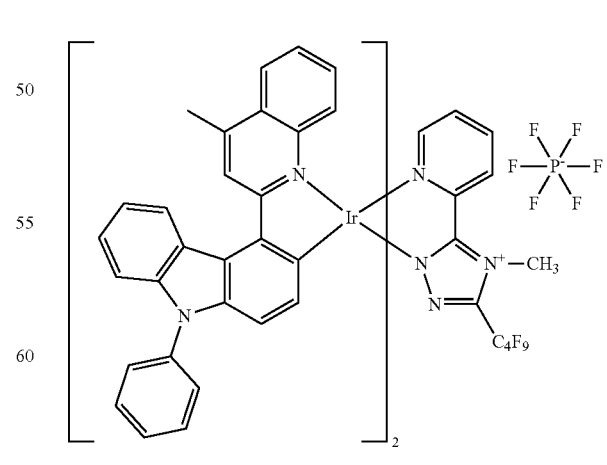
Ir(L42)ftmpi

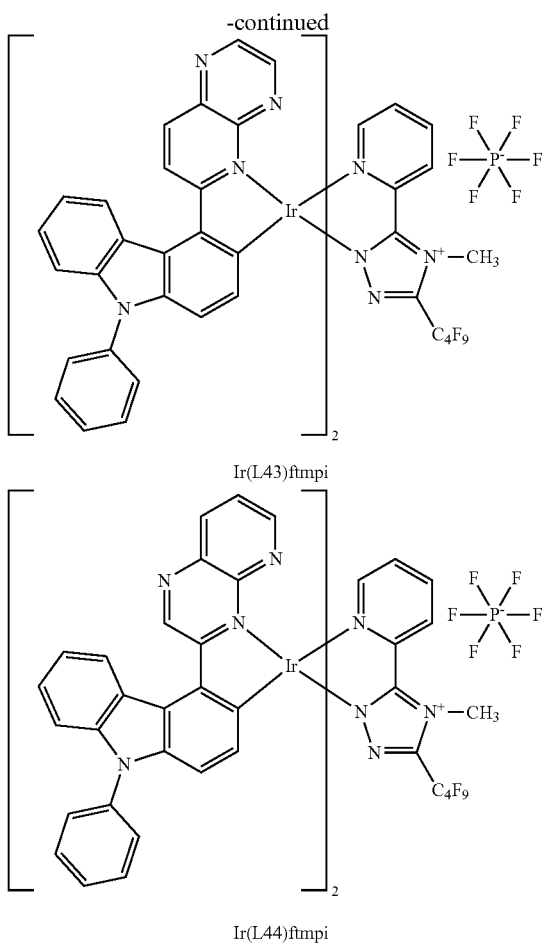

Ir(L43)ftmpi

Ir(L44)ftmpi

Example 14

Electroluminescent Devices

Organic light emitting diodes (OLEDs) comprising materials according to this invention are made according to processes that are well known to one skilled in the art and that have been described in the literature many times (for example in WO 2004/037887 A2 for OLEDs made from solution, and WO 2004/058911 for OLEDs made by thermal evaporation).

Emitters from the present invention are particularly well suited for OLEDs made from solution. A typical OLED device has the following layered structure: Ba/Al cathode (3 nm/100 nm)/EML (80 nm; 6-7 wt.-% emitter)/Interlayer (20 nm; HIL-012)/PEDOT (80 nm; Clevios P 4083 Al)/ITO, wherein EML represents the emissive layer. ITO-coated glass substrates are purchased from Technoprint, the cathode is deposited by vapour-deposition through an evaporation mask.

The substrates are cleaned with de-ionised water and a detergent (Deconex 15 PF) in a clean room and then activated by UV/ozone plasma treatment. An 80 nm PEDOT layer (PEDOT is a polythiophene derivative (Clevios P 4083 Al) from H. C. Starck, Goslar, which is supplied as an aqueous dispersion) is then applied by spin coating, likewise in a clean room. The required spin rate depends on the degree of dilution and the specific spin-coater geometry (typical for 80 nm: 4500 rpm). In order to remove residual water from the layer, the substrates are dried by heating on a hotplate at 180° C. for 10 minutes. The substrates are transferred into a glove box and all subsequent coating and annealing steps are carried out in an inert-gas atmosphere (nitrogen or argon). A 20 nm film of an interlayer (typically a hole-dominated polymer, here HIL-012 from Merck) is spin-coated onto the substrate from a 5 g/L toluene solution and heated for 60 min. at 180° C. A particular advantage of some of the devices shown here is that even the interlayer can be omitted and thus very simple devices can be made. In the device setup 80 nm of an EML are applied from toluene solution. The concentrations depend on the specific composition of the EML: For EMLs that contain polymeric host materials, the concentration is 10 g/L, for EMLs based on soluble small molecules 18 to 20 g/L. The solvent for spin-coating is toluene. After the film is applied, the layers are annealed at 180° C. for 10 minutes. The Ba/Al cathode is then vapour-deposited, (high-purity metals from Aldrich, particularly barium 99.99% (Order No. 474711); typical vacuum level $5 \times 10^{-6}$ mbar). Alternatively, an organic electron transport layer (ETL) may be vapour-deposited between the solution processed EML and the cathode which then typically does not contain a Ba-layer. Finally, the device is encapsulated in order to protect the layers from air and atmospheric moisture.

Devices are characterized in holders manufactured specifically for the substrate size. Electrical contact is made with spring contacts. A photodiode with eye response filter is placed directly on the measurement holder in order to exclude influences from extraneous light. Voltages are typically increased from 0 to max. 12 V in 0.2 V steps and reduced again. For each voltage, the current through the device and the photocurrent through the photodiode are measured. This way, the IUL data of the test devices are obtained. Important parameters are the efficiency and required voltage for 1000 cd/m² as well as the external quantum efficiency (EQE, in %). To determine the colour and the precise electroluminescence spectrum of the test devices, the voltage required for 1000 cd/m² is applied again and the photodiode is replaced by a cover that connects the sample holder with an Ocean Optics spectrometer via an optical fibre. The colour coordinates (CIE: Commission Internationale de l'Eclairage, standard observer from 1931) can be derived from the measured spectrum.

Device lifetimes are measured in a separate setup, but in a very similar way. Based on the characterization data, voltage and current are provided to reach an initial luminance of 2000 to 6000 cd/m² (chosen based on the initial efficiency of the specific device). Then the current is kept constant, which typically leads to an increase in voltage while the device is driven. Here, the lifetimes are determined as T50, the time when the initial luminance has degraded to 50% of the initial value. In order to compare lifetimes for devices with different starting brightnesses, the lifetimes are extrapolated to a starting brightness of 1000 cd/m² with an extrapolation factor of 1.9 for devices with interlayer and 1.625 for devices without.

The examples of solution processed devices with polymer matrices are mainly intended for cheap monochrome applications. They need sufficient lifetime, but mainly good efficiency and "unusual" (not display-type) colour. Solution processed devices with soluble small molecules can still be used for these applications, but are a little more demanding in terms of processing. They will therefore more likely be used in high-end applications where lifetime is also very important.

Simplified Devices without Interlayer (Devices 1-17):

80 nm of the EML are spin-coated directly onto PEDOT. The concentration of the emitters is 7% by weight based on the polymer matrix P1. The overall concentration is 10 g/L, i.e. 9.3 g/L P1 and 0.7 g/L emitter, the spin-rate is ~1200 rpm. The matrix of choice for these simple devices is P1, the polymerization of the monomers is carried out according to WO 2005/040302:

Devices with Interlayer and a Polymer Matrix (Devices 18-6):

80 nm of the EML are spin-coated onto HIL-012. The concentration of the emitters is 7% by weight based on the polymer matrix P2. The overall concentration is 10 g/L, i.e. 9.3 g/L P2 and 0.7 g/L emitter, the spin-rate is ~1200 rpm. The matrix of choice for these devices is P2, the polymerization of the monomers is carried out according to WO 2005/040302:

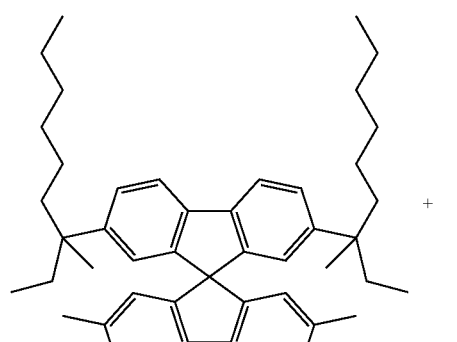

77%

+

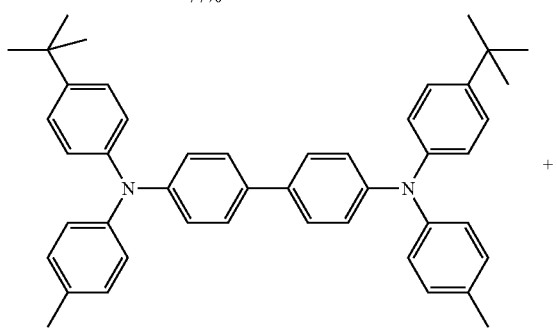

8%

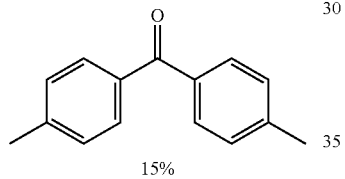

15%

+

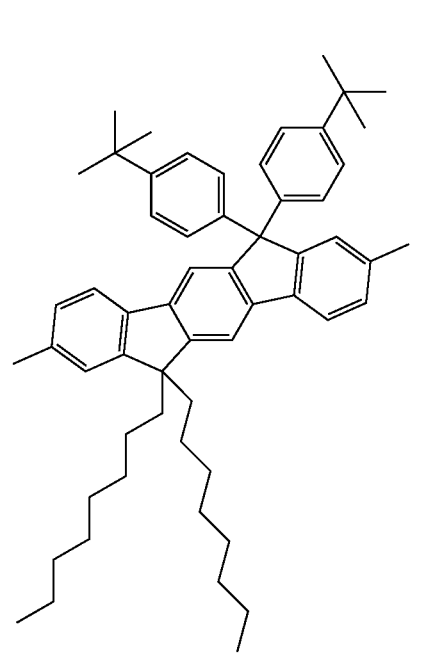

50%

(monomer concentrations in the matrix polymer are given in mol-% with respect to the polymer)

The results are summarized in Table 1. The new emitters have a reasonable lifetime even in these simple and, thus, cheap devices. The colour is more orange, as intended, the efficiencies are very high for such a simple setup.

TABLE 1

| Device | Emitter | Host | ETL/Cathode | Eff.*/(cd/A) | EQE* | U*/V | CIE* | LT50*/h |
|---|---|---|---|---|---|---|---|---|
| 1 | V1 | P1 | Ba/Al | 10.4 | 6.4% | 4.2 | 0.63/0.37 | 840 |
| 2 | (Ir(L1)fppz) | P1 | Ba/Al | 11.4 | 6.0% | 5.1 | 0.61/0.39 | 460 |
| 3 | (Ir(L1)fptz) | P1 | Ba/Al | 10.8 | 5.2% | 4.9 | 0.59/0.41 | 320 |
| 4 | (Ir(L3)tptz) | P1 | Ba/Al | 10.1 | 6.1 | 4.9 | 0.59/0.38 | 530 |
| 5 | (Ir(L5)bppz) | P1 | Ba/Al | 10.5 | 5.9 | 5.0 | 0.58/0.39 | 350 |
| 6 | (Ir(L6)hppz) | P1 | Ba/Al | 10.9 | 5.7 | 4.5 | 0.62/0.35 | 480 |
| 7 | (Ir(L9)pptz) | P1 | Ba/Al | 10.8 | 6.2 | 4.8 | 0.61/0.37 | 340 |
| 8 | (Ir(L11)fptz) | P1 | Ba/Al | 11.0 | 6.1 | 4.7 | 0.59/0.39 | 510 |
| 9 | (Ir(L14)mptz) | P1 | Ba/Al | 11.3 | 5.9 | 5.1 | 0.61/0.38 | 490 |
| 10 | (Ir(L16)pptz) | P1 | Ba/Al | 10.6 | 5.6 | 4.3 | 0.61/0.36 | 400 |
| 11 | (Ir(L19)pptz) | P1 | Ba/Al | 10.3 | 5.2 | 4.4 | 0.60/0.37 | 420 |
| 12 | (Ir(L22)hppz) | P1 | Ba/Al | 11.1 | 5.3 | 5.1 | 0.58/0.37 | 500 |
| 13 | (Ir(L26)mptz) | P1 | Ba/Al | 9.8 | 5.9 | 5.3 | 0.59/0.35 | 390 |
| 14 | (Ir(L35)bppz) | P1 | Ba/Al | 10.7 | 5.7 | 4.8 | 0.56/0.40 | 450 |
| 16 | (Ir(L41)pptz) | P1 | Ba/Al | 11.2 | 6.0 | 5.1 | 0.60/0.39 | 380 |
| 17 | (Ir(L44)mppz) | P1 | Ba/Al | 10.7 | 5.7 | 5.0 | 0.61/0.36 | 430 |

*all values at 1000 cd/m$^2$

-continued

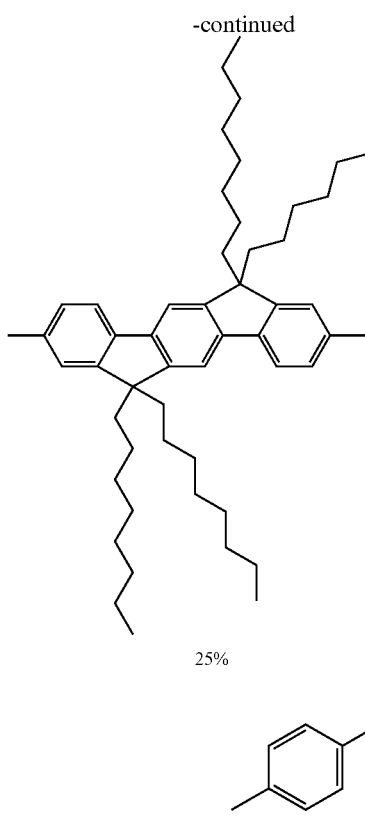

25%

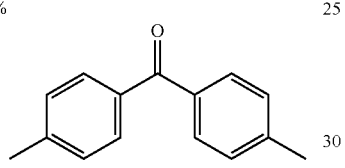

25%

(monomer concentrations in the matrix polymer are given in mol-% with respect to the polymer.)

The results are summarized in Table 2.

TABLE 2

| Device | Inter-layer | Emitter | Host | ETL/Cathode | Eff.*/(cd/A) | EQE* | U*/V | CIE* | LT50*/h |
|---|---|---|---|---|---|---|---|---|---|
| 18 | HIL-012 | V2 | P2 | Ba/Al | 0.70 | 0.4% | 10.1 | 0.57/0.41 | NA |
| 19 | HIL-012 | (Ir(L1)fppz) | P2 | Ba/Al | 9.3 | 4.7% | 6.0 | 0.60/0.39 | 550 |
| 20 | HIL-012 | (Ir(L1)fptz) | P2 | Ba/Al | 7.3 | 3.4% | 6.2 | 0.58/0.41 | 450 |
| 21 | HIL-012 | (Ir(L3)tptz) | P2 | Ba/Al | 7.1 | 4.0 | 5.9 | 0.58/0.38 | 737 |
| 22 | HIL-012 | (Ir(L5)bppz) | P2 | Ba/Al | 7.8 | 4.4 | 6.3 | 0.57/0.39 | 473 |
| 23 | HIL-012 | (Ir(L6)hppz) | P2 | Ba/Al | 8.6 | 4.2 | 5.4 | 0.61/0.35 | 667 |
| 24 | HIL-012 | (Ir(L9)pptz) | P2 | Ba/Al | 8.3 | 4.8 | 5.7 | 0.60/0.37 | 425 |
| 25 | HIL-012 | (Ir(L11)fptz) | P2 | Ba/Al | 7.7 | 4.3 | 5.6 | 0.58/0.39 | 658 |
| 26 | HIL-012 | (Ir(L14)mptz) | P2 | Ba/Al | 7.4 | 4.5 | 6.4 | 0.60/0.38 | 686 |
| 27 | HIL-012 | (Ir(L16)pptz) | P2 | Ba/Al | 7.9 | 3.9 | 5.3 | 0.60/0.36 | 520 |
| 28 | HIL-012 | (Ir(L19)pptz) | P2 | Ba/Al | 7.9 | 3.1 | 5.5 | 0.59/0.37 | 512 |
| 29 | HIL-012 | (Ir(L22)hppz) | P2 | Ba/Al | 7.4 | 3.6 | 6.2 | 0.57/0.37 | 625 |
| 30 | HIL-012 | (Ir(L26)mptz) | P2 | Ba/Al | 7.4 | 4.2 | 6.4 | 0.58/0.35 | 534 |
| 31 | HIL-012 | (Ir(L35)bppz) | P2 | Ba/Al | 9.3 | 3.8 | 5.7 | 0.55/0.40 | 599 |
| 33 | HIL-012 | (Ir(L41)pptz) | P2 | Ba/Al | 7.9 | 4.4 | 6.3 | 0.59/0.39 | 532 |
| 34 | HIL-012 | (Ir(L44)mppz) | P2 | Ba/Al | 7.1 | 4.3 | 6.1 | 0.60/0.36 | 563 |

*all values at 1000 cd/m$^2$

Devices with Interlayer and Soluble Small Molecule Matrix 1 (Comp. 1) (Devices 35 to 58):

80 nm of the EML are spin-coated onto HIL-012. The soluble small molecule matrix consists of 30 wt.-% SSM1, 42 wt.-% SSM2 and 22 wt.-% SSM3 (=composition 1). The emitter concentration is 6 wt.-%. The overall concentration is 18 g/L, the spin-rates are between 650 and 1300 rpm. The results are summarized in Table 3.

TABLE 3

| Device | Inter-layer | Emitter | Host | ETL/Cathode | Eff.*/(cd/A) | EQE* | U*/V | CIE* | LT50*/h |
|---|---|---|---|---|---|---|---|---|---|
| 35 | HIL-012 | V1 | Comp. 1 | Ba/Al | 11.0 | 7.5% | 7.3 | 0.63/0.37 | 8000 |
| 36 | HIL-012 | V2 | Comp. 1 | Ba/Al | 7.3 | 3.9% | 10.1 | 0.58/0.41 | 330 |
| 37 | HIL-012 | V3 | Comp. 1 | Ba/Al | 15.6 | 7.9% | 7.4 | 0.59/0.41 | 3900 |
| 38 | HIL-012 | V4 | Comp. 1 | Ba/Al | 13.9 | 9.5% | 6.7 | 0.64/0.36 | 21000 |
| 39 | HIL-012 | (Ir(L1)fppz) | Comp. 1 | Ba/Al | 24.2 | 11.5% | 6.7 | 0.59/0.41 | 31000 |
| 40 | HIL-012 | (Ir(L1)fptz) | Comp. 1 | Ba/Al | 25.3 | 11.1% | 6.6 | 0.57/0.42 | 12000 |
| 41 | HIL-012 | (Ir(L1)hptz) | Comp. 1 | Ba/Al | 15.3 | 7.9% | 7.1 | 0.58/0.42 | 12000 |
| 42 | HIL-012 | (Ir(L1)mptz) | Comp. 1 | Ba/Al | 13.0 | 7.0% | 7.5 | 0.58/0.42 | 8000 |
| 43 | HIL-012 | (Ir(L2)fppz) | Comp. 1 | Ba/Al | 23.7 | 9.9% | 6.5 | 0.60/0.40 | 12000 |
| 44 | HIL-012 | (Ir(L2)fptz) | Comp. 1 | Ba/Al | 17.4 | 7.2% | 7.1 | 0.55/0.45 | 8000 |
| 45 | HIL-012 | (Ir(L3)tptz) | Comp. 1 | Ba/Al | 20.1 | 11.4% | 6.5 | 0.57/0.39 | 32000 |
| 46 | HIL-012 | (Ir(L5)bppz) | Comp. 1 | Ba/Al | 24.1 | 12.5% | 6.8 | 0.56/0.38 | 16000 |
| 47 | HIL-012 | (Ir(L6)hppz) | Comp. 1 | Ba/Al | 28.0 | 12.6% | 5.8 | 0.60/0.34 | 29000 |
| 48 | HIL-012 | (Ir(L9)pptz) | Comp. 1 | Ba/Al | 26.0 | 15.3% | 6.4 | 0.59/0.36 | 13000 |
| 49 | HIL-012 | (Ir(L11)fptz) | Comp. 1 | Ba/Al | 26.3 | 11.0% | 6.1 | 0.57/0.38 | 19000 |
| 50 | HIL-012 | (Ir(L14)mptz) | Comp. 1 | Ba/Al | 22.6 | 13.3% | 6.9 | 0.59/0.37 | 25000 |
| 51 | HIL-012 | (Ir(L16)pptz) | Comp. 1 | Ba/Al | 21.9 | 11.4% | 5.7 | 0.59/0.35 | 22000 |
| 52 | HIL-012 | (Ir(L19)pptz) | Comp. 1 | Ba/Al | 22.9 | 10.0% | 6.0 | 0.58/0.36 | 15000 |
| 53 | HIL-012 | (Ir(L22)hppz) | Comp. 1 | Ba/Al | 22.7 | 11.0% | 6.8 | 0.56/0.36 | 23000 |
| 54 | HIL-012 | (Ir(L26)mptz) | Comp. 1 | Ba/Al | 24.4 | 13.7% | 7.1 | 0.57/0.34 | 29000 |
| 55 | HIL-012 | (Ir(L35)bppz) | Comp. 1 | Ba/Al | 28.3 | 12.1% | 6.3 | 0.54/0.39 | 23000 |
| 57 | HIL-012 | (Ir(L41)pptz) | Comp. 1 | Ba/Al | 24.2 | 12.6% | 6.9 | 0.58/0.38 | 15000 |
| 58 | HIL-012 | (Ir(L44)mppz) | Comp. 1 | Ba/Al | 21.9 | 10.9% | 6.8 | 0.59/0.35 | 26000 |

*all values at 1000 cd/m$^2$

Compared to the two standard emitters V1 and V2, the emitters according to the invention show an overall much improved set of device characteristics. The co-ligand in V3 shortens the lifetime significantly. V4 is deep-red, the co-ligand thus introduces a strong batho-chromic shift. It is also worse in all parameters than the 1:1 comparison (Ir(L1)fppz).

Devices with Interlayer, Soluble Small Molecule Matrix 1 (Comp. 1) and Additional Evaporated ETL:
(Devices 59 to 75):

60 nm of the EML in composition 1 are spin-coated onto HIL-012. The emitter concentration is 6 wt.-%. The overall concentration is 18 g/L, the spin-rate is increased to ~1900 rpm (due to the thinner EML-layer). A 50 nm ETL consisting of 50 wt.-% ET1 and 50 wt.-% ET2 is vapour-deposited on top of the spin-coated layer and capped with 100 nm of Al. The results are summarized in Table 4.

Again the new materials result in much improved devices, especially in terms of efficiency, lifetime and color.

The invention claimed is:
1. A compound of the general Formula (1)

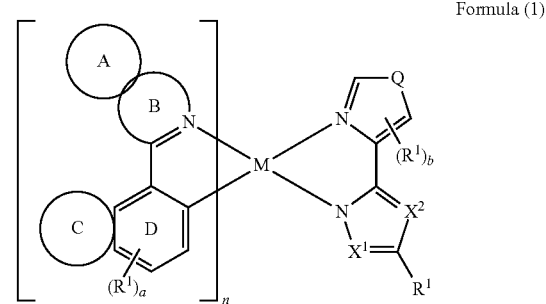

Formula (1)

TABLE 4

| Device | Inter-layer | Emitter | Host | ETL/Cathode | Eff.*/(cd/A) | EQE* | U*/V | CIE* | LT50*/h |
|---|---|---|---|---|---|---|---|---|---|
| 59 | HIL-012 | V1 | Comp. 1 | ET1:ET2/Al | 19.5 | 11.7 | 6.4 | 0.63/0.37 | 11500 |
| 60 | HIL-012 | (Ir(L1)fppz) | Comp. 1 | ET1:ET2/Al | 23.1 | 12.4 | 7.0 | 0.60/0.40 | 18000 |
| 61 | HIL-012 | (Ir(L1)fptz) | Comp. 1 | ET1:ET2/Al | 24.9 | 12.7 | 6.6 | 0.59/0.41 | 18000 |
| 62 | HIL-012 | (Ir(L3)tptz) | Comp. 1 | ET1:ET2/Al | 20.1 | 11.4% | 6.5 | 0.58/0.40 | 41000 |
| 63 | HIL-012 | (Ir(L5)bppz) | Comp. 1 | ET1:ET2/Al | 24.1 | 12.5% | 6.8 | 0.57/0.39 | 19000 |
| 64 | HIL-012 | (Ir(L6)hppz) | Comp. 1 | ET1:ET2/Al | 28.0 | 12.6% | 5.8 | 0.61/0.35 | 18000 |
| 65 | HIL-012 | (Ir(L9)pptz) | Comp. 1 | ET1:ET2/Al | 26.0 | 15.3% | 6.4 | 0.60/0.35 | 19000 |
| 66 | HIL-012 | (Ir(L11)fptz) | Comp. 1 | ET1:ET2/Al | 26.3 | 11.0% | 6.1 | 0.58/0.37 | 22000 |
| 67 | HIL-012 | (Ir(L14)mptz) | Comp. 1 | ET1:ET2/Al | 22.6 | 13.3% | 6.9 | 0.60/0.36 | 30000 |
| 68 | HIL-012 | (Ir(L16)pptz) | Comp. 1 | ET1:ET2/Al | 21.9 | 11.4% | 5.7 | 0.60/0.34 | 23000 |
| 69 | HIL-012 | (Ir(L19)pptz) | Comp. 1 | ET1:ET2/Al | 22.9 | 10.0% | 6.0 | 0.59/0.35 | 9000 |
| 70 | HIL-012 | (Ir(L22)hppz) | Comp. 1 | ET1:ET2/Al | 22.7 | 11.0% | 6.8 | 0.57/0.35 | 33000 |
| 71 | HIL-012 | (Ir(L26)mptz) | Comp. 1 | ET1:ET2/Al | 24.4 | 13.7% | 7.1 | 0.58/0.35 | 28780 |
| 72 | HIL-012 | (Ir(L35)bppz) | Comp. 1 | ET1:ET2/Al | 28.3 | 12.1% | 6.3 | 0.55/0.40 | 33437 |
| 74 | HIL-012 | (Ir(L41)pptz) | Comp. 1 | ET1:ET2/Al | 24.2 | 12.6% | 6.9 | 0.59/0.39 | 17234 |
| 75 | HIL-012 | (Ir(L44)mppz) | Comp. 1 | ET1:ET2/Al | 21.9 | 10.9% | 6.8 | 0.60/0.34 | 25384 | wherein A and B together represent a condensed heteroaromatic ring system wherein both A and B can be unsubstituted or identically or differently be substituted with one or more R¹;

wherein A can be any aromatic or heteroaromatic ring or any aromatic or heteroaromatic polycyclic ring system;

wherein B represents any monocyclic heteroaromatic ring;

wherein C represents a chemical structure having the Formula (2) which is condensed to ring D at any positions via the positions indicated by the sign # in Formula (2);

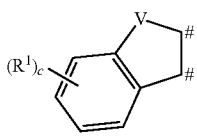

Formula (2)

and where the remaining indices and symbols are defined as follows:

a is 0, 1 or 2;
b is 0, 1 or 2;
c is 0, 1, 2, 3 or 4;
M is a metal selected from the group consisting of iridium, rhodium, platinum and palladium;
n is 2 for M equal to iridium or rhodium and n is 1 for M equal to platinum or palladium; if n is 2, the two ligands comprising the rings A, B, C and D can be identical or different from each other;
R¹ is identical or different from each other on each occurrence and selected from H, D, F, Cl, Br, I, N(R²)₂, CN, NO₂, Si(R²)₃, B(R²)₂, C(=O)R², P(=O)(R²)₂, S(=O)R², S(=O)₂R², OSO₂R², a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more substituents R², where one or more non-adjacent CH₂ groups may be replaced by R²C=CR², C=C, Si(R²)₂, Ge(R²)₂, Sn(R²)₂, C=O, C=S, C=Se, C=NR², P(=O)(R²), SO, SO₂, NR², O, S or CONR² and where one or more H atoms may be replaced by D, F, Cl, Br, I, CN or NO₂, or an aromatic or heteroaromatic ring system having 5 to 60 aromatic ring atoms which may in each case be substituted by one or more substituents R², or an aryloxy or heteroaryloxy group having 5 to 60 aromatic ring atoms, which may be substituted by one or more substituents R², or a diarylamino group, diheteroarylamino group or arylheteroarylamino group having 10 to 40 aromatic ring atoms, which may be substituted by one or more substituents R², or a combination of two or more of these groups; two or more groups R¹ here may also form a mono- or poly-cyclic, aliphatic, aromatic and/or benzo-fused ring system with one another;
R² is, identical or different on each occurrence, H, D, F, Cl, Br, I, N(R³)₂, CN, NO₂, Si(R³)₃, B(R³)₂, C(=O)R³, P(=O)(R³)₂, S(=O)R³, S(=O)₂R³, OSO₂R³, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more substituents R³, where one or more non-adjacent CH₂ groups may be replaced by R³C=CR³, C=C, Si(R³)₂, Ge(R³)₂, Sn(R³)₂, C=O, C=S, C=Se, C=NR³, P(=O)(R³), SO, SO₂, NR³, O, S or CONR³ and where one or more H atoms may be replaced by D, F, Cl, Br, I, CN or NO₂, or an aromatic or heteroaromatic ring system having 5 to 60 aromatic ring atoms, which may in each case be substituted by one or more substituents R³, or an aryloxy or heteroaryloxy group having 5 to 60 aromatic ring atoms, which may be substituted by one or more substituents R³, or a diarylamino group, diheteroarylamino group or arylheteroarylamino group having 10 to 40 aromatic ring atoms, which may be substituted by one or more substituents R³, or a combination of two or more of these groups; two or more adjacent substituents R² here may form a mono- or polycyclic, aliphatic or aromatic ring system with one another;

R³ is identical or different on each occurrence and selected from H, D, F or an aliphatic, aromatic and/or heteroaromatic hydrocarbon having 1 to 20 C atoms, in which, in addition, one or more H atoms may be replaced by F; two or more substituents R³ here may also form a mono-or polycyclic, aliphatic or aromatic ring system with one another;

Q is identical or different on each occurrence and selected from R¹C=CR¹, R¹C=N, O, S, SO₂, SiR¹₂, Se or NR¹;

X¹ and X² are identical or different on each occurrence, selected from CR¹ or N, wherein at least one of X¹ and X² is N;

V is identical or different on each occurrence and selected from NR¹, O, S, SO₂, SiR¹₂, BR¹ or Se.

2. The compound according to claim 1, wherein ring A is a ring or ring system according to Formula (3)

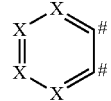

Formula (3)

wherein X is identical or different on each occurrence and selected from CR¹ or N, and wherein the signs # indicate the positions in ring A which are condensed to ring B.

3. The compound according to claim 1, wherein the compound has one of the following general Formulae (9) to (26)

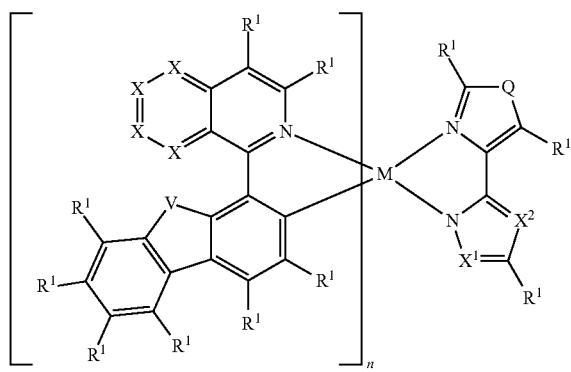

Formula (9)

Formula (10)
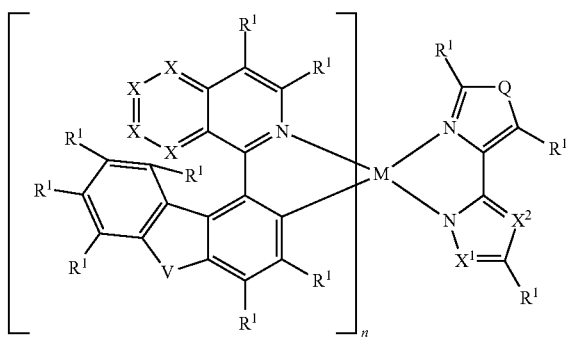
Formula (11)
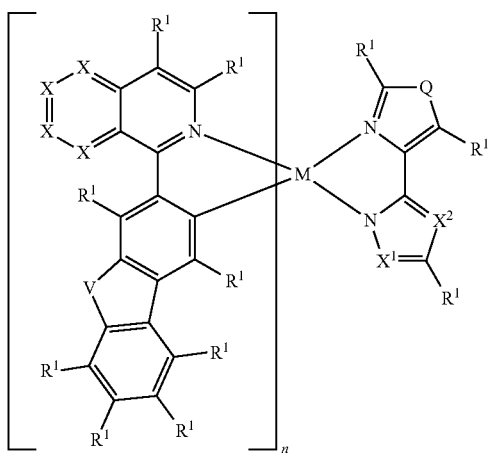
Formula (12)
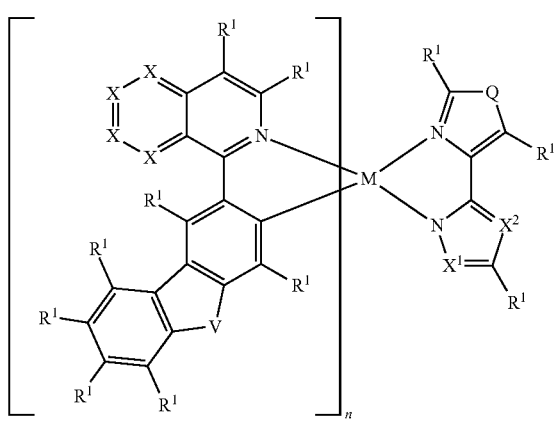
Formula (13)
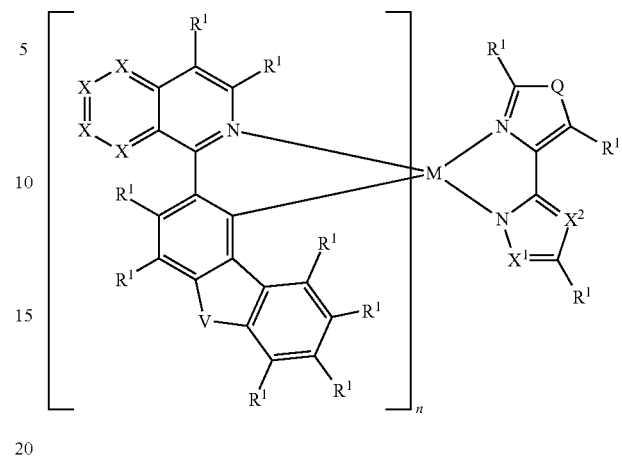
Formula (14)
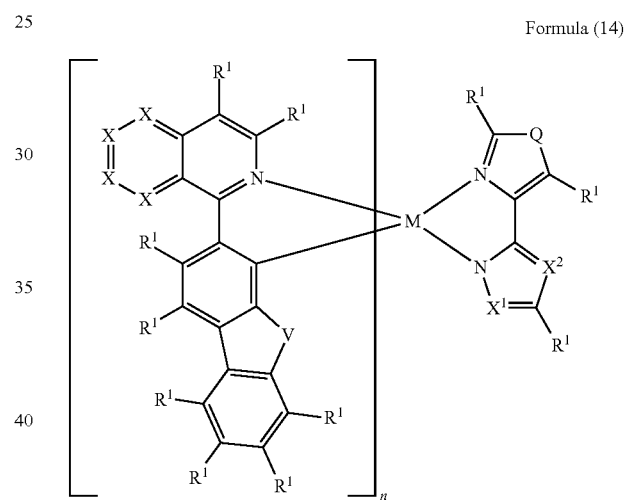
Formula (15)
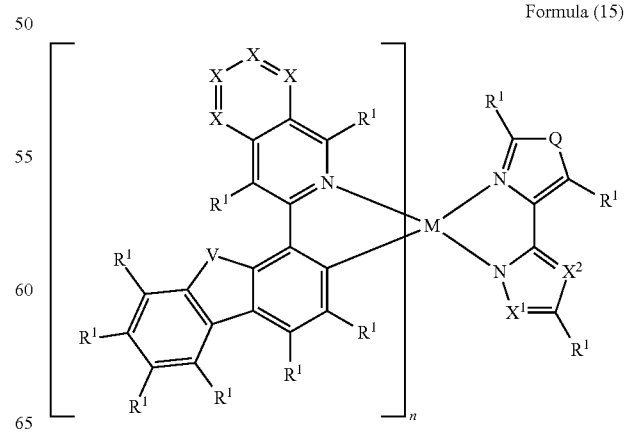

Formula (16)
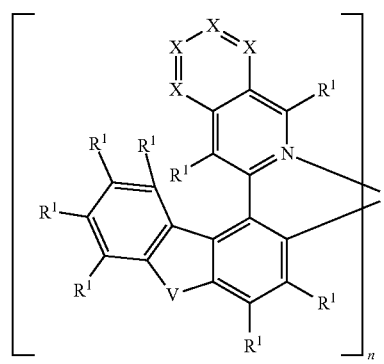
Formula (17)
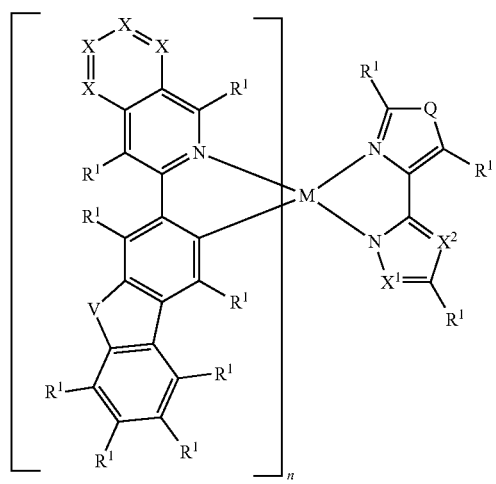
Formula (18)
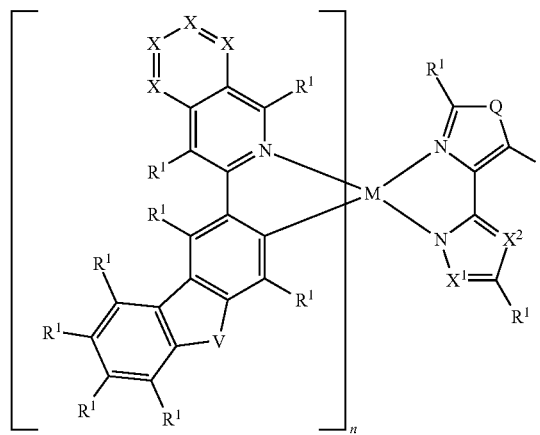
Formula (19)
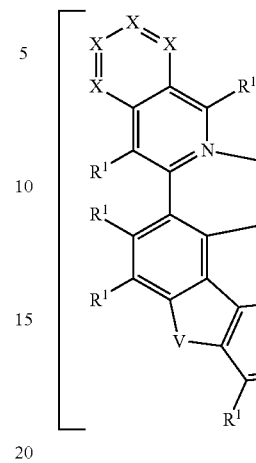
Formula (20)
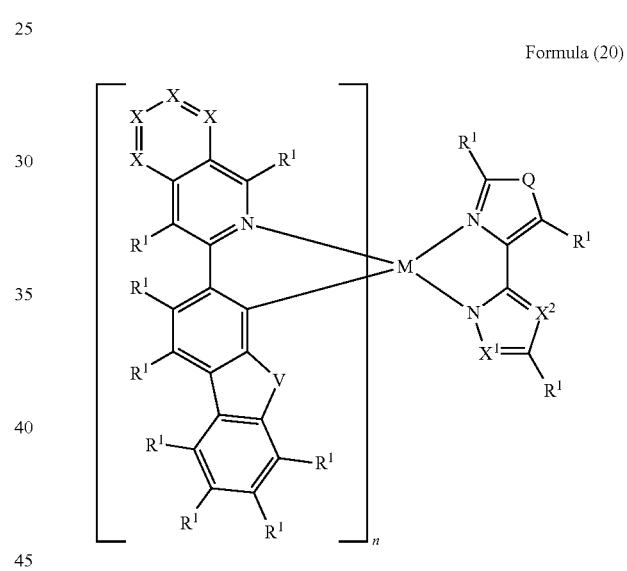
Formula (21)
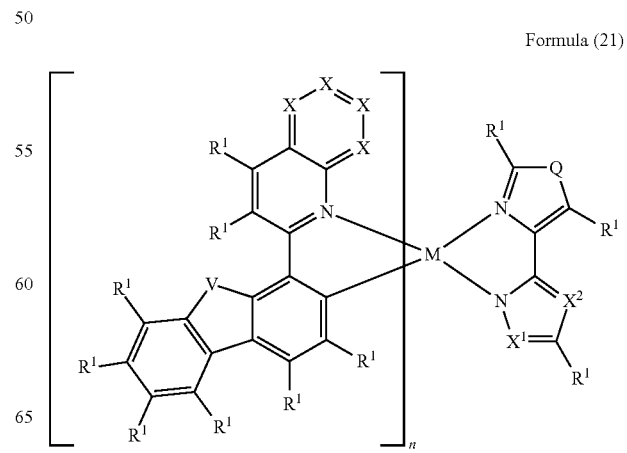

311
-continued
Formula (22)
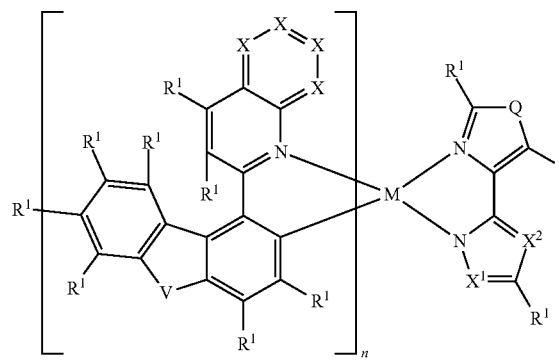
Formula (23)
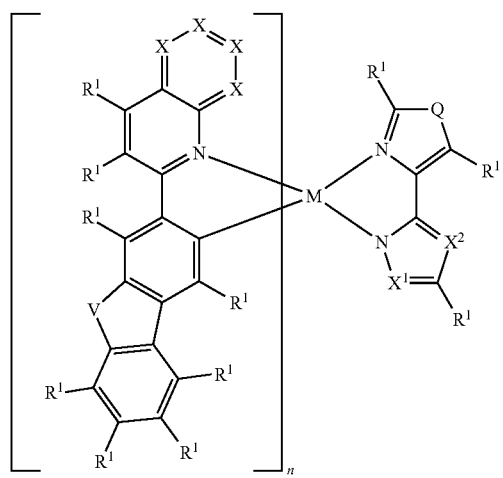
Formula (24)
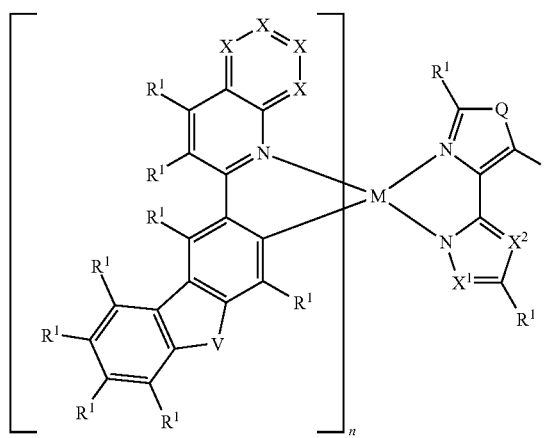
312
-continued
Formula (25)
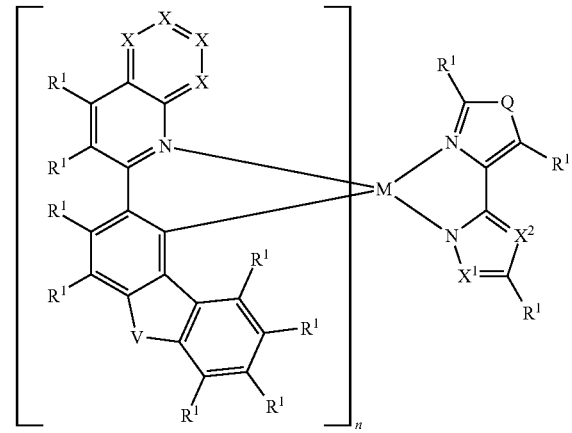
Formula (26)
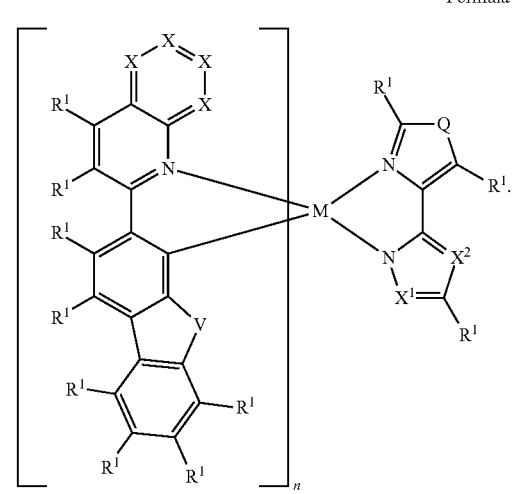
4. The compound according to claim 1, wherein the compound has the following general Formula (65)
Formula (65)
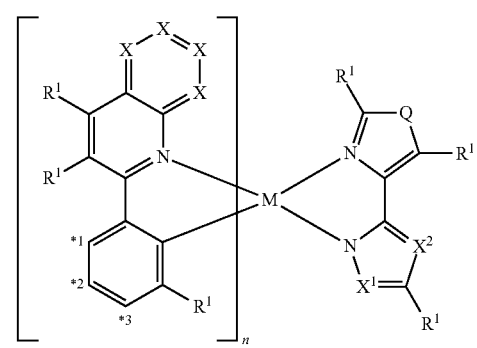
wherein compound of Formula (66) is condensed via positions #1 and #2 to compound of Formula (65) via positions *1, *2 or *3

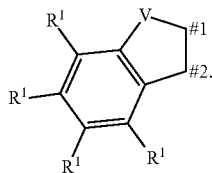

Formula (66)

5. The compound according to claim 4, wherein condensation occurs via position #1 to *1 or to *3 and #2 to *2.

6. The compound according to claim 4, wherein condensation occurs via position #1 to *1 and #2 to *2.

7. The compound according to claim 1, wherein $X^1$ is N and $X^2$ is $CR^1$.

8. The compound according to claim 1, wherein both $X^1$ and $X^2$ are N.

9. The compound according to claim 1, wherein the substituents $R^1$ do not form mono or polycyclic, aliphatic and/or aromatic and/or benzo-fused ring systems with one another.

10. A composition comprising at least one compound according to claim 1 and at least one further organic functional material selected from hole transport material (HTM), hole injection material (HIM), electron transport material (ETM), electron injection material (EIM), hole blocking material (HBM), exciton blocking material (ExBM), host or matrix material, fluorescent emitter, phosphorescent emitter.

11. The composition according to claim 10, wherein the at least one organic functional material is a matrix material selected from ketones, phosphinoxides, sulfoxides, sulfones, triarylamines, carbazoles, indolocarbazoles, indenocarbazoles, azacarbazoles, bipolar matrix materials, silanes, azaborolenes, boronesters, triazines, zinc complexes, diaza- or tetraazasiloles or diazaphospholes or mixtures thereof.

12. A formulation comprising at least one compound according to claim 1 and at least one solvent.

13. An electronic device comprising at least one compound according to claim 1.

14. The electronic device as claimed in claim 13, wherein the device is organic electroluminescent device (OLED), organic light emitting diode, PLED(polymer light emitting diode), organic integrated cicuit (O-IC), organic field effect transistor (O-FET), organic thin film transistor (O-TFT), organic light emitting transistor (O-LET), organic solar cell (O-SC), organic optical detector, organic photoreceptor, organic field quenching device (O-FQD), light emitting electrochemical cell (LEC, OLEC, LEEC) or organic laser diode (O-Laser).

15. An electronic device which comprises the composition according to claim 10 in one or more light emitting layers.

16. An electroluminescent device comprising at least one compound according to claim 1.

17. A method for the medical treatment which comprises phototherapy with the electroluminescent device as claimed in claim 16.

18. The compound according to claim 1, wherein
M is iridium;
Q is $R^1C=CR^1$; and
V is O.

19. The compound according to claim 2, wherein X is $CR^1$.

20. A process for a cosmetic application which comprises irradiation of the skin by means of phototherapy using the electroluminescent device according to claim 16.

21. The process according to claim 20, wherein the cosmetic application is an application in the area of acne, cellulite, skin reddening, skin wrinkling or skin rejuvenation.

22. A method for the treatment of the skin which comprises treating the skin by means of phototherapy through the use of a luminescent comprising the composition according to claim 16.

* * * * *